United States Patent
Bur et al.

(10) Patent No.: US 8,288,419 B2
(45) Date of Patent: Oct. 16, 2012

(54) AMINOPYRAZOLE DERIVATIVES

(75) Inventors: Daniel Bur, Therwil (CH); Oliver Corminboeuf, Allschwil (CH); Sylvaine Cren, Zürich (CH); Heinz Fretz, Riehen (CH); Corinna Grisostomi, Allschwil (CH); Xavier Leroy, Steinsoultz (FR); Julien Pothier, Saint-Louis (FR); Sylvia Richard-Bildstein, Dietwiller (FR)

(73) Assignee: Actelion Pharmaceuticals, Ltd, Allschwil (CH)

( * ) Notice: Subject to any disclaimer, the term of this patent is extended or adjusted under 35 U.S.C. 154(b) by 148 days.

(21) Appl. No.: 12/808,137

(22) PCT Filed: Dec. 12, 2008

(86) PCT No.: PCT/IB2008/055251
§ 371 (c)(1),
(2), (4) Date: Jun. 14, 2010

(87) PCT Pub. No.: WO2009/077954
PCT Pub. Date: Jun. 25, 2009

(65) Prior Publication Data
US 2011/0034516 A1 Feb. 10, 2011

(30) Foreign Application Priority Data

Dec. 14, 2007 (WO) .................. PCT/IB2007/055111
Sep. 10, 2008 (WO) .................. PCT/IB2008/053648

(51) Int. Cl.
*A61K 31/44* (2006.01)
*C07D 231/00* (2006.01)

(52) U.S. Cl. ..... 514/341; 514/406; 514/374; 548/374.1; 548/365.7; 546/275.4

(58) Field of Classification Search .................. 514/341, 514/374, 406; 548/374.1, 365.7; 546/275.4
See application file for complete search history.

(56) References Cited

U.S. PATENT DOCUMENTS

| 7,799,782 B2 * | 9/2010 | Munson et al. ............ 514/234.5 |
| 2004/0043904 A1 | 3/2004 | Yamaguchi et al. |

FOREIGN PATENT DOCUMENTS

| JP | 62-234018 | 10/1987 |
| WO | WO 03/082314 | 10/2003 |
| WO | WO 2005/047899 | 5/2005 |
| WO | WO 2007/055941 | 5/2007 |
| WO | WO 2009/025793 | 2/2009 |
| WO | WO 2009/077990 | 6/2009 |
| WO | WO 2010/134014 | 11/2010 |
| WO | WO 2010/143116 | 12/2010 |
| WO | WO 2010/143158 | 12/2010 |

OTHER PUBLICATIONS

Burli et al., Bioorganic & Medicinal Chemistry Letters, Pergamon, Elsevier Science, GB, vol. 16, No. 14, pp. 3713-3718 (2006).
Chiang et al., Pharmacological Reviews, vol. 58, pp. 463-487 (2006).
Gould, International Journal of Pharmacology, vol. 33, pp. 201-217 (1986).
Greene, Index of Protective Groups in Organic Synthesis, P.G.M. Wuts, Wiley Interscience (1999).
Le et al., Protein Peptide Letters, vol. 14, pp. 846-853 (2007).
Serhan et al., Current Opinion in Pharmacology, vol. 6, pp. 414-420 (2006).
Unknown, Index of The Science and Practice of Pharmacy, 21st Edition, Part 5, "Pharmaceutical Manufacturing" [published by Lippincott Williams & Wilkins] (2005).
Yamaguchi, U.S. Appl. No. 10/380,753, filed Mar. 19, 2003.
Yazawa et al., The FASEB Journal, vol. 15, pp. 2454-2462 (2001).
Ying et al., Journal Immunology, vol. 172, pp. 7078-7085 (2004).
Mallamo et al. (1992) Journal of Medicinal Chemistry 35(10): 1663-1670.
Obushak et al. (2004) Russian Journal of Organic Chemistry 40(3): 383-389.
Satoshi et al., U.S. Appl. No. 10/380,783, entitled "Pyridazinones and Triazinones and Medicinal Use Thereof," filed Mar. 18, 2003.
Wermuth (1996) The Practice of Medicinal Chemistry 13: 203-237.
Yamaguchi et al., U.S. Appl. No. 10/380,753, entitled "N-(4-Pyrazolyl) Amide Derivatives, Chemicals for Agricultural and Horticultural, Use, and Usage of the Same" Mar. 19, 2003.

* cited by examiner

*Primary Examiner* — Rei-tsang Shiao
(74) *Attorney, Agent, or Firm* — Hunton & Williams LLP

(57) ABSTRACT

The invention relates to aminopyrazole derivatives of formula (I),

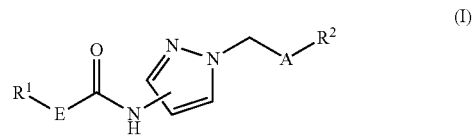

wherein A, E, $R^1$ and $R^2$ are as defined in the description, their preparation and their use as pharmaceutically active compounds.

17 Claims, No Drawings

AMINOPYRAZOLE DERIVATIVES

This application is a national phase filing of International Patent Application No. PCT/IB2008/055251, filed Dec. 12, 2008, which claims priority to PCT/IB2007/055111, filed Dec. 14, 2007, and to PCT/IB2008/053648, filed Sep. 10, 2008. The disclosures of each of these applications are hereby incorporated by reference in their entirety.

The present invention relates to novel aminopyrazole derivatives of formula (I) and their use as pharmaceuticals. The invention also concerns related aspects including processes for the preparation of the compounds, pharmaceutical compositions containing one or more compounds of formula (I), and especially their use as ALX receptor agonists.

BACKGROUND

ALXR (alias Lipoxin A4 Receptor, FPRL1; disclosed in WO2003/082314 as nucleotide sequence SEQ ID NO:1) is a member of the G-protein coupled receptor family. ALXR was found to mediate calcium mobilization in response to high concentration of the formyl-methionine-leucyl-phenylalanine peptide. Furthermore, a lipid metabolite, lipoxin A4 (LXA4), and its analogs, were found to bind ALXR with high affinity and increase arachidonic acid production and G-protein activation in ALXR transfected cells (Chiang et al., Pharmacol. Rev., 2006, 58, 463-487). The effects of LXA4 have been evaluated in a variety of animal models of diseases and LXA4 was demonstrated to have potent anti-inflammatory and pro-resolution activities. The disease models where LXA4, or derivatives, or stable analogs, demonstrated in vivo activities are for example dermal inflammation, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, and graft-vs-host disease (GvHD) (Serhan and Chiang, Br. J. Pharmacol., 2007, 1-16). ALXR was also identified as a functional receptor of a various number of peptides, including a fragment of the prion protein, a peptide derived from gp120 of the Human Immunodeficiency Virus (HIV)-$1_{LAI}$ strain, and amyloid-beta 1-42 (Ab42) (for review, Le et al., Protein Pept Lett., 2007, 14, 846-853), and has been suggested to participate in the pathogenesis of Alzheimer's Disease (AD) in several crucial ways (Yazawa et al., FASEB J., 2001, 15, 2454-2462). Activation of ALXR on macrophages and microglial cells initiates a G protein-mediated signaling cascade that increases directional cell migration, phagocytosis, and mediator release. These events may account for the recruitment of mononuclear cells to the vicinity of senile plaques in the diseased areas of AD brain where Ab42 is overproduced and accumulated. Although accumulation of leukocytes at the sites of tissue injury may be considered an innate host response aimed at the clearance of noxious agents, activated mononuclear phagocytes also release a variety of substances such as superoxide anions that may be toxic to neurons. Thus, ALXR may mediate pro-inflammatory responses elicited by Ab42 in AD brain and exacerbate disease progression. It was also reported that humanin (HN), a peptide with neuroprotective capabilities, shares the human ALXR with Ab42 on mononuclear phagocytes and neuronal cell lines and it has been suggested that the neuroprotective activity of HN may be attributed to its competitive occupation of ALXR (Ying et al., J. Immunol., 2004, 172, 7078-7085).

The biological properties of ALXR agonists include, but are not limited to, monocyte/macrophage/microglia migration/activation, neutrophil migration/activation, regulation of lymphocyte activation, proliferation and differentiation regulation of inflammation, regulation of cytokine production and/or release, regulation of proinflammatory mediator production and/or release, regulation of immune reaction.

SUMMARY OF INVENTION

The present invention provides aminopyrazole derivatives, which are non-peptide agonists of human ALX receptor. The compounds are useful for the prevention or treatment of diseases, which respond to the modulation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the prevention or treatment of autoimmune diseases and for the modulation of immune responses (especially those elicited by vaccination).

Various embodiments of the invention are presented hereafter:

1) The present invention relates to aminopyrazole derivatives of the formula (I),

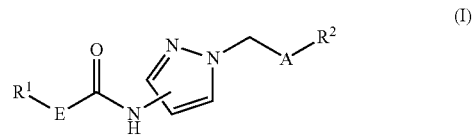

wherein
A represents a phenyl- or a monocyclic heterocyclyl-group, wherein the two substituents are in a 1,3-arrangement; or A represents propan-1,3-diyl;
E represents *-(C$_1$-C$_4$)alkyl-O—, —CH=CH— or

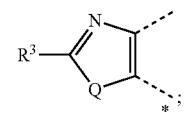

wherein the asterisks indicate the bond which is linked to R$^1$;
Q represents O, or S;
R$^3$ represents hydrogen, (C$_1$-C$_4$)alkyl, cyclopropyl, (C$_1$-C$_4$) alkoxy-(C$_1$-C$_2$)alkyl, —CH$_2$NH$_2$, —CH$_2$NHBoc, —CH$_2$CH$_2$C(O)OtBu or benzyl;
R$^1$ represents a heterocyclyl- or an aryl-group, which groups are unsubstituted, mono-, di- or tri-substituted, wherein the substituents are independently selected from the group consisting of halogen, (C$_1$-C$_4$)alkyl, (C$_1$-C$_4$)alkoxy, (C$_1$-C$_4$) fluoroalkyl, (C$_1$-C$_4$)fluoroalkoxy, phenyl, cyano, di-[(C$_1$-C$_3$) alkyl]-amino, —C(O)—NH$_2$, —C(O)OtBu, (C$_1$-C$_4$)alkoxy-(C$_1$-C$_2$)alkyl, hydroxy-(C$_1$-C$_2$)alkyl and dimethylamino-(C$_1$-C$_2$)alkyl; and
R$^2$ represents —CO—(C$_1$-C$_3$)alkyl, —CO-cyclopropyl, —CF$_2$—(C$_1$-C$_3$)alkyl, —CHF—(C$_1$-C$_3$)alkyl or —SO$_2$—(C$_1$-C$_3$)alkyl.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

In case E represents —CH=CH— the double bond may be present in (Z)- or (E)-configuration, preferably it is present in (E)-configuration.

The following paragraphs provide definitions of the various chemical moieties for the compounds according to the invention and are intended to apply uniformly throughout the specification and claims unless an otherwise expressly set out definition provides a broader or narrower definition.

The term "alkyl", used alone or in combination, refers to a straight or branched chain alkyl group containing one to four carbon atoms. The term "$(C_x-C_y)$alkyl" (x and y each being an integer), refers to an alkyl group as defined before containing x to y carbon atoms. For example a $(C_1-C_4)$alkyl group contains from one to four carbon atoms. Representative examples of alkyl groups include methyl, ethyl, n-propyl, iso-propyl, n-butyl, iso-butyl, sec-butyl and tert-butyl. Preferred are $(C_1-C_3)$alkyl groups such as methyl, ethyl, n-propyl and iso-propyl. Most preferred are ethyl and methyl.

Examples of $(C_1-C_3)$alkyl groups as used in $R^2$ representing —CO—$(C_1-C_3)$alkyl, —CHF—$(C_1-C_3)$alkyl, —$CF_2$—$(C_1-C_3)$alkyl or —$SO_2$—$(C_1-C_3)$alkyl are methyl, ethyl and iso-propyl. Preferred is methyl.

In a bridging $(C_1-C_4)$alkyl group as used in E representing *-$(C_1-C_4)$alkyl-O—, the oxygen atom and the rest $R^1$ are preferably attached to the same carbon atom of the bridging $(C_1-C_4)$alkyl group. Examples of such bridging $(C_1-C_4)$alkyl groups are a methylene or an ethane-1,1-diyl group, wherein the chiral carbon atom of the ethane-1,1-diyl group may be in absolute (R)- or (S)-configuration. Preferred is a methylene group.

The term "alkoxy", used alone or in combination, refers to an alkyl-O— group wherein the alkyl group is as defined before. The term "$(C_x-C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy. Preferred are ethoxy and methoxy. Most preferred is methoxy. The term "fluoroalkyl" refers to an alkyl group as defined before containing one to four (preferably one to three) carbon atoms in which one or more (and possibly all) hydrogen atoms have been replaced with fluorine. The term "$(C_x-C_y)$fluoroalkyl" (x and y each being an integer) refers to a fluoroalkyl group as defined before containing x to y carbon atoms. For example a $(C_1-C_3)$fluoroalkyl group contains from one to three carbon atoms in which one to seven hydrogen atoms have been replaced with fluorine. Representative examples of fluoroalkyl groups include trifluoromethyl and 2,2,2-trifluoroethyl. Preferred is $(C_1)$fluoroalkyl such as trifluoromethyl and difluoromethyl. Most preferred is trifluoromethyl.

The term "fluoroalkoxy" refers to an alkoxy group as defined before containing one to four (preferably one to three) carbon atoms in which one or more (and possibly all) hydrogen atoms have been replaced with fluorine. The term "$(C_x-C_y)$fluoroalkoxy" (x and y each being an integer) refers to a fluoroalkoxy group as defined before containing x to y carbon atoms. For example a $(C_1-C_3)$fluoroalkoxy group contains from one to three carbon atoms in which one to seven hydrogen atoms have been replaced with fluorine. Representative examples of fluoroalkoxy groups include trifluoromethoxy, difluoromethoxy and 2,2,2-trifluoroethoxy. Preferred are $(C_1)$fluoroalkoxy groups such as trifluoromethoxy and difluoromethoxy. Most preferred is trifluoromethoxy.

The term "$(C_1-C_4)$alkoxy-$(C_1-C_2)$alkyl" refers to an alkyl group as defined before containing one or two carbon atoms in which one hydrogen atom has been replaced with $(C_1-C_4)$alkoxy as defined before. Representative examples of $(C_1-C_4)$alkoxy-$(C_1-C_2)$alkyl groups include methoxy-methyl, methoxy-ethyl, ethoxy-methyl, ethoxy-ethyl, isopropoxy-methyl and isopropoxy-ethyl (and preferably methoxy-methyl, methoxy-ethyl, ethoxy-methyl and ethoxy-ethyl).

Preferred examples of $(C_1-C_4)$alkoxy-$(C_1-C_2)$alkyl groups as used in $R^1$ are methoxy-methyl, methoxy-ethyl, ethoxy-methyl, ethoxy-ethyl, isopropoxy-methyl and isopropoxy-ethyl. Most preferred are methoxy-methyl and methoxy-ethyl.

Preferred examples of $(C_1-C_4)$alkoxy-$(C_1-C_2)$alkyl groups as used in $R^3$ are methoxy-methyl and methoxy-ethyl. Most preferred is methoxy-methyl.

The term "hydroxy-$(C_1-C_2)$alkyl" refers to an alkyl group as defined before containing one or two carbon atoms in which one hydrogen atom has been replaced with hydroxy. Examples of hydroxy-$(C_1-C_2)$alkyl groups include hydroxy-methyl, 1-hydroxy-ethyl and 2-hydroxy-ethyl.

The term "di-[$(C_1-C_3)$alkyl]-amino" refers to an amino group which is substituted by two $(C_1-C_3)$alkyl groups as defined above, wherein the two $(C_1-C_3)$alkyl groups may be the same or different. Representative examples of di-[$(C_1-C_3)$alkyl]-amino groups include, but are not limited to dimethylamino, methyl-ethyl-amino and diethylamino. Preferred is dimethylamino.

The term "dimethylamino-$(C_1-C_2)$alkyl" refers to an alkyl group as defined before containing one or two carbon atoms in which one hydrogen atom has been replaced with dimethylamino. Representative examples of dimethylamino-$(C_1-C_2)$alkyl groups include dimethylamino-methyl and dimethylamino-ethyl.

The term halogen means fluoro, chloro, bromo or iodo, preferably fluoro, chloro or bromo and most preferably fluoro or chloro.

The term "aryl", alone or in any combination, means phenyl (preferred) or naphthyl. The aryl group is unsubstituted, mono-, di-, or tri-substituted, wherein the substituents are independently selected from the group consisting of halogen, $(C_1-C_4)$alkyl, $(C_1-C_4)$alkoxy, $(C_1-C_4)$fluoroalkyl, $(C_1-C_4)$fluoroalkoxy, phenyl, cyano, di-[$(C_1-C_3)$-alkyl]-amino, —C(O)—$NH_2$, —C(O)OtBu, $(C_1-C_4)$alkoxy-$(C_1-C_2)$alkyl, hydroxy-$(C_1-C_2)$alkyl and dimethylamino-$(C_1-C_2)$alkyl. Examples are phenyl, naphthyl, 2-chlorophenyl, 3-chlorophenyl, 4-chlorophenyl, 2,3-dichlorophenyl, 2,4-dichlorophenyl, 2,6-dichlorophenyl, 2-chloro-4-fluorophenyl, 2-chloro-6-fluorophenyl, 3-chloro-2-fluorophenyl, 3-chloro-4-fluorophenyl, 2-chloro-3,6-difluorophenyl, 3-chloro-2,6-difluorophenyl, 4-chloro-3,5-difluorophenyl 2-chloro-6-fluoro-3-methylphenyl, 2-chloro-6-fluoro-5-methylphenyl, 2-fluorophenyl, 3-fluorophenyl, 4-fluorophenyl, 2,3-difluorophenyl, 3,4-difluorophenyl, 2,3,4-trifluorophenyl, 2,3,5-trifluorophenyl, 2,4,5-trifluorophenyl, 2,4,6-trifluorophenyl, 2,6-difluoro-3-methyl-phenyl, 2-fluoro-3-trifluoromethyl-phenyl, 2-fluoro-5-trifluoromethyl-phenyl, 2,3-difluoro-4-trifluoromethyl-phenyl, 2,5-difluoro-4-trifluoromethyl-phenyl, 3-bromophenyl, 4-bromophenyl, 2-methylphenyl, 3-methylphenyl, 4-methylphenyl, 2,5-dimethylphenyl, 3,4-dimethylphenyl, 3,5-dimethylphenyl, 2-ethylphenyl, 2-methoxyphenyl, 3-methoxyphenyl, 4-methoxyphenyl, 3-methoxy-4-methylphenyl, 2,3-dimethoxyphenyl, 2,4-dimethoxyphenyl, 3-cyanophenyl, 3-hydroxymethyl-phenyl, 3-hydroxyethyl-phenyl, 3-methoxymethyl-phenyl, 3-methoxyethyl-phenyl, 3-dimethylamino-phenyl, 3-dimethylaminomethyl-phenyl, 3-dimethylaminoethyl-phenyl, 3-carbamoyl-phenyl, 3-tert-butoxy-carbonylphenyl, 2-trifluoromethylphenyl, 3-trifluoromethylphenyl, 4-trifluoromethylphenyl, 3-trifluoromethoxyphenyl, 4-trifluoromethoxyphenyl and biphenyl-3-yl. Preferred examples are phenyl, naphthyl, 2-chlorophenyl, 3-chlorophenyl, 4-chlorophenyl, 2,3-dichlorophenyl, 2,4-dichlorophenyl, 2,6-dichlorophenyl, 2-chloro-4-fluorophenyl, 2-chloro-6-fluorophenyl, 3-chloro-2-fluorophenyl, 3-chloro-4-fluorophenyl, 2-chloro-3,6-difluorophenyl, 3-chloro-2,6-difluorophenyl, 2-chloro-6-fluoro-3-methylphenyl, 2-chloro-6-fluoro-5-methylphenyl, 4-fluorophenyl, 2,3-difluorophenyl, 3,4-difluorophenyl, 2,3,4-trifluorophenyl, 2,3,5-trifluorophenyl, 2,4,5-trifluorophenyl, 2,4,6-trifluorophenyl, 2,6-difluoro-3-methyl-phenyl, 2-fluoro-3-trifluoromethyl-phenyl, 2-fluoro-5-trifluoromethyl-phenyl, 4-bromophenyl, 2-methylphenyl, 3-methylphenyl, 4-methylphenyl, 2,5-dimethylphenyl, 3,4-dimethylphenyl, 3,5-dimethylphenyl, 2-ethylphenyl, 2-methoxyphenyl, 3-methoxyphenyl, 4-methoxyphenyl, 2,3-dimethoxyphenyl, 2-trifluoromethylphenyl, 3-trifluoromethylphenyl, 4-trifluoromethylphenyl, and 3-trifluoromethoxyphenyl. Further examples are 3-isopropoxymethyl-phenyl and 3-(2-isopropoxy-ethyl)-phenyl.

The term "heterocyclyl", alone or in combination, means a 5- to 10-membered monocyclic or bicyclic aromatic ring containing 1, 2 or 3 heteroatoms independently selected from oxygen, nitrogen and sulfur. Examples of such heterocyclyl groups are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, naphthyridinyl, cinnolinyl, quinazolinyl, quinoxalinyl and phthalazinyl, which groups are unsubstituted, mono-, di- or tri-substituted, wherein the substituents are independently selected from the group consisting of halogen, $(C_1-C_4)$alkyl, $(C_1-C_4)$alkoxy, $(C_1-C_4)$fluoroalkyl, $(C_1-C_4)$fluoroalkoxy, phenyl, cyano, di-$[(C_1-C_3)$alkyl]-amino, —C(O)—NH$_2$, —C(O)OtBu, $(C_1-C_4)$alkoxy-$(C_1-C_2)$alkyl, hydroxy-$(C_1-C_2)$alkyl and dimethylamino-$(C_1-C_2)$alkyl (and preferably from halogen, $(C_1-C_4)$alkyl and $(C_1-C_4)$fluoroalkyl). Preferred examples of such heterocyclyl groups are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, pyridyl, pyrimidyl, pyridazinyl and pyrazinyl, which groups are unsubstituted, mono-, di- or tri-substituted (preferably unsubstituted or mono-substituted), wherein the substituents are independently selected from the group consisting of halogen, $(C_1-C_4)$alkyl, $(C_1-C_4)$alkoxy, $(C_1-C_4)$fluoroalkyl, $(C_1-C_4)$fluoroalkoxy, phenyl, cyano, di-$[(C_1-C_3)$alkyl]-amino, —C(O)—NH$_2$, —C(O)OtBu, $(C_1-C_4)$alkoxy-$(C_1-C_2)$alkyl, hydroxy-$(C_1-C_2)$alkyl and dimethylamino-$(C_1-C_2)$alkyl (and preferably from halogen, $(C_1-C_4)$alkyl and $(C_1-C_4)$fluoroalkyl).

In case "$R^1$" represents "heterocyclyl" the term preferably means a group selected from isoxazolyl (especially isoxazol-5-yl), pyridyl (especially pyridin-2-yl and pyridin-4-yl), indolyl (especially indol-3-yl) and benzothiazolyl (especially benzothiazol-2-yl), which group is unsubstituted or mono- or di-substituted (preferably unsubstituted or mono-substituted), wherein the substituents are independently selected from halogen, $(C_1-C_4)$alkyl and $(C_1-C_4)$fluoroalkyl.

In case "$R^1$" represents "heterocyclyl" the term most preferably means a group selected from isoxazolyl (especially isoxazol-5-yl) and pyridyl (especially pyridin-2-yl and pyridin-4-yl), which group is unsubstituted or mono- or di-substituted (preferably unsubstituted or mono-substituted), wherein the substituents are independently selected from halogen, $(C_1-C_4)$alkyl and $(C_1-C_4)$fluoroalkyl.

The term "monocyclic heterocyclyl", alone or in combination, means a 5- or 6-membered monocyclic aromatic ring containing 1, 2 or 3 heteroatoms independently selected from oxygen, nitrogen and sulfur. Examples of such "monocyclic heterocyclyl" groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, and pyrazinyl. Preferred examples are furanyl (especially furan-2,5-diyl), oxazolyl (especially oxazol-2,4-diyl and oxazol-2,5-diyl), isoxazolyl (especially isoxazol-3,5-diyl), thienyl (especially thiophen-2,4-diyl and thiophen-2,5-diyl), thiazolyl (especially thiazol-2,4-diyl and thiazol-2,5-diyl), and pyridyl (especially pyridin-2,4-diyl, pyridin-2,6-diyl and pyridin-3,5-diyl). More preferred examples are furan-2,5-diyl, oxazol-2,4-diyl, oxazol-2,5-diyl, thiophen-2,5-diyl and thiazol-2,4-diyl. Most preferred examples are furan-2,5-diyl and thiophen-2,5-diyl and especially furan-2,5-diyl. Another most preferred example is oxazol-2,4-diyl.

The term "1,3-arrangement" as used in the specification of "A" means that the two atoms of the phenyl or monocyclic heterocyclyl group which are attached to the pyrazole-methyl moiety and to the residue $R^2$ respectively are separated from each other by one atom; for example, if "A" represents phenyl the arrangement of the substituents is as shown in the figure below

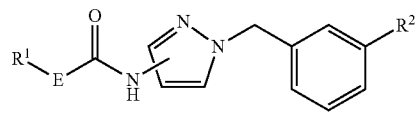

In this patent application, a dotted line shows the point of attachment of the radical drawn. For example, the radical drawn below

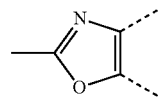

is the 2-methyl-oxazole-4,5-diyl group.

In this patent application, variably attached bonds may be used for substituents or groups. In such case it is meant that the substituent or group is attached to either atom linked by the bond into which the variably attached bond is drawn into. For example, the compound drawn below

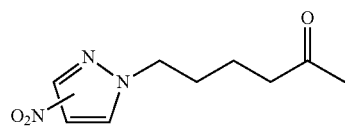

is either 6-(4-nitro-pyrazol-1-yl)-hexan-2-one or 6-(3-nitro-pyrazol-1-yl)-hexan-2-one.

2) A further embodiment of the invention relates to aminopyrazole derivatives of the formula (I) according to embodiment 1), wherein A represents phenyl-1,3-diyl, furan-2,5-diyl, thiophen-2,4-diyl, thiophen-2,5-diyl, thiazol-2,4-diyl, isoxazole-3,5-diyl, pyridin-2,4-diyl, pyridin-2,6-diyl, pyridin-3,5-diyl or propan-1,3-diyl;

E represents *-$(C_1$-$C_4)$alkyl-O—, —CH=CH— or

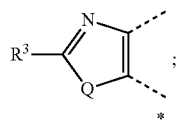

wherein the asterisks indicate the bond which is linked to $R^1$;

Q represents O, or S;

$R^3$ represents hydrogen, $(C_1$-$C_4)$alkyl, cyclopropyl, —$CH_2NH_2$ or —$CH_2NHBoc$;

$R^1$ represents a pyridyl- or an aryl-group, which groups are unsubstituted, mono-, di- or tri-substituted, wherein the substituents are independently selected from the group consisting of halogen, $(C_1$-$C_4)$alkyl, $(C_1$-$C_4)$alkoxy, $(C_1$-$C_4)$fluoroalkyl, $(C_1$-$C_4)$fluoroalkoxy, phenyl, cyano, di-[$(C_1$-$C_3)$alkyl]-amino, —C(O)—$NH_2$, —C(O)OtBu, $(C_1$-$C_4)$alkoxy-$(C_1$-$C_2)$alkyl, hydroxy-$(C_1$-$C_2)$alkyl and dimethylamino-$(C_1$-$C_2)$alkyl; and $R^2$ represents —CO—$(C_1$-$C_3)$alkyl, —CO-cyclopropyl, —$CF_2$—$(C_1$-$C_3)$alkyl, —CHF—$(C_1$-$C_3)$alkyl or —$SO_2$—$(C_1$-$C_3)$alkyl.

3) A further embodiment of the invention relates to aminopyrazole derivatives of the formula (I) according to embodiment 1), wherein at least one, preferably all of the following characteristics are present:

A represents phenyl-1,3-diyl, furan-2,5-diyl, oxazol-2,4-diyl (with $R^2$ being attached in 2-position or in 4-position and notably in 4-position), oxazol-2,5-diyl (with $R^2$ being attached in 2-position or in 5-position), thiophen-2,4-diyl (with $R^2$ being attached in 2-position or in 4-position), thiophen-2,5-diyl, thiazol-2,4-diyl (notably with $R^2$ being attached in 4-position), thiazol-2,5-diyl (notably with $R^2$ being attached in 2-position), pyridin-2,4-diyl (notably with $R^2$ being attached in 2-position), pyridin-2,6-diyl, pyridin-3,5-diyl or propan-1,3-diyl;

E represents *-$(C_1$-$C_4)$alkyl-O—, —CH=CH— or

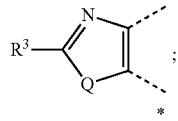

wherein the asterisks indicate the bond which is linked to $R^1$;

Q represents O, or S;

$R^3$ represents hydrogen, $(C_1$-$C_4)$alkyl, cyclopropyl, $(C_1$-$C_4)$alkoxy-$(C_1$-$C_2)$alkyl, or —$CH_2NHBoc$;

$R^1$ represents a pyridyl-group (preferably pyridin-2-yl or pyridin-4-yl), which group is unsubstituted or monosubstituted with halogen or trifluoromethyl; or an aryl-group, which group is unsubstituted, mono-, di- or tri-substituted, wherein the substituents are independently selected from the group consisting of halogen, $(C_1$-$C_4)$alkyl, $(C_1$-$C_4)$-alkoxy, $(C_1$-$C_4)$fluoroalkyl, $(C_1$-$C_4)$fluoroalkoxy, phenyl, cyano, di-[$(C_1$-$C_3)$alkyl]-amino, —C(O)—$NH_2$, —C(O)OtBu and $(C_1$-$C_4)$alkoxy-$(C_1$-$C_2)$alkyl; and $R^2$ represents —CO—$(C_1$-$C_3)$alkyl, —CO-cyclopropyl, —$CF_2$—$(C_1$-$C_3)$alkyl, —CHF—$(C_1$-$C_3)$alkyl or —$SO_2$—$(C_1$-$C_3)$alkyl.

4) A further embodiment of the invention relates to aminopyrazole derivatives of the formula (I) according to embodiment 1) or 2), wherein at least one, preferably all of the following characteristics are present:

A represents phenyl-1,3-diyl, furan-2,5-diyl, thiophen-2,4-diyl (with $R^2$ preferably being attached in 2-position), thiophen-2,5-diyl, thiazol-2,4-diyl (with $R^2$ preferably being attached in 4-position), pyridin-2,4-diyl (with $R^2$ preferably being attached in 2-position), pyridin-2,6-diyl, pyridin-3,5-diyl or propan-1,3-diyl;

E represents *-$(C_1$-$C_4)$alkyl-O—, —CH=CH— or

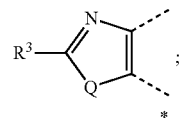

wherein the asterisks indicate the bond which is linked to $R^1$;

Q represents O, or S;

$R^3$ represents hydrogen, $(C_1$-$C_4)$alkyl, cyclopropyl or —$CH_2NHBoc$;

$R^1$ represents a pyridyl-group (preferably pyridin-2-yl or pyridin-4-yl and most preferably pyridin-4-yl), which group is unsubstituted or monosubstituted with halogen; or an aryl-group, which group is unsubstituted, mono-, di- or tri-substituted, wherein the substituents are independently selected from the group consisting of halogen, $(C_1$-$C_4)$alkyl, $(C_1$-$C_4)$-alkoxy, $(C_1$-$C_4)$fluoroalkyl, $(C_1$-$C_4)$fluoroalkoxy, phenyl, cyano, di-[$(C_1$-$C_3)$alkyl]-amino, —C(O)—$NH_2$, —C(O)OtBu and $(C_1$-$C_4)$alkoxy-$(C_1$-$C_2)$alkyl; and $R^2$ represents —CO—$(C_1$-$C_3)$alkyl, —CO-cyclopropyl, —$CF_2$—$(C_1$-$C_3)$alkyl, —CHF—$(C_1$-$C_3)$alkyl or —$SO_2$—$(C_1$-$C_3)$alkyl.

5) A further embodiment of the invention relates to aminopyrazole derivatives of the formula (I) according to any one of embodiments 1) to 4), wherein at least one, preferably all of the following characteristics are present:

A represents furan-2,5-diyl or propan-1,3-diyl;

E represents *-$(C_1$-$C_4)$alkyl-O—, —CH=CH— or

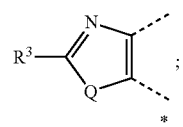

wherein the asterisks indicate the bond which is linked to $R^1$;

Q represents O, or S;

$R^3$ represents hydrogen, $(C_1$-$C_4)$alkyl or cyclopropyl;

$R^1$ represents aryl, which is unsubstituted, mono-, di- or tri-substituted, wherein the substituents are independently selected from the group consisting of halogen, $(C_1$-$C_4)$alkyl, $(C_1$-$C_4)$alkoxy, $(C_1$-$C_4)$fluoroalkyl and $(C_1$-$C_4)$fluoroalkoxy; and $R^2$ represents —CO—$(C_1$-$C_3)$alkyl, —CO-cyclopropyl, —$CF_2$—$(C_1$-$C_3)$alkyl or —CHF—$(C_1$-$C_3)$alkyl.

6) A further embodiment of the invention relates to aminopyrazole derivatives of the formula (I) according to embodiment 1) or 3), wherein at least one, preferably all of the following characteristics are present:

A represents furan-2,5-diyl, oxazol-2,4-diyl (notably with $R^2$ being attached in 4-position), oxazol-2,5-diyl (notably with $R^2$ being attached in 5-position), thiophen-2,4-diyl (notably with R² being attached in 2-position or in 4-position), thiophen-2,5-diyl, thiazol-2,4-diyl (notably with R² being attached in 4-position) or pyridin-2,4-diyl (notably with R² being attached in 2-position);
E represents *-($C_1$-$C_4$)alkyl-O—, —CH=CH— or

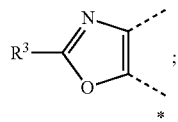

wherein the asterisks indicate the bond which is linked to R¹;
R³ represents hydrogen, ($C_1$-$C_4$)alkyl, cyclopropyl or methoxy-methyl;
R¹ represents an aryl-group, which group is unsubstituted, mono-, di- or tri-substituted,
wherein the substituents are independently selected from the group consisting of halogen, ($C_1$-$C_4$)alkyl, ($C_1$-$C_4$)alkoxy, ($C_1$-$C_4$)fluoroalkyl, ($C_1$-$C_4$)fluoroalkoxy, phenyl, cyano, dimethylamino, —C(O)OtBu and ($C_1$-$C_4$)alkoxy-($C_1$-$C_2$)alkyl; and
R² represents —CO—($C_1$-$C_3$)alkyl, —$CF_2$—($C_1$-$C_3$)alkyl or —CHF—($C_1$-$C_3$)alkyl.

7) A further embodiment of the invention relates to aminopyrazole derivatives of the formula (I) according to any one of embodiments 1) to 4), wherein at least one, preferably all of the following characteristics are present:
A represents furan-2,5-diyl, thiophen-2,4-diyl (with R² being attached in 2-position), thiophen-2,5-diyl, thiazol-2,4-diyl (with R² being attached in 4-position) or pyridin-2,4-diyl (with R² being attached in 2-position);
E represents *-($C_1$-$C_4$)alkyl-O—, —CH=CH— or

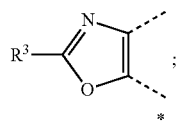

wherein the asterisks indicate the bond which is linked to R¹;
R³ represents hydrogen, ($C_1$-$C_4$)alkyl or cyclopropyl;
R¹ represents an aryl-group, which group is unsubstituted, mono-, di- or tri-substituted, wherein the substituents are independently selected from the group consisting of halogen, ($C_1$-$C_4$)alkyl, ($C_1$-$C_4$)alkoxy, ($C_1$-$C_4$)fluoroalkyl, ($C_1$-$C_4$)fluoroalkoxy, phenyl, cyano, dimethylamino, —C(O)OtBu and ($C_1$-$C_4$)alkoxy-($C_1$-$C_2$)alkyl; and
R² represents —CO—($C_1$-$C_3$)alkyl, —$CF_2$—($C_1$-$C_3$)alkyl or —CHF—($C_1$-$C_3$)alkyl.

8) A further embodiment of the invention relates to aminopyrazole derivatives of the formula (I) according to any one of embodiments 1) to 4), wherein at least one, preferably all of the following characteristics are present:
A represents propan-1,3-diyl;
E represents *-($C_1$-$C_4$)alkyl-O—, —CH=CH— or

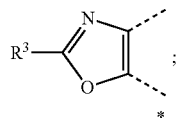

wherein the asterisks indicate the bond which is linked to R¹;
R³ represents hydrogen or ($C_1$-$C_4$)alkyl;
R¹ represents an aryl-group, which group is unsubstituted, mono-, di- or tri-substituted, wherein the substituents are independently selected from the group consisting of halogen, ($C_1$-$C_4$)alkyl, ($C_1$-$C_4$)alkoxy, ($C_1$-$C_4$)fluoroalkyl, ($C_1$-$C_4$)fluoroalkoxy, phenyl, cyano, dimethylamino, —C(O)OtBu and ($C_1$-$C_4$)alkoxy-($C_1$-$C_2$)alkyl; and
R² represents —CO—($C_1$-$C_3$)alkyl, —$CF_2$—($C_1$-$C_3$)alkyl or —CHF—($C_1$-$C_3$)alkyl.

9) A further embodiment of the invention relates to aminopyrazole derivatives of the formula (I) according to any one of embodiments 1), 3) or 6), wherein A represents furan-2,5-diyl, oxazol-2,4-diyl (notably with R² being attached in 4-position), oxazol-2,5-diyl (notably with R² being attached in 5-position), thiophen-2,4-diyl (notably with R² being attached in 2-position or in 4-position), thiophen-2,5-diyl, thiazol-2,4-diyl (notably with R² being attached in 4-position) or pyridin-2,4-diyl (notably with R² being attached in 2-position).

10) A further embodiment of the invention relates to aminopyrazole derivatives of the formula (I) according to any one of embodiments 1) to 4), 6) to 7) or 9), wherein A represents furan-2,5-diyl, thiophen-2,4-diyl (with R² being attached in 2-position), thiophen-2,5-diyl, thiazol-2,4-diyl (with R² being attached in 4-position) or pyridin-2,4-diyl (with R² being attached in 2-position).

11) A further embodiment of the invention relates to aminopyrazole derivatives of the formula (I) according to any one of embodiments 1) to 7), wherein A represents furan-2,5-diyl.

12) A further embodiment of the invention relates to aminopyrazole derivatives of the formula (I) according to any one of embodiments 1), 3) or 6), wherein A represents oxazol-2,4-diyl or oxazol-2,5-diyl; and preferably oxazol-2,4-diyl with R² being attached in 4-position or oxazol-2,5-diyl with R² being attached in 5-position; and most preferably oxazol-2,4-diyl with R² being attached in 4-position.

13) A further embodiment of the invention relates to aminopyrazole derivatives of the formula (I) according to any one of embodiments 1) to 4), 6) or 7), wherein A represents thiophen-2,4-diyl (with R² being attached in 2-position or in 4-position and notably in 2-position).

14) A further embodiment of the invention relates to aminopyrazole derivatives of the formula (I) according to any one of embodiments 1) to 4), 6) or 7), wherein A represents thiophen-2,5-diyl.

15) A further embodiment of the invention relates to aminopyrazole derivatives of the formula (I) according to any one of embodiments 1) to 4), 6) or 7), wherein A represents thiazol-2,4-diyl (with R² preferably being attached in 4-position).

16) A further embodiment of the invention relates to aminopyrazole derivatives of the formula (I) according to any one of embodiments 1) to 4), wherein A represents pyridin-2,4-diyl (with R² preferably being attached in 2-position), pyridin-2,6-diyl or pyridin-3,5-diyl.

17) A further embodiment of the invention relates to aminopyrazole derivatives of the formula (I) according to any one of embodiments 1) to 4), 6) or 7), wherein A represents pyridin-2,4-diyl (with R² being attached in 2-position).

18) A further embodiment of the invention relates to aminopyrazole derivatives of the formula (I) according to any one of embodiments 1) to 4), wherein A represents phenyl-1,3-diyl.

19) A further embodiment of the invention relates to aminopyrazole derivatives of the formula (I) according to any one of embodiments 1) to 5) or 8), wherein A represents propan-1,3-diyl.

20) A further embodiment of the invention relates to aminopyrazole derivatives of the formula (I) according to any one of embodiments 1) to 5) or 9) to 19), wherein E represents

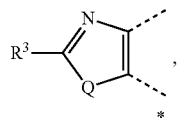

wherein the asterisk indicates the bond which is linked to $R^1$.

21) A further embodiment of the invention relates to aminopyrazole derivatives of the formula (I) according to any one of embodiments 1) to 19), wherein
E represents *-(C$_1$-C$_4$)alkyl-O— or —CH=CH—;
wherein the asterisk indicates the bond which is linked to $R^1$.

22) A further embodiment of the invention relates to aminopyrazole derivatives of the formula (I) according to any one of embodiments 1) to 19) or 21), wherein E represents *-(C$_1$-C$_4$)alkyl-O— (preferably *-CH$_2$—O—),
wherein the asterisks indicate the bond which is linked to $R^1$.

23) A further embodiment of the invention relates to aminopyrazole derivatives of the formula (I) according to any one of embodiments 1) to 19) or 21), wherein E represents —CH=CH—.

24) A further embodiment of the invention relates to aminopyrazole derivatives of the formula (I) according to any one of embodiments 1) to 20), wherein Q represents O.

25) A further embodiment of the invention relates to aminopyrazole derivatives of the formula (I) according to any one of embodiments 1), 3), 6), 9) to 20) or 24), wherein $R^3$ represents hydrogen, methyl, ethyl, iso-propyl, n-butyl, cyclopropyl or methoxy-methyl.

26) A further embodiment of the invention relates to aminopyrazole derivatives of the formula (I) according to any one of embodiments 1) to 7), 9) to 20) or 24), wherein $R^3$ represents hydrogen, methyl, ethyl or cyclopropyl.

27) A further embodiment of the invention relates to aminopyrazole derivatives of the formula (I) according to any one of embodiments 1) to 20) or 24) to 26), wherein $R^3$ represents hydrogen or methyl.

28) A further embodiment of the invention relates to aminopyrazole derivatives of the formula (I) according to any one of embodiments 1) or 9) to 27), wherein $R^1$ represents a heterocyclyl-group, which group is unsubstituted, mono-, di- or tri-substituted, wherein the substituents are independently selected from the group consisting of halogen, (C$_1$-C$_4$)alkyl, (C$_1$-C$_4$)alkoxy, (C$_1$-C$_4$)fluoroalkyl, (C$_1$-C$_4$)fluoroalkoxy, phenyl, cyano, di-[(C$_1$-C$_3$)alkyl]-amino, —C(O)—NH$_2$, —C(O)OtBu, (C$_1$-C$_4$)alkoxy-(C$_1$-C$_2$)alkyl, hydroxy-(C$_1$-C$_2$)alkyl and dimethylamino-(C$_1$-C$_2$)alkyl (and preferably from halogen, (C$_1$-C$_4$)alkyl and (C$_1$-C$_4$)fluoroalkyl).

29) A further embodiment of the invention relates to aminopyrazole derivatives of the formula (I) according to any one of embodiments 1) or 9) to 28), wherein $R^1$ represents a heterocyclyl group selected from isoxazolyl (especially isoxazol-5-yl), pyridyl (especially pyridin-2-yl and pyridin-4-yl), indolyl (especially indol-3-yl) and benzothiazolyl (especially benzothiazol-2-yl), which group is unsubstituted or mono- or di-substituted (preferably unsubstituted or mono-substituted), wherein the substituents are independently selected from halogen, (C$_1$-C$_4$)alkyl and (C$_1$-C$_4$)fluoroalkyl.

30) A further embodiment of the invention relates to aminopyrazole derivatives of the formula (I) according to any one of embodiments 1) to 4) or 6) to 27), wherein $R^1$ represents phenyl, which is unsubstituted, mono-, di- or tri-substituted wherein the substituents are independently selected from the group consisting of halogen, (C$_1$-C$_4$)alkyl, (C$_1$-C$_4$)alkoxy, (C$_1$-C$_4$)fluoroalkyl, (C$_1$-C$_4$)fluoroalkoxy, phenyl, cyano, dimethylamino, —C(O)OtBu and (C$_1$-C$_4$)alkoxy-(C$_1$-C$_2$)alkyl.

31) A further embodiment of the invention relates to aminopyrazole derivatives of the formula (I) according to any one of embodiments 1) to 27), wherein $R^1$ represents phenyl, which is unsubstituted, mono-, di- or tri-substituted wherein the substituents are independently selected from the group consisting of halogen, (C$_1$-C$_4$)alkyl, (C$_1$-C$_4$)alkoxy, trifluoromethyl and trifluoromethoxy.

32) A further embodiment of the invention relates to aminopyrazole derivatives of the formula (I) according to any one of embodiments 1) to 5) or 9) to 31), wherein $R^2$ represents —CO—(C$_1$-C$_3$)alkyl or —CO-cyclopropyl.

33) A further embodiment of the invention relates to aminopyrazole derivatives of the formula (I) according to any one of embodiments 1) to 31), wherein $R^2$ represents —CO—(C$_1$-C$_3$)alkyl or —CF$_2$—(C$_1$-C$_3$)alkyl.

34) A further embodiment of the invention relates to aminopyrazole derivatives of the formula (I) according to any one of embodiments 1) to 33), wherein $R^2$ represents —CO—(C$_1$-C$_3$)alkyl.

35) A further embodiment of the invention relates to aminopyrazole derivatives of the formula (I) according to any one of embodiments 1) to 31), wherein $R^2$ represents —CF$_2$—(C$_1$-C$_3$)alkyl.

36) A further embodiment of the invention relates to aminopyrazole derivatives of the formula (I) according to any one of embodiments 1) to 4) or 9) to 31), wherein $R^2$ represents —SO$_2$—(C$_1$-C$_3$)alkyl.

37) A further embodiment of the invention relates to aminopyrazole derivatives of the formula (I) according to any of the embodiments 1) to 36), wherein the aminopyrazole is a 3-amino-pyrazole group.

38) A further embodiment of the invention relates to aminopyrazole derivatives of the formula (I) according to any of the embodiments 1) to 36), wherein the aminopyrazole is a 4-amino-pyrazole group.

39) Preferred compounds of formula (I) as defined in embodiment 1) are selected from the group consisting of:
[1-(5-Acetyl-furan-2-ylmethyl)-1H-pyrazol-4-yl]-carbamic acid 2-chloro-benzyl ester;
[1-(5-Propionyl-furan-2-ylmethyl)-1H-pyrazol-4-yl]-carbamic acid 2-chloro-benzyl ester;
[1-(5-Cyclopropanecarbonyl-furan-2-ylmethyl)-1H-pyrazol-4-yl]-carbamic acid 2-chloro-benzyl ester;
[1-(5-Acetyl-furan-2-ylmethyl)-1H-pyrazol-3-yl]-carbamic acid benzyl ester;
[1-(5-Acetyl-furan-2-ylmethyl)-1H-pyrazol-3-yl]-carbamic acid 2-methyl-benzyl ester;
[1-(5-Acetyl-furan-2-ylmethyl)-1H-pyrazol-3-yl]-carbamic acid 4-trifluoromethyl-benzyl ester;
[1-(5-Acetyl-furan-2-ylmethyl)-1H-pyrazol-3-yl]-carbamic acid 3-trifluoromethyl-benzyl ester;
[1-(5-Acetyl-furan-2-ylmethyl)-1H-pyrazol-3-yl]-carbamic acid 3-chloro-benzyl ester;
[1-(5-Acetyl-furan-2-ylmethyl)-1H-pyrazol-3-yl]-carbamic acid 2-chloro-4-fluoro-benzyl ester;

[1-(5-Acetyl-furan-2-ylmethyl)-1H-pyrazol-3-yl]-carbamic acid 2-ethyl-benzyl ester;
[1-(5-Acetyl-furan-2-ylmethyl)-1H-pyrazol-3-yl]-carbamic acid 2,6-dichloro-benzyl ester;
[1-(5-Acetyl-furan-2-ylmethyl)-1H-pyrazol-3-yl]-carbamic acid 3,4-dimethyl-benzyl ester;
[1-(5-Acetyl-furan-2-ylmethyl)-1H-pyrazol-3-yl]-carbamic acid 3,4-difluoro-benzyl ester;
[1-(5-Acetyl-furan-2-ylmethyl)-1H-pyrazol-3-yl]-carbamic acid 2-chloro-6-fluoro-benzyl ester;
[1-(5-Acetyl-furan-2-ylmethyl)-1H-pyrazol-3-yl]-carbamic acid naphthalen-1-ylmethyl ester;
[1-(5-Acetyl-furan-2-ylmethyl)-1H-pyrazol-3-yl]-carbamic acid 2,5-dimethyl-benzyl ester;
[1-(5-Acetyl-furan-2-ylmethyl)-1H-pyrazol-3-yl]-carbamic acid 2,4,6-trifluoro-benzyl ester;
[1-(5-Acetyl-furan-2-ylmethyl)-1H-pyrazol-3-yl]-carbamic acid 2,3-difluoro-benzyl ester;
[1-(5-Acetyl-furan-2-ylmethyl)-1H-pyrazol-3-yl]-carbamic acid 3-chloro-2,6-difluoro-benzyl ester;
[1-(5-Acetyl-furan-2-ylmethyl)-1H-pyrazol-3-yl]-carbamic acid 6-chloro-2-fluoro-3-methyl-benzyl ester;
[1-(5-Acetyl-furan-2-ylmethyl)-1H-pyrazol-3-yl]-carbamic acid 3-chloro-2-fluoro-benzyl ester;
[1-(5-Acetyl-furan-2-ylmethyl)-1H-pyrazol-3-yl]-carbamic acid 2-chloro-6-fluoro-3-methyl-benzyl ester;
[1-(5-Acetyl-furan-2-ylmethyl)-1H-pyrazol-3-yl]-carbamic acid 2,4,5-trifluoro-benzyl ester;
[1-(5-Acetyl-furan-2-ylmethyl)-1H-pyrazol-3-yl]-carbamic acid 2,3,4-trifluoro-benzyl ester;
[1-(5-Acetyl-furan-2-ylmethyl)-1H-pyrazol-3-yl]-carbamic acid 4-bromo-benzyl ester;
[1-(5-Acetyl-furan-2-ylmethyl)-1H-pyrazol-3-yl]-carbamic acid 2-trifluoromethyl-benzyl ester;
[1-(5-Acetyl-furan-2-ylmethyl)-1H-pyrazol-3-yl]-carbamic acid 2-fluoro-benzyl ester;
[1-(5-Acetyl-furan-2-ylmethyl)-1H-pyrazol-3-yl]-carbamic acid 4-chloro-benzyl ester;
[1-(5-Acetyl-furan-2-ylmethyl)-1H-pyrazol-3-yl]-carbamic acid 3-methyl-benzyl ester;
[1-(5-Acetyl-furan-2-ylmethyl)-1H-pyrazol-3-yl]-carbamic acid 2,6-difluoro-3-methyl-benzyl ester;
5-Phenyl-oxazole-4-carboxylic acid [1-(5-acetyl-furan-2-ylmethyl)-1H-pyrazol-3-yl]-amide;
N-[1-(5-Acetyl-furan-2-ylmethyl)-1H-pyrazol-3-yl]-3-phenyl-acrylamide;
N-[1-(5-Acetyl-furan-2-ylmethyl)-1H-pyrazol-3-yl]-3-(2-trifluoromethyl-phenyl)-acrylamide;
N-[1-(5-Acetyl-furan-2-ylmethyl)-1H-pyrazol-3-yl]-3-(4-trifluoromethyl-phenyl)-acrylamide;
N-[1-(5-Acetyl-furan-2-ylmethyl)-1H-pyrazol-3-yl]-3-(2-chloro-6-fluoro-phenyl)-acrylamide;
N-[1-(5-Acetyl-furan-2-ylmethyl)-1H-pyrazol-3-yl]-3-(2,3-dimethoxy-phenyl)-acrylamide;
N-[1-(5-Acetyl-furan-2-ylmethyl)-1H-pyrazol-3-yl]-3-(2,3-dichloro-phenyl)-acrylamide;
N-[1-(5-Acetyl-furan-2-ylmethyl)-1H-pyrazol-3-yl]-3-(3-trifluoromethoxy-phenyl)-acrylamide;
N-[1-(5-Acetyl-furan-2-ylmethyl)-1H-pyrazol-3-yl]-3-(3-chloro-4-fluoro-phenyl)-acrylamide;
N-[1-(5-Acetyl-furan-2-ylmethyl)-1H-pyrazol-3-yl]-3-(2-chloro-3,6-difluoro-phenyl)-acrylamide;
N-[1-(5-Acetyl-furan-2-ylmethyl)-1H-pyrazol-3-yl]-3-(2,4-dichloro-phenyl)-acrylamide;
N-[1-(5-Acetyl-furan-2-ylmethyl)-1H-pyrazol-3-yl]-3-(2-chloro-4-fluoro-phenyl)-acrylamide;
N-[1-(5-Acetyl-furan-2-ylmethyl)-1H-pyrazol-3-yl]-3-(2-methoxy-phenyl)-acrylamide;
N-[1-(5-Acetyl-furan-2-ylmethyl)-1H-pyrazol-3-yl]-3-(2-fluoro-3-trifluoromethyl-phenyl)-acrylamide;
N-[1-(5-Acetyl-furan-2-ylmethyl)-1H-pyrazol-3-yl]-3-o-tolyl-acrylamide;
N-[1-(5-Acetyl-furan-2-ylmethyl)-1H-pyrazol-3-yl]-3-(3-chloro-phenyl)-acrylamide;
5-(4-Methoxy-phenyl)-oxazole-4-carboxylic acid [1-(5-acetyl-furan-2-ylmethyl)-1H-pyrazol-3-yl]-amide;
2-Methyl-5-m-tolyl-oxazole-4-carboxylic acid [1-(5-acetyl-furan-2-ylmethyl)-1H-pyrazol-3-yl]-amide;
N-[1-(5-Acetyl-furan-2-ylmethyl)-1H-pyrazol-3-yl]-3-(3-trifluoromethyl-phenyl)-acrylamide;
N-[1-(5-Acetyl-furan-2-ylmethyl)-1H-pyrazol-3-yl]-3-(4-methoxy-phenyl)-acrylamide;
N-[1-(5-Acetyl-furan-2-ylmethyl)-1H-pyrazol-3-yl]-3-p-tolyl-acrylamide;
N-[1-(5-Acetyl-furan-2-ylmethyl)-1H-pyrazol-3-yl]-3-(3-methoxy-phenyl)-acrylamide;
N-[1-(5-Acetyl-furan-2-ylmethyl)-1H-pyrazol-3-yl]-3-m-tolyl-acrylamide;
5-(3-Methoxy-phenyl)-oxazole-4-carboxylic acid [1-(5-acetyl-furan-2-ylmethyl)-1H-pyrazol-3-yl]-amide;
5-(4-Methoxy-phenyl)-2-methyl-oxazole-4-carboxylic acid [1-(5-acetyl-furan-2-ylmethyl)-1H-pyrazol-3-yl]-amide;
2-Methyl-5-o-tolyl-oxazole-4-carboxylic acid [1-(5-acetyl-furan-2-ylmethyl)-1H-pyrazol-3-yl]-amide;
[1-(5-Acetyl-furan-2-ylmethyl)-1H-pyrazol-4-yl]-carbamic acid benzyl ester;
[1-(5-Acetyl-furan-2-ylmethyl)-1H-pyrazol-4-yl]-carbamic acid 2-methyl-benzyl ester;
[1-(5-Acetyl-furan-2-ylmethyl)-1H-pyrazol-4-yl]-carbamic acid 4-trifluoromethyl-benzyl ester;
[1-(5-Acetyl-furan-2-ylmethyl)-1H-pyrazol-4-yl]-carbamic acid 3-trifluoromethyl-benzyl ester;
[1-(5-Acetyl-furan-2-ylmethyl)-1H-pyrazol-4-yl]-carbamic acid 3-chloro-benzyl ester;
[1-(5-Acetyl-furan-2-ylmethyl)-1H-pyrazol-4-yl]-carbamic acid 2-chloro-4-fluoro-benzyl ester;
[1-(5-Acetyl-furan-2-ylmethyl)-1H-pyrazol-4-yl]-carbamic acid 2-ethyl-benzyl ester;
[1-(5-Acetyl-furan-2-ylmethyl)-1H-pyrazol-4-yl]-carbamic acid 2,6-dichloro-benzyl ester;
[1-(5-Acetyl-furan-2-ylmethyl)-1H-pyrazol-4-yl]-carbamic acid 3,4-dimethyl-benzyl ester;
[1-(5-Acetyl-furan-2-ylmethyl)-1H-pyrazol-4-yl]-carbamic acid 3,4-difluoro-benzyl ester;
[1-(5-Acetyl-furan-2-ylmethyl)-1H-pyrazol-4-yl]-carbamic acid 2-chloro-6-fluoro-benzyl ester;
[1-(5-Acetyl-furan-2-ylmethyl)-1H-pyrazol-4-yl]-carbamic acid naphthalen-1-ylmethyl ester;
[1-(5-Acetyl-furan-2-ylmethyl)-1H-pyrazol-4-yl]-carbamic acid 2,5-dimethyl-benzyl ester;
[1-(5-Acetyl-furan-2-ylmethyl)-1H-pyrazol-4-yl]-carbamic acid 2,4,6-trifluoro-benzyl ester;
[1-(5-Acetyl-furan-2-ylmethyl)-1H-pyrazol-4-yl]-carbamic acid 2,3-difluoro-benzyl ester;
[1-(5-Acetyl-furan-2-ylmethyl)-1H-pyrazol-4-yl]-carbamic acid 3-chloro-2,6-difluoro-benzyl ester;
[1-(5-Acetyl-furan-2-ylmethyl)-1H-pyrazol-4-yl]-carbamic acid 6-chloro-2-fluoro-3-methyl-benzyl ester;
[1-(5-Acetyl-furan-2-ylmethyl)-1H-pyrazol-4-yl]-carbamic acid 3-chloro-2-fluoro-benzyl ester;
[1-(5-Acetyl-furan-2-ylmethyl)-1H-pyrazol-4-yl]-carbamic acid 2-chloro-6-fluoro-3-methyl-benzyl ester;

[1-(5-Acetyl-furan-2-ylmethyl)-1H-pyrazol-4-yl]-carbamic acid 2,4,5-trifluoro-benzyl ester;
[1-(5-Acetyl-furan-2-ylmethyl)-1H-pyrazol-4-yl]-carbamic acid 2,6-difluoro-3-methyl-benzyl ester;
[1-(5-Acetyl-furan-2-ylmethyl)-1H-pyrazol-4-yl]-carbamic acid 2,3,4-trifluoro-benzyl ester;
[1-(5-Acetyl-furan-2-ylmethyl)-1H-pyrazol-4-yl]-carbamic acid 4-bromo-benzyl ester;
[1-(5-Acetyl-furan-2-ylmethyl)-1H-pyrazol-4-yl]-carbamic acid 2-trifluoromethyl-benzyl ester;
[1-(5-Acetyl-furan-2-ylmethyl)-1H-pyrazol-4-yl]-carbamic acid 2-fluoro-benzyl ester;
[1-(5-Acetyl-furan-2-ylmethyl)-1H-pyrazol-4-yl]-carbamic acid 4-chloro-benzyl ester;
[1-(5-Acetyl-furan-2-ylmethyl)-1H-pyrazol-4-yl]-carbamic acid 3-methyl-benzyl ester;
5-Phenyl-oxazole-4-carboxylic acid [1-(5-acetyl-furan-2-ylmethyl)-1H-pyrazol-4-yl]-amide;
N-[1-(5-Acetyl-furan-2-ylmethyl)-1H-pyrazol-4-yl]-3-(2-trifluoromethyl-phenyl)-acrylamide;
N-[1-(5-Acetyl-furan-2-ylmethyl)-1H-pyrazol-4-yl]-3-(4-trifluoromethyl-phenyl)-acrylamide;
N-[1-(5-Acetyl-furan-2-ylmethyl)-1H-pyrazol-4-yl]-3-(2-chloro-6-fluoro-phenyl)-acrylamide;
N-[1-(5-Acetyl-furan-2-ylmethyl)-1H-pyrazol-4-yl]-3-(2,3-dimethoxy-phenyl)-acrylamide;
N-[1-(5-Acetyl-furan-2-ylmethyl)-1H-pyrazol-4-yl]-3-(2,3-dichloro-phenyl)-acrylamide;
N-[1-(5-Acetyl-furan-2-ylmethyl)-1H-pyrazol-4-yl]-3-(3-trifluoromethoxy-phenyl)-acrylamide;
N-[1-(5-Acetyl-furan-2-ylmethyl)-1H-pyrazol-4-yl]-3-(2-chloro-3,6-difluoro-phenyl)-acrylamide;
N-[1-(5-Acetyl-furan-2-ylmethyl)-1H-pyrazol-4-yl]-3-(2,4-dichloro-phenyl)-acrylamide;
N-[1-(5-Acetyl-furan-2-ylmethyl)-1H-pyrazol-4-yl]-3-(2-chloro-4-fluoro-phenyl)-acrylamide;
N-[1-(5-Acetyl-furan-2-ylmethyl)-1H-pyrazol-4-yl]-3-o-tolyl-acrylamide;
N-[1-(5-Acetyl-furan-2-ylmethyl)-1H-pyrazol-4-yl]-3-(3-chloro-phenyl)-acrylamide;
5-(4-Methoxy-phenyl)-oxazole-4-carboxylic acid [1-(5-acetyl-furan-2-ylmethyl)-1H-pyrazol-4-yl]-amide;
2-Methyl-5-m-tolyl-oxazole-4-carboxylic acid [1-(5-acetyl-furan-2-ylmethyl)-1H-pyrazol-4-yl]-amide;
5-(4-Methoxy-phenyl)-2-methyl-oxazole-4-carboxylic acid [1-(5-acetyl-furan-2-ylmethyl)-1H-pyrazol-4-yl]-amide;
2-Methyl-5-m-tolyl-thiazole-4-carboxylic acid [1-(5-acetyl-furan-2-ylmethyl)-1H-pyrazol-4-yl]-amide;
N-[1-(5-Acetyl-furan-2-ylmethyl)-1H-pyrazol-4-yl]-3-(3-trifluoromethyl-phenyl)-acrylamide;
5-(3-Methoxy-phenyl)-2-methyl-oxazole-4-carboxylic acid [1-(5-acetyl-furan-2-ylmethyl)-1H-pyrazol-4-yl]-amide;
2-Methyl-5-phenyl-oxazole-4-carboxylic acid [1-(5-acetyl-furan-2-ylmethyl)-1H-pyrazol-4-yl]-amide;
N-[1-(5-Acetyl-furan-2-ylmethyl)-1H-pyrazol-4-yl]-3-(2-chloro-phenyl)-acrylamide;
5-m-Tolyl-oxazole-4-carboxylic acid [1-(5-acetyl-furan-2-ylmethyl)-1H-pyrazol-4-yl]-amide;
N-[1-(5-Acetyl-furan-2-ylmethyl)-1H-pyrazol-4-yl]-3-p-tolyl-acrylamide;
5-(3-Methoxy-phenyl)-oxazole-4-carboxylic acid [1-(5-acetyl-furan-2-ylmethyl)-1H-pyrazol-4-yl]-amide;
2-Methyl-5-o-tolyl-oxazole-4-carboxylic acid [1-(5-acetyl-furan-2-ylmethyl)-1H-pyrazol-4-yl]-amide;
5-(3-Chloro-phenyl)-thiazole-4-carboxylic acid [1-(5-acetyl-furan-2-ylmethyl)-1H-pyrazol-4-yl]-amide;
5-(2-Fluoro-phenyl)-thiazole-4-carboxylic acid [1-(5-acetyl-furan-2-ylmethyl)-1H-pyrazol-4-yl]-amide;
[1-(5-Oxo-hexyl)-1H-pyrazol-4-yl]-carbamic acid 2-chloro-benzyl ester;
[1-(5-Oxo-hexyl)-1H-pyrazol-4-yl]-carbamic acid 1-phenyl-ethyl ester;
[1-(5-Oxo-hexyl)-1H-pyrazol-4-yl]-carbamic acid 4-bromo-benzyl ester;
[1-(5-Oxo-hexyl)-1H-pyrazol-4-yl]-carbamic acid 2-trifluoromethyl-benzyl ester;
[1-(5-Oxo-hexyl)-1H-pyrazol-4-yl]-carbamic acid 2-fluoro-benzyl ester;
[1-(5-Oxo-hexyl)-1H-pyrazol-4-yl]-carbamic acid 4-chloro-benzyl ester;
[1-(5-Oxo-hexyl)-1H-pyrazol-4-yl]-carbamic acid 3-methyl-benzyl ester;
[1-(5-Oxo-hexyl)-1H-pyrazol-4-yl]-carbamic acid 3-trifluoromethyl-benzyl ester;
[1-(5-Oxo-hexyl)-1H-pyrazol-4-yl]-carbamic acid 3-chloro-benzyl ester;
[1-(5-Oxo-hexyl)-1H-pyrazol-4-yl]-carbamic acid 2-chloro-4-fluoro-benzyl ester;
[1-(5-Oxo-hexyl)-1H-pyrazol-4-yl]-carbamic acid 2-ethyl-benzyl ester;
[1-(5-Oxo-hexyl)-1H-pyrazol-4-yl]-carbamic acid 2,6-dichloro-benzyl ester;
[1-(5-Oxo-hexyl)-1H-pyrazol-4-yl]-carbamic acid 3,4-dimethyl-benzyl ester;
[1-(5-Oxo-hexyl)-1H-pyrazol-4-yl]-carbamic acid 3,4-difluoro-benzyl ester;
[1-(5-Oxo-hexyl)-1H-pyrazol-4-yl]-carbamic acid naphthalen-1-ylmethyl ester;
[1-(5-Oxo-hexyl)-1H-pyrazol-4-yl]-carbamic acid 2,5-dimethyl-benzyl ester;
[1-(5-Oxo-hexyl)-1H-pyrazol-4-yl]-carbamic acid 2,4,6-trifluoro-benzyl ester;
[1-(5-Oxo-hexyl)-1H-pyrazol-4-yl]-carbamic acid 2,3-difluoro-benzyl ester;
[1-(5-Oxo-hexyl)-1H-pyrazol-4-yl]-carbamic acid 3-chloro-2,6-difluoro-benzyl ester;
[1-(5-Oxo-hexyl)-1H-pyrazol-4-yl]-carbamic acid 6-chloro-2-fluoro-3-methyl-benzyl ester;
[1-(5-Oxo-hexyl)-1H-pyrazol-4-yl]-carbamic acid 3-chloro-2-fluoro-benzyl ester;
[1-(5-Oxo-hexyl)-1H-pyrazol-4-yl]-carbamic acid 2-chloro-6-fluoro-3-methyl-benzyl ester;
[1-(5-Oxo-hexyl)-1H-pyrazol-4-yl]-carbamic acid 2,6-difluoro-3-methyl-benzyl ester;
[1-(5-Oxo-hexyl)-1H-pyrazol-4-yl]-carbamic acid 2-fluoro-5-trifluoromethyl-benzyl ester;
[1-(5-Oxo-hexyl)-1H-pyrazol-4-yl]-carbamic acid 2,3,5-trifluoro-benzyl ester;
[1-(5-Oxo-hexyl)-1H-pyrazol-4-yl]-carbamic acid 2,3,4-trifluoro-benzyl ester;
5-Phenyl-oxazole-4-carboxylic acid [1-(5-oxo-hexyl)-1H-pyrazol-4-yl]-amide;
N-[1-(5-oxo-hexyl)-1H-pyrazol-4-yl]-3-(2-trifluoromethyl-phenyl)-acrylamide;
N-[1-(5-oxo-hexyl)-1H-pyrazol-4-yl]-3-o-tolyl-acrylamide;
3-(2-Chloro-phenyl)-N-[1-(5-oxo-hexyl)-1H-pyrazol-4-yl]-acrylamide;
2-Methyl-5-m-tolyl-oxazole-4-carboxylic acid [1-(5-oxo-hexyl)-1H-pyrazol-4-yl]-amide;
[1-(5-Oxo-hexyl)-1H-pyrazol-3-yl]-carbamic acid 2-chloro-benzyl ester;
[1-(5-Oxo-hexyl)-1H-pyrazol-3-yl]-carbamic acid benzyl ester;

[1-(5-Oxo-hexyl)-1H-pyrazol-3-yl]-carbamic acid 2-methyl-benzyl ester;
[1-(5-Oxo-hexyl)-1H-pyrazol-3-yl]-carbamic acid 3-trifluoromethyl-benzyl ester;
[1-(5-Oxo-hexyl)-1H-pyrazol-3-yl]-carbamic acid 3-chloro-benzyl ester;
[1-(5-Oxo-hexyl)-1H-pyrazol-3-yl]-carbamic acid 2-chloro-4-fluoro-benzyl ester;
[1-(5-Oxo-hexyl)-1H-pyrazol-3-yl]-carbamic acid 3,4-dimethyl-benzyl ester;
[1-(5-Oxo-hexyl)-1H-pyrazol-3-yl]-carbamic acid 3,4-difluoro-benzyl ester;
[1-(5-Oxo-hexyl)-1H-pyrazol-3-yl]-carbamic acid 2-chloro-6-fluoro-benzyl ester;
[1-(5-Oxo-hexyl)-1H-pyrazol-3-yl]-carbamic acid naphthalen-1-ylmethyl ester;
[1-(5-Oxo-hexyl)-1H-pyrazol-3-yl]-carbamic acid 2,5-dimethyl-benzyl ester;
[1-(5-Oxo-hexyl)-1H-pyrazol-3-yl]-carbamic acid 2,3-difluoro-benzyl ester;
[1-(5-Oxo-hexyl)-1H-pyrazol-3-yl]-carbamic acid 6-chloro-2-fluoro-3-methyl-benzyl ester;
[1-(5-Oxo-hexyl)-1H-pyrazol-3-yl]-carbamic acid 3-chloro-2-fluoro-benzyl ester;
[1-(5-Oxo-hexyl)-1H-pyrazol-3-yl]-carbamic acid 2-chloro-6-fluoro-3-methyl-benzyl ester;
[1-(5-Oxo-hexyl)-1H-pyrazol-3-yl]-carbamic acid 2,6-difluoro-3-methyl-benzyl ester;
[1-(5-Oxo-hexyl)-1H-pyrazol-3-yl]-carbamic acid 2-ethyl-benzyl ester;
5-Phenyl-oxazole-4-carboxylic acid [1-(5-oxo-hexyl)-1H-pyrazol-3-yl]-amide;
N-[1-(5-oxo-hexyl)-1H-pyrazol-3-yl]-3-(2-trifluoromethyl-phenyl)-acrylamide;
N-[1-(5-oxo-hexyl)-1H-pyrazol-3-yl]-3-(4-trifluoromethyl-phenyl)-acrylamide;
3-(2,3-Dichloro-phenyl)-N-[1-(5-oxo-hexyl)-1H-pyrazol-3-yl]-acrylamide;
3-(2,4-Dichloro-phenyl)-N-[1-(5-oxo-hexyl)-1H-pyrazol-3-yl]-acrylamide;
3-(2-Chloro-4-fluoro-phenyl)-N-[1-(5-oxo-hexyl)-1H-pyrazol-3-yl]-acrylamide;
N-[1-(5-oxo-hexyl)-1H-pyrazol-3-yl]-3-o-tolyl-acrylamide;
2-Methyl-5-m-tolyl-oxazole-4-carboxylic acid [1-(5-oxo-hexyl)-1H-pyrazol-3-yl]-amide;
3-(3-Chloro-phenyl)-N-[1-(5-oxo-hexyl)-1H-pyrazol-3-yl]-acrylamide;
{1-[5-(1,1-Difluoro-ethyl)-furan-2-ylmethyl]-1H-pyrazol-3-yl}-carbamic acid 2-chloro-benzyl ester;
5-Phenyl-oxazole-4-carboxylic acid {1-[5-(1,1-difluoro-ethyl)-furan-2-ylmethyl]-1H-pyrazol-3-yl}-amide;
{1-[5-(1,1-Difluoro-ethyl)-furan-2-ylmethyl]-1H-pyrazol-4-yl}-carbamic acid 2-chloro-benzyl ester;
5-Phenyl-oxazole-4-carboxylic acid {1-[5-(1,1-difluoro-ethyl)-furan-2-ylmethyl]-1H-pyrazol-4-yl}-amide;
[1-(5,5-Difluoro-hexyl)-1H-pyrazol-3-yl]-carbamic acid 2-chloro-benzyl ester;
5-Phenyl-oxazole-4-carboxylic acid [1-(5,5-difluoro-hexyl)-1H-pyrazol-3-yl]-amide;
[1-(5,5-Difluoro-hexyl)-1H-pyrazol-4-yl]-carbamic acid 2-chloro-benzyl ester;
5-Phenyl-oxazole-4-carboxylic acid [1-(5,5-difluoro-hexyl)-1H-pyrazol-4-yl]-amide;
2-Cyclopropyl-5-phenyl-oxazole-4-carboxylic acid [1-(5-acetyl-furan-2-ylmethyl)-1H-pyrazol-4-yl]-amide;
2-Ethyl-5-phenyl-oxazole-4-carboxylic acid [1-(5-acetyl-furan-2-ylmethyl)-1H-pyrazol-4-yl]-amide;
{1-[5-(1,1-Difluoro-ethyl)-furan-2-ylmethyl]-1H-pyrazol-3-yl}-carbamic acid 6-chloro-2-fluoro-3-methyl-benzyl ester;
{1-[5-(1,1-Difluoro-ethyl)-furan-2-ylmethyl]-1H-pyrazol-3-yl}-carbamic acid 2-chloro-6-fluoro-3-methyl-benzyl ester;
[1-(5,5-Difluoro-hexyl)-1H-pyrazol-3-yl]-carbamic acid 2-chloro-6-fluoro-3-methyl-benzyl ester;
[1-(5,5-Difluoro-hexyl)-1H-pyrazol-3-yl]-carbamic acid 6-chloro-2-fluoro-3-methyl-benzyl ester;
2-Methyl-5-phenyl-oxazole-4-carboxylic acid [1-(5,5-difluoro-hexyl)-1H-pyrazol-4-yl]-amide;
2-Methyl-5-m-tolyl-oxazole-4-carboxylic acid [1-(5,5-difluoro-hexyl)-1H-pyrazol-4-yl]-amide;
N-[1-(5,5-Difluoro-hexyl)-1H-pyrazol-3-yl]-3-(4-trifluoromethyl-phenyl)-acrylamide;
N-[1-(5,5-Difluoro-hexyl)-1H-pyrazol-3-yl]-3-(2-trifluoromethyl-phenyl)-acrylamide;
[1-(5-Acetyl-furan-2-ylmethyl)-1H-pyrazol-3-yl]-carbamic acid 2-chloro-benzyl ester;
[1-(5-Fluoro-hexyl)-1H-pyrazol-4-yl]-carbamic acid 2-chloro-benzyl ester;
N-[1-(5-Acetyl-furan-2-ylmethyl)-1H-pyrazol-3-yl]-3-(2-chloro-phenyl)-acrylamide;
{1-[5-(1,1-Difluoro-ethyl)-furan-2-ylmethyl]-1H-pyrazol-4-yl}-carbamic acid 6-chloro-2-fluoro-3-methyl-benzyl ester;
{1-[5-(1,1-Difluoro-ethyl)-furan-2-ylmethyl]-1H-pyrazol-4-yl}-carbamic acid 2-chloro-6-fluoro-3-methyl-benzyl ester;
[1-(5,5-Difluoro-hexyl)-1H-pyrazol-4-yl]-carbamic acid 2-chloro-6-fluoro-3-methyl-benzyl ester;
[1-(5,5-Difluoro-hexyl)-1H-pyrazol-4-yl]-carbamic acid 6-chloro-2-fluoro-3-methyl-benzyl ester;
5-m-Tolyl-oxazole-4-carboxylic acid {1-[5-(1,1-difluoro-ethyl)-furan-2-ylmethyl]-1H-pyrazol-4-yl}-amide;
5-(4-Methoxy-phenyl)-oxazole-4-carboxylic acid {1-[5-(1,1-difluoro-ethyl)-furan-2-ylmethyl]-1H-pyrazol-4-yl}-amide;
5-(4-Methoxy-phenyl)-2-methyl-oxazole-4-carboxylic acid {1-[5-(1,1-difluoro-ethyl)-furan-2-ylmethyl]-1H-pyrazol-4-yl}-amide;
N-{1-[5-(1,1-Difluoro-ethyl)-furan-2-ylmethyl]-1H-pyrazol-4-yl}-3-(4-trifluoromethyl-phenyl)-acrylamide;
N-{1-[5-(1,1-Difluoro-ethyl)-furan-2-ylmethyl]-1H-pyrazol-4-yl}-3-(2,3-dimethoxy-phenyl)-acrylamide;
N-{1-[5-(1,1-Difluoro-ethyl)-furan-2-ylmethyl]-1H-pyrazol-4-yl}-3-p-tolyl-acrylamide;
5-(3-Methoxy-phenyl)-2-methyl-oxazole-4-carboxylic acid {1-[5-(1,1-difluoro-ethyl)-furan-2-ylmethyl]-1H-pyrazol-4-yl}-amide;
5-(3-Chloro-phenyl)-thiazole-4-carboxylic acid {1-[5-(1,1-difluoro-ethyl)-furan-2-ylmethyl]-1H-pyrazol-4-yl}-amide;
N-{1-[5-(1,1-Difluoro-ethyl)-furan-2-ylmethyl]-1H-pyrazol-4-yl}-3-(4-methoxy-phenyl)-acrylamide;
N-{1-[5-(1,1-Difluoro-ethyl)-furan-2-ylmethyl]-1H-pyrazol-3-yl}-3-(3-trifluoromethyl-phenyl)-acrylamide;
3-(2,3-Dichloro-phenyl)-N-{1-[5-(1,1-difluoro-ethyl)-furan-2-ylmethyl]-1H-pyrazol-3-yl}-acrylamide;
N-{1-[5-(1,1-Difluoro-ethyl)-furan-2-ylmethyl]-1H-pyrazol-3-yl}-3-(2,3-dimethoxy-phenyl)-acrylamide;
3-(2-Chloro-4-fluoro-phenyl)-N-{1-[5-(1,1-difluoro-ethyl)-furan-2-ylmethyl]-1H-pyrazol-3-yl}-acrylamide;
N-{1-[5-(1,1-Difluoro-ethyl)-furan-2-ylmethyl]-1H-pyrazol-3-yl}-3-p-tolyl-acrylamide;

3-(2,4-Dichloro-phenyl)-N-{1-[5-(1,1-difluoro-ethyl)-furan-2-ylmethyl]-1H-pyrazol-3-yl}-acrylamide;
3-(2-Chloro-6-fluoro-phenyl)-N-{1-[5-(1,1-difluoro-ethyl)-furan-2-ylmethyl]-1H-pyrazol-3-yl}-acrylamide;
3-(2-Chloro-3,6-difluoro-phenyl)-N-{1-[5-(1,1-difluoro-ethyl)-furan-2-ylmethyl]-1H-pyrazol-3-yl}-acrylamide;
3-(3-Chloro-phenyl)-N-{1-[5-(1,1-difluoro-ethyl)-furan-2-ylmethyl]-1H-pyrazol-3-yl}-acrylamide;
N-{1-[5-(1,1-Difluoro-ethyl)-furan-2-ylmethyl]-1H-pyrazol-3-yl}-3-(2-fluoro-3-trifluoromethyl-phenyl)-acrylamide;
N-{1-[5-(1,1-Difluoro-ethyl)-furan-2-ylmethyl]-1H-pyrazol-3-yl}-3-m-tolyl-acrylamide;
N-{1-[5-(1,1-Difluoro-ethyl)-furan-2-ylmethyl]-1H-pyrazol-3-yl}-3-(3-methoxy-phenyl)-acrylamide;
N-{1-[5-(1,1-Difluoro-ethyl)-furan-2-ylmethyl]-1H-pyrazol-3-yl}-3-(4-methoxy-phenyl)-acrylamide;
2-Methyl-5-phenyl-oxazole-4-carboxylic acid {1-[5-(1,1-difluoro-ethyl)-furan-2-ylmethyl]-1H-pyrazol-4-yl}-amide;
2-Methyl-5-m-tolyl-oxazole-4-carboxylic acid {1-[5-(1,1-difluoro-ethyl)-furan-2-ylmethyl]-1H-pyrazol-4-yl}-amide;
2-Methyl-5-m-tolyl-oxazole-4-carboxylic acid {1-[5-(1,1-difluoro-ethyl)-furan-2-ylmethyl]-1H-pyrazol-3-yl}-amide;
5-(3-Methoxy-phenyl)-2-methyl-oxazole-4-carboxylic acid {1-[5-(1,1-difluoro-ethyl)-furan-2-ylmethyl]-1H-pyrazol-3-yl}-amide;
5-(3-Methoxy-phenyl)-oxazole-4-carboxylic acid {1-[5-(1,1-difluoro-ethyl)-furan-2-ylmethyl]-1H-pyrazol-4-yl}-amide;
5-(3-Methoxy-phenyl)-oxazole-4-carboxylic acid {1-[5-(1,1-difluoro-ethyl)-furan-2-ylmethyl]-1H-pyrazol-3-yl}-amide; and
5-(4-Methoxy-phenyl)-oxazole-4-carboxylic acid {1-[5-(1,1-difluoro-ethyl)-furan-2-ylmethyl]-1H-pyrazol-3-yl}-amide;
wherein the double bond of acrylamide derivatives cited in the above list may be in (E)- or (Z)-configuration (preferably in (E)-configuration); and
carbamic acid 1-phenyl-ethyl ester derivatives as well as 5-fluoro-hexyl derivatives may be in absolute (R)- or (S)-configuration.

40) In addition to the compounds of formula (I) as listed in embodiment 39) further preferred compounds are selected from the group consisting of:
N-[1-(5-Acetyl-furan-2-ylmethyl)-1H-pyrazol-4-yl]-3-(2-trifluoromethyl-phenyl)-acrylamide;
N-[1-(5-Acetyl-furan-2-ylmethyl)-1H-pyrazol-4-yl]-3-(4-trifluoromethyl-phenyl)-acrylamide;
N-[1-(5-Acetyl-furan-2-ylmethyl)-1H-pyrazol-3-yl]-3-(2-trifluoromethyl-phenyl)-acrylamide;
N-[1-(5-Acetyl-furan-2-ylmethyl)-1H-pyrazol-3-yl]-3-(4-trifluoromethyl-phenyl)-acrylamide;
N-[1-(5-Acetyl-furan-2-ylmethyl)-1H-pyrazol-3-yl]-3-(4-methoxy-phenyl)-acrylamide;
{1-[5-(1,1-Difluoro-ethyl)-furan-2-ylmethyl]-1H-pyrazol-4-yl}-carbamic acid 3-chloro-2-fluoro-benzyl ester;
{1-[5-(1,1-Difluoro-ethyl)-furan-2-ylmethyl]-1H-pyrazol-3-yl}-carbamic acid 3-trifluoromethyl-benzyl ester;
{1-[5-(1,1-Difluoro-ethyl)-furan-2-ylmethyl]-1H-pyrazol-4-yl}-carbamic acid 2-chloro-4-fluoro-benzyl ester;
[1-(5,5-Difluoro-hexyl)-1H-pyrazol-3-yl]-carbamic acid 2,6-difluoro-3-methyl-benzyl ester;
{1-[5-(1,1-Difluoro-ethyl)-furan-2-ylmethyl]-1H-pyrazol-4-yl}-carbamic acid 2-chloro-6-fluoro-benzyl ester;
{1-[5-(1,1-Difluoro-ethyl)-furan-2-ylmethyl]-1H-pyrazol-3-yl}-carbamic acid 2-fluoro-benzyl ester;
[1-(5,5-Difluoro-hexyl)-1H-pyrazol-3-yl]-carbamic acid 3-trifluoromethyl-benzyl ester;
{1-[5-(1,1-Difluoro-ethyl)-furan-2-ylmethyl]-1H-pyrazol-3-yl}-carbamic acid 3-chloro-benzyl ester;
[1-(5,5-Difluoro-hexyl)-1H-pyrazol-4-yl]-carbamic acid 3-trifluoromethyl-benzyl ester;
{1-[5-(1,1-Difluoro-ethyl)-furan-2-ylmethyl]-1H-pyrazol-4-yl}-carbamic acid 2,6-difluoro-3-methyl-benzyl ester;
{1-[5-(1,1-Difluoro-ethyl)-furan-2-ylmethyl]-1H-pyrazol-4-yl}-carbamic acid 2-fluoro-benzyl ester;
[1-(5,5-Difluoro-hexyl)-1H-pyrazol-3-yl]-carbamic acid 2-fluoro-benzyl ester;
{1-[5-(1,1-Difluoro-ethyl)-furan-2-ylmethyl]-1H-pyrazol-3-yl}-carbamic acid benzyl ester;
{1-[5-(1,1-Difluoro-ethyl)-furan-2-ylmethyl]-1H-pyrazol-4-yl}-carbamic acid 3-trifluoromethyl-benzyl ester;
[1-(5,5-Difluoro-hexyl)-1H-pyrazol-4-yl]-carbamic acid 2-fluoro-benzyl ester;
[1-(5,5-Difluoro-hexyl)-1H-pyrazol-3-yl]-carbamic acid 3-chloro-benzyl ester;
[1-(5,5-Difluoro-hexyl)-1H-pyrazol-3-yl]-carbamic acid 3,4-dimethyl-benzyl ester;
[1-(5,5-Difluoro-hexyl)-1H-pyrazol-3-yl]-carbamic acid 2-ethyl-benzyl ester;
{1-[5-(1,1-Difluoro-ethyl)-furan-2-ylmethyl]-1H-pyrazol-3-yl}-carbamic acid 3-methyl-benzyl ester;
[1-(5,5-Difluoro-hexyl)-1H-pyrazol-4-yl]-carbamic acid 3-chloro-benzyl ester;
{1-[5-(1,1-Difluoro-ethyl)-furan-2-ylmethyl]-1H-pyrazol-3-yl}-carbamic acid 2-ethyl-benzyl ester;
{1-[5-(1,1-Difluoro-ethyl)-furan-2-ylmethyl]-1H-pyrazol-4-yl}-carbamic acid benzyl ester;
[1-(5,5-Difluoro-hexyl)-1H-pyrazol-3-yl]-carbamic acid benzyl ester;
[1-(5,5-Difluoro-hexyl)-1H-pyrazol-4-yl]-carbamic acid 3,4-dimethyl-benzyl ester;
{1-[5-(1,1-Difluoro-ethyl)-furan-2-ylmethyl]-1H-pyrazol-4-yl}-carbamic acid 2-methyl-benzyl ester;
{1-[5-(1,1-Difluoro-ethyl)-furan-2-ylmethyl]-1H-pyrazol-4-yl}-carbamic acid 3-chloro-benzyl ester;
[1-(5,5-Difluoro-hexyl)-1H-pyrazol-3-yl]-carbamic acid 2-methyl-benzyl ester;
{1-[5-(1,1-Difluoro-ethyl)-furan-2-ylmethyl]-1H-pyrazol-4-yl}-carbamic acid 3,4-dimethyl-benzyl ester;
[1-(5,5-Difluoro-hexyl)-1H-pyrazol-4-yl]-carbamic acid benzyl ester;
[1-(5,5-Difluoro-hexyl)-1H-pyrazol-3-yl]-carbamic acid 2,5-dimethyl-benzyl ester;
[1-(5,5-Difluoro-hexyl)-1H-pyrazol-3-yl]-carbamic acid 3-methyl-benzyl ester;
[1-(5,5-Difluoro-hexyl)-1H-pyrazol-4-yl]-carbamic acid 2-ethyl-benzyl ester;
[1-(5,5-Difluoro-hexyl)-1H-pyrazol-4-yl]-carbamic acid 2-methyl-benzyl ester;
[1-(5,5-Difluoro-hexyl)-1H-pyrazol-4-yl]-carbamic acid 3-methyl-benzyl ester;
[1-(5,5-Difluoro-hexyl)-1H-pyrazol-4-yl]-carbamic acid 2,5-dimethyl-benzyl ester;
{1-[5-(1,1-Difluoro-ethyl)-furan-2-ylmethyl]-1H-pyrazol-4-yl}-carbamic acid 2-ethyl-benzyl ester;
{1-[5-(1,1-Difluoro-ethyl)-furan-2-ylmethyl]-1H-pyrazol-4-yl}-carbamic acid 3-methyl-benzyl ester;
{1-[5-(1,1-Difluoro-ethyl)-furan-2-ylmethyl]-1H-pyrazol-4-yl}-carbamic acid 2,5-dimethyl-benzyl ester;

N-[1-(5-Acetyl-furan-2-ylmethyl)-1H-pyrazol-3-yl]-3-(2,4-dimethoxy-phenyl)-acrylamide;
5-(3-Fluoro-phenyl)-2-methyl-oxazole-4-carboxylic acid [1-(5-acetyl-furan-2-ylmethyl)-1H-pyrazol-3-yl]-amide;
N-[1-(5-Acetyl-furan-2-ylmethyl)-1H-pyrazol-3-yl]-3-(4-chloro-phenyl)-acrylamide;
2-Methyl-5-(3-trifluoromethoxy-phenyl)-oxazole-4-carboxylic acid [1-(5-acetyl-furan-2-ylmethyl)-1H-pyrazol-3-yl]-amide;
5-(3,4-Dimethyl-phenyl)-oxazole-4-carboxylic acid [1-(5-acetyl-furan-2-ylmethyl)-1H-pyrazol-4-yl]-amide;
N-[1-(5-Acetyl-furan-2-ylmethyl)-1H-pyrazol-4-yl]-3-(2,4-dimethoxy-phenyl)-acrylamide;
5-(3,4-Dimethyl-phenyl)-oxazole-4-carboxylic acid [1-(5-acetyl-furan-2-ylmethyl)-1H-pyrazol-3-yl]-amide;
5-(3-Fluoro-phenyl)-2-methyl-oxazole-4-carboxylic acid [1-(5-acetyl-furan-2-ylmethyl)-1H-pyrazol-4-yl]-amide;
N-[1-(5-Acetyl-furan-2-ylmethyl)-1H-pyrazol-4-yl]-3-(4-methoxy-phenyl)-acrylamide;
2-Methyl-5-(3-trifluoromethyl-phenyl)-oxazole-4-carboxylic acid [1-(5-acetyl-furan-2-ylmethyl)-1H-pyrazol-4-yl]-amide;
N-[1-(5-Acetyl-furan-2-ylmethyl)-1H-pyrazol-4-yl]-3-(4-chloro-phenyl)-acrylamide;
5-(3-Chloro-phenyl)-2-methyl-oxazole-4-carboxylic acid [1-(5-acetyl-furan-2-ylmethyl)-1H-pyrazol-4-yl]-amide;
2-Methyl-5-(3-trifluoromethoxy-phenyl)-oxazole-4-carboxylic acid [1-(5-acetyl-furan-2-ylmethyl)-1H-pyrazol-4-yl]-amide;
5-Biphenyl-3-yl-2-methyl-oxazole-4-carboxylic acid [1-(5-acetyl-furan-2-ylmethyl)-1H-pyrazol-4-yl]-amide;
5-p-Tolyl-oxazole-4-carboxylic acid [1-(5-acetyl-furan-2-ylmethyl)-1H-pyrazol-4-yl]-amide;
5-p-Tolyl-oxazole-4-carboxylic acid [1-(5-acetyl-furan-2-ylmethyl)-1H-pyrazol-3-yl]-amide;
2-Methyl-5-(3-trifluoromethyl-phenyl)-oxazole-4-carboxylic acid [1-(5-acetyl-furan-2-ylmethyl)-1H-pyrazol-3-yl]-amide;
[1-(5-Acetyl-furan-2-ylmethyl)-1H-pyrazol-3-yl]-carbamic acid 4-fluoro-benzyl ester;
[1-(5-Acetyl-furan-2-ylmethyl)-1H-pyrazol-3-yl]-carbamic acid 3-bromo-benzyl ester;
[1-(5-Acetyl-furan-2-ylmethyl)-1H-pyrazol-4-yl]-carbamic acid 4-fluoro-benzyl ester;
[1-(5-Acetyl-furan-2-ylmethyl)-1H-pyrazol-4-yl]-carbamic acid 3-bromo-benzyl ester;
N-[1-(5-Acetyl-furan-2-ylmethyl)-1H-pyrazol-4-yl]-3-(2,3-difluoro-4-trifluoromethyl-phenyl)-acrylamide;
N-[1-(5-Acetyl-furan-2-ylmethyl)-1H-pyrazol-4-yl]-3-(2,5-difluoro-4-methoxy-phenyl)-acrylamide;
5-(4-Trifluoromethyl-phenyl)-oxazole-4-carboxylic acid [1-(5-acetyl-furan-2-ylmethyl)-1H-pyrazol-3-yl]-amide;
5-(3-Trifluoromethyl-phenyl)-oxazole-4-carboxylic acid [1-(5-acetyl-furan-2-ylmethyl)-1H-pyrazol-3-yl]-amide;
5-(3-Fluoro-phenyl)-oxazole-4-carboxylic acid [1-(5-acetyl-furan-2-ylmethyl)-1H-pyrazol-3-yl]-amide;
5-(4-Chloro-phenyl)-oxazole-4-carboxylic acid [1-(5-acetyl-furan-2-ylmethyl)-1H-pyrazol-3-yl]-amide;
5-(4-Fluoro-phenyl)-oxazole-4-carboxylic acid [1-(5-acetyl-furan-2-ylmethyl)-1H-pyrazol-3-yl]-amide;
5-(4-Trifluoromethoxy-phenyl)-oxazole-4-carboxylic acid [1-(5-acetyl-furan-2-ylmethyl)-1H-pyrazol-3-yl]-amide;
5-(4-Trifluoromethoxy-phenyl)-oxazole-4-carboxylic acid [1-(5-acetyl-furan-2-ylmethyl)-1H-pyrazol-4-yl]-amide;
5-(3-Trifluoromethyl-phenyl)-oxazole-4-carboxylic acid [1-(5-acetyl-furan-2-ylmethyl)-1H-pyrazol-4-yl]-amide;
N-[1-(5-Acetyl-furan-2-ylmethyl)-1H-pyrazol-3-yl]-3-(4-chloro-3,5-difluoro-phenyl)-acrylamide;
N-[1-(5-Acetyl-furan-2-ylmethyl)-1H-pyrazol-4-yl]-3-(2,5-difluoro-4-trifluoromethyl-phenyl)-acrylamide;
5-(4-Chloro-phenyl)-oxazole-4-carboxylic acid [1-(5-acetyl-furan-2-ylmethyl)-1H-pyrazol-4-yl]-amide;
5-(3-Chloro-phenyl)-oxazole-4-carboxylic acid [1-(5-acetyl-furan-2-ylmethyl)-1H-pyrazol-4-yl]-amide;
5-(3-Chloro-phenyl)-oxazole-4-carboxylic acid [1-(5-acetyl-furan-2-ylmethyl)-1H-pyrazol-3-yl]-amide;
5-(3-Fluoro-phenyl)-oxazole-4-carboxylic acid [1-(5-acetyl-furan-2-ylmethyl)-1H-pyrazol-4-yl]-amide;
5-Biphenyl-3-yl-2-methyl-oxazole-4-carboxylic acid [1-(5-acetyl-furan-2-ylmethyl)-1H-pyrazol-3-yl]-amide;
5-(3-Chloro-phenyl)-2-methyl-oxazole-4-carboxylic acid [1-(5-acetyl-furan-2-ylmethyl)-1H-pyrazol-3-yl]-amide;
5-Biphenyl-3-yl-oxazole-4-carboxylic acid [1-(5-acetyl-furan-2-ylmethyl)-1H-pyrazol-3-yl]-amide;
5-Biphenyl-3-yl-oxazole-4-carboxylic acid [1-(5-acetyl-furan-2-ylmethyl)-1H-pyrazol-4-yl]-amide;
5-(3-Methoxy-phenyl)-2-methyl-oxazole-4-carboxylic acid [1-(5-acetyl-furan-2-ylmethyl)-1H-pyrazol-3-yl]-amide;
5-m-Tolyl-oxazole-4-carboxylic acid [1-(5-acetyl-furan-2-ylmethyl)-1H-pyrazol-3-yl]-amide;
2-Methyl-5-phenyl-oxazole-4-carboxylic acid [1-(5-acetyl-furan-2-ylmethyl)-1H-pyrazol-3-yl]-amide;
[1-(5-Acetyl-thiophen-2-ylmethyl)-1H-pyrazol-4-yl]-carbamic acid 2-chloro-benzyl ester;
5-Phenyl-oxazole-4-carboxylic acid [1-(3-acetyl-isoxazol-5-ylmethyl)-1H-pyrazol-4-yl]-amide;
[1-(6-Acetyl-pyridin-2-ylmethyl)-1H-pyrazol-4-yl]-carbamic acid 2-chloro-benzyl ester;
5-Phenyl-oxazole-4-carboxylic acid [1-(6-acetyl-pyridin-2-ylmethyl)-1H-pyrazol-4-yl]-amide;
N-[1-(6-Acetyl-pyridin-2-ylmethyl)-1H-pyrazol-4-yl]-3-(4-trifluoromethyl-phenyl)-acrylamide;
[1-(3-Acetyl-benzyl)-1H-pyrazol-4-yl]-carbamic acid 2-chloro-benzyl ester;
5-Phenyl-oxazole-4-carboxylic acid [1-(3-acetyl-benzyl)-1H-pyrazol-4-yl]-amide;
5-Pyridin-2-yl-oxazole-4-carboxylic acid [1-(5-acetyl-furan-2-ylmethyl)-1H-pyrazol-4-yl]-amide;
5-Phenyl-oxazole-4-carboxylic acid [1-(5-acetyl-thiophen-2-ylmethyl)-1H-pyrazol-4-yl]-amide;
N-[1-(5-Acetyl-thiophen-2-ylmethyl)-1H-pyrazol-4-yl]-3-(4-trifluoromethyl-phenyl)-acrylamide;
5-(3-Trifluoromethoxy-phenyl)-oxazole-4-carboxylic acid [1-(5-acetyl-furan-2-ylmethyl)-1H-pyrazol-3-yl]-amide;
5-(3-Trifluoromethoxy-phenyl)-oxazole-4-carboxylic acid [1-(5-acetyl-furan-2-ylmethyl)-1H-pyrazol-4-yl]-amide;
5-(3-Cyano-phenyl)-oxazole-4-carboxylic acid [1-(5-acetyl-furan-2-ylmethyl)-1H-pyrazol-4-yl]-amide;
5-(3-Carbamoyl-phenyl)-oxazole-4-carboxylic acid [1-(5-acetyl-furan-2-ylmethyl)-1H-pyrazol-4-yl]-amide;
5-(3-Dimethylamino-phenyl)-oxazole-4-carboxylic acid [1-(5-acetyl-furan-2-ylmethyl)-1H-pyrazol-4-yl]-amide;
5-Phenyl-oxazole-4-carboxylic acid [1-(5-acetyl-thiophen-2-ylmethyl)-1H-pyrazol-3-yl]-amide;
N-[1-(5-Acetyl-thiophen-2-ylmethyl)-1H-pyrazol-3-yl]-3-(4-trifluoromethyl-phenyl)-acrylamide;
[1-(5-Acetyl-thiophen-2-ylmethyl)-1H-pyrazol-3-yl]-carbamic acid 2-chloro-benzyl ester;
5-[3-(2-Methoxy-ethyl)-phenyl]-oxazole-4-carboxylic acid [1-(5-acetyl-furan-2-ylmethyl)-1H-pyrazol-3-yl]-amide;
5-(3-Cyano-phenyl)-oxazole-4-carboxylic acid [1-(5-acetyl-furan-2-ylmethyl)-1H-pyrazol-3-yl]-amide;

3-{4-[1-(5-Acetyl-furan-2-ylmethyl)-1H-pyrazol-3-ylcarbamoyl]-oxazol-5-yl}-benzoic acid tert-butyl ester;

[1-(5-Acetyl-pyridin-3-ylmethyl)-1H-pyrazol-4-yl]-carbamic acid 2-chloro-benzyl ester;

5-[3-(2-Hydroxy-ethyl)-phenyl]-oxazole-4-carboxylic acid [1-(5-acetyl-furan-2-ylmethyl)-1H-pyrazol-3-yl]-amide;

5-(3-Methoxymethyl-phenyl)-oxazole-4-carboxylic acid [1-(5-acetyl-furan-2-ylmethyl)-1H-pyrazol-3-yl]-amide;

[1-(4-Acetyl-pyridin-2-ylmethyl)-1H-pyrazol-4-yl]-carbamic acid 2-chloro-benzyl ester;

{4-[1-(5-Acetyl-furan-2-ylmethyl)-1H-pyrazol-3-ylcarbamoyl]-5-phenyl-oxazol-2-ylmethyl}-carbamic acid tert-butyl ester;

[1-(4-Acetyl-thiazol-2-ylmethyl)-1H-pyrazol-4-yl]-carbamic acid 2-chloro-benzyl ester;

5-Phenyl-oxazole-4-carboxylic acid [1-(4-acetyl-thiazol-2-ylmethyl)-1H-pyrazol-4-yl]-amide;

N-[1-(4-Acetyl-thiazol-2-ylmethyl)-1H-pyrazol-4-yl]-3-(4-trifluoromethyl-phenyl)-acrylamide;

2-Aminomethyl-5-phenyl-oxazole-4-carboxylic acid [1-(5-acetyl-furan-2-ylmethyl)-1H-pyrazol-3-yl]-amide;

2-Methyl-5-(3-trifluoromethoxy-phenyl)-oxazole-4-carboxylic acid [1-(5-acetyl-thiophen-2-ylmethyl)-1H-pyrazol-4-yl]-amide;

2-Methyl-5-(3-trifluoromethoxy-phenyl)-oxazole-4-carboxylic acid [1-(5-acetyl-thiophen-2-ylmethyl)-1H-pyrazol-3-yl]-amide;

5-m-Tolyl-oxazole-4-carboxylic acid [1-(5-acetyl-thiophen-2-ylmethyl)-1H-pyrazol-4-yl]-amide;

5-m-Tolyl-oxazole-4-carboxylic acid [1-(5-acetyl-thiophen-2-ylmethyl)-1H-pyrazol-3-yl]-amide;

2-Methyl-5-m-tolyl-thiazole-4-carboxylic acid [1-(5-acetyl-thiophen-2-ylmethyl)-1H-pyrazol-4-yl]-amide;

5-(4-Chloro-phenyl)-2-methyl-thiazole-4-carboxylic acid [1-(5-acetyl-thiophen-2-ylmethyl)-1H-pyrazol-4-yl]-amide;

5-(3-Cyano-phenyl)-oxazole-4-carboxylic acid [1-(5-acetyl-thiophen-2-ylmethyl)-1H-pyrazol-4-yl]-amide;

5-(3-Cyano-phenyl)-oxazole-4-carboxylic acid [1-(5-acetyl-thiophen-2-ylmethyl)-1H-pyrazol-3-yl]-amide;

5-(3-Dimethylamino-phenyl)-oxazole-4-carboxylic acid [1-(5-acetyl-thiophen-2-ylmethyl)-1H-pyrazol-4-yl]-amide;

5-(3-Dimethylamino-phenyl)-oxazole-4-carboxylic acid [1-(5-acetyl-thiophen-2-ylmethyl)-1H-pyrazol-3-yl]-amide;

2-Cyclopropyl-5-phenyl-oxazole-4-carboxylic acid [1-(5-acetyl-thiophen-2-ylmethyl)-1H-pyrazol-4-yl]-amide;

2-Cyclopropyl-5-phenyl-oxazole-4-carboxylic acid [1-(5-acetyl-thiophen-2-ylmethyl)-1H-pyrazol-3-yl]-amide;

5-(3-Methoxy-4-methyl-phenyl)-oxazole-4-carboxylic acid [1-(5-acetyl-thiophen-2-ylmethyl)-1H-pyrazol-4-yl]-amide;

5-(3-Hydroxymethyl-phenyl)-oxazole-4-carboxylic acid [1-(5-acetyl-furan-2-ylmethyl)-1H-pyrazol-3-yl]-amide;

5-[3-(2-Dimethylamino-ethyl)-phenyl]-oxazole-4-carboxylic acid [1-(5-acetyl-furan-2-ylmethyl)-1H-pyrazol-3-yl]-amide;

5-(3-Dimethylaminomethyl-phenyl)-oxazole-4-carboxylic acid [1-(5-acetyl-furan-2-ylmethyl)-1H-pyrazol-3-yl]-amide;

[1-(2-Acetyl-pyridin-4-ylmethyl)-1H-pyrazol-4-yl]-carbamic acid 2-chloro-benzyl ester;

5-Phenyl-oxazole-4-carboxylic acid [1-(5-acetyl-thiophen-3-ylmethyl)-1H-pyrazol-4-yl]-amide;

[1-(2-Acetyl-thiazol-4-ylmethyl)-1H-pyrazol-4-yl]-carbamic acid 2-chloro-benzyl ester;

N-[1-(6-Acetyl-pyridin-2-ylmethyl)-1H-pyrazol-3-yl]-3-(4-trifluoromethyl-phenyl)-acrylamide;

[1-(6-Acetyl-pyridin-2-ylmethyl)-1H-pyrazol-3-yl]-carbamic acid 2-chloro-benzyl ester;

5-(2-Fluoro-pyridin-4-yl)-oxazole-4-carboxylic acid [1-(5-acetyl-furan-2-ylmethyl)-1H-pyrazol-4-yl]-amide; and 5-Phenyl-oxazole-4-carboxylic acid [1-(5-methanesulfonyl-furan-2-ylmethyl)-1H-pyrazol-4-yl]-amide;

wherein the double bond of acrylamide derivatives cited in the above list may be in (E)- or (Z)-configuration (preferably in (E)-configuration); and carbamic acid 1-phenyl-ethyl ester derivatives as well as 5-fluoro-hexyl derivatives may be in absolute (R)- or (S)-configuration.

41) In addition to the compounds of formula (I) as listed in embodiments 39) and 40) further preferred compounds are selected from the group consisting of:

5-Pyridin-4-yl-oxazole-4-carboxylic acid [1-(5-acetyl-furan-2-ylmethyl)-1H-pyrazol-4-yl]-amide;

5-(6-Methyl-pyridin-2-yl)-oxazole-4-carboxylic acid [1-(5-acetyl-furan-2-ylmethyl)-1H-pyrazol-4-yl]-amide;

2-Methoxymethyl-5-phenyl-oxazole-4-carboxylic acid [1-(5-acetyl-furan-2-ylmethyl)-1H-pyrazol-4-yl]-amide;

2-Methoxymethyl-5-phenyl-oxazole-4-carboxylic acid [1-(5-acetyl-furan-2-ylmethyl)-1H-pyrazol-3-yl]-amide;

{4-[1-(5-Acetyl-furan-2-ylmethyl)-1H-pyrazol-4-ylcarbamoyl]-5-phenyl-oxazol-2-ylmethyl}-carbamic acid tert-butyl ester;

5-(6-Trifluoromethyl-pyridin-2-yl)-oxazole-4-carboxylic acid [1-(5-acetyl-furan-2-ylmethyl)-1H-pyrazol-4-yl]-amide;

5-Isoxazol-5-yl-oxazole-4-carboxylic acid [1-(5-acetyl-furan-2-ylmethyl)-1H-pyrazol-4-yl]-amide;

5-Phenyl-oxazole-4-carboxylic acid [1-(2-acetyl-thiazol-4-ylmethyl)-1H-pyrazol-3-yl]-amide;

2-(2-Methoxy-ethyl)-5-phenyl-oxazole-4-carboxylic acid [1-(5-acetyl-furan-2-ylmethyl)-1H-pyrazol-4-yl]-amide;

2-(2-Methoxy-ethyl)-5-phenyl-oxazole-4-carboxylic acid [1-(5-acetyl-furan-2-ylmethyl)-1H-pyrazol-3-yl]-amide;

2-Isopropyl-5-phenyl-oxazole-4-carboxylic acid [1-(5-acetyl-furan-2-ylmethyl)-1H-pyrazol-4-yl]-amide;

2-Butyl-5-phenyl-oxazole-4-carboxylic acid [1-(5-acetyl-furan-2-ylmethyl)-1H-pyrazol-4-yl]-amide;

2-Isopropyl-5-phenyl-oxazole-4-carboxylic acid [1-(5-acetyl-furan-2-ylmethyl)-1H-pyrazol-3-yl]-amide;

2-Butyl-5-phenyl-oxazole-4-carboxylic acid [1-(5-acetyl-furan-2-ylmethyl)-1H-pyrazol-3-yl]-amide;

5-(3-Isopropoxymethyl-phenyl)-oxazole-4-carboxylic acid [1-(5-acetyl-furan-2-ylmethyl)-1H-pyrazol-3-yl]-amide;

5-[3-(2-Isopropoxy-ethyl)-phenyl]-oxazole-4-carboxylic acid [1-(5-acetyl-furan-2-ylmethyl)-1H-pyrazol-3-yl]-amide;

[1-(4-Acetyl-thiazol-2-ylmethyl)-1H-pyrazol-3-yl]-carbamic acid 2-chloro-benzyl ester;

5-Phenyl-oxazole-4-carboxylic acid [1-(4-acetyl-thiazol-2-ylmethyl)-1H-pyrazol-3-yl]-amide;

2-Benzyl-5-phenyl-oxazole-4-carboxylic acid [1-(5-acetyl-furan-2-ylmethyl)-1H-pyrazol-4-yl]-amide;

2-Benzyl-5-phenyl-oxazole-4-carboxylic acid [1-(5-acetyl-furan-2-ylmethyl)-1H-pyrazol-3-yl]-amide;

3-{4-[1-(5-Acetyl-furan-2-ylmethyl)-1H-pyrazol-3-ylcarbamoyl]-5-phenyl-oxazol-2-yl}-propionic acid tert-butyl ester;

5-Phenyl-oxazole-4-carboxylic acid [1-(5-acetyl-thiazol-2-ylmethyl)-1H-pyrazol-4-yl]-amide;

[1-(5-Acetyl-thiazol-2-ylmethyl)-1H-pyrazol-4-yl]-carbamic acid 2-chloro-benzyl ester;

5-Phenyl-oxazole-4-carboxylic acid [1-(2-acetyl-thiazol-5-ylmethyl)-1H-pyrazol-4-yl]-amide;

N-[1-(2-Acetyl-thiazol-5-ylmethyl)-1H-pyrazol-4-yl]-3-(4-trifluoromethyl-phenyl)-acrylamide;
[1-(2-Acetyl-thiazol-5-ylmethyl)-1H-pyrazol-4-yl]-carbamic acid 2-chloro-benzyl ester;
5-Phenyl-oxazole-4-carboxylic acid [1-(2-acetyl-oxazol-5-ylmethyl)-1H-pyrazol-3-yl]-amide;
5-Phenyl-oxazole-4-carboxylic acid [1-(4-acetyl-thiophen-2-ylmethyl)-1H-pyrazol-4-yl]-amide;
[1-(4-Acetyl-thiophen-2-ylmethyl)-1H-pyrazol-4-yl]-carbamic acid 2-chloro-benzyl ester;
2-Methyl-5-m-tolyl-oxazole-4-carboxylic acid [1-(4-acetyl-thiazol-2-ylmethyl)-1H-pyrazol-3-yl]-amide;
5-(3-Chloro-phenyl)-2-methyl-oxazole-4-carboxylic acid [1-(4-acetyl-thiazol-2-ylmethyl)-1H-pyrazol-3-yl]-amide;
5-m-Tolyl-oxazole-4-carboxylic acid [1-(4-acetyl-thiazol-2-ylmethyl)-1H-pyrazol-3-yl]-amide;
2-Methyl-5-phenyl-oxazole-4-carboxylic acid [1-(4-acetyl-thiazol-2-ylmethyl)-1H-pyrazol-3-yl]-amide;
2-Methyl-5-(3-trifluoromethyl-phenyl)-oxazole-4-carboxylic acid [1-(4-acetyl-thiazol-2-ylmethyl)-1H-pyrazol-3-yl]-amide;
5-(3-Fluoro-phenyl)-oxazole-4-carboxylic acid [1-(4-acetyl-thiazol-2-ylmethyl)-1H-pyrazol-3-yl]-amide;
5-(3-Dimethylamino-phenyl)-oxazole-4-carboxylic acid [1-(4-acetyl-thiazol-2-ylmethyl)-1H-pyrazol-3-yl]-amide;
5-(3-Chloro-phenyl)-oxazole-4-carboxylic acid [1-(4-acetyl-thiazol-2-ylmethyl)-1H-pyrazol-3-yl]-amide;
2-Methyl-5-(3-trifluoromethoxy-phenyl)-oxazole-4-carboxylic acid [1-(4-acetyl-thiazol-2-ylmethyl)-1H-pyrazol-3-yl]-amide;
5-(3-Trifluoromethoxy-phenyl)-oxazole-4-carboxylic acid [1-(4-acetyl-thiazol-2-ylmethyl)-1H-pyrazol-3-yl]-amide;
5-(3-Methoxy-phenyl)-oxazole-4-carboxylic acid [1-(4-acetyl-thiazol-2-ylmethyl)-1H-pyrazol-3-yl]-amide;
N-[1-(4-Acetyl-thiazol-2-ylmethyl)-1H-pyrazol-3-yl]-3-(4-trifluoromethyl-phenyl)-acrylamide;
N-[1-(4-Acetyl-thiazol-2-ylmethyl)-1H-pyrazol-3-yl]-3-(2-trifluoromethyl-phenyl)-acrylamide;
N-[1-(4-Acetyl-thiazol-2-ylmethyl)-1H-pyrazol-3-yl]-3-(3-trifluoromethoxy-phenyl)-acrylamide;
N-[1-(4-Acetyl-thiazol-2-ylmethyl)-1H-pyrazol-3-yl]-3-(2-chloro-4-fluoro-phenyl)-acrylamide;
5-(3-Methoxy-phenyl)-2-methyl-oxazole-4-carboxylic acid [1-(4-acetyl-thiazol-2-ylmethyl)-1H-pyrazol-3-yl]-amide;
5-(3-Fluoro-phenyl)-2-methyl-oxazole-4-carboxylic acid [1-(4-acetyl-thiazol-2-ylmethyl)-1H-pyrazol-3-yl]-amide;
5-Phenyl-oxazole-4-carboxylic acid [1-(4-acetyl-oxazol-2-ylmethyl)-1H-pyrazol-3-yl]-amide;
5-Phenyl-oxazole-4-carboxylic acid {1-[4-(1,1-difluoro-ethyl)-thiazol-2-ylmethyl]-1H-pyrazol-3-yl}-amide;
[1-(5-Oxo-hexyl)-1H-pyrazol-4-yl]-carbamic acid benzothiazol-2-ylmethyl ester;
5-(6-Trifluoromethyl-pyridin-2-yl)-oxazole-4-carboxylic acid [1-(5-acetyl-furan-2-ylmethyl)-1H-pyrazol-3-yl]-amide;
N-[1-(5-Acetyl-furan-2-ylmethyl)-1H-pyrazol-4-yl]-3-(1H-indol-3-yl)-acrylamide;
5-Phenyl-oxazole-4-carboxylic acid [1-(5-acetyl-oxazol-2-ylmethyl)-1H-pyrazol-3-yl]-amide; and
[1-(2-Acetyl-oxazol-4-ylmethyl)-1H-pyrazol-4-yl]-carbamic acid 2-chloro-benzyl ester;
wherein the double bond of acrylamide derivatives cited in the above list may be in (E)- or (Z)-configuration (preferably in (E)-configuration).

Any reference hereinbefore or hereinafter to a compound of formula (I) is to be understood as referring also to the salts, especially the pharmaceutically acceptable salts, of such compound of formula (I), as appropriate and expedient.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to embodiment 1), or pharmaceutically acceptable salts thereof, are suitable for use as medicament. In particular, compounds of formula (I) modulate the ALX receptor, i.e. they act as ALX receptor agonists, and are useful for the prevention or treatment of diseases which respond to the activation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the modulation of immune responses (especially those elicited by vaccination). Especially, compounds of formula (I) are useful for the prevention or treatment of diseases such as inflammatory diseases, obstructive airway diseases, allergic conditions, autoimmune diseases, cardiovascular disorders, neuroinflammation, neurological disorders, pain, prion-mediated diseases and amyloid-mediated disorders (especially Alzheimer's disease).

In particular, the compounds of formula (I) according to embodiment 1), or pharmaceutically acceptable salts thereof, are suitable for the prevention or treatment of diseases selected from inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.

2) Further inflammatory diseases, obstructive airway diseases and allergic conditions include bronchitis of whatever type or genesis.

3) Further inflammatory diseases, obstructive airway diseases and allergic conditions include bronchiectasis and pneumoconiosis of whatever type or genesis.

4) Further inflammatory diseases, obstructive airway diseases and allergic conditions include asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection.

5) In a further embodiment the compounds of formula (I) according to embodiment 1), or pharmaceutically acceptable salts thereof, are particularly suitable for the prevention or treatment of inflammatory diseases. Inflammatory diseases include one, several or all of the following groups of diseases and disorders:

5a) In particular, inflammatory diseases refer to neutrophil related disorders, especially neutrophil related disorders of the airway including hyper-neutrophilia as it affects the airway and/or lungs. Further neutrophil related disorders also include periodontitis, glomerulonephritis, and cystic fibrosis.

5b) Further inflammatory diseases include skin diseases such as psoriasis, contact dermatitis, atopic dermatitis, dermatitis herpetiformis, scleroderma, hypersensitivity angiitis, urticaria, lupus erythematosus, and epidermolysis.

5c) Further inflammatory diseases also relate to diseases or conditions having an inflammatory component. Diseases or conditions having an inflammatory component include, but are not limited to, diseases and conditions affecting the eye such as conjunctivitis, keratoconjunctivitis sicca, and vernal conjunctivitis; diseases affecting the nose including allergic rhinitis; and inflammatory diseases in which autoimmune reactions are implicated or which have an autoimmune component or aetiology, such as systemic lupus erythematosus, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis.

5d) Further inflammatory diseases in which autoimmune reactions are implicated or which have an autoimmune component or aetiology include rheumatoid arthritis, hishimoto's thyroid and diabetes type I or II.

Further, the compounds of formula (I) according to embodiment 1), or pharmaceutically acceptable salts thereof, are suitable for the prevention or treatment of HIV-mediated retroviral infections.

HIV-mediated retroviral infections include, but are not limited to, one, several or all of the groups of diseases and disorders caused by HIV-1 and HIV-2 strains such as GUN-4-v, GUN-7wt, AG204, AG206, AG208, HCM305, HCM308, HCM342, mSTD104, and HCM309.

Further, the compounds of formula (I) according to embodiment 1), or pharmaceutically acceptable salts thereof, are suitable for the prevention or treatment of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Further, the compounds of formula (I) according to embodiment 1), or pharmaceutically acceptable salts thereof, are suitable for the prevention or treatment of neuroinflammation. Neuroinflammation refers to cell signaling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Further, the compounds of formula (I) according to embodiment 1), or pharmaceutically acceptable salts thereof, are suitable for the prevention or treatment of neurological disorders.

In particular, neurological disorders include, but are not limited to, epilepsy, stroke, cerebral ischemia, cerebral palsy, relapsing multiple sclerosis, progressive multiple sclerosis, Alpers' disease, amyotrophic lateral sclerosis (ALS), senile dementia, dementia with Lewy bodies, Rhett syndrome, spinal cord trauma, traumatic brain injury, trigeminal neuralgia, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea.

Further, the compounds of formula (I) according to embodiment 1), or pharmaceutically acceptable salts thereof, are suitable for the prevention or treatment of pain. Pain includes, but is not limited to, neuropathic pain exemplified by conditions such as diabetic neuropathy, postherpetic neuralgia, trigeminal neuralgia, painful diabetic polyneuropathy, post-stroke pain, post-amputation pain, myelopathic or radiculopathic pain, atypical facial pain and causalgia-like syndromes.

Further, the compounds of formula (I) according to embodiment 1), or pharmaceutically acceptable salts thereof, are suitable for the prevention or treatment of prion-mediated diseases. Prion-mediated diseases, also known as transmissible spongiform encephalopathies (TSEs), include, but are not limited to, kuru, Gerstmann-Sträussler-Scheinker syndrome (GSS), Fatal Familial Insomnia (FFI) and Creutzfeldt-Jakob Disease (CJD).

Further, the compounds of formula (I) according to embodiment 1), or pharmaceutically acceptable salts thereof, are suitable for the treatment of amyloid-mediated disorders. Amyloid-mediated disorders are defined as diseases and disorders, that are caused by or associated with amyloid or amyloid-like proteins. Diseases and disorders caused by or associated with amyloid or amyloid-like proteins include, but are not limited to, Alzheimer's Disease (AD), including diseases or conditions characterized by a loss of cognitive memory capacity such as, for example, mild cognitive impairment (MCI); dementia with Lewy bodies; Down's syndrome; cerebral hemorrhage with amyloidosis. In another embodiment, diseases and disorders caused by or associated with amyloid or amyloid-like proteins include progressive supranuclear palsy, multiple sclerosis, Creutzfeld Jakob disease, Parkinson's disease, HIV-related dementia, Amyotropic Lateral Sclerosis (ALS), inclusion-body myositis (IBM), Adult Onset Diabetes, and senile cardiac amyloidosis.

Further, the compounds of formula (I) according to embodiment 1), or pharmaceutically acceptable salts thereof, are suitable for the modulation of immune responses. The modulation of immune responses includes, but is not limited to, methods based on the administration to a subject a composition of at least one antigen and at least one compound of formula (I) according to embodiment 1), or pharmaceutically acceptable salts thereof. In some cases, the antigen-containing composition is administrated first, followed by administration of a composition of at least one compounds of formula (I) according to embodiment 1), or pharmaceutically acceptable salts thereof. In other cases, the antigen-containing composition is administrated last. The different compositions may be administrated simultaneously, closely in sequence, or separated in time. Those methods and compositions are provided for therapeutic and prophylactic immunisation (i.e., the deliberate provocation, enhancement, intensification or modulation of an adaptative and/or innate immune response). Particular advantages may include one or more of the following:

1) An accelerated immune response following administration of at least one compound of formula (I) according to embodiment 1), or pharmaceutically acceptable salts thereof, and the antigen, as compared to sole administration of the antigen;

2) A greater sensitivity to small amounts of antigen (e.g., toxin or pathogen) or antigens that do not habitually induce strong immune responses; and 3) More effective anti-tumor therapies.

Further, the compounds of formula (I) according to embodiment 1), or pharmaceutically acceptable salts thereof, are suitable for the prevention or treatment of cystic fibrosis, pulmonary fibrosis, pulmonary hypertension, wound healing, diabetic nephropathy, reduction of inflammation in transplanted tissue, inflammatory diseases caused by pathogenic organisms.

Especially, compounds of formula (I) according to embodiment 1), or pharmaceutically acceptable salts thereof, are suitable for the prevention or treatment of diseases selected from one, several or all of the following groups of diseases and disorders:

1) Inflammatory diseases, obstructive airway diseases and allergic conditions such as acute lung injury (ALI); adult/acute respiratory distress syndrome (ARDS); and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection;

2) Inflammatory diseases such as neutrophil related disorders, especially neutrophil related disorders of the airway including hyper-neutrophilia as it affects the airway and/or lungs; periodontitis; glomerulonephritis; cystic fibrosis; and skin diseases such as psoriasis, contact dermatitis, atopic dermatitis, dermatitis herpetiformis, scleroderma, hypersensitivity angiitis, urticaria, lupus erythematosus, and epidermolysis;

3) Diseases having an inflammatory component such as diseases and conditions affecting the eye such as conjunctivitis, keratoconjunctivitis sicca, and vernal conjunctivitis; inflammatory disease in which autoimmune reactions are implicated or which have an autoimmune component or aetiology; and autoimmune inflammatory bowel disease (e.g. ulcerative colitis and Crohn's disease);

4) HIV-mediated retroviral infections such as diseases and disorders caused by HIV-1 and HIV-2 strains such as GUN-4-v, GUN-7wt, AG204, AG206, AG208, HCM305, HCM308, HCM342, mSTD104, and HCM309;

5) Neuroinflammation which refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as amyloid β deposition of amyloid plaques;

6) Neurological disorders such as stroke, cerebral ischemia, Alzheimer's disease, and Parkinson's disease;

7) Prion-mediated diseases, also known as transmissible spongiform encephalopathies (TSEs), such as kuru, Gerstmann-Sträussler-Scheinker syndrome (GSS), Fatal Familial Insomnia (FFI) and Creutzfeldt-Jakob Disease (CJD);

8) Amyloid-mediated disorders;

9) Cystic fibrosis, wound healing and inflammatory diseases caused by pathogenic organisms.

The invention also relates to the use of a compound of formula (I) according to embodiment 1) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to embodiment 1).

A pharmaceutical composition according to the present invention contains at least one compound of formula (I) according to embodiment 1) (or a pharmaceutically acceptable salt thereof) as the active agent and optionally carriers and/or diluents and/or adjuvants. The compounds of formula (I) according to embodiment 1) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to embodiment 1), or a pharmaceutically acceptable salt thereof.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C.

to Y plus 5° C. Besides, the term "room temperature" (rt) as used herein refers to a temperature of about 25° C.

The compounds of formula (I) can be manufactured by the methods given below, by the methods given in the Examples or by analogous methods. Optimum reaction conditions may vary with the particular reactants or solvents used, but such conditions can be determined by a person skilled in the art by routine optimization procedures.

If not indicated otherwise, the generic groups A, E, Q, $R^1$, $R^2$ and $R^3$ are as defined for formula (I). Other abbreviations used are defined in the experimental section. Generic group $R''$ as used in structures 4c, 4d and 7b below represents hydrogen or $(C_1-C_3)$alkyl. Generic groups $R^x$ as used in structures 4 and 6 below represent $(C_1-C_2)$alkyl or both $R^x$ together form an ethane-1,2-diyl bridge. Generic group $R^y$ as used in structures 4, 4b, 6 and 7 below represents $(C_1-C_3)$alkyl or cyclopropyl. Generic group $R^z$ as used in scheme 6 below represents $(C_1-C_4)$alkyl. The generic carboxyl protecting group R as used e.g. in structures 3 and 5, in schemes 1 to 8 and in the general procedures of the experimental part below represents $(C_1-C_4)$alkyl, preferably methyl or ethyl.

Reactions of alcohols with methanesulfonyl chloride may result in the formation of the respective chloride or the respective mesylate derivative depending on the reaction conditions used; it is well known in the art that already small changes in such reaction conditions may have an influence on the outcome of said reactions; it should be understood that normally both reagents, the chloride and the mesylate, might be useful as electrophiles in reactions discussed below.

In some instances the generic groups A, E, Q, $R^1$, $R^2$ and $R^3$ might be incompatible with the assembly illustrated in the schemes below and will therefore require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups are as necessary in place.

DETAILED DESCRIPTION OF THE INVENTION

Preparation of the Compounds of Formula (I):

A. Synthesis of Final Products

Sections A.a) to A.e) hereafter describe general methods for preparing compounds of formula (I).

A.a) The compounds of formula (I) can be prepared from amines of structure 1 by reaction with the appropriate chloroformate $R^1$-E-COCl (E represents *-$(C_1-C_4)$alkyl-O—) at a temperature about rt or the appropriate carboxylic acid chloride of formula $R^1$-E-COCl (E represents an oxazole or a thiazole radical as defined in formula (I) or —CH=CH—) at a temperature about rt in a suitable solvent such as $CH_2Cl_2$ in presence of a base such as $Et_3N$ or DIPEA. If not commercially available, the appropriate chloroformate can be prepared at a temperature about rt from the corresponding alcohol by reaction with phosgene in a suitable solvent such as $CH_2Cl_2$ in presence of a base such as $Et_3N$. If not commercially available, the appropriate carboxylic acid chloride can be prepared at a temperature about rt from the corresponding carboxylic acid by reaction with a reagent such as oxalyl chloride in presence of DMF in a suitable solvent such as toluene. Alternatively, amines of structure 1 can be coupled with the corresponding carboxylic acid of formula $R^1$-E-COOH using standard amide coupling conditions such as EDC/HOBt/DMAP, TBTU, HBTU or PyBOP in presence of a base such as DIPEA or $Et_3N$ at a temperature about rt in a suitable solvent such as $CH_2Cl_2$. In case E represents *-$(C_1-C_4)$alkyl-O—, amines of structure 1 can be coupled with the corresponding alcohol of formula $R^1$-E-H by activation of the compounds of structure 1 e.g. with 4-nitrophenyl chloroformate in a suitable solvent such as AcCN in presence of a base such as $Et_3N$ or DIPEA or, alternatively, by in-situ formation of the chloroformate from $R^1$-E-H (E represents *-$(C_1-C_4)$alkyl-O—) with, for example, phosgene in a suitable solvent such as $CH_2Cl_2$ in presence of a base such as $Et_3N$ or DIPEA.

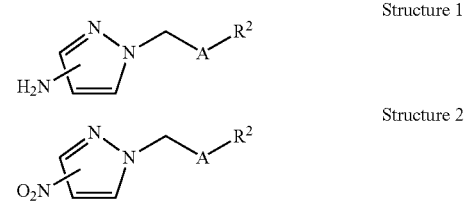

Structure 1

Structure 2

Compounds of structure 1 can be obtained from compounds of structure 2 by reduction of the nitro group either by hydrogenation in the presence of a metal catalyst such as Pd/C, Pt/C or $PtO_2$ in a suitable solvent such as MeOH or EtOH at a temperature about rt, or by reduction with a metal such as iron in a solvent mixture such as $H_2O$/EtOH in the presence of ammonium chloride at a temperature ranging from rt to 95° C.

A.b) Alternatively, the compounds of formula (I) wherein $R^2$ represents —CO—$(C_1-C_3)$alkyl or —CO-cyclopropyl may be prepared by a sequence comprising:

Reduction of an ester of structure 3 to the corresponding alcohol under standard reducing conditions using a reagent such as $NaBH_4$ in a solvent such as MeOH at a temperature about rt or, alternatively, a reagent such as DiBAL in a solvent such as THF at a temperature ranging from −78° C. to rt;

Oxidation of the alcohol to the corresponding aldehyde under standard oxidative conditions using reagents such as $MnO_2$, pyridinium chlorochromate or NMO/TPAP in a solvent such as AcCN or $CH_2Cl_2$ at a temperature about rt;

Addition of an alkyl Grignard reagent at a temperature below rt (preferably about −78° C.) in a solvent such as THF, or, alternatively, addition of a trialkylaluminum reagent at a temperature about 0° C. in a solvent such as $CH_2Cl_2$ providing the corresponding secondary alcohol; and Oxidation of the alcohol under standard oxidative conditions using reagents such as TPAP/NMO or $MnO_2$ in a solvent such as $CH_2Cl_2$ or AcCN at a temperature about rt to provide the compound of formula (I).

Structure 3

A.c) Alternatively, the compounds of formula (I) can be prepared by deprotecting a ketal of structure 4 using standard conditions like:

using an acid such as diluted aqueous HCl in a solvent such as THF at a temperature about rt; or using SCX silica gel in a solvent such as MeOH; or using a silica gel bound acid such as tosic acid in a solvent such as MeOH; or using an acid such as formic acid in a solvent such as water at a temperature ranging from about 0° C. to about 50° C.

Structure 4

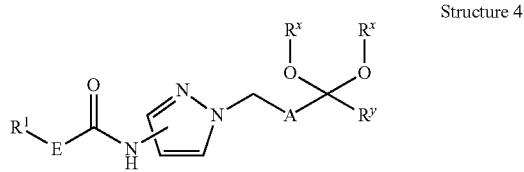

A.d) Alternatively, the compounds of formula (I) wherein $R^1$ is an aminoalkylaryl derivative may be prepared by a sequence comprising:

Activation of an alcohol of structure 4b by formation of a mesylate or the like under standard conditions such as using mesyl chloride and a base such as DIPEA in a solvent such as $CH_2Cl_2$; and Displacement of the mesylate with an amine under standard conditions in a solvent such as $CH_2Cl_2$ or THF at a temperature ranging from rt to reflux.

Structure 4b

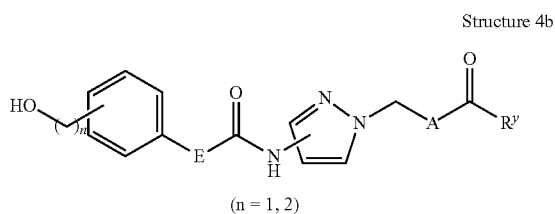

(n = 1, 2)

A.e) Alternatively, the compounds of formula (I) wherein $R^2$ represents —CO—$(C_1$-$C_3)$alkyl may be prepared either by:

Oxidation of an alcohol of structure 4c ($R^u$ represents $(C_1$-$C_3)$alkyl) under standard oxidative conditions using reagents such as TPAP/NMO or $MnO_2$ in a solvent such as $CH_2Cl_2$ or AcCN at a temperature about rt;

or by:

The oxidation-addition-oxidation sequence described in the last three steps under A.b) starting from an alcohol of structure 4c ($R^u$ represents hydrogen).

Structure 4c

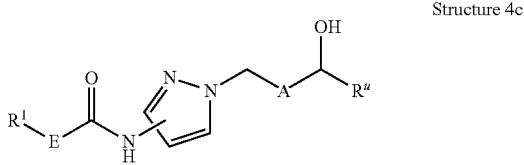

B. Synthesis of Intermediates:

Compounds of structure 2 wherein $R^2$ represents —CO—$(C_1$-$C_3)$alkyl can be prepared from compounds of structure 5 following the procedure as described in section A.b) or from compounds of structure 6 following the procedure as described in section A.c) above. Compounds of structure 2 wherein $R^2$ represents —$CF_2$—$(C_1$-$C_3)$alkyl may be prepared from compounds of structure 2 wherein $R^2$ represents —CO—$(C_1$-$C_3)$alkyl with a fluorinating agent such as (diethylamino)sulphur trifluoride or (bis(2-methoxyethyl)amino)sulphur trifluoride in a solvent such as toluene at a temperature about 60° C. Compounds of structure 2 wherein $R^2$ represents —CHF—$(C_1$-$C_3)$alkyl may be prepared from secondary alcohols of structure 7 using a fluorinating agent such as perfluoro-1-butanesulfonyl fluoride or triethylamine trihydrofluoride in the presence of a base such as $Et_3N$ in a solvent such as THF at a temperature about rt.

Structure 5

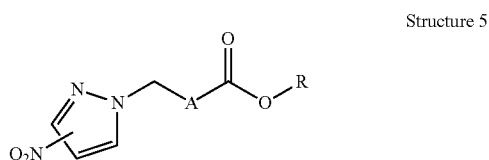

Structure 6

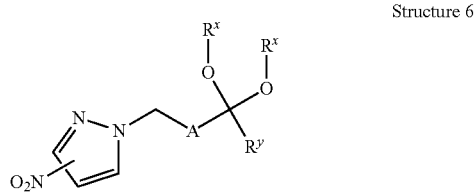

Structure 7

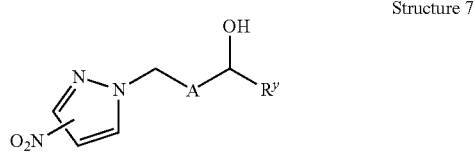

Compounds of structure 2 wherein A represents pyridine-2,4-diyl may be prepared by reacting methanesulfonic acid 2-acetyl-pyridin-4-ylmethyl ester with 4-nitro-1H-pyrazole or 5-nitro-1H-pyrazole in the presence of a base such as $K_2CO_3$ or $Cs_2CO_3$ in a solvent such as acetone or AcCN at a temperature about rt or 80° C. (with or without addition of tetrabutylammonium bromide).

Compounds of structure 2 wherein A represents oxazole-2,4-diyl may be prepared by reacting methanesulfonic acid 4-acetyl-oxazol-2-ylmethyl ester with 4-nitro-1H-pyrazole or 5-nitro-1H-pyrazole in the presence of a base such as $K_2CO_3$ or $Cs_2CO_3$ in a solvent such as acetone or AcCN at a temperature about rt or 80° C. (with or without addition of tetrabutylammonium bromide).

Compounds of structure 2 wherein $R^2$ represents —$SO_2$—$(C_1$-$C_3)$alkyl may be prepared by reacting commercially available 4-nitro-1H-pyrazole or 5-nitro-1H-pyrazole in the presence of a base such as $K_2CO_3$ or $Cs_2CO_3$ (with or without addition of tetrabutylammonium bromide) in a solvent such as acetone or AcCN at a temperature about rt or 80° C. with Cl—$CH_2$-A-$SO_2$—$(C_1$-$C_3)$alkyl (especially 2-chloromethyl-5-methanesulfonyl-furan).

Compounds of structures 3 and 4 can be prepared in analogy to the procedures described in section A.a) from compounds of structure 5 and 6 respectively.

Compounds of structure 4b can be prepared starting from the respective compounds of structure 4 (wherein $R^1$ equals hydroxymethyl-phenyl or hydroxyethyl-phenyl) by ketal deprotection with an aqueous acid such as hydrochloric acid in a solvent like THF; in the starting material of structure 4 the hydroxy function of the hydroxymethyl-phenyl or hydroxyethyl-phenyl group might be protected, for example, as a silyl ether (especially as a TBDMS ether) which protecting group might be removed during ketal deprotection or in an additional deprotection step using standard conditions.

Compounds of structure 4c can be prepared starting from the respective compounds of structure 3 by the first step ($R^u$ represents hydrogen) or the first three steps ($R^u$ represents ($C_1$-$C_3$)alkyl) of the sequence described under A.b).

Alternatively, compounds of structure 4c can be prepared starting from the respective compounds of structure 4d by silyl deprotection using TBAF in a solvent like THF.

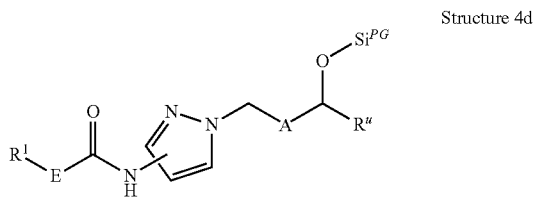

Structure 4d $Si^{PG}$ represents an appropriate silyl protecting group such as TMS, TIPS, TBDMS or TBDPS (preferably TBDMS)

Compounds of structure 4d may be prepared in analogy to the procedures described in section A.a) from compounds of structure 7b

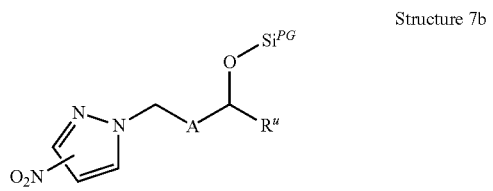

Structure 7b

Compounds of structure 5 may be prepared by reacting commercially available 4-nitro-1H-pyrazole or 5-nitro-1H-pyrazole with, for instance, a commercially available 5-chloromethyl-furan-2-carboxylic acid ester (A represents furan-2,5-diyl), a commercially available 5-bromo-pentanoic acid ester (A represents propan-1,3-diyl), a 5-chloromethyl-isoxazole-3-carboxylic acid ester (A represents isoxazole-3,5-diyl) or a 4-chloromethyl-thiazole-2-carboxylic acid ester (A represents thiazol-2-4-diyl). The reaction may be performed in the presence of a base such as $K_2CO_3$ or $Cs_2CO_3$ in a solvent such as acetone or AcCN at a temperature about rt or 80° C. with addition of tetrabutylammonium bromide, where appropriate.

Compounds of structure 6 may be prepared in analogy to those of structure 5 using, in case A represents furan-2,5-diyl, an appropriate protected furane derivative such as 2-(5-chloromethyl-furan-2-yl)-2-methyl-[1,3]dioxolane or, in case A represents propan-1,3-diyl, an appropriate protected 4-bromo-butyl ketone derivative such as 2-(4-bromo-butyl)-2-methyl-[1,3]dioxolane or, in case A represents thiophen-2,5-diyl, an appropriate protected thiophene derivative such as 2-(5-chloromethyl-thiophen-2-yl)-2-methyl-[1,3]dioxolane or, in case A represents phenyl-1,3-diyl, an appropriate protected phenyl derivative such as methanesulfonic acid 3-(2-methyl-[1,3]dioxolan-2-yl)-benzyl ester or, in case A represents pyridine-2,6-diyl, an appropriate protected pyridine derivative such as methanesulfonic acid 6-(2-methyl-[1,3]dioxolan-2-yl)-pyridin-2-ylmethyl ester or, in case A represents pyridine-3,5-diyl, an appropriate protected pyridine derivative such as methanesulfonic acid 5-(2-methyl-[1,3]dioxolan-2-yl)-pyridin-3-ylmethyl ester or, in case A represents pyridine-2,4-diyl, an appropriate protected pyridine derivative such as methanesulfonic acid 4-(2-methyl-[1,3]dioxolan-2-yl)-pyridin-2-ylmethyl ester or methanesulfonic acid 2-(2-methyl-[1,3]dioxolan-2-yl)-pyridin-4-ylmethyl ester or, in case A represents thiazol-2,4-diyl, an appropriate protected thiazole derivative such as methanesulfonic acid 4-(2-methyl-[1,3]dioxolan-2-yl)-thiazol-2-ylmethyl ester or 4-chloromethyl-2-(2-methyl-[1,3]dioxolan-2-yl)-thiazole or, in case A represents thiophen-2,4-diyl, an appropriate protected thiophene derivative such as 2-(4-chloromethyl-thiophen-2-yl)-2-methyl-[1,3]dioxolane or methanesulfonic acid 4-(2-methyl-[1,3]dioxolan-2-yl)-thiophen-2-ylmethyl ester or, in case A represents thiazol-2,5-diyl, an appropriate protected thiazole derivative such as methanesulfonic acid 5-(2-methyl-[1,3]dioxolan-2-yl)-thiazol-2-ylmethyl ester or 5-chloromethyl-2-(2-methyl-[1,3]dioxolan-2-yl)-thiazole or in case A represents oxazole-2,5-diyl, an appropriate protected oxazole derivative such as 2-chloromethyl-5-(2-methyl-[1,3]dioxolan-2-yl)-oxazole.

Compounds of structure 6 can also be obtained from compounds of structure 2 wherein $R^2$ represents —CO—($C_1$-$C_3$) alkyl using a reagent such as ethylene glycol in the presence of a reagent such as TsOH in a solvent such as toluene at a temperature about 110° C.; or from compounds of structure 2 wherein $R^2$ represents —CO—($C_1$-$C_3$)alkyl using reagents such as $LiBF_4$ and trimethylorthoformate in a solvent such as ethylene glycol at a temperature about 95° C.

Alternatively, compounds of structure 6 may be synthesized from compounds of structure 5 in analogy to the sequence described in section A.b), followed by protection of the keto function using a reagent such as ethylene glycol in the presence of a reagent such as TsOH in a solvent such as toluene at a temperature about 110° C. Alternatively, the ketal formation can be performed using reagents such as $LiBF_4$ and trimethylorthoformate in a solvent such as ethylene glycol at a temperature about 95° C.

Secondary alcohols of structure 7 may be synthesized from compounds of structure 5 in analogy to the first three steps of the sequence described in A.b).

Compounds of structure 7b may be prepared from commercially available 4-nitro-1H-pyrazole or 5-nitro-1H-pyrazole in analogy to those of structure 5 using, in case A represents oxazole-2,5-diyl, an oxazole derivative such as 2-[1-(tert-butyl-dimethyl-silanyloxy)-ethyl]-5-chloromethyl-oxazole or, in case A represents oxazole-2,4-diyl and $R^u$ represents hydrogen, an appropriate protected oxazole derivative such as methanesulfonic acid 2-(tert-butyl-dimethyl-silanyloxymethyl)-oxazol-4-ylmethyl ester.

2-[1-(tert-Butyl-dimethyl-silanyloxy)-ethyl]-5-chloromethyl-oxazole may be prepared using the following sequence: a) reaction of commercially available oxazole with an organomagnesium reagent such as isopropylmagnesium chloride in a solvent such as THF at a temperature about −15° C. and subsequent acetylation with N-methoxy-N-methylacetamide at a temperature ranging from −15° C. to rt; b) reduction with a reducing agent such as $NaBH_4$ in a solvent such as MeOH at a temperature about rt; c) protection of the alcohol using tert-butyldimethylsilyl chloride in the presence of a base such as imidazole in a solvent such as THF; d) reaction of the protected alcohol with an organolithium reagent such as t-butyl lithium in a solvent such as THF at a temperature ranging from −78° C. to −40° C. and subsequent formylation with N,N-dimethyl-formamide at a temperature ranging from −78° C. to rt; e) reduction with a reducing agent such as $NaBH_4$ in a solvent such as MeOH at a temperature about rt; g) chlorination using a reagent such as methanesulfonyl chloride in a solvent such as $CH_2Cl_2$ in the presence of a base such as $Et_3N$ and DMAP at a temperature about 0° C.

5-Chloromethyl-isoxazole-3-carboxylic acid ethyl ester may be prepared by chlorination of commercially available 5-hydroxymethyl-isoxazole-3-carboxylic acid ethyl ester using for example Ms-Cl in presence of a base such as $Et_3N$ and DMAP in a solvent such as $CH_2Cl_2$ at a temperature about rt.

2-(5-Chloromethyl-furan-2-yl)-2-methyl-[1,3]dioxolane may be prepared using the following sequence: a) protection of commercially available 1-furan-2-yl-ethanone in the presence of trimethylorthoformate and a catalyst such as $LiBF_4$ in a solvent such as ethylene glycol at a temperature about 95° C.; b) lithiation with an organolithium reagent such as n-butyl lithium in a solvent such as THF at a temperature about −78° C. and subsequent addition of DMF; c) reduction with a reducing agent such as $NaBH_4$ in a solvent such as MeOH at a temperature about 0° C.; and d) chlorination of the alcohol using for example Ms-Cl in presence of a base such as $Et_3N$ and DMAP in a solvent such as $CH_2Cl_2$ at a temperature about 0° C.

2-(5-Chloromethyl-thiophen-2-yl)-2-methyl-[1,3]dioxolane may be prepared using the following sequence: a) lithiation of commercially available 2-methyl-2-thiophen-2-yl-[1,3]dioxolane with an organolithium reagent such as n-butyl lithium in the presence of N,N,N',N'-tetramethyl-ethylenediamine in a solvent such as THF at a temperature about −78° C. and subsequent addition of DMF; b) reduction with a reducing agent such as $NaBH_4$ in a solvent such as MeOH at a temperature about 0° C.; and c) chlorination of the alcohol using for example Ms-Cl in presence of a base such as $Et_3N$ and DMAP in a solvent such as $CH_2Cl_2$ at a temperature about 0° C.

Methanesulfonic acid 6-(2-methyl-[1,3]dioxolan-2-yl)-pyridin-2-ylmethyl ester may be prepared by the following sequence: a) reaction of commercially available 2,6-dibromopyridine with an organolithium reagent such as n-butyl lithium in a solvent such as ether at a temperature about −78° C. and subsequent acetylation with N,N-dimethylacetamide at a temperature ranging from −78° C. to rt; b) ketal formation in the presence of trimethylorthoformate and a catalyst such as $LiBF_4$ in a solvent such as ethylene glycol at a temperature about 95° C.; c) lithiation with an organolithium reagent such as n-butyl lithium in a solvent such as ether at a temperature about −78° C. and subsequent formylation with DMF; d) reduction with a reducing agent such as $NaBH_4$ in a solvent such as MeOH at a temperature about rt; and e) mesylation using a reagent such as methanesulfonyl chloride in a solvent such as $CH_2Cl_2$ in the presence of a base such as $Et_3N$ and DMAP at a temperature about 0° C.

Methanesulfonic acid 2-(2-methyl-[1,3]dioxolan-2-yl)-pyridin-4-ylmethyl ester may be prepared by the following sequence: a) reaction of commercially available 2,4-dibromopyridine with an organolithium reagent such as n-butyl lithium in a solvent such as ether at a temperature about −78° C. and subsequent formylation with N,N-dimethyl-formamide at a temperature ranging from −78° C. to rt; b) reduction with a reducing agent such as $NaBH_4$ in a solvent such as MeOH at a temperature about rt; c) protection of the alcohol using tert-butyldimethylsilyl chloride in the presence of a base such as imidazole in a solvent such as dichloromethane; d) reaction of the protected alcohol with an organolithium reagent such as n-butyl lithium in a solvent such as ether at a temperature about −78° C. and subsequent acetylation with N,N-dimethylacetamide at a temperature ranging from −78° C. to rt; e) ketal formation in the presence of trimethylorthoformate and a catalyst such as $LiBF_4$ in a solvent such as ethylene glycol at a temperature about 95° C.; f) deprotection of the silyl protecting group under standard conditions such as TBAF in a solvent such as THF at a temperature about rt or 0° C.; g) mesylation using a reagent such as methanesulfonyl chloride in a solvent such as $CH_2Cl_2$ in the presence of a base such as $Et_3N$ and DMAP at a temperature about 0° C.

2-(4-Bromo-butyl)-2-methyl-[1,3]dioxolane may be prepared by reacting commercially available 1-methylcyclopentanol with bromine in the presence of a base such as $K_2CO_3$ in a solvent such as chloroform at a temperature about 0° C. followed by protection with ethylene glycol in the presence of a catalyst such as TsOH.

Methanesulfonic acid 3-(2-methyl-[1,3]dioxolan-2-yl)-benzyl ester may be prepared as described for methanesulfonic acid 6-(2-methyl-[1,3]dioxolan-2-yl)-pyridin-2-ylmethyl ester but starting with commercially available 1,3-dibromobenzene.

Methanesulfonic acid 5-(2-methyl-[1,3]dioxolan-2-yl)-pyridin-3-ylmethyl ester may be prepared as described for methanesulfonic acid 6-(2-methyl-[1,3]dioxolan-2-yl)-pyridin-2-ylmethyl ester but starting with commercially available 3,5-dibromopyridine.

Methanesulfonic acid 4-(2-methyl-[1,3]dioxolan-2-yl)-pyridin-2-ylmethyl ester may be prepared as described for methanesulfonic acid 6-(2-methyl-[1,3]dioxolan-2-yl)-pyridin-2-ylmethyl ester but starting with commercially available 2,4-dibromopyridine.

Methanesulfonic acid 2-acetyl-pyridin-4-ylmethyl ester may be prepared by the following sequence: a) reaction of commercially available 2,4-dibromopyridine with an organolithium reagent such as n-butyl lithium in a solvent such as ether at a temperature about −78° C. and subsequent formylation with N,N-dimethylformamide; b) reduction with a reducing agent such as $NaBH_4$ in a solvent such as MeOH at a temperature about rt; c) protection of the alcohol using tert-butyldimethylsilyl chloride in a solvent such as $CH_2Cl_2$ in the presence of a base such as imidazole; d) lithiation with an organolithium reagent such as n-butyl lithium in a solvent such as ether at a temperature about −78° C. and subsequent acetylation with N,N-dimethylacetamide; e) deprotection of the silyl ether derivative using a fluorinated agent such as TBAF in a solvent such as THF at a temperature about rt; and f) mesylation using a reagent such as methanesulfonyl chloride in a solvent such as $CH_2Cl_2$ in the presence of a base such as $Et_3N$ and DMAP at a temperature about 0° C.

Methanesulfonic acid 4-(2-methyl-[1,3]dioxolan-2-yl)-thiazol-2-ylmethyl ester may be prepared as described for methanesulfonic acid 2-(2-methyl-[1,3]dioxolan-2-yl)-pyridin-4-ylmethyl ester but starting with commercially available 2,4-dibromo-thiazole.

2-(4-Chloromethyl-thiophen-2-yl)-2-methyl-[1,3]dioxolane may be prepared as described for 2-(5-chloromethyl-furan-2-yl)-2-methyl-[1,3]dioxolane but starting with commercially available 1-(4-bromo-2-thienyl)-ethan-1-one.

4-Chloromethyl-thiazole-2-carboxylic acid ethyl ester may be prepared by the following sequence: a) reaction of commercially available oxalamic acid ethyl ester with Lawesson's reagent in a solvent such as toluene at a temperature about 80° C.; and b) cyclization with 1,3-dichloroacetone in a solvent such as toluene at a temperature about 110° C.

4-Chloromethyl-2-(2-methyl-[1,3]dioxolan-2-yl)-thiazole may be prepared from 4-chloromethyl-thiazole-2-carboxylic acid ethyl ester by the sequence described under A.b) using trimethylaluminium in step 3, followed by subsequent ketal formation in the presence of trimethylorthoformate and a catalyst such as $LiBF_4$ in a solvent such as ethylene glycol at a temperature about 90° C.

2-Chloromethyl-5-methanesulfonyl-furan may be prepared by the following sequence: a) reaction of commercially available 5-nitro-furan-2-carboxylic acid ethyl ester with sodium methanethiolate in a solvent such as DMSO at a temperature about 100° C.; b) oxidation with an oxidative agent such as, m-CPBA in a solvent such as $CH_2Cl_2$ at a temperature about rt; c) reduction with a reducing agent such as DiBAL in a solvent such as THF at a temperature below rt; and d) chlorination using a reagent such as methanesulfonyl chloride in a solvent such as dichloromethane in the presence of a base such as $Et_3N$ and DMAP at a temperature about 0° C.

Methanesulfonic acid 5-(2-methyl-[1,3]dioxolan-2-yl)-thiazol-2-ylmethyl ester may be prepared by the following sequence: a) reaction of commercially available 2-bromo-thiazole-5-carbaldehyde with trimethylaluminum in a solvent such as dichloromethane at a temperature about 0° C.; b) oxidation with an oxidative agent such as MnO2 in a solvent such as acetonitrile at a temperature about rt; c) ketal formation in the presence of trimethylorthoformate and a catalyst such as $LiBF_4$ in a solvent such as ethylene glycol at a temperature about 95° C.; d) lithiation with an organolithium reagent such as n-butyl lithium in a solvent such as ether at a temperature about −78° C. and subsequent formylation with N,N-dimethylformamide; e) reduction with a reducing agent such as $NaBH_4$ in a solvent such as MeOH at a temperature about rt; f) mesylation using a reagent such as methanesulfonyl chloride in a solvent such as $CH_2Cl_2$ in the presence of a base such as $Et_3N$ and DMAP at a temperature about 0° C.

5-Chloromethyl-2-(2-methyl-[1,3]dioxolan-2-yl)-thiazole may be prepared by the following sequence: a) reduction of commercially available 2-bromo-thiazole-5-carbaldehyde with a reducing agent such as $NaBH_4$ in a solvent such as MeOH at a temperature about rt; b) protection of the alcohol using as tert-butyldimethylsilyl chloride in a solvent such as $CH_2Cl_2$ in the presence of a base such as imidazole; c) lithiation with an organolithium reagent such as n-butyl lithium in a solvent such as ether at a temperature about −78° C. and subsequent acetylation with N,N-dimethylacetamide; d) ketal formation in the presence of trimethylorthoformate and a catalyst such as $LiBF_4$ in a solvent such as ethylene glycol at a temperature about 95° C.; e) deprotection of the silyl ether derivative using a fluorinated agent such as TBAF in a solvent such as THF at a temperature about rt; and f) chlorination using a reagent such as methanesulfonyl chloride in a solvent such as $CH_2Cl_2$ in the presence of a base such as $Et_3N$ and DMAP at a temperature about 0° C.

Methanesulfonic acid 4-(2-methyl-[1,3]dioxolan-2-yl)-thiophen-2-ylmethyl ester may be prepared as described for 5-chloromethyl-2-(2-methyl-[1,3]dioxolan-2-yl)-thiazole but starting with commercially available 4-bromo-thiophene-2-carbaldehyde.

Methanesulfonic acid 4-acetyl-oxazol-2-ylmethyl ester may be prepared by the following sequence: a) oxazole formation reacting commercially available 3-phenyl-acrylamide with 3-bromo-2-oxo-propionic acid ethyl ester in the presence of a base such as $NaHCO_3$ in a solvent such as THF at a temperature around 60° C.; b) oxidative cleavage using for example silica gel supported $NaIO_4$ and a metal complex such as $RuCl_3$ hydrate in a solvent such as dichloromethane at a temperature about rt; c) reduction with a reducing agent such as $NaBH_4$ in a solvent such as EtOH at a temperature about 0° C.; d) protection of the alcohol using tert-butyldimethylsilyl chloride in a solvent such as $CH_2Cl_2$ in the presence of a base such as imidazole; e) reduction to the aldehyde with a reducing agent such as DiBAL in a solvent such as $CH_2Cl_2$ at a temperature about −78° C.; f) reaction with trimethylaluminum in a solvent such as dichloromethane at a temperature about 0° C.; g) oxidation with an oxidative agent such as $MnO_2$ in a solvent such as acetonitrile at a temperature about rt; h) deprotection of the silyl ether derivative using a fluorinated agent such as TBAF in a solvent such as THF at a temperature about rt; and i) mesylation using a reagent such as methanesulfonyl chloride in a solvent such as $CH_2Cl_2$ in the presence of a base such as $Et_3N$ and DMAP at a temperature about 0° C.

2-Chloromethyl-5-(2-methyl-[1,3]dioxolan-2-yl)-oxazole may be prepared using the following sequence: a) lithiation of commercially available oxazole with an organolithium reagent such as n-butyl lithium in a solvent such as THF at a temperature about −78° C. and subsequent addition of DMF; b) reduction with a reducing agent such as $NaBH_4$ in a solvent such as MeOH at a temperature about 0° C.; c) protection of the alcohol using tert-butyldimethylsilyl chloride in the presence of a base such as imidazole in a solvent such as THF; d) lithiation with an organolithium reagent such as t-butyl lithium in a solvent such as THF at a temperature ranging from −78° C. to −40° C. and subsequent acetylation with N,N-dimethylacetamide at a temperature ranging from −78° C. to rt; e) ketal formation and deprotection of the silyl protection group in the presence of trimethylorthoformate and a catalyst such as $LiBF_4$ in a solvent such as ethylene glycol at a temperature about 95° C.; f) chlorination of the alcohol using for example Ms-Cl in the presence of a base such as $Et_3N$ and DMAP in a solvent such as $CH_2Cl_2$ at a temperature about 0° C.

Methanesulfonic acid 2-(tert-butyl-dimethyl-silanyloxymethyl)-oxazol-4-ylmethyl ester may be prepared by the following sequence: a) oxazole formation reacting commercially available 3-phenyl-acrylamide with 3-bromo-2-oxo-propionic acid ethyl ester in the presence of a base such as $NaHCO_3$ in a solvent such as THF at a temperature around 60° C.; b) oxidative cleavage using for example silica gel supported $NaIO_4$ and a metal complex such as $RuCl_3$ hydrate in a solvent such as $CH_2Cl_2$ at a temperature about rt; c) reduction with a reducing agent such as $NaBH_4$ in a solvent such as EtOH at a temperature about 0° C.; d) protection of the alcohol using tert-butyldimethylsilyl chloride in a solvent such as $CH_2Cl_2$ in the presence of a base such as imidazole; e) reduction to the alcohol with a reducing agent such as DiBAL in a solvent such as THF at a temperature about 0° C.; f) mesylation using a reagent such as methanesulfonyl chloride in a solvent such as $CH_2Cl_2$ in the presence of a base such as $Et_3N$ and DMAP at a temperature about 0° C.

Chloroformates or acid chlorides of formula $R^1$-E-COCl or carboxylic acids of formula $R^1$-E-COOH are commercially available or synthesized according to well known methods e.g. from commercially available benzoic acids, benzaldehydes, benzyl alcohols or their heterocyclic analogues.

Acids of formula $R^1$-E-COOH, which are also compounds of structure 8, are well known in the art or are prepared according to the methods described below.

Structure 8

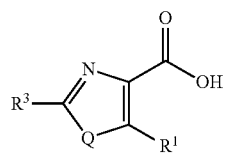

Compounds of structure 8 wherein Q represents O and $R^3$ represents Me may be prepared as described in Scheme 1 by reacting 3-oxo-propionic acid ester derivatives with an aqueous solution of sodium nitrite in presence of an acid such as glacial acetic acid. Subsequent transformation of the oxime with acetic anhydride in presence of an acid such as glacial acetic acid and catalytic amounts of metal chlorides such as mercury chloride or zinc chloride and zinc powder followed by cyclization under dehydrating conditions such as thionyl chloride in a solvent such as chloroform followed by saponification of the ester function using methods known in the art such as treatment with a base such as NaOH in a solvent or a solvent mixture such as ethanol/water or THF afforded the desired acid derivative. The respective 3-oxo-propionic acid ester derivatives are commercially available or well known in the art.

Scheme 1: Oxazole synthesis (1).

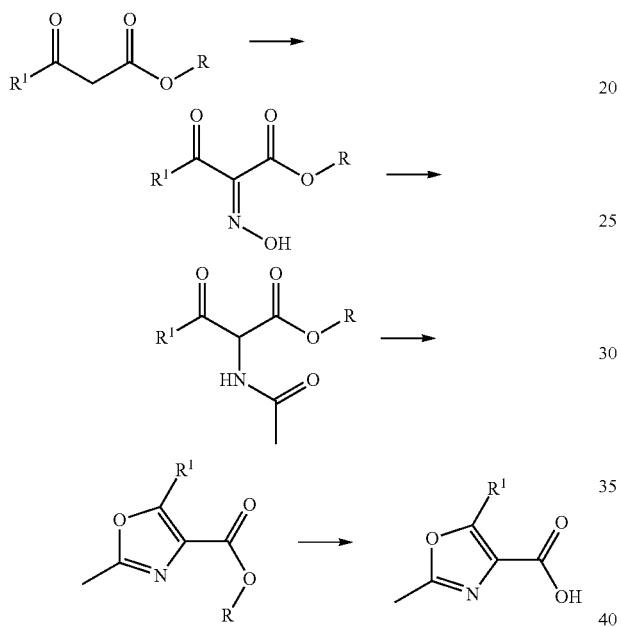

Alternatively, compounds of structure 8 wherein Q represents O may be prepared as described in Scheme 2 by reacting 3-oxo-propionic acid ester derivatives with a solution of 4-acetamidobenzenesulfonyl azide and a base such as $Et_3N$. Subsequent treatment with a carboxamide derivative and a catalyst such as tetrakis(acetato)dirhodium(II) dihydrate followed by cyclization using triphenylphosphine and iodine in the presence of a base such as $Et_3N$ afforded the respective ester derivative. Saponification of the ester function using methods known in the art such as treatment with a base such as NaOH in a solvent or a solvent mixture such as ethanol/water or THF afforded the desired acid derivative. The respective 3-oxo-propionic acid ester derivatives are commercially available or well known in the art.

Scheme 2: Oxazole synthesis (2).

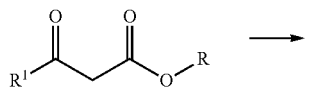

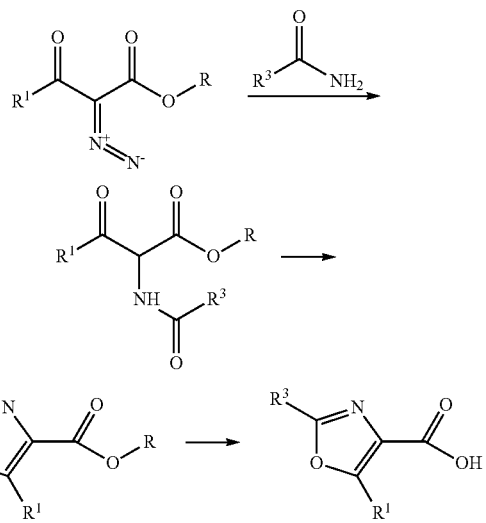

Alternatively, compounds of structure 8 wherein Q represents O and $R^3$ represents hydrogen may be prepared as described in Scheme 2b by reacting a solution of an acid derivative of formula $R^1COOH$ with methyl isocyanoacetate in the presence of a base such as potassium carbonate sesquihydrate or DIPEA and DPPA in a solvent such as DMF. Saponification of the ester function using methods known in the art such as treatment with a base such as NaOH in a solvent or a solvent mixture such as ethanol/water or THF afforded the respective acid derivative. The respective acids $R^1COOH$ are commercially available or well known in the art.

Scheme 2b: Oxazole synthesis (3).

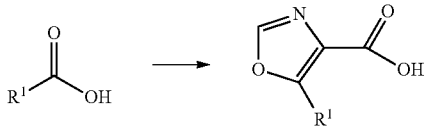

Compounds of structure 8 wherein Q represents S may be prepared by first reacting methyl dichloroacetate with commercially available benzaldehyde derivatives $R^1$—CHO in the presence of a base such as KOt-Bu in a solvent such as THF. The desired compounds of structure 8 wherein $R^3$ represents $(C_1-C_4)$alkyl or cyclopropyl are obtained as described in Scheme 3 by subsequent transformation (cyclization) with the respective thioamides in a solvent such as MeCN followed by saponification of the ester function using methods known in the art such as treatment with a base such as NaOH in a solvent such as MeOH. The respective benzaldehydes $R^1$—CHO are commercially available or well known in the art. The thioamides are commercially available or, alternatively, can be synthesized from commercially available carboxamides with Lawesson's reagent.

Scheme 3: Thiazole synthesis (1), wherein $R^3$ represents ($C_1$-$C_4$) alkyl or cyclopropyl.

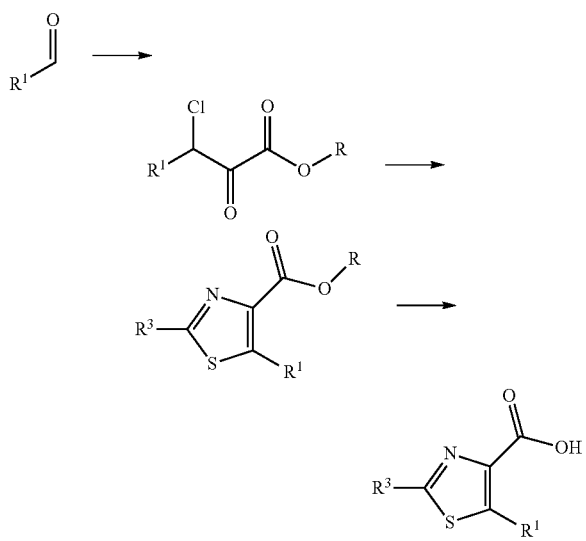

Alternatively, the desired compounds of structure 8 wherein Q represents S and $R^3$ represents hydrogen are obtained as described in Scheme 4 by reacting methyl dichloroacetate with commercially available benzaldehyde derivatives $R^1$—CHO in the presence of a base such as KOt-Bu in a solvent such as THF. A subsequent transformation with commercially available thiourea followed by treatment with a base such as sodium bicarbonate afforded the amino-thiazole derivative. Sandmeyer transformation using a Cu(II) derivative such as $CuBr_2$ followed by hydrogenation in the presence of a metal catalyst such as Pd/C, Pt/C or $PtO_2$ afforded the desired ester. Saponification of the ester function was performed using methods known in the art such as treatment with a base such as NaOH in a solvent such as MeOH.

Scheme 4: Thiazole synthesis (2).

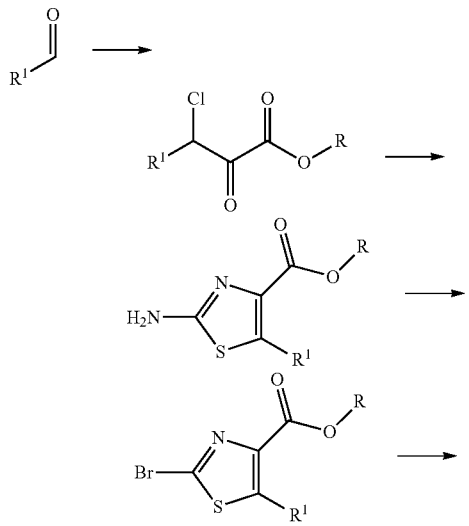

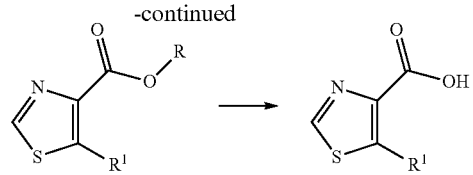

Alternatively, compounds of structure 8 wherein Q represents O may be prepared as described in Scheme 5 by esterification of a 3-phenylserine derivative using a reagent such as thionylchloride in a solvent such as MeOH at a temperature about 0° C. followed by coupling with an carboxylic acid derivative $R^3$—COOH using standard conditions such as HOBt, DCC, N-methylmorpholine in a solvent such as $CH_2Cl_2$ at a temperature about 0° C. Oxidation of the alcohol with an oxidative reagent such as Dess-Martin periodinane in a solvent such as $CH_2Cl_2$ followed by cyclization using triphenylphosphine and iodine in the presence of a base such as $Et_3N$ afforded the respective oxazole derivative. The desired acid derivatives may be obtained by saponification of the ester function using methods known in the art such as treatment with a base such as aq. LiOH in a solvent such as dioxane.

Scheme 5: Oxazole synthesis (4).

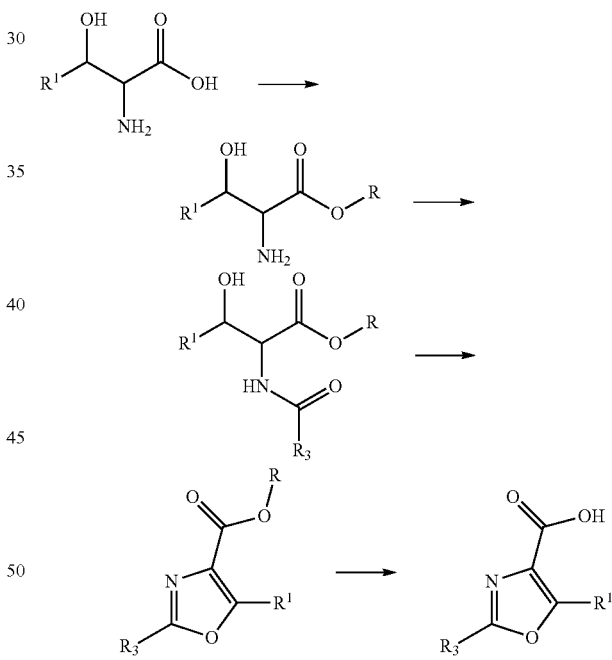

Compounds of structure 8 wherein $R^1$ is an aryl group, which group is substituted with ($C_1$-$C_4$)alkoxy-($C_1$-$C_2$)alkyl can be obtained, for instance, according to Scheme 6 by a sequence comprising:

Saponification of the hydroxy-($C_1$-$C_2$)alkyl-substituted 5-phenyl-oxazole derivative (prepared according to Scheme 7 or 8) using methods known in the art such as treatment with a base such as aq. LiOH in a solvent such as THF;

Alkylation of the corresponding alcohol with an alkyl halogenide such as alkyl iodide in presence of a base such as NaH in a solvent such as DMF;

Saponification of the resulting ester using a method known in the art such as treatment with a base such as NaOH in a solvent or a solvent mixture such as ethanol/water or THF.

Scheme 6: Synthesis of (C$_1$-C$_4$)alkoxy-(C$_1$-C$_2$)alkyl substituted 5-phenyl-oxazole derivatives (R$^Z$ represents (C$_1$-C$_4$)alkyl and n represents 1 or 2).

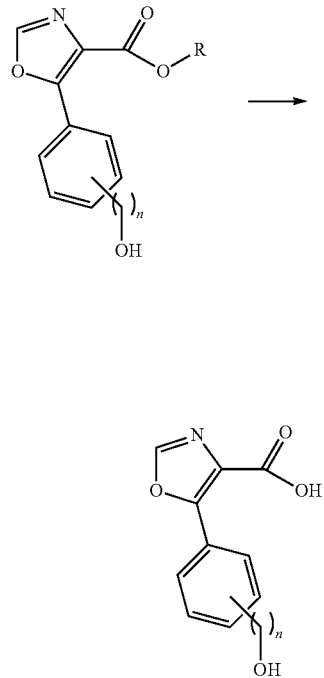

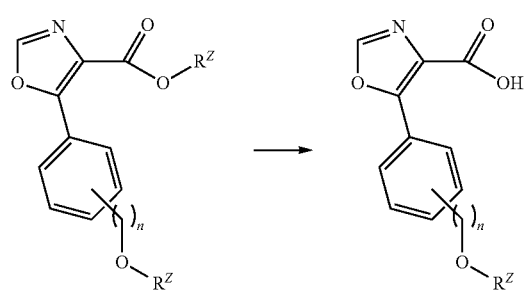

Hydroxy-(C$_1$-C$_2$)alkyl-substituted 5-phenyl-oxazole derivatives can be obtained, for instance, according to Scheme 7 by a sequence comprising:

Oxazole formation by reacting a phenyl-dicarboxylic acid mono-ester derivative with methyl isocyanoacetate in analogy to the method described in Scheme 2b;

Selective saponification of the phenyl-bound ester group using any of the methods known in the art (e.g. by acid catalyzed cleavage of a tert-butyl ester with, for instance, TFA);

Reduction of the obtained acid to the respective primary alcohol with a reducing agent like borane;

Scheme 7: Synthesis of hydroxy-(C$_1$-C$_2$)alkyl substituted 5-phenyl-oxazole derivatives.

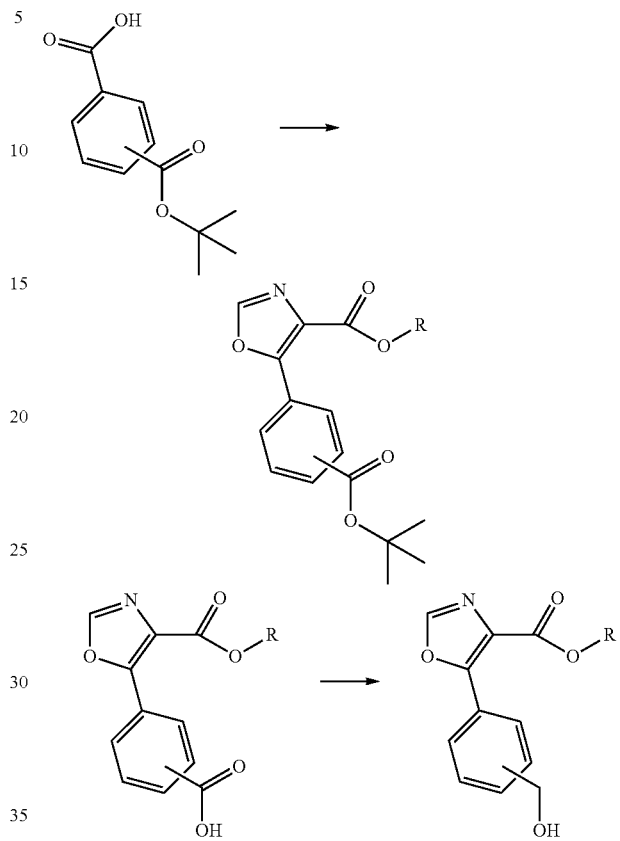

Alternatively, hydroxy-(C$_1$-C$_2$)alkyl-substituted 5-phenyl-oxazole derivatives can be obtained, for instance, according to Scheme 8 by a sequence comprising:

Oxazole formation by reacting a hydroxy-(C$_1$-C$_2$)alkyl-substituted benzoic acid derivative with methyl isocyanoacetate in analogy to the method described in Scheme 2b;

Scheme 8: Synthesis of hydroxy-(C$_1$-C$_2$)alkyl substituted 5-phenyl-oxazole derivatives (2).

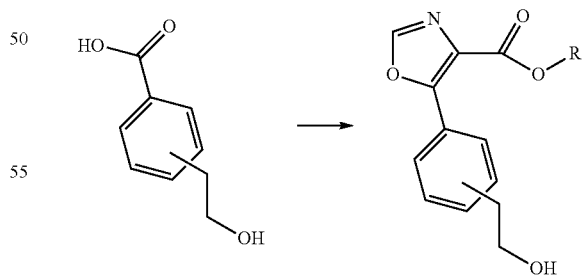

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5

μm) column. Typical conditions of chiral HPLC are an isocratic mixture of eluent A (EtOH, in presence or absence of an amine such as Et$_3$N or diethylamine) and eluent B (hexane), at a flow rate of 0.8 to 150 mL/min.

EXPERIMENTAL PART

Abbreviations

As Used Herein and in the Description Above

| | |
|---|---|
| Ac | acetyl |
| AcCl | acetyl chloride |
| AcCN | acetonitrile |
| AcOH | acetic acid |
| aq. | aqueous |
| atm | atmosphere |
| Boc | tert-butoxycarbonyl |
| BSA | bovine serum albumin |
| Bu | butyl |
| BuLi | n-butyllithium |
| ca. | about |
| cat. | catalytic |
| DCC | N,N'-dicyclohexylcarbodiimide |
| DIPEA | diisopropylethylamine |
| DiBAL | di-iso-butylaluminum hydride |
| DMAP | 4-N,N-dimethylaminopyridine |
| DMF | dimethylformamide |
| DMSO | dimethylsulfoxide |
| DPPA | diphenyl phosphoryl azide |
| EA | ethyl acetate |
| EIA | enzyme immunoassay |
| EDC | N-(3-dimethylaminopropyl)-N'-ethyl-carbodiimide hydrochloride |
| ELSD | evaporative light-scattering detection |
| eq. | equivalent(s) |
| ES+ | electro-spray, positive ionization |
| Et | ethyl |
| ether | diethylether |
| Et$_3$N | triethylamine |
| EtOH | ethanol |
| FC | flash column chromatography on silica gel |
| h | hour(s) |
| HATU | 2-(7-aza-1H-benzotriazol-1-yl)-1,1,3,3-tetramethyluronium hexafluorophosphate |
| HBTU | O-(benzotriazol-1-yl)-N,N,N',N'-tetramethyluronium hexafluorophosphate |
| hept | heptane |
| HOBt | hydroxybenzotriazole |
| HPLC | high performance liquid chromatography |
| LC-MS | liquid chromatography - mass spectrometry |
| m-CPBA | meta-chloroperbenzoic acid |
| Me | methyl |
| MeOH | methanol |
| min | minute(s) |
| MPLC | medium pressure liquid chromatography |
| MS | mass spectrometry |
| Ms | methanesulfonyl |
| NMO | N-methyl-morpholine-N-oxide |
| NMR | nuclear magnetic resonance |
| OAc | acetate |
| org. | organic |
| p | para |
| p-TsOH | para-toluene sulfonic acid |
| PG | protecting group |
| PyBOP | benzotriazol-1-yl-oxy-tris-pyrrolidino-phosphonium-hexafluoro-phosphate |
| Rochelle's salt | potassium sodium tartrate |
| rf | retention factor |
| rt | room temperature |
| sat. | saturated |
| SCX | strong cation exchanger |
| sol. | solution |
| TBA | tetra-n-butylammonium |

-continued

| | |
|---|---|
| TBAF | tetra-n-butylammonium fluoride |
| TBDMS | tert-butyl-dimethyl-silyl |
| TBDPS | tert-butyl-diphenyl-silyl |
| TBTU | O-(benzotriazol-1-yl)-N,N,N',N'-tetramethyluronium tetrafluoroborate |
| tBu | tert-butyl, tertiary butyl |
| TFA | trifluoroacetic acid |
| THF | tetrahydrofuran |
| TIPS | tri-isopropyl-silyl |
| TLC | thin layer chromatography |
| TMS | trimethyl-silyl |
| TPAP | tetrapropylammonium perruthenate |
| $t_R$ | retention time |
| TsOH | p-toluene sulfonic acid monohydrate |
| UV | ultra violet |
| Vis | visible |

I Chemistry

General. All temperatures are stated in degrees Celsius (° C.). Unless otherwise indicated, the reactions take place at rt.

As SCX material SiliaBond® SCX from Silicycle was used.

Analytical thin layer chromatography (TLC) was performed with 0.2 mm plates: Merck, Silica gel 60 $F_{254}$. Preparative thin layer chromatography (TLC) was performed with 0.2 or 0.5 mm plates: Merck, Silica gel 60 $F_{254}$. Detection was done with UV or with a solution of KMnO$_4$ (3 g), K$_2$CO$_3$ (20 g), NaOH 5% (3 mL) and H$_2$O (300 mL) with subsequent heating.

Flash column chromatography (FC) and filtration were performed using silica gel 60 Merck (0.063-0.200 mm) or Macherey-Nagel silica gel (0.063-0.200 mm): elution with EA, hept, CH$_2$Cl$_2$, CHCl$_3$, MeOH or mixtures thereof.

MPLC were performed using Isolute® SPE Flash SI II columns from international sorbent technology, elution with EA, hept, CH$_2$Cl$_2$, MeOH or mixture thereof.

LC-MS-conditions 01 (if not indicated otherwise): Analytical: Thermo Finnigan MSQ Surveyor MS with Agilent 1100 Binary Pump and DAD. Column: Zorbax SB-AQ 5 μm, 4.6×50 mm ID from Agilent Technologies. Eluents: A: H$_2$O+0.04% TFA; B: AcCN; Gradient: 5% B→95% B over 1 min. Flow: 4.50 mL/min. Detection: UV/Vis+MS, $t_R$ is given in min.

LC-MS-conditions 01b (if not indicated otherwise): Analytical: Thermo Finnigan MSQ Surveyor MS with Agilent 1100 Binary Pump and DAD. Column: Xbridge C18 5 μM, 4.6×50 mm ID from Waters. Eluents: A: H$_2$O+0.04% TFA; B: AcCN; Gradient: 5% B→95% B over 1 min. Flow: 4.50 mL/min. Detection: UV/Vis+MS, $t_R$ is given in min.

LC-MS-conditions 02 (if not indicated otherwise): Analytical: Thermo Finnigan MSQ Plus MS with Agilent 1100 Binary Pump and DAD. Column: Zorbax SB-AQ 5 μm, 4.6×50 mm ID from Agilent Technologies. Eluents: A: H$_2$O+0.04% TFA; B: AcCN; Gradient: 5% B→95% B over 1 min. Flow: 4.50 mL/min. Detection: UV/Vis and/or ELSD+MS, $t_R$ is given in min.

LC-MS-conditions 05 (if not indicated otherwise): Analytical: Dionex GHP 3200 Binary Pump, MS: Thermo MSQ Plus, DAD: Dionex PDA 3000, ELSD: Sedere Sedex 85, column: Xbridge C18 5 μM, 4.6×50 mm ID from Waters, thermostated in the Dionex TCC-3200 compartment. Eluents: A: H$_2$O+0.04% TFA; B: AcCN. Method: Gradient: 5% B→95% B over 1 min. Flow: 4.5 mL/min. Detection: UV/Vis and/or ELSD, and MS, $t_R$ is given in min.

LC-MS-conditions 05b (if not indicated otherwise): Analytical: Dionex GHP 3200 Binary Pump, MS: Thermo MSQ Plus, DAD: Dionex PDA 3000, ELSD: Sedere Sedex 85, Column: Zorbax Extend C18 1.8 µM, 4.6×20 mm from Agilent Technologies, thermostated in the Dionex TCC-3200 compartment. Eluents: A: $H_2O$+0.04% TFA; B: AcCN. Method: Gradient: 2% B→95% B over 1.20 min. Flow: 4.5 mL/min. Detection: UV/Vis and/or ELSD, and MS, $t_R$ is given in min.

LC-MS-conditions 05c (if not indicated otherwise): Analytical: Dionex GHP 3200 Binary Pump, MS: Thermo MSQ Plus, DAD: Dionex PDA 3000, ELSD: Sedere Sedex 85. Column: Zorbax SB-AQ 4.6×20 mm ID from Agilent Technologies, thermostated in the Dionex TCC-3200 compartment. Eluents: A: $H_2O$+0.04% TFA; B: AcCN. Method: Gradient: 5% B→95% B over 1 min. Flow: 4.5 mL/min. Detection: UV/Vis and/or ELSD, and MS, $t_R$ is given in min.

HPLC preparative: X-Bridge C18 5 µm, 50×19 mm ID from Waters. Eluents: A: $H_2O$+0.5% $NH_4OH$; B: AcCN; Gradient: 10% B→90% B over 5 min. Flow: 40.0 mL/min. Detection: UV/Vis and/or ELSD.

HPLC chiral, analytical: a) Regis Whelk column, 4.6×250 mm, 10 µm. Eluent A: EtOH+0.05% $Et_3N$. Eluent B: hexane. Flow: 1 mL/min. b) ChiralPak AD, 4.6×250 mm, 5 µm. Eluent A: EtOH+0.05% $Et_3N$. Eluent B: hexane. Flow: 1 mL/min. c) ChiralCel OD, 4.6×250 mm, 10 µm. Eluent A: EtOH+0.1% $Et_3N$. Eluent B: hexane. Flow: 0.8 mL/min.

HPLC chiral, preparative: a) Regis Whelk 01 column, 50×250 mm. Flow: 100 mL/min. b) ChiralPak AD, 20×250 mm. Flow: 10 mL/min. c) ChiralCel OD, 20 µm, 50 mm×250 mm. Flow: 100 mL/min.

NMR: Bruker Avance 400 (400 MHz); Varian Mercury 300 (300 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

The following examples illustrate the invention but do not at all limit the scope thereof.

General Procedures

General Procedure A

Carbamate Formation (1)

In a glass vial, under inert atmosphere ($N_2$), to a solution of the appropriate aminopyrazole derivative (1.0 eq.) in AcCN (or $CH_2Cl_2$) (0.05M solution), was added 4-nitrophenyl chloroformate (1.1 eq.) and DIPEA (1.0 eq.). The mixture was stirred for 30 min, and then it was transferred to glass vials containing the appropriate alcohol (1.4 eq.), under inert atmosphere. After adding DIPEA (1.0 eq.), the mixture was stirred at 60° C. for 12 h. The reaction mixture was poured on a syringe containing diatomaceous earth (Isolute® HM-N from Separtis) treated with 1M NaOH (1.25 mL per g of Isolute®). The product was eluted with $CH_2Cl_2$ (3×1 mL). The solvent was removed under reduced pressure. Purification of the residue by FC or HPLC gave the desired compound.

General Procedure B

Amide Coupling

In a glass vial, under inert atmosphere ($N_2$), to an acid (1.5 eq.), was added a solution of the amine (1.0 eq.) in $CH_2Cl_2$ (0.1M). A solution of HOBt (2.0 eq.), DMAP (0.25 eq.), and DIPEA (2.0 eq.) in $CH_2Cl_2$ (10 mL per mmol of HOBt), was added, followed by EDC (1.5 eq.). The resulting mixture was stirred at rt overnight. The reaction mixture was poured on a syringe containing diatomaceous earth (Isolute® HM-N from Separtis) treated with 1M HCl (1.0 mL per g of Isolute®). The product was eluted with $CH_2Cl_2$ (3×1 mL) and the solvent was removed under reduced pressure. Purification of the residue by FC or HPLC gave the desired compound.

General Procedure C

Dioxolane Deprotection (1)

In a glass vial, under inert atmosphere ($N_2$), a 0.07M solution of the dioxolane (1.0 eq.) in THF was treated with 1N HCl (2.7 eq.) and the reaction mixture was stirred at rt until completion. Water was added and the product was extracted twice with EA. The org. layer was dried over $MgSO_4$ filtered, and the solvent was removed under reduced pressure. Purification of the residue by FC or HPLC gave the desired compound.

General Procedure D

Dioxolane Deprotection (2)

To a glass vial containing a 0.05M solution of the dioxolane in MeOH was added SCX silica gel (70 mg per 0.05 mmol of dioxolane) and the reaction mixture was stirred at rt for 18 h. The mixture was filtered and the solvent was removed under reduced pressure. Purification of the residue by FC or HPLC gave the desired compound.

General Procedure E

Condensation

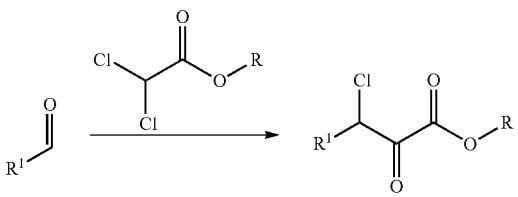

In a flame dried round-bottomed flask equipped with a magnetic stir bar and under inert atmosphere ($N_2$), a solution of the aldehyde derivative (1 eq.) in dichloro-acetic acid methyl ester (1.0 eq.) was added over 1 h to a 1.45M suspension of KOt-Bu (1.0 eq.) in THF at −78° C. The reaction mixture was stirred at −78° C. for 5 h at rt overnight. The solvent was removed under reduced pressure and the residue was dissolved in EA and washed with water. The organic layer was dried over $MgSO_4$ and concentrated under reduced pressure to afford the corresponding 3-chloro-2-oxo-propionic acid methyl ester derivative.

General Procedure F

Cyclization (1)

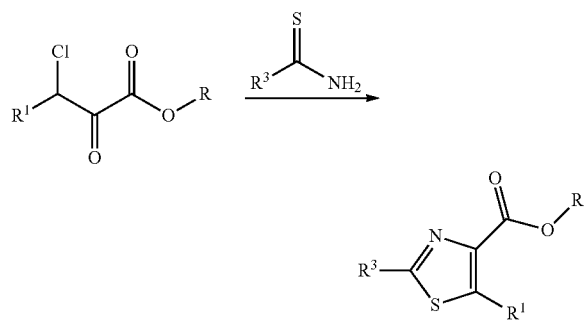

$R^3$ represents $(C_1-C_4)$alkyl or cyclopropyl.

In a flame dried round-bottomed flask equipped with a magnetic stir bar and under inert atmosphere ($N_2$), a 0.5M solution of the respective thioamide (1.0 eq.) in MeCN was added to a 2.2M solution of the respective 3-chloro-2-oxo-propionic acid ester derivative (1.0 eq.) in MeCN along with molecular sieves 4 Å (91 mg per mmol of thioacetamide). After stirring at rt for 5 h, the mixture was cooled with an ice-bath and the resulting precipitate was filtered off. The residue was washed with cold MeCN, dried, dissolved in MeOH (1.12 times the amount of MeCN as used for the thioacetamide) and stirred at 50° C. for 6 h. The solvents were removed under reduced pressure to give the corresponding thiazole-4-carboxylic acid ester derivative.

General Procedure G

Grignard Addition

In a flame dried round-bottomed flask equipped with a magnetic stir bar and under inert atmosphere ($N_2$), a 0.1M solution of the aldehyde (1.0 eq.) in THF was treated at −78° C. with the appropriate cyclopropyl- or alkyl-magnesium bromide (4.0 eq.). The reaction mixture was stirred at −78° C. for 90 min and at rt for 45 min before being quenched by pouring in sat. aq. $NH_4Cl$, extracted with EA and the combined org. extracts were dried over $MgSO_4$, filtered, and the solvents were removed under reduced pressure. Purification of the residue by FC gave the desired compound.

General Procedure H

Alcohol Oxidation

In a flame dried round-bottomed flask equipped with a magnetic stir bar and under inert atmosphere ($N_2$), a 0.1M solution of the alcohol (1.0 eq.) in $CH_2Cl_2$ was treated at rt with NMO (3.0 eq.) and the reaction mixture was stirred for 5 min. TPAP (0.1 eq.) was then added and the reaction mixture was stirred for 2 h at rt and then the solvent was removed under reduced pressure. Purification of the residue by FC gave the desired compound.

General Procedure I

Carbamate Formation (2)

Step 1:

In a glass vial, under inert atmosphere ($N_2$), a 0.065M solution of the alcohol (1.3 eq.) in $CH_2Cl_2$ was treated with phosgene (1.3 eq., 20% solution in toluene). The resulting mixture was stirred at rt overnight. The reaction mixture was then poured on a syringe containing diatomaceous earth (Isolute® HM-N from Separtis) treated with 1M NaOH (1.25 mL per g of Isolute®). The product was eluted with $CH_2Cl_2$ (3×1 mL) and the solvents were removed under reduced pressure.

Step 2:

The residue was treated with a solution of the appropriate aminopyrazole derivative (1.0 eq.) and DIPEA (2.0 eq.) in $CH_2Cl_2$ (20 mL per mmol of aminopyrazole derivative) and the resulting mixture was stirred at rt overnight. The reaction mixture was poured on a syringe containing diatomaceous earth (Isolute® HM-N from Separtis) treated with 1M HCl (1.0 mL per g of Isolute®). The product was eluted with $CH_2Cl_2$ (3×1 mL) and the solvent was removed under reduced pressure. Purification of the residue by HPLC gave the desired compound.

General Procedure J

Ester Hydrolysis

A 0.5M solution of the respective carboxylic acid ester (1.0 eq.) in a 3:1 mixture of THF and the corresponding alkyl alcohol, e.g. MeOH or EtOH, was treated with 1M aq. NaOH (2.0 eq.). After stirring for 3 h, a white suspension was formed and the org. volatiles were removed under reduced pressure. The remaining mixture was diluted with water (half the amount of the 3:1 mixture of THF and MeOH), cooled with an ice-bath and acidified (pH=3-4) by addition of 1M aq. HCl. The suspension was filtered and the residue was washed with cold water to afford the desired carboxylic acid derivative after drying.

General Procedure K

Synthesis of 2-acetylamino-3-oxo-propionic acid ester derivatives

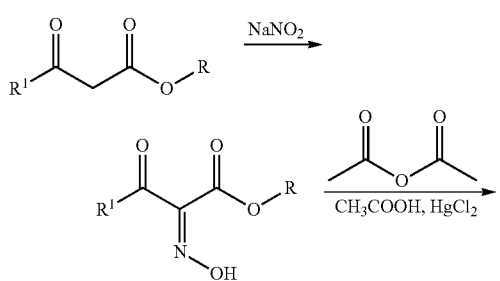

-continued

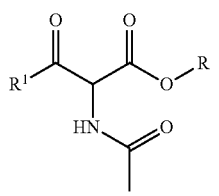

In a flame dried round-bottomed flask equipped with a magnetic stir bar and under inert atmosphere (N$_2$), a 2.5M solution of the respective 3-oxo-propionic acid ester derivative (1.0 eq.) in glacial acetic acid was cooled to 10° C. and at this temperature was added a 8.2M solution of NaNO$_2$ (1.16 eq.) in water. After the addition was complete (15 min), the solution was allowed to warm to rt and stirred for 2 h. The solution was then poured into water (5.3 times the volume of glacial acetic acid) and after a few minutes crystals began to appear. This suspension was cooled with an ice-bath and crystals were collected by filtration. The cake was washed several times with cold water and the water was removed by azeotrope distillation with toluene under reduced pressure to give the respective 2-hydroxyimino-3-oxo-propionic acid ester derivative, which was dissolved in a 1:1.3 mixture of acetic anhydride and glacial acetic acid (0.66 mL for 1.0 mmol of the respective 3-oxo-propionic acid ester derivative). To this solution was added sodium acetate (0.06 eq.) and HgCl$_2$ (0.002 eq.). The mixture was refluxed for 1 h, then cooled to rt and filtered. The solid was rinsed with ether, the organic filtrate was recovered, washed 3 times with water and once with 1M aq. K$_2$CO$_3$. The organic layer was dried over MgSO$_4$, filtered and the solvent was removed under reduced pressure. The crude product was purified by FC to afford the desired 2-acetylamino-3-oxo-propionic acid ester derivative.

General Procedure L

Cyclization (2)

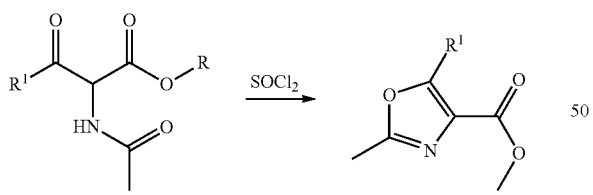

In a flame dried round-bottomed flask equipped with a magnetic stir bar and under inert atmosphere (N$_2$), a 1.6M solution of the respective 2-acetylamino-3-oxo-propionic acid ester derivative (1.0 eq.) in chloroform was cooled to about 0° C. in an ice/NaCl bath. SOCl$_2$ (1.4 eq.) was added to the stirred solution and the temperature was maintained at about 0° C. for 30 minutes. Then the solution was stirred at reflux for one hour. Another 0.25 eq. of SOCl$_2$ was added and the reaction mixture was refluxed for an additional hour. The excess SOCl$_2$ was quenched with 1M aq. K$_2$CO$_3$. The aq. layer was extracted twice with ether. The combined organic phases were washed once with water and dried over MgSO$_4$, filtered and the solvent was removed under reduced pressure to afford the desired oxazole derivative.

General Procedure M

Dehalogenation

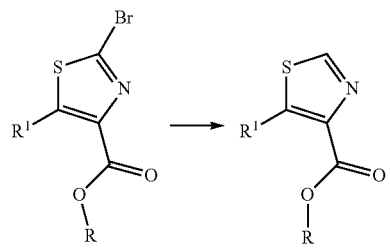

In a flame dried round-bottomed flask equipped with a magnetic stir bar and under an H$_2$ atmosphere, a 0.16M solution of the bromide (1.0 eq.), in EtOH was reduced with Pd/C (10% Pd, 200 mg for 1 mmol of the bromide). The reaction mixture was filtered over Celite and the solvent was removed under reduced pressure to afford the desired reduced derivative.

General Procedure N

Sandmeyer Reaction

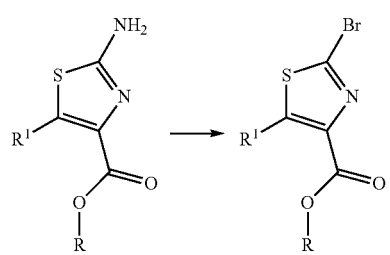

In a flame dried round-bottomed flask equipped with a magnetic stir bar and under an inert atmosphere (N$_2$) atmosphere, a 0.18M solution of CuBr$_2$ (0.97 eq.) in AcCN was carefully treated with isoamylnitrite (1.45 eq.) at 5° C. The reaction mixture was stirred for 30 min and the 2-amino-thiazole-4-carboxylic acid ester derivative (0.86 eq.) was then added portionwise. The resulting mixture was stirred at rt for 15 min, then at 40° C. for 30 min and at 65° C. for 1 h. The solvent was removed under reduced pressure and the residue was purified by FC to afford the desired bromo derivative.

General Procedure O Cyclization (3)

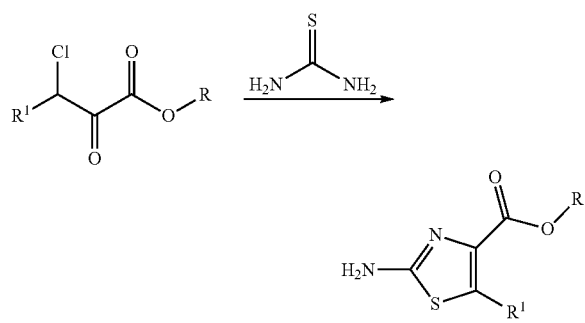

In a flame dried round-bottomed flask equipped with a magnetic stir bar and under an inert atmosphere (N$_2$), a 0.57M solution of the 3-chloro-2-oxo-propionic acid ester derivative (1.0 eq.) in acetone was added to a 0.72M solution of thiourea (1.0 eq.) in acetone. The reaction mixture was stirred overnight at 57° C. The cooled reaction mixture was filtered and the solvent was removed under reduced pressure. The residue was dissolved in water to obtain a 0.2M solution, which was treated with sat. aq. NaHCO$_3$ until pH 7 was reached. The mixture was then extracted with ether, organic layers were combined, dried over MgSO$_4$ and the solvent was removed under reduced pressure to afford the desired 2-amino-thiazole derivative.

General Procedure P

Cyclization (4)

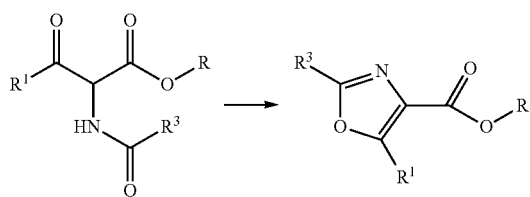

In a flame dried round-bottomed flask equipped with a magnetic stir bar and under an inert atmosphere (N$_2$), Et$_3$N (4.1 eq.) followed by a 0.1M solution of the respective 2-(carbonyl-amino)-3-oxo-propionic acid ester derivative (1.0 eq.) in CH$_2$Cl$_2$ were added to a 0.2M solution of triphenylphosphine (2.0 eq.) and iodine (2.0 eq.) in CH$_2$Cl$_2$. The reaction mixture was stirred at rt for 1.5 h. The solvent was removed under reduced pressure and the residue purified by FC to afford the desired oxazole derivative.

General Procedure Q

N-Insertion

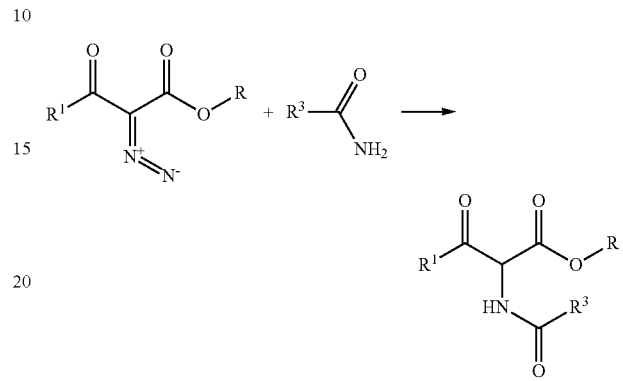

In a flame dried round-bottomed flask equipped with a magnetic stir bar and under an inert atmosphere (N$_2$), a 0.5M solution of the diazo derivative (1.0 eq.) in 1,2-dichloroethane was added over 1.5 h to a refluxing solution of the carboxamide derivative (1.0 eq.) and rhodium(II) acetate tetrakis (acetato)dirhodium(II) dihydrate (0.05 eq.) in 1,2-dichloroethane (3 mL per mmol of carboxamide derivative). The reaction mixture was then stirred at reflux for 1.5 h. The solvent was removed under reduced pressure and the residue purified by FC to afford the desired 2-(carbonyl-amino)-3-oxo-propionic acid ester derivative.

General Procedure R

Diazotation

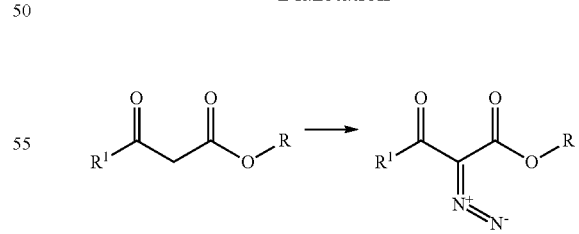

In a flame dried round-bottomed flask equipped with a magnetic stir bar and under an inert atmosphere (N$_2$), a 0.17M solution of the 3-oxo-propionic acid ester derivative (1.0 eq.) in AcCN was treated at 0° C. with 4-acetamidobenzenesulfonyl azide (1.0 eq.) followed by Et$_3$N (3.0 eq.). The reaction mixture was stirred at rt for 1 h. The solvent was removed under reduced pressure, the residue triturated in ether-light petroleum and filtered. The solvent was removed under reduced pressure and the residue was purified by FC to afford the desired diazo derivative.

General Procedure S

Claisen Condensation

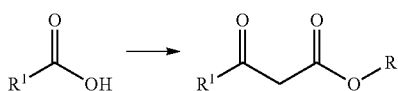

A) In a flame dried round-bottomed flask equipped with a magnetic stir bar and under an inert atmosphere ($N_2$), a 1.3M solution of the acid derivative (1.0 eq.) in 1,2-dichloroethane was treated at rt with a few drop of DMF followed by oxalyl chloride (1.3 eq.). The reaction mixture was stirred at rt for 3 h and at 80° C. for 20 min. The solvent was removed under reduced pressure.

B) In a flame dried round-bottomed flask equipped with a magnetic stir bar and under an inert atmosphere ($N_2$), a 0.83M solution of potassium malonic acid monoethyl ester (2 eq.) in acetonitrile was treated at 10° C. with magnesium chloride (2.5 eq.) and the suspension was stirred at 10° C. for 30 min and at rt for 3 h. The reaction mixture was cooled to 0° C. and treated dropwise over 15 min with the solution of the acid chloride prepared under A, followed by $Et_3N$ (2 eq.). The resulting suspension was stirred at rt for 20 h. The solvent was removed under reduced pressure and the residue was striped with toluene. The residue was taken in toluene (1.5 mL per mmol of potassium malonic acid monoethyl ester) and treated at 10° C. with the same amount of 4M HCl as of toluene. The organic layer was washed twice with 4M HCl, water, dried over $MgSO_4$, filtered, and the solvent was removed under reduced pressure. The residue was purified by FC to afford the desired derivative.

General Procedure T

Dioxolane Deprotection (3)

To a glass vial containing a 0.05M solution of the dioxolane in MeOH was added silica gel bound tosic acid (70 mg per 0.05 mmol of dioxolane, R60530B silica gel bound tosic acid from Silicycle) and the reaction mixture was stirred at rt for 18 h. The mixture was filtered. Purification of the residue by FC or HPLC gave the desired compound.

General Procedure U

Cyclization (5)

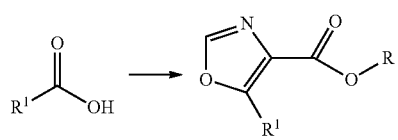

In a flame dried round-bottomed flask equipped with a magnetic stir bar and under an inert atmosphere ($N_2$), a 0.5M solution of the acid (1.0 eq.) in DMF was treated at rt with potassium carbonate sesquihydrate or, alternatively DIPEA (from 1.2 eq. to 1.5 eq.) followed by a 2.0M solution of methyl isocyanoacetate (from 1.5 eq. to 3.2 eq.) in DMF and the mixture was stirred at rt for 5 min. The reaction mixture was cooled to 0° C. and treated with a 0.67M solution of DPPA (1.1 eq.) in DMF. The resulting suspension was stirred at 0° C. for 2 h and at rt for 15 h. It was then poured in a 1:1 mixture of EA and toluene and the organic layer was washed with water, 10% citric acid, water and sat. aq. $NaHCO_3$. The organic layer was dried over $MgSO_4$, filtered, and the solvent was removed under reduced pressure. The residue was purified by FC to afford the desired derivative.

General Procedure V

Ester Hydrolysis

A 0.25M solution of the respective carboxylic acid ester (1.0 eq.) in dioxane was treated with 1M aq. LiOH (4.0 eq.). After reaction completion, EA (10 times the volume of dioxane) was added and the organic phase was washed with 1N HCl (3 times the volume of dioxane). The organic layer was dried over $MgSO_4$, filtered, and the solvent was removed under reduced pressure to afford the desired carboxylic acid derivative after drying.

General Procedure W

Boc Deprotection

A 0.25M solution of the respective Boc protected amine (1.0 eq.) in TFA was stirred for 1 h at rt. TFA was removed under reduced pressure, $CH_2Cl_2$ (10 times the initial volume of TFA) was added followed by sat. aq. $NaHCO_3$ (same volume as $CH_2Cl_2$). The aqueous phase was extracted again with the same amount of $CH_2Cl_2$ and the combined organic layers were dried over $MgSO_4$, filtered, and the solvent was removed under reduced pressure to afford the desired carboxylic acid derivative after drying. Purification of the residue by FC or HPLC gave the pure compound.

General Procedure X

Amide Coupling

In a glass vial, under inert atmosphere ($N_2$), to a 0.1M solution of the acid (1.5 eq.) in toluene, was added DMF (0.1 eq.) followed by oxalyl chloride (3.9 eq). The resulting mixture was stirred at rt for 30 min. The solvent was removed under reduced pressure and $CH_2Cl_2$ (half the amount of toluene used earlier) was added. This solution was added to a solution of the amine (1 eq) and $Et_3N$ (3 eq) in $CH_2Cl_2$ (half the amount of toluene used earlier). The reaction mixture was stirred at rt for 45 min and the solvent was removed under reduced pressure. Purification of the residue by FC or HPLC gave the desired compound.

General Procedure Y

Esterification

In a flame dried round-bottomed flask equipped with a magnetic stir bar and under inert atmosphere ($N_2$), a 1M solution of the acid (1.0 eq) in MeOH was treated at 0° C. with thionylchloride (1.1 eq). The resulting mixture was then stirred at rt overnight. The volatiles were removed under reduced pressure and the residue was triturated in EA and filtered to give the desired compound. Purification of the residue by FC or HPLC gave the desired compound.

General Procedure Z

Amide Coupling

In a flame dried round-bottomed flask equipped with a magnetic stir bar and under inert atmosphere ($N_2$), a 0.2M solution of the acid (1.0 eq) in $CH_2Cl_2$ was treated at 0° C. with HOBt (1.1 eq), DCC (1.1 eq) N-methylmorpholine (1.5 eq) and the amine (1 eq). The resulting mixture was stirred at rt for 2 h, poured in 5% $KHSO_4$, stirred for 15 min, filtered and washed with $CH_2Cl_2$. The aqueous phase was extracted with $CH_2Cl_2$ and the combined organic phases were washed with sat. aq. $NaHCO_3$, brine, dried over $MgSO_4$, filtered, and the solvent removed under reduced pressure. Purification of the residue gave the title compound.

General Procedure Z1

Cyclization

In a flame dried round-bottomed flask equipped with a magnetic stir bar and under inert atmosphere ($N_2$), a 0.13M solution of the amide (1 eq) in $CH_2Cl_2$ was treated at 0° C. with Dess-Martin periodinane (1.0 eq). The resulting mixture was stirred at rt for 1 h and filtered through a short plug of basic alumina (activity I) and sand into a flask containing a freshly prepared solution of triphenylphosphine (2.02 eq), $I_2$ (2.0 eq) and $Et_3N$ (4.0 eq) in $CH_2Cl_2$ (same amount as in the oxidation step). The filter cake was washed with $CH_2Cl_2$. After 15 min, the reaction mixture was transferred to a separatory funnel, treated with sat. aq. $Na_2S_2O_3$ and extracted with $CH_2Cl_2$. The organic layer was washed with sat. aq. $NaHCO_3$, filtered, and the solvent was removed under reduced pressure. Purification of the residue gave the desired compound.

General Procedure Z2

Ester Hydrolysis

A 0.2M solution of the respective carboxylic acid ester (1.0 eq.) in a 1:1 mixture of THF and the corresponding alkyl alcohol, e.g. MeOH or EtOH, was treated with 1M aq. NaOH (5.0 eq.) and the reaction mixture was stirred at rt until completion. The reaction mixture was acidified (pH=3-4) by addition of 1M aq. HCl and the mixture was extracted with EtOAc. The combined org. extracts were dried over $MgSO_4$, filtered, and the solvents were removed under reduced pressure to afford the desired carboxylic acid derivative after drying.

General Procedure Z3

Amide Coupling

In a glass vial, under inert atmosphere ($N_2$), a 0.1M solution of the acid (1.0 eq.) in DMF was treated with HATU (1.0 eq) and the reaction mixture was stirred at rt for 10 min. A 0.07M solution of the amine (1.0 eq) in DMF was then added followed by DIPEA (2.84 eq) and the resulting mixture was stirred at rt until completion. Water was added and the aq. layer was extracted twice with EtOAc. The combined org. extracts were dried over $Na_2SO_4$, filtered, and the solvents were removed under reduced pressure. Purification of the residue by FC or HPLC gave the desired compound.

Synthesis of Intermediates 5-(4-Nitro-pyrazol-1-ylmethyl)-furan-2-carboxylic acid methyl ester In a flame dried round-bottomed flask equipped with a magnetic stir bar and under inert atmosphere ($N_2$), a solution of 4-nitro-1H-pyrazole (6.22 g, 55.0 mmol) in acetone (130 mL) was treated with 5-chloromethyl-furan-2-carboxylic acid methyl ester (9.61 g, 55.0 mmol) followed by $K_2CO_3$ (38.04 g, 275.2 mmol) and TBA bromide (3.55 g, 11.0 mmol). The reaction mixture was stirred at rt for 2 h before being quenched with water (500 mL), extracted with EA (3×100 mL) and the combined org. extracts were dried over $MgSO_4$, filtered, and the solvents were removed under reduced pressure. Purification of the residue by FC (50:50 hept-EA) gave the title compound as a yellowish solid. TLC: rf (50:50 hept-EA)=0.35. LC-MS-conditions 02: $t_R$=0.88 min. $^1$H NMR (400 MHz, $CDCl_3$) δ 3.91 (s, 3H), 5.39 (s, 2H), 6.59 (d, J=3.3 Hz, 1H), 7.17 (d, J=3.3 Hz, 1H), 8.09 (s, 1H), 8.23 (s, 1H).

5-(4-Amino-pyrazol-1-ylmethyl)-furan-2-carboxylic acid methyl ester

In a flame dried round-bottomed flask equipped with a magnetic stir bar and under inert atmosphere ($N_2$), a solution of 5-(4-nitro-pyrazol-1-ylmethyl)-furan-2-carboxylic acid methyl ester (4.45 g, 17.7 mmol) in MeOH (100 mL) was treated with Pd/C (445 mg, 10% Pd). The $N_2$ atmosphere was replaced by an $H_2$ atmosphere ($H_2$ balloon) and the reaction mixture was stirred at rt for 4 h before being filtered through Celite and the solvent was removed under reduced pressure to give the title compound as an oil. LC-MS-conditions 02: $t_R$=0.50 min; $[M+H]^+$=222.27. $^1$H NMR (400 MHz, DMSO-$d_6$) $^1$H NMR 83.79 (s, 3H), 3.88 (s, 2H), 5.24 (s, 2H), 6.54 (d, J=3.3 Hz, 1H), 6.96 (s, 1H), 7.08 (s, 1H), 7.25 (d, J=3.5 Hz, 1H).

5-[4-(2-Chloro-benzyloxycarbonylamino)-pyrazol-1-ylmethyl]-furan-2-carboxylic acid methyl ester In a flame dried round-bottomed flask equipped with a magnetic stir bar and under inert atmosphere ($N_2$), a solution of 5-(4-amino-pyrazol-1-ylmethyl)-furan-2-carboxylic acid methyl ester (2.90 g, 13.10 mmol) in $CH_2Cl_2$ (58.0 mL) was treated with DIPEA (3.37 mL, 19.66 mmol) followed by 2-chlorobenzylchloroformate (2.69 mL, 17.04 mmol). The reaction mixture was stirred at rt for 4 h before being quenched with water (100 mL), extracted with $CH_2Cl_2$ (3×50 mL). The combined org. extracts were dried over $MgSO_4$, filtered, and the solvent was removed under reduced pressure. Purification of the residue by FC (50:50 hept-EA) gave the title compound as a solid. TLC: rf (50:50 hept-EA)=0.22. LC-MS-conditions 02: $t_R$=0.94 min; $[M+H]^+$=390.37. $^1$H NMR (400 MHz, $CDCl_3$) δ 3.89 (s, 3H), 5.29 (s, 2H), 5.31 (s, 2H), 6.39 (d, J=2.5 Hz, 1H), 6.75 (s, 1H), 7.12 (d, J=3.0 Hz, 1H), 7.23-7.31 (m, 2H), 7.38-7.42 (m, 1H), 7.43-7.46 (m, 2H), 7.75 (s, 1H).

[1-(5-Hydroxymethyl-furan-2-ylmethyl)-1H-pyrazol-4-yl]-carbamic acid 2-chloro-benzyl ester In a flame dried round-bottomed flask equipped with a magnetic stir bar and under inert atmosphere ($N_2$), a solution of 5-[4-(2-chloro-benzyloxycarbonylamino)-pyrazol-1-ylmethyl]-furan-2-carboxylic acid methyl ester (3.30 g, 8.46 mmol) in MeOH (33.0 mL) was treated portionwise, at rt with NaBH$_4$ (3.33 g, 84.60 mmol). The reaction mixture was stirred at rt overnight before being quenched by pouring in sat. aq. NH$_4$Cl (100 mL), extracted with EA (3×100 mL). The combined org. extracts were dried over MgSO$_4$, filtered, and the solvents were removed under reduced pressure. Purification of the residue by FC (30:70 hept-EA) gave the title compound. TLC: rf (30:70 hept-EA)=0.22. LC-MS-conditions 02: t$_R$=0.86 min; [M+H]$^+$=362.32. $^1$H NMR (400 MHz, CDCl$_3$) δ 2.94 (s, 1H), 4.52 (s, 2H), 5.15 (s, 2H), 5.28 (s, 2H), 6.21 (s, 1H), 6.28 (s, 1H), 7.04 (s, 1H), 7.22-7.35 (m, 2H), 7.35 (s, 1H), 7.35-7.46 (m, 2H), 7.69 (s, 1H).

[1-(5-Formyl-furan-2-ylmethyl)-1H-pyrazol-4-yl]-carbamic acid 2-chloro-benzyl ester In a flame dried round-bottomed flask equipped with a magnetic stir bar and under inert atmosphere (N$_2$), a solution of [1-(5-hydroxymethyl-furan-2-ylmethyl)-1H-pyrazol-4-yl]-carbamic acid 2-chloro-benzyl ester (300 mg, 0.83 mmol) in AcCN (8.0 mL) was treated at rt with MnO$_2$ (400 mg, 4.15 mmol). The reaction mixture was stirred at rt overnight before being filtered through Celite and the solvent was removed under reduced pressure to give the title compound as a yellow oil. LC-MS-conditions 02: t$_R$=0.90 min; [M+H]$^+$=360.28. $^1$H NMR (400 MHz, CDCl$_3$) δ 5.32 (s, 5H), 6.47 (s, 1H), 6.64 (s, 1H), 7.20 (s, 1H), 7.30 (s, 1H), 7.37-7.45 (m, 1H), 7.45 (s, 2H), 7.79 (s, 1H), 9.63 (s, 1H).

[5-(4-Nitro-pyrazol-1-ylmethyl)-furan-2-yl]-methanol

In a flame dried round-bottomed flask equipped with a magnetic stir bar and under inert atmosphere (N$_2$), a solution of 5-(4-nitro-pyrazol-1-ylmethyl)-furan-2-carboxylic acid methyl ester (10.0 g, 39.81 mmol) in THF (300.0 mL) was treated dropwise, at −78° C. with DiBAL (160.0 mL of a 1M solution in toluene, 160.0 mmol). The reaction mixture was stirred at −78° C. for 1.5 h and at rt for 1 h. Sat. aq. Rochelle's salt (600 mL) was added and the reaction mixture was stirred at rt for 1 h. The aq. layer was extracted with EA (2×350 mL). The combined org. extracts were dried over MgSO$_4$, filtered, and the solvents were removed under reduced pressure. Purification of the residue by FC (40:60 hept-EA) gave the title compound. TLC: rf (40:60 hept-EA)=0.28. LC-MS-conditions 02: t$_R$=0.74 min. $^1$H NMR (400 MHz, CDCl$_3$) δ 2.10 (s, 1H), 4.62 (s, 2H), 5.31 (s, 2H), 6.33 (d, J=3.0 Hz, 1H), 6.47 (d, J=3.0 Hz, 1H), 8.08 (s, 1H), 8.15 (s, 1H).

5-(4-Nitro-pyrazol-1-ylmethyl)-furan-2-carbaldehyde

In a flame dried round-bottomed flask equipped with a magnetic stir bar and under inert atmosphere (N$_2$), a solution of [5-(4-nitro-pyrazol-1-ylmethyl)-furan-2-yl]-methanol (7.0 g, 15.68 mmol) in AcCN (320.0 mL) was treated at rt with MnO$_2$ (18.2 g, 188.18 mmol). The reaction mixture was stirred at rt overnight before being filtered through Celite and the solvent was removed under reduced pressure. Purification of the residue by FC (60:40 hept-EA) gave the title compound. TLC: rf (60:40 hept-EA)=0.16. LC-MS-conditions 02: t$_R$=0.80 min. $^1$H NMR (400 MHz, CDCl$_3$) δ 5.44 (s, 2H), 6.66 (d, J=3.5 Hz, 1H), 7.25 (d, J=3.5 Hz, 1H), 8.10 (s, 1H), 8.28 (s, 1H), 9.65 (s, 1H).

1-[5-(4-Nitro-pyrazol-1-ylmethyl)-furan-2-yl]-ethanol

In a flame dried round-bottomed flask equipped with a magnetic stir bar and under inert atmosphere (N$_2$), a solution of 5-(4-nitro-pyrazol-1-ylmethyl)-furan-2-carbaldehyde (3.79 g, 17.14 mmol) in THF (173.0 mL) was treated at −78° C. with methylmagnesium bromide (17.1 mL of a 1M solution in THF, 17.14 mmol). The reaction mixture was stirred at −78° C. for 4 h then poured on sat. aq. NH$_4$Cl (150 mL) and extracted with EA (2×300 mL). The combined org. extracts were dried over MgSO$_4$, filtered, and the solvents were removed under reduced pressure. Purification of the residue by FC (50:50 hept-EA) gave the title compound as a yellow oil. TLC: rf (50:50 hept-EA)=0.24. LC-MS-conditions 02: t$_R$=0.79 min. $^1$H NMR (400 MHz, CDCl$_3$) δ 1.55 (d, J=6.5 Hz, 3H), 2.09 (d, J=5.0 Hz, 1H), 4.83-4.95 (m, 1H), 5.31 (s, 2H), 6.28 (d, J=3.0 Hz, 1H), 6.46 (d, J=3.0 Hz, 1H), 8.09 (s, 1H), 8.13 (s, 1H).

1-[5-(4-Nitro-pyrazol-1-ylmethyl)-furan-2-yl]-ethanone

In a flame dried round-bottomed flask equipped with a magnetic stir bar and under inert atmosphere (N$_2$), a solution of 1-[5-(4-nitro-pyrazol-1-ylmethyl)-furan-2-yl]-ethanol (4.94 g, 20.82 mmol) in AcCN (200.0 mL) was treated at rt with MnO$_2$ (12.07 g, 124.90 mmol) and the reaction mixture was stirred at rt overnight before being filtered through Celite. The solvent was removed under reduced pressure. Purification of the residue by FC (50:00 hept-EA) gave the title compound as a yellow solid. TLC: rf (50:50 hept-EA)=0.26. LC-MS-conditions 02: t$_R$=0.83 min. $^1$H NMR (400 MHz, CDCl$_3$) δ 2.47 (s, 3H), 5.41 (s, 2H), 6.60 (d, J=3.3 Hz, 1H), 7.17 (d, J=3.3 Hz, 1H), 8.10 (s, 1H), 8.25 (s, 1H).

1-[5-(1,1-Difluoro-ethyl)-furan-2-ylmethyl]-4-nitro-1H-pyrazole

In a flame dried round-bottomed flask equipped with a magnetic stir bar and under inert atmosphere (N$_2$), a solution of 1-[5-(4-nitro-pyrazol-1-ylmethyl)-furan-2-yl]-ethanone (4.20 g, 17.86 mmol) was dissolved at rt in (bis(2-methoxyethyl)amino)sulphur trifluoride (33.0 mL of a 50% solution in toluene, 178.6 mmol). EtOH (1.1 mL) was added at rt and the reaction mixture was stirred at 60° C. overnight. Sat. aq. Na$_2$CO$_3$ (65 mL) was added dropwise and the mixture was extracted with CH$_2$Cl$_2$ (2×100 mL), washed with water (100 mL), dried over MgSO$_4$, filtered, and the solvents were removed under reduced pressure. Purification of the residue by FC (2:1 hept-EA) gave the title compound as a red oil. TLC: rf (2:1 hept-EA)=0.31. LC-MS-conditions 02: t$_R$=0.97 min.

1-[5-(1,1-Difluoro-ethyl)-furan-2-ylmethyl]-1H-pyrazol-4-ylamine

In a flame dried round-bottomed flask equipped with a magnetic stir bar and under inert atmosphere (N$_2$), a mixture of 1-[5-(1,1-difluoro-ethyl)-furan-2-ylmethyl]-4-nitro-1H-pyrazole (234 mg, 0.91 mmol), iron powder (154 mg, 2.73 mmol) and NH$_4$Cl (246 mg, 4.55 mmol) in a mixture of EtOH (4.0 mL) and water (2.0 mL) was stirred at 75° C. for 1 h. The reaction mixture was filtered while hot and concentrated under reduced pressure. CH$_2$Cl$_2$ (20 mL) was added followed by 1M NaOH (20 mL). The aq. layer was extracted with CH$_2$Cl$_2$ (2×20 mL). The combined org. extracts were dried over MgSO$_4$, filtered, and the solvents were removed under reduced pressure to give the title compound as an orange oil. LC-MS-conditions 02: t$_R$=0.65 min; [M+AcCN+H]$^+$= 269.07.

1-[5-(2-Methyl-[1,3]dioxolan-2-yl)-furan-2-ylmethyl]-4-nitro-1H-pyrazole

In a flame dried round-bottomed flask equipped with a magnetic stir bar and a Dean-Stark apparatus under inert atmosphere (N$_2$), a solution of 1-[5-(4-nitro-pyrazol-1-ylmethyl)-furan-2-yl]-ethanone (3.40 g, 14.46 mmol), ethylene glycol (8.1 mL, 144.84 mmol) and TsOH (28 mg, 0.15 mmol) in toluene (150.0 mL) was heated to reflux for 4 h. The reaction mixture was allowed to cool to rt. Water (200 mL) and EA (40 mL) were added and the aq. phase was extracted with EA (2×80 mL). The combined org. extracts were washed with sat. aq. NaHCO$_3$ (200 mL), dried over MgSO$_4$, filtered, and the solvents were removed under reduced pressure. Purification of the residue by FC (60:40 hept-EA) gave the title compound as a yellow oil. TLC: rf (60:40 hept-EA)=0.31. LC-MS-conditions 02: t$_R$=0.91 min. $^1$H NMR (400 MHz, CDCl$_3$) δ 1.72 (s, 3H), 3.99 (dd, J=4.5, 2.5 Hz, 2H), 4.06 (dd, J=4.4, 2.5 Hz, 2H), 5.31 (s, 2H), 6.35 (d, J=3.3 Hz, 1H), 6.42 (d, J=3.3 Hz, 1H), 8.09 (s, 1H), 8.12 (s, 1H).

1-[5-(2-Methyl-[1,3]dioxolan-2-yl)-furan-2-ylmethyl]-1H-pyrazol-4-ylamine

In a flame dried round-bottomed flask equipped with a magnetic stir bar and under inert atmosphere (N$_2$), a mixture of 1-[5-(2-methyl-[1,3]dioxolan-2-yl)-furan-2-ylmethyl]-4-nitro-1H-pyrazole (427 mg, 1.53 mmol), iron powder (258 mg, 4.59 mmol) and NH$_4$Cl (413 mg, 7.65 mmol) in a mixture of EtOH (8.0 mL) and water (4.0 mL) was stirred at 75° C. for 2.5 h. The reaction mixture was filtered while hot and concentrated under reduced pressure. CH$_2$Cl$_2$ (30 mL) was added followed by 1M NaOH (30 mL). The aq. layer was extracted with CH$_2$Cl$_2$ (2×20 mL). The combined org. extracts were dried over MgSO$_4$, filtered, and the solvents were removed under reduced pressure to give the title compound as a deep red oil. LC-MS-conditions 02: t$_R$=0.58 min; [M+H]$^+$=250.4.

5-(3-Nitro-pyrazol-1-ylmethyl)-furan-2-carboxylic acid methyl ester

In a flame dried round-bottomed flask equipped with a magnetic stir bar and under inert atmosphere (N$_2$), a solution of 5-nitro-1H-pyrazole (10.95 g, 96.89 mmol) in dry acetone (219 mL) was treated with 5-chloromethyl-furan-2-carboxylic acid methyl ester (17.80 g, 96.89 mmol) followed by K$_2$CO$_3$ (67.61 g, 484.29 mmol) and TBA bromide (6.24 g, 19.37 mmol). The reaction mixture was stirred at rt overnight. Water (500 mL) was added followed by EA (1000 mL). The aq. layer was extracted with EA (2×500 mL) and the combined org. extracts were dried over MgSO$_4$, filtered, and the solvents were removed under reduced pressure. Purification of the residue by FC (50:50 hept-EA) gave the title compound as a yellow oil. TLC: rf (50:50 hept-EA)=0.26. LC-MS-conditions 02: t$_R$=0.84 min. $^1$H NMR (400 MHz, CDCl$_3$) δ 3.90 (s, 3H), 5.44 (s, 2H), 6.58 (d, J=3.5 Hz, 1H), 6.93 (d, J=2.5 Hz, 1H), 7.15 (d, J=3.5 Hz, 1H), 7.60 (d, J=2.3 Hz, 1H).

[5-(3-Nitro-pyrazol-1-ylmethyl)-furan-2-yl]-methanol

In a flame dried round-bottomed flask equipped with a magnetic stir bar and under inert atmosphere (N$_2$), a solution of 5-(3-nitro-pyrazol-1-ylmethyl)-furan-2-carboxylic acid methyl ester (25.40 g, 61.31 mmol) in THF (154.0 mL) was treated dropwise, at −78° C. with DiBAL (165.0 mL of a 1.7M solution in toluene, 245.22 mmol). The reaction mixture was stirred at −78° C. for 1 h and then allowed to warm up to rt. Sat. aq. Rochelle's salt (600 mL) was added and the reaction mixture was stirred at rt for 2 h. The aq. layer was extracted with EA (2×500 mL) and the combined org. extracts were dried over MgSO$_4$, filtered, and the solvents were removed under reduced pressure. Purification of the residue by FC (40:60 hept-EA) gave the title compound. TLC: rf (40:60 hept-EA)=0.28. LC-MS-conditions 02: t$_R$=0.75 min. $^1$H NMR (400 MHz, CDCl$_3$) δ 2.05 (s, 1H), 4.60 (s, 2H), 5.36 (s, 2H), 6.31 (d, J=3.0 Hz, 1H), 6.46 (d, J=3.0 Hz, 1H), 6.91 (d, J=2.5 Hz, 1H), 7.51 (d, J=2.5 Hz, 1H).

5-(3-Nitro-pyrazol-1-ylmethyl)-furan-2-carbaldehyde

In a flame dried round-bottomed flask equipped with a magnetic stir bar and under inert atmosphere (N$_2$), a solution of [5-(3-nitro-pyrazol-1-ylmethyl)-furan-2-yl]-methanol (13.80 g, 61.83 mmol) in AcCN (631.0 mL) was treated at rt with MnO$_2$ (35.84 g, 370.98 mmol). The reaction mixture was stirred at rt for 16 h before being filtered through Celite and the solvent was removed under reduced pressure. Purification of the residue by FC (40:60 hept-EA) gave the title compound. TLC: rf (60:40 hept-EA)=0.16. LC-MS-conditions 02: t$_R$=0.81 min. $^1$H NMR (400 MHz, CDCl$_3$) δ 5.48 (s, 2H), 6.67 (d, J=3.5 Hz, 1H), 6.96 (d, J=2.5 Hz, 1H), 7.24 (d, J=3.8 Hz, 1H), 7.64 (d, J=2.5 Hz, 1H), 9.65 (s, 1H).

1-[5-(3-Nitro-pyrazol-1-ylmethyl)-furan-2-yl]-ethanol

In a flame dried round-bottomed flask equipped with a magnetic stir bar and under inert atmosphere (N$_2$), a solution of 5-(3-nitro-pyrazol-1-ylmethyl)-furan-2-carbaldehyde (10.50 g, 47.47 mmol) in THF (479.2 mL) was treated at −78° C. with methylmagnesium bromide (47.47 mL of a 1M solution in THF, 47.47 mmol). The reaction mixture was stirred at −78° C. for 4 h. It was then poured in sat. aq. NH$_4$Cl (450 mL). The aq. phase was extracted with EA (2×500 mL) and the combined org. extracts were dried over MgSO$_4$, filtered, and the solvents were removed under reduced pressure. Purification of the residue by FC (50:50 hept-EA) gave the title compound as a mixture with 5-(3-nitro-pyrazol-1-ylmethyl)-furan-2-carbaldehyde. TLC: rf (50:50 hept-EA)=0.24. LC-MS-conditions 02: t$_R$=0.78 min. $^1$H NMR (400 MHz, CDCl$_3$) characteristic signals 81.53 (d, J=6.5 Hz, 3H), 2.15-2.24 (m, 1H), 4.81-4.91 (m, 1H), 5.35 (s, 2H), 6.24 (d, J=3.0 Hz, 1H), 6.43 (d, J=3.3 Hz, 1H), 6.89 (d, J=2.3 Hz, 1H), 7.49 (d, J=2.5 Hz, 1H).

1-[5-(3-Nitro-pyrazol-1-ylmethyl)-furan-2-yl]-ethanone

In a flame dried round-bottomed flask equipped with a magnetic stir bar and under inert atmosphere (N$_2$), a solution of 1-[5-(3-nitro-pyrazol-1-ylmethyl)-furan-2-yl]-ethanol (6.50 g, 27.40 mmol) in AcCN (269.0 mL) was treated at rt with MnO$_2$ (15.881 g, 164.40 mmol) and the reaction mixture was stirred at rt for 16 h before being filtered through Celite. The solvent was removed under reduced pressure. Purification of the residue by FC (50:50 hept-EA) gave the title compound as a mixture with 5-(3-nitro-pyrazol-1-ylmethyl)-furan-2-carbaldehyde. TLC: rf (50:50 hept-EA)=0.20. LC- MS-conditions 02: $t_R$=0.83 min. $^1$H NMR (400 MHz, CDCl$_3$) characteristic signals δ 2.47 (s, 3H), 5.46 (s, 2H), 6.61 (d, J=3.5 Hz, 1H), 6.95 (d, J=2.3 Hz, 1H), 7.16 (d, J=3.5 Hz, 1H), 7.61 (d, J=2.3 Hz, 1H).

1-[5-(1,1-Difluoro-ethyl)-furan-2-ylmethyl]-3-nitro-1H-pyrazole

In a flame dried round-bottomed flask equipped with a magnetic stir bar and under inert atmosphere (N$_2$), a solution of 1-[5-(3-nitro-pyrazol-1-ylmethyl)-furan-2-yl]-ethanone (3.1 g, 13.18 mmol) was dissolved at rt in (bis(2-methoxyethyl)amino)sulphur trifluoride (24.3 mL of a 50% solution in toluene, 131.81 mmol). EtOH (0.81 mL) was added at rt and the reaction mixture was stirred at 60° C. overnight. Sat. aq. Na$_2$CO$_3$ (50 mL) was added dropwise and the mixture was extracted with CH$_2$Cl$_2$ (2×65 mL), washed with water (60 mL), dried over MgSO$_4$, filtered, and the solvents were removed under reduced pressure. Purification of the residue by FC (2:1 hept-EA) gave the title compound as a red oil. TLC: rf (2:1 hept-EA)=0.24. LC-MS-conditions 02: $t_R$=0.98 min.

1-[5-(1,1-Difluoro-ethyl)-furan-2-ylmethyl]-1H-pyrazol-3-ylamine

In a flame dried round-bottomed flask equipped with a magnetic stir bar and under inert atmosphere (N$_2$), a mixture of 1-[5-(1,1-difluoro-ethyl)-furan-2-ylmethyl]-3-nitro-1H-pyrazole (208 mg, 0.81 mmol), iron powder (137 mg, 2.43 mmol) and NH$_4$Cl (218 mg, 4.04 mmol) in a mixture of EtOH (4.0 mL) and water (2.0 mL) was stirred at 75° C. for 45 min. The reaction mixture was filtered while hot and concentrated under reduced pressure. CH$_2$Cl$_2$ (20 mL) was added followed by 1M NaOH (20 mL). The aq. layer was extracted with CH$_2$Cl$_2$ (2×20 mL) and the combined org. extracts were dried over MgSO$_4$, filtered, and the solvents were removed under reduced pressure to give the title compound as a deep orange oil. LC-MS-conditions 02: $t_R$=0.73 min; [M+H]$^+$=228.13

1-[5-(2-Methyl-[1,3]dioxolan-2-yl)-furan-2-ylmethyl]-3-nitro-1H-pyrazole

In a flame dried round-bottomed flask equipped with a magnetic stir bar and a Dean-Stark apparatus under inert atmosphere (N$_2$), a solution of 1-[5-(3-nitro-pyrazol-1-ylmethyl)-furan-2-yl]-ethanone (1.760 g, 7.48 mmol), ethylene glycol (4.18 mL, 74.98 mmol) and TsOH (14 mg, 0.08 mmol) in toluene (74.8 mL) was heated to reflux for 4 h. The reaction mixture was allowed to cool to rt. Water (125 mL) and EA (25 mL) were added and the aq. phase was extracted with EA (2×50 mL). The combined org. extracts were washed with sat. aq. NaHCO$_3$, dried over MgSO$_4$, filtered, and the solvents were removed under reduced pressure. Purification of the residue by FC (60:40 hept-EA) gave the title compound as a yellow oil. TLC: rf (60:40 hept-EA)=022. LC-MS-conditions 02: $t_R$=0.92 min; [M+H]$^+$=280.04. $^1$H NMR (400 MHz, CDCl$_3$) δ 1.71 (s, 3H), 3.95-4.02 (m, 2H), 4.02-4.09 (m, 2H), 5.36 (s, 2H), 6.33 (d, J=3.3 Hz, 1H), 6.41 (d, J=3.0 Hz, 1H), 6.91 (d, J=2.5 Hz, 1H), 7.48 (d, J=2.3 Hz, 1H).

1-[5-(2-Methyl-[1,3]dioxolan-2-yl)-furan-2-ylmethyl]-1H-pyrazol-3-ylamine

In a flame dried round-bottomed flask equipped with a magnetic stir bar and under inert atmosphere (N$_2$), a mixture of 1-[5-(2-methyl-[1,3]dioxolan-2-yl)-furan-2-ylmethyl]-3-nitro-1H-pyrazole (173 mg, 0.62 mmol), iron powder (105 mg, 1.86 mmol) and NH$_4$Cl (167 mg, 3.10 mmol) in a mixture of EtOH (4.0 mL) and water (2.0 mL) was stirred at 75° C. for 40 min. The reaction mixture was filtered while hot and concentrated under reduced pressure. CH$_2$Cl$_2$ (15 mL) was added followed by water (15 mL). The aq. layer was extracted with CH$_2$Cl$_2$ (2×15 mL) and the combined org. extracts were dried over MgSO$_4$, filtered, and the solvents were removed under reduced pressure to give the title compound as a yellow oil. LC-MS-conditions 02: $t_R$=0.62 min; [M+H]$^+$=250.34.

6-Bromo-hexan-2-one

In a flame dried round-bottomed flask equipped with a magnetic stir bar and under inert atmosphere (N$_2$), a solution of commercially available 1-methylcyclopentanol (4.00 g, 39.94 mmol) in CHCl$_3$ at 0° C. (2.6 mL) was treated with K$_2$CO$_3$ (33.11 g, 239.62 mmol) and the reaction mixture was stirred for 15 min. Bromine (10.23 mL, 199.68 mmol) was then added and the reaction mixture was stirred at 0° C. for 2.5 h. The reaction mixture was slowly poured onto an ice-chilled sat. aq. Na$_2$S$_2$O$_3$ solution (100 mL). The org. layer was washed with water (2×100 mL), dried over MgSO$_4$, filtered, and the solvent was removed under reduced pressure. Purification of the residue by FC (gradient hept→75:25 hept-EA) gave the title compound as a yellow oil. TLC: rf (75:25 hept-EA)=0.36. $^1$H NMR (400 MHz, CDCl$_3$) δ 1.66-1.80 (m, 2H), 1.82-1.93 (m, 2H), 2.15 (s, 3H), 2.48 (t, J=7.3 Hz, 2H), 3.41 (t, J=6.5 Hz, 2H).

2-(4-Bromo-butyl)-2-methyl-[1,3]dioxolane

In a flame dried round-bottomed flask equipped with a magnetic stir bar and a Dean-Stark apparatus under inert atmosphere (N$_2$), a solution of 6-bromo-hexan-2-one (3.34 g, 18.65 mmol) in toluene (71.3 mL) was treated with ethylene glycol (10.4 mL, 186.92 mmol) and TsOH (35 mg, 0.19 mmol). The reaction mixture was heated to reflux for 3 h, allowed to cool to rt and sat. aq. NaHCO$_3$ (100 mL) and ether (100 mL) were added and the aq. phase was washed with water (2×100 mL), dried over MgSO$_4$, filtered, and the solvents were removed under reduced pressure to give the title compound. $^1$H NMR (400 MHz, CDCl$_3$) δ 1.34 (s, 3H), 1.50-1.65 (m, 2H), 1.65-1.75 (m, 2H), 1.84-1.98 (m, 2H), 3.43 (t, J=6.8 Hz, 2H), 3.90-4.04 (m, 4H).

1-[4-(2-Methyl-[1,3]dioxolan-2-yl)-butyl]-4-nitro-1H-pyrazole

In a flame dried round-bottomed flask equipped with a magnetic stir bar and under inert atmosphere (N$_2$), a solution of 4-nitro-1H-pyrazole (2.10 g, 18.68 mmol) and Cs$_2$CO$_3$ (6.67 g, 20.46 mmol) in AcCN (18.9 mL) was treated with a solution of 2-(4-bromo-butyl)-2-methyl-[1,3]dioxolane (4.15 g, 18.60 mmol) in AcCN (18.9 mL). The reaction mixture was stirred at 80° C. for 2 h. Water (100 mL) was added followed by EA (100 mL). The aq. layer was extracted with EA (200 mL) and the combined org. extracts were dried over MgSO$_4$, filtered, and the solvents were removed under reduced pressure. Purification of the residue by FC (50:50 hept-EA) gave the title compound. TLC: rf (50:50 hept-EA)=0.46. LC-MS-conditions 02: $t_R$=0.89 min; [M+H]$^+$=256.36. $^1$H NMR (400 MHz, CDCl$_3$) δ 1.31 (s, 3H), 1.38-1.53 (m, 2H), 1.65-1.77 (m, 2H), 1.90-2.02 (m, 2H), 3.88-3.94 (m, 2H), 3.94-3.99 (m, 2H), 4.17 (t, J=7.0 Hz, 2H), 8.08 (s, 1H), 8.14 (s, 1H).

1-[4-(2-Methyl-[1,3]dioxolan-2-yl)-butyl]-1H-pyrazol-4-ylamine

In a flame dried round-bottomed flask equipped with a magnetic stir bar and under inert atmosphere ($N_2$), a mixture of 1-[4-(2-methyl-[1,3]dioxolan-2-yl)-butyl]-4-nitro-1H-pyrazole (1.80 g, 7.05 mmol), iron powder (1.20 g, 21.26 mmol) and $NH_4Cl$ (1.90 g, 35.25 mmol) in a mixture of EtOH (46.0 mL) and water (23.0 mL) was stirred at 75° C. for 30 min. The reaction mixture was filtered while hot and concentrated under reduced pressure. $CH_2Cl_2$ (400 mL) was added followed by 1M NaOH (100 mL). The aq. layer was extracted with $CH_2Cl_2$ (2×100 mL) and the combined org. extracts were dried over $MgSO_4$, filtered, and the solvents were removed under reduced pressure to give the title compound as a deep red oil. LC-MS-conditions 02: $t_R$=0.56 min; $[M+H]^+$=226.53. $^1$H NMR (400 MHz, $CDCl_3$) δ 1.29 (s, 3H), 1.34-1.46 (m, 2H), 1.61-1.70 (m, 2H), 1.77-1.88 (m, 2H), 2.85 (s, 2H), 3.86-3.92 (m, 2H), 3.92-3.96 (m, 2H), 3.99 (t, J=7.3 Hz, 2H), 7.00 (s, 1H), 7.14 (s, 1H).

6-(4-Nitro-pyrazol-1-yl)-hexan-2-one

In a flame dried round-bottomed flask equipped with a magnetic stir bar and under inert atmosphere ($N_2$), a suspension of 4-nitro-1H-pyrazole (8.29 g, 64.99 mmol) and $Cs_2CO_3$ (31.87 g, 71.49 mmol) in AcCN (75.0 mL) was treated with a solution of 6-bromo-hexan-2-one (12.80 g, 71.49 mmol) in AcCN (58.0 mL). The reaction mixture was stirred at 80° C. for 2 h. Water (270 mL) and EA (400 mL) were added to the cooled reaction mixture. The aq. layer was extracted with EA (400 mL) and the combined org. extracts were dried over $MgSO_4$, filtered, and the solvents were removed under reduced pressure. Purification of the residue by FC (50:50 hept-EA) gave the title compound. TLC: rf (50:50 hept-EA)=0.29. LC-MS-conditions 02: $t_R$=0.82 min; $[M+H]^+$=212.18.

1-(5,5-Difluoro-hexyl)-4-nitro-1H-pyrazole

In a flame dried round-bottomed flask equipped with a magnetic stir bar and under inert atmosphere ($N_2$), a solution of 6-(4-nitro-pyrazol-1-yl)-hexan-2-one (9.20 g, 43.55 mmol) was dissolved at rt in (diethylamino)sulphur trifluoride (12.0 mL, 87.10 mmol) and the reaction mixture was stirred at 50° C. overnight. The reaction mixture was poured onto ice (150 mL) and the mixture was extracted with $CH_2Cl_2$ (2×60 mL), washed with water (60 mL), brine (60 mL), dried over $MgSO_4$, filtered, and the solvents were removed under reduced pressure. Purification of the residue by FC (3:1 hept-EA) gave the title compound as an orange oil. TLC: rf (3:1 hept-EA)=0.26. LC-MS-conditions 02: $t_R$=0.99 min; $[M+H]^+$=234.07.

1-(5,5-Difluoro-hexyl)-1H-pyrazol-4-ylamine

In a flame dried round-bottomed flask equipped with a magnetic stir bar and under inert atmosphere ($N_2$), a mixture of 1-(5,5-difluoro-hexyl)-4-nitro-1H-pyrazole (400 mg, 1.72 mmol), iron powder (290 mg, 5.15 mmol) and $NH_4Cl$ (463 mg, 8.58 mmol) in a mixture of EtOH (8.0 mL) and water (4.0 mL) was stirred at 75° C. for 40 min. The reaction mixture was filtered while hot and concentrated under reduced pressure. $CH_2Cl_2$ (30 mL) was added followed by 1M NaOH (30 mL). The aq. layer was extracted with $CH_2Cl_2$ (2×30 mL) and the combined org. extracts were dried over $MgSO_4$, filtered, and the solvents were removed under reduced pressure to give the title compound as a deep red oil. LC-MS-conditions 02: $t_R$=0.60 min; $[M+H]^+$=204.27.

1-[4-(2-Methyl-[1,3]dioxolan-2-yl)-butyl]-3-nitro-1H-pyrazole

In a flame dried round-bottomed flask equipped with a magnetic stir bar and under inert atmosphere ($N_2$), a solution of 5-nitro-1H-pyrazole (2.97 g, 18.68 mmol) and $Cs_2CO_3$ (6.67 g, 26.22 mmol) in AcCN (27.0 mL) was treated with a solution of 2-(4-bromo-butyl)-2-methyl-[1,3]dioxolane (5.85 g, 26.22 mmol) in AcCN (27.0 mL). The reaction mixture was stirred at 80° C. for 2.5 h. Water (100 mL) and EA (200 mL) were added to the cooled reaction mixture. The aq. layer was extracted with EA (100 mL) and the combined org. extracts were dried over $MgSO_4$, filtered, and the solvents were removed under reduced pressure. Purification of the residue by FC (60:40 hept-EA) gave the title compound. TLC: rf (60:40 hept-EA)=0.17. LC-MS-conditions 02: $t_R$=0.89 min; $[M+H]^+$=256.32. $^1$H NMR (400 MHz, $CDCl_3$) δ 1.31 (s, 3H), 1.39-1.50 (m, 2H), 1.67-1.75 (m, 2H), 1.92-2.02 (m, 2H), 3.88-3.94 (m, 2H), 3.94-4.00 (m, 2H), 4.22 (t, J=7.0 Hz, 2H), 6.91 (d, J=2.3 Hz, 1H), 7.46 (d, J=2.3 Hz, 1H).

1-[4-(2-Methyl-[1,3]dioxolan-2-yl)-butyl]-1H-pyrazol-3-ylamine

In a flame dried round-bottomed flask equipped with a magnetic stir bar and under inert atmosphere ($N_2$), a mixture of 1-[4-(2-methyl-[1,3]dioxolan-2-yl)-butyl]-3-nitro-1H-pyrazole (300 mg, 1.18 mmol), iron powder (199 mg, 3.53 mmol) and $NH_4Cl$ (317 mg, 5.88 mmol) in a mixture of EtOH (4.0 mL) and water (2.0 mL) was stirred at 75° C. for 30 min. The reaction mixture was filtered while hot and concentrated under reduced pressure. $CH_2Cl_2$ (20 mL) was added followed by water (20 mL). The aq. layer was extracted with $CH_2Cl_2$ (3×10 mL) and the combined org. extracts were dried over $MgSO_4$, filtered, and the solvents were removed under reduced pressure to give the title compound as a colorless oil. LC-MS-conditions 02: $t_R$=0.59 min; $[M+H]^+$=226.47.

6-(3-Nitro-pyrazol-1-yl)-hexan-2-one

In a flame dried round-bottomed flask equipped with a magnetic stir bar and under inert atmosphere ($N_2$), a suspension of 5-nitro-1H-pyrazole (3.69 g, 29.35 mmol) and $Cs_2CO_3$ (10.53 g, 32.28 mmol) in AcCN (34.0 mL) was treated with a solution of 6-bromo-hexan-2-one (5.78 g, 32.28 mmol) in AcCN (26.0 mL). The reaction mixture was stirred at 80° C. for 2 h. Water (123 mL) and EA (185 mL) were added to the cooled reaction mixture. The aq. layer was extracted with EA (185 mL) and the combined org. extracts were dried over $MgSO_4$, filtered, and the solvents were removed under reduced pressure. Purification of the residue by FC (50:50 hept-EA) gave the title compound. TLC: rf (50:50 hept-EA)=0.21. LC-MS-conditions 02: $t_R$=0.82 min; $[M+H]^+$=212.28.

1-(5,5-Difluoro-hexyl)-3-nitro-1H-pyrazole

In a flame dried round-bottomed flask equipped with a magnetic stir bar and under inert atmosphere ($N_2$), a solution of 6-(3-nitro-pyrazol-1-yl)-hexan-2-one (4.60 g, 21.78 mmol) was dissolved at rt in (diethylamino)sulphur trifluoride (6.01 mL, 43.55 mmol) and the reaction mixture was stirred at 50° C. overnight. The reaction mixture was poured onto ice (75 mL) and the mixture was extracted with $CH_2Cl_2$ (2×30 mL), washed with water (30 mL), brine (30 mL), dried over $MgSO_4$, filtered, and the solvents were removed under reduced pressure. Purification of the residue by FC (3:1 hept-EA) gave the title compound as an orange oil. TLC: rf (3:1 hept-EA)=0.29. LC-MS-conditions 02: $t_R$=0.99 min; $[M+H]^+$=234.13.

1-(5,5-Difluoro-hexyl)-1H-pyrazol-3-ylamine

In a flame dried round-bottomed flask equipped with a magnetic stir bar and under inert atmosphere ($N_2$), a mixture of 1-(5,5-difluoro-hexyl)-3-nitro-1H-pyrazole (400 mg, 1.72 mmol), iron powder (290 mg, 5.15 mmol) and $NH_4Cl$ (463 mg, 8.58 mmol) in a mixture of EtOH (8.0 mL) and water (4.0 mL) was stirred at 75° C. for 40 min. The reaction mixture was filtered while hot and concentrated under reduced pressure. $CH_2Cl_2$ (30 mL) was added followed by 1M NaOH (30 mL). The aq. layer was extracted with $CH_2Cl_2$ (2×30 mL) and the combined org. extracts were dried over $MgSO_4$, filtered, and the solvents were removed under reduced pressure to give the title compound as a yellow oil. LC-MS-conditions 02: $t_R$=0.66 min; $[M+H]^+$=204.25.

2-Furan-2-yl-2-methyl-[1,3]dioxolane

In a flame dried round-bottomed flask equipped with a magnetic stir bar and under inert atmosphere ($N_2$), a solution of 1-furan-2-yl-ethanone (50.00 g, 454.0 mmol) in ethylene glycol (500.0 mL) was treated with trimethylorthoformate (100.0 mL, 908.0 mmol) followed by $LiBF_4$ (7.00 g, 75 mmol). The reaction mixture was heated at 92° C. overnight. Sat. aq. $NaHCO_3$ (500 mL) was added and the mixture was extracted with EA (500 mL). The org. extracts were washed with brine (2×250 mL), dried over $MgSO_4$, filtered, and the solvent was removed under reduced pressure. Purification of the residue by distillation (11 mbar, 71-73° C.) gave the title compound as colorless oil. LC-MS-conditions 02: $t_R$=0.50 min.

[5-(2-Methyl-[1,3]dioxolan-2-yl)-furan-2-yl]-methanol

In a flame dried round-bottomed flask equipped with a magnetic stir bar and under inert atmosphere ($N_2$), to a solution of n-BuLi (14.6 mL of a 1.6M solution in hexane, 23.35 mmol) in THF (21 mL) at −78° C. was added dropwise a solution of 2-furan-2-yl-2-methyl-[1,3]dioxolane (3.00 g, 19.46 mmol) in THF (6.0 mL). The reaction mixture was then stirred for 1 h at −78° C. before DMF (4.52 mL, 58.38 mmol) was added dropwise. The reaction mixture was stirred for 1 h at −78° C. Sat. aq. $NaH_4Cl$ (50 mL) was added and the mixture was extracted with EA (2×50 mL). The combined org. extracts were dried over $MgSO_4$, filtered, and the solvent was removed under reduced pressure to give 5.91 g of crude 5-(2-methyl-[1,3]dioxolan-2-yl)-furan-2-carbaldehyde as an orange oil. LC-MS-conditions 02: $t_R$=0.75 min; $[M+H]^+$= 183.23. The crude material was dissolved, under inert atmosphere ($N_2$) in MeOH (59.0 mL) and treated at 0° C., portion-wise, over 20 min, with $NaBH_4$ (1.53 g, 38.92 mmol in five equal portions). The reaction mixture was stirred at rt for 45 min. The reaction mixture was poured in water (80 mL) and the aq. layer was extracted with EA (2×60 mL). The combined org. extracts were dried over $MgSO_4$, filtered, and the solvents were removed under reduced pressure. Purification of the residue by FC (50:50 hept-EA) gave the title compound. TLC: rf (50:50 hept-EA)=0.27. LC-MS-conditions 02: $t_R$=0.65 min; $[M+H]^+$=185.28.

1-[5-(2-Methyl-[1,3]dioxolan-2-yl)-furan-2-ylm-ethyl]-4-nitro-1H-pyrazole

In a flame dried round-bottomed flask equipped with a magnetic stir bar and under inert atmosphere ($N_2$), a solution of [5-(2-methyl-[1,3]dioxolan-2-yl)-furan-2-yl]-methanol (3.52 g, 19.11 mmol) in dry $CH_2Cl_2$ (35.2 mL) was treated at 0° C. with $Et_3N$ (3.20 mL, 22.93 mmol) followed by DMAP (233 mg, 1.91 mmol) and Ms-Cl (1.63 mL, 21.02 mmol). After stirring at rt for 2 h, the reaction mixture was quenched with water (35 mL), extracted with $CH_2Cl_2$ (30 mL) and the combined org. extracts were dried over $MgSO_4$, filtered, and the solvents were removed under reduced pressure to give 3.65 g of crude 2-(5-chloromethyl-furan-2-yl)-2-methyl-[1, 3]dioxolane as an orange oil. The crude material in acetone (20 mL) was added, under inert atmosphere ($N_2$) to a solution of 4-nitro-1H-pyrazole (1.57 g, 13.91 mmol) in acetone (20 mL). $K_2CO_3$ (7.69 g, 55.66 mmol) followed by TBA iodide (1.03 g, 2.73 mmol) were added and the reaction mixture was stirred at rt overnight. Water (100 mL) and EA (100 mL) were added. The aq. layer was extracted with EA (100 mL) and the combined org. extracts were dried over $MgSO_4$, filtered, and the solvents were removed under reduced pressure. Purification of the residue by FC (50:50 hept-EA) gave the title compound as an orange oil. TLC: rf (60:40 hept-EA)=0.31. LC-MS-conditions 02: $t_R$=0.91 min. $^1$H NMR (400 MHz, $CDCl_3$) δ 1.72 (s, 3H), 3.99 (dd, J=4.5, 2.5 Hz, 2H), 4.06 (dd, J=4.4, 2.5 Hz, 2H), 5.31 (s, 2H), 6.35 (d, J=3.3 Hz, 1H), 6.42 (d, J=3.3 Hz, 1H), 8.09 (s, 1H), 8.12 (s, 1H).

5-Methylsulfanyl-furan-2-carboxylic acid ethyl ester

In a flame dried round-bottomed flask equipped with a magnetic stir bar and under inert atmosphere ($N_2$), a solution of commercially available 5-nitro-furan-2-carboxylic acid ethyl ester (5.00 g, 27.01 mmol) in DMSO (34.5 mL) was treated at rt with sodium methanethiolate (2.05 g 27.82 mmol). The mixture was then stirred at 100° C. overnight, cooled down to rt and treated with sat. aq. $NH_4Cl$ (250 mL). The aqueous layer was extracted with EA (3×100 mL). The combined org. extracts were washed with sat. aq. $NaHCO_3$ (100 mL) and brine (100 mL), dried over $MgSO_4$, filtered, and the solvents were removed under reduced pressure. Purification of the residue by FC (70:30 hept-EA) gave the title compound. TLC: rf (70:30 hept-EA)=0.52. LC-MS-conditions 02: $t_R$=0.96 min; $[M+AcCN+H]^+$=228.23.

5-Methanesulfonyl-furan-2-carboxylic acid ethyl ester

In a flame dried round-bottomed flask equipped with a magnetic stir bar and under inert atmosphere ($N_2$), a solution of 5-methylsulfanyl-furan-2-carboxylic acid ethyl ester (1.74 g, 9.34 mmol) in $CH_2Cl_2$ (16.0 mL) was carefully treated at rt with m-CPBA (3.28 g, 13.32 mmol). The mixture was then stirred at rt for 2 h, treated at rt with sat. aq. $Na_2CO_3$ and the organic layer was washed with water and brine, dried over $MgSO_4$, filtered, and the solvents were removed under reduced pressure to give the title compound as a yellow solid. LC-MS-conditions 02: $t_R$=0.83 min.

(5-Methanesulfonyl-furan-2-yl)-methanol

In a flame dried round-bottomed flask equipped with a magnetic stir bar and under inert atmosphere ($N_2$), a solution of 5-methanesulfonyl-furan-2-carboxylic acid ethyl ester (1.26 g) in THF (57.0 mL) was treated at −78° C. with DiBAL (19.50 mL of a 1M solution in THF, 19.50 mmol) and the reaction mixture was stirred at this temperature for 2 h. The reaction mixture was poured on Rochelle's salt (100 mL) and stirred at rt for 12 h. The aq. layer was extracted with EA (2×100 mL). The combined org. extracts were dried over $MgSO_4$, filtered, and the solvents were removed under reduced pressure. Purification of the residue by FC (30:70 hept-EA) gave the title compound as a yellow oil. TLC: rf (30:70 hept-EA)=0.28. LC-MS-conditions 02: $t_R$=0.50 min.

1-(5-Methanesulfonyl-furan-2-ylmethyl)-4-nitro-1H-pyrazole

In a flame dried round-bottomed flask equipped with a magnetic stir bar and under inert atmosphere ($N_2$), a solution of (5-methanesulfonyl-furan-2-yl)-methanol (692 mg, 3.93 mmol) in dry $CH_2Cl_2$ (7.0 mL) was treated at 0° C. with $Et_3N$ (0.71 mL, 5.11 mmol) followed by DMAP (50 mg, 0.39 mmol) and Ms-Cl (0.37 mL, 4.71 mmol). After stirring at rt for 2 h, the reaction mixture was quenched with water (10 mL), extracted with $CH_2Cl_2$ (20 mL) and the combined org. extracts were dried over $MgSO_4$, filtered, and the solvents were removed under reduced pressure to give 868 mg of crude 2-chloromethyl-5-methanesulfonyl-furan as a yellow oil. 150 mg of this crude material in acetone (2.0 mL) was added, under inert atmosphere ($N_2$) to a solution of 4-nitro-1H-pyrazole (87 mg, 0.77 mmol) in acetone (2.0 mL). $K_2CO_3$ (320 mg, 2.13 mmol) followed by TBA bromide (50 mg, 0.15 mmol) were added and the reaction mixture was stirred at rt overnight. Water (10 mL) and EA (10 mL) were added. The aq. layer was extracted with EA (10 mL) and the combined org. extracts were dried over $MgSO_4$, filtered, and the solvents were removed under reduced pressure. Purification of the residue by FC (40:60 hept-EA) gave the title compound as a yellow oil. TLC: rf (40:60 hept-EA)=0.27. LC-MS-conditions 02: $t_R$=0.82 min.

1-(5-Methanesulfonyl-furan-2-ylmethyl)-1H-pyrazol-4-ylamine

In a flame dried round-bottomed flask equipped with a magnetic stir bar and under inert atmosphere ($N_2$), a mixture of 1-(5-methanesulfonyl-furan-2-ylmethyl)-4-nitro-1H-pyrazole (150 mg, 0.55 mmol), iron powder (94 mg, 1.66 mmol) and $NH_4Cl$ (149 mg, 2.77 mmol) in a mixture of EtOH (2.0 mL) and water (1.0 mL) was stirred at 85° C. for 40 min. The reaction mixture was filtered while hot and concentrated under reduced pressure. $CH_2Cl_2$ (10 mL) was added followed by water (10 mL). The aq. layer was extracted with $CH_2Cl_2$ (2×10 mL) and the combined org. extracts were dried over $MgSO_4$, filtered, and the solvents were removed under reduced pressure to give the title compound as an orange oil. LC-MS-conditions 02: $t_R$=0.37 min; [M+H]$^+$=242.32.

1-[5-(2-Methyl-[1,3]dioxolan-2-yl)-furan-2-ylmethyl]-3-nitro-1H-pyrazole

In a flame dried round-bottomed flask equipped with a magnetic stir bar and under inert atmosphere ($N_2$), a solution of [5-(2-methyl-[1,3]dioxolan-2-yl)-furan-2-yl]-methanol (6.00 g, 32.58 mmol) in dry $CH_2Cl_2$ (60.0 mL) was treated at 0° C. with $Et_3N$ (5.89 mL, 42.35 mmol) followed by DMAP (398 mg, 3.26 mmol) and Ms-Cl (3.03 mL, 39.09 mmol). The reaction mixture was stirred at rt for 2 h before being quenched with water (60 mL), extracted with $CH_2Cl_2$ (60 mL) and the combined org. extracts were dried over $MgSO_4$, filtered, and the solvents were removed under reduced pressure to give 6.66 g of crude 2-(5-chloromethyl-furan-2-yl)-2-methyl-[1,3]dioxolane as an orange oil. A solution of the crude material in acetone (82.0 mL) was treated, under inert atmosphere ($N_2$) with $K_2CO_3$ (13.50 g, 97.71 mmol) followed by 5-nitro-1H-pyrazole (3.68 g, 32.57 mmol) and TBA bromide (2.10 g, 6.51 mmol). The resulting mixture was stirred overnight at rt. Water (50 mL) and EA (75 mL) were added. The aq. layer was extracted with EA (100 mL) and the combined org. extracts were dried over $MgSO_4$, filtered, and the solvents were removed under reduced pressure. Purification of the residue by FC (60:40 hept-EA) gave the title compound as a yellow oil. TLC: rf (60:40 hept-EA)=022. LC-MS-conditions 02: $t_R$=0.92 min; [M+H]$^+$=280.04. $^1$H NMR (400 MHz, $CDCl_3$) δ 1.71 (s, 3H), 3.95-4.02 (m, 2H), 4.02-4.09 (m, 2H), 5.36 (s, 2H), 6.33 (d, J=3.3 Hz, 1H), 6.41 (d, J=3.0 Hz, 1H), 6.91 (d, J=2.5 Hz, 1H), 7.48 (d, J=2.3 Hz, 1H).

6-(4-Nitro-pyrazol-1-yl)-hexan-2-ol

In a flame dried round-bottomed flask equipped with a magnetic stir bar and under inert atmosphere ($N_2$), a 0.1M solution of 6-(4-nitro-pyrazol-1-yl)-hexan-2-one (250 mg, 1.18 mmol) in THF was treated dropwise, at −78° C. with DiBAL (1.5 mL of a 1M solution in toluene, 1.5 mmol). The reaction mixture was stirred at −78° C. for 1 h. Sat. aq. Rochelle's salt (10 mL) was added and the reaction mixture was stirred for 2 h at rt. The aq. layer was extracted with EA (2×25 mL). The combined org. extracts were dried over $MgSO_4$, filtered, and the solvents were removed under reduced pressure. Purification of the residue by FC (50:50 hept-EA) gave the title compound. TLC: rf (40:60 hept-EA)= 0.2. LC-MS-conditions 02: $t_R$=0.78 min; [M+H]$^+$=214.23.

1-(5-Fluoro-hexyl)-4-nitro-1H-pyrazole

In a flame dried round-bottomed flask equipped with a magnetic stir bar and under inert atmosphere ($N_2$), a solution of 6-(4-nitro-pyrazol-1-yl)-hexan-2-ol (213 mg, 1.00 mmol) in THF (3.0 mL) was treated at rt with perfluoro-1-butane-sulfonyl fluoride (0.36 mL, 2.00 mmol), triethylamine trihydrofluoride (0.33 mL, 2.00 mmol) and $Et_3N$ and the reaction mixture was stirred at rt overnight. Purification of the residue by FC (80:10 hept-EA) gave the title compound. TLC: rf (80:20 hept-EA)=0.28. LC-MS-conditions 02: $t_R$=0.97 min; [M+H]$^+$=216.20.

1-(5-Fluoro-hexyl)-1H-pyrazol-4-ylamine

In a flame dried round-bottomed flask equipped with a magnetic stir bar and under inert atmosphere ($N_2$), a mixture of 1-(5-fluoro-hexyl)-4-nitro-1H-pyrazole (135 mg, 0.63 mmol), iron powder (106 mg, 1.88 mmol) and $NH_4Cl$ (169 mg, 3.13 mmol) in a mixture of EtOH (4.0 mL) and water (2.0 mL) was stirred at 75° C. for 40 min. The reaction mixture was filtered while hot and concentrated under reduced pressure. $CH_2Cl_2$ (10 mL) was added followed by 1M NaOH (10 mL). The aq. layer was extracted with $CH_2Cl_2$ (2×10 mL) and the combined org. extracts were dried over $MgSO_4$, filtered, and the solvents were removed under reduced pressure to give the title compound as a red solid. LC-MS-conditions 02: $t_R$=0.60 min.

[5-(2-Methyl-[1,3]dioxolan-2-yl)-thiophen-2-yl]-methanol

In a flame dried round-bottomed flask equipped with a magnetic stir bar and under inert atmosphere ($N_2$), to a solution of commercially available 2-methyl-2-thiophen-2-yl-[1,3]dioxolane (5.00 g, 28.49 mmol) in THF (145.0 mL) at −78° C. was added dropwise N,N,N',N'-tetramethyl-ethylendiamine (4.41 mL, 29.06 mmol) followed by n-BuLi (18.14 mL of a 1.6M solution in hexane, 29.06 mmol), maintaining the temperature at −78° C. The reaction mixture was then stirred for 2 h at −78° C. before DMF (6.74 mL, 87.22 mmol) was added dropwise. The cooling bath was removed and the reaction mixture was stirred for 16 h. The reaction mixture was poured in sat. aq. $NaH_4Cl$ (200 mL) and extracted with EA (2×200 mL). The combined org. extracts were dried over $MgSO_4$, filtered, and the solvent was removed under reduced pressure to give crude 5-(2-methyl-[1,3]dioxolan-2-yl)-thiophene-2-carbaldehyde as an yellow oil. LC-MS-conditions 02: $t_R$=0.87 min; $[M+AcCN+H]^+$=240.32. The crude material was dissolved, under inert atmosphere ($N_2$) in MeOH (51.2 mL) and treated at 0° C., portionwise, over 20 min, with $NaBH_4$ (1.35 g, 34.19 mmol in five equal portions). The reaction mixture was stirred at rt for 45 min. The reaction mixture was poured in water (90 mL) and the aq. layer was extracted with EA (2×225 mL). The combined org. extracts were dried over $MgSO_4$, filtered, and the solvents were removed under reduced pressure. Purification of the residue by FC (50:50 hept-EA) gave the title compound. TLC: rf (50:50 hept-EA)=0.40. LC-MS-conditions 02: $t_R$=0.72 min; $[M+H]^+$=201.46.

1-[5-(2-Methyl-[1,3]dioxolan-2-yl)-thiophen-2-ylmethyl]-4-nitro-1H-pyrazole

In a flame dried round-bottomed flask equipped with a magnetic stir bar and under inert atmosphere ($N_2$), a solution of [5-(2-methyl-[1,3]dioxolan-2-yl)-thiophen-2-yl]-methanol (2.00 g, 19.11 mmol) in dry $CH_2Cl_2$ (18.4 mL) was treated at 0° C. with $Et_3N$ (1.81 mL, 12.98 mmol) followed by DMAP (122 mg, 1.00 mmol) and Ms-Cl (0.93 mL, 11.98 mmol). After stirring at rt for 2 h, the reaction mixture was quenched with water (15 mL), extracted with $CH_2Cl_2$ (30 mL) and the combined org. extracts were dried over $MgSO_4$, filtered, and the solvents were removed under reduced pressure to give crude 2-(5-chloromethyl-thiophen-2-yl)-2-methyl-[1,3]dioxolane as a yellow oil. The crude material in acetone (12 mL) was added, under inert atmosphere ($N_2$) to a solution of 4-nitro-1H-pyrazole (1.23 g, 9.60 mmol) in acetone (12 mL). $K_2CO_3$ (3.98 g, 28.81 mmol) followed by TBA bromide (619 mg, 1.92 mmol) were added and the reaction mixture was stirred at rt overnight. Water (60 mL) and EA (80 mL) were added. The aq. layer was extracted with EA (80 mL) and the combined org. extracts were dried over $MgSO_4$, filtered, and the solvents were removed under reduced pressure. Purification of the residue by FC (60:40 hept-EA) gave the title compound as a yellow oil. TLC: rf (60:40 hept-EA)=0.35. LC-MS-conditions 02: $t_R$=0.96 min.

1-[5-(2-Methyl-[1,3]dioxolan-2-yl)-thiophen-2-ylmethyl]-3-nitro-1H-pyrazole

In a flame dried round-bottomed flask equipped with a magnetic stir bar and under inert atmosphere ($N_2$), a solution of [5-(2-methyl-[1,3]dioxolan-2-yl)-thiophen-2-yl]-methanol (400 mg, 2.00 mmol) in dry $CH_2Cl_2$ (3.7 mL) was treated at 0° C. with $Et_3N$ (0.36 mL, 2.60 mmol) followed by DMAP (24 mg, 0.20 mmol) and Ms-Cl (0.19 mL, 2.40 mmol). The reaction mixture was stirred at rt for 2 h before being quenched with water (5 mL), extracted with $CH_2Cl_2$ (10 mL) and the combined org. extracts were dried over $MgSO_4$, filtered, and the solvents were removed under reduced pressure to give crude 2-(5-chloromethyl-thiophen-2-yl)-2-methyl-[1,3]dioxolane as an orange oil. A solution of the crude material in acetone (5.0 mL) was treated, under inert atmosphere ($N_2$) with $K_2CO_3$ (829 mg, 6.00 mmol) followed by 5-nitro-1H-pyrazole (226 mg, 2.00 mmol) and TBA bromide (129 mg, 0.40 mmol). The resulting mixture was stirred at rt overnight. Water (15 mL) and EA (20 mL) were added. The aq. layer was extracted with EA (20 mL) and the combined org. extracts were dried over $MgSO_4$, filtered, and the solvents were removed under reduced pressure. Purification of the residue by FC (60:40 hept-EA) gave the title compound as a yellow oil. TLC: rf (60:40 hept-EA)=0.24. LC-MS-conditions 02: $t_R$=0.96 min; $[M+H]^+$=296.20.

1-[5-(2-Methyl-[1,3]dioxolan-2-yl)-thiophen-2-ylmethyl]-1H-pyrazol-4-ylamine

In a flame dried round-bottomed flask equipped with a magnetic stir bar and under inert atmosphere ($N_2$), a mixture of 1-[5-(2-methyl-[1,3]dioxolan-2-yl)-thiophen-2-ylmethyl]-4-nitro-1H-pyrazole (390 mg, 1.32 mmol), iron powder (223 mg, 3.96 mmol) and $NH_4Cl$ (357 mg, 6.60 mmol) in a mixture of EtOH (7.0 mL) and water (3.5 mL) was stirred at 75° C. for 30 min. The reaction mixture was filtered while hot and concentrated under reduced pressure. $CH_2Cl_2$ (40 mL) was added followed by 1M NaOH (40 mL). The aq. layer was extracted with $CH_2Cl_2$ (2×20 mL). The combined org. extracts were dried over $MgSO_4$, filtered, and the solvents were removed under reduced pressure to give the title compound as a deep red oil. LC-MS-conditions 02: $t_R$=0.63 min; $[M+H]^+$=266.34.

1-[5-(2-Methyl-[1,3]dioxolan-2-yl)-thiophen-2-ylmethyl]-1H-pyrazol-3-ylamine

In a flame dried round-bottomed flask equipped with a magnetic stir bar and under inert atmosphere ($N_2$), a mixture of 1-[5-(2-methyl-[1,3]dioxolan-2-yl)-thiophen-2-ylmethyl]-3-nitro-1H-pyrazole (230 mg, 0.78 mmol), iron powder (132 mg, 2.34 mmol) and $NH_4Cl$ (210 mg, 3.85 mmol) in a mixture of EtOH (4.0 mL) and water (2.0 mL) was stirred at 75° C. for 30 min. The reaction mixture was filtered while hot and concentrated under reduced pressure. $CH_2Cl_2$ (40 mL) was added followed by 1M NaOH (40 mL). The aq. layer was extracted with $CH_2Cl_2$ (2×20 mL) and the combined org. extracts were dried over $MgSO_4$, filtered, and the solvents were removed under reduced pressure to give the title compound as a red oil. LC-MS-conditions 02: $t_R$=0.69 min; $[M+H]^+$=266.38.

5-(4-Nitro-pyrazol-1-ylmethyl)-isoxazole-3-carboxylic acid ethyl ester

In a flame dried round-bottomed flask equipped with a magnetic stir bar and under inert atmosphere ($N_2$), a solution of 5-hydroxymethyl-isoxazole-3-carboxylic acid ethyl ester (3.00 g, 17.53 mmol) in dry $CH_2Cl_2$ (30.0 mL) was treated at 0° C. with $Et_3N$ (3.17 mL, 22.79 mmol) followed by DMAP (214 mg, 1.75 mmol) and Ms-Cl (2.04 mL, 26.29 mmol). The reaction mixture was stirred at rt for 4 h before being quenched with water (50 mL), extracted with $CH_2Cl_2$ (50 mL) and the combined org. extracts were dried over $MgSO_4$, filtered, and the solvents were removed under reduced pressure to give crude 5-chloromethyl-isoxazole-3-carboxylic acid ethyl ester as an orange oil. A solution of 1.01 g of this crude material in acetone (8.0 mL) was treated, under inert atmosphere ($N_2$) with $K_2CO_3$ (1.260 g, 9.12 mmol) followed by 4-nitro-1H-pyrazole (343 mg, 3.04 mmol) and TBA bromide (195 mg, 0.61 mmol). The resulting mixture was stirred at rt overnight. Water (50 mL) and EA (50 mL) were added. The aq. layer was extracted with EA (50 mL) and the combined org. extracts were dried over $MgSO_4$, filtered, and the solvents were removed under reduced pressure. Purification of the residue by FC (50:50 hept-EA) gave the title compound as a yellow oil. TLC: rf (50:50 hept-EA)=0.31. LC-MS-conditions 02: $t_R$=0.86 min.

[5-(4-Nitro-pyrazol-1-ylmethyl)-isoxazol-3-yl]-methanol

In a flame dried round-bottomed flask equipped with a magnetic stir bar and under inert atmosphere ($N_2$), a solution of 5-(4-nitro-pyrazol-1-ylmethyl)-isoxazole-3-carboxylic acid ethyl ester (3.477 g, 13.061 mmol) in THF (130.0 mL) was treated dropwise, at −78° C. with DiBAL (44.4 mL of a 1M solution in toluene, 44.41 mmol). The reaction mixture was stirred at −78° C. for 1 h followed by 1 h at rt. Sat. aq. Rochelle's salt (300 mL) was added and the reaction mixture was stirred for 2 h at rt. The aq. layer was extracted with EA (2×300 mL). The combined org. extracts were dried over $MgSO_4$, filtered, and the solvents were removed under reduced pressure. Purification of the residue by FC (20:80 hept-EA) gave the title compound as a yellow oil. TLC: rf (20:80 hept-EA)=0.33. LC-MS-conditions 02: $t_R$=0.68 min.

5-(4-Nitro-pyrazol-1-ylmethyl)-isoxazole-3-carbaldehyde

In a flame dried round-bottomed flask equipped with a magnetic stir bar and under inert atmosphere ($N_2$), a solution of [5-(4-nitro-pyrazol-1-ylmethyl)-isoxazol-3-yl]-methanol (1.82 g, 8.20 mmol) in $CH_2Cl_2$ (25.0 mL) was added to an ice-chilled suspension of pyridinium chlorochromate (5.35 g, 24.36 mmol) in $CH_2Cl_2$ (25.0 mL). The reaction mixture was stirred for 4.5 h at rt. It was filtered over celite and the solvent was removed under reduced pressure. Purification of the residue by FC (50:50 hept-EA) gave the title compound as a colorless oil. TLC: rf (50:50 hept-EA)=0.36. LC-MS-conditions 02: $t_R$=0.60 min.

1-[5-(4-Nitro-pyrazol-1-ylmethyl)-isoxazol-3-yl]-ethanol

In a flame dried round-bottomed flask equipped with a magnetic stir bar and under inert atmosphere ($N_2$), a solution of 5-(4-nitro-pyrazol-1-ylmethyl)-isoxazole-3-carbaldehyde (666 mg, 3.00 mmol) in $CH_2Cl_2$ (22.0 mL) was treated at 0° C. with trimethylaluminum (15 mL of a 1M solution in heptane, 15.00 mmol). The reaction mixture was then stirred at 0° C. for 2 h. $CH_2Cl_2$ (100.0 mL) followed by sat. aq. $NH_4Cl$ (50 mL) was then added. The mixture was then treated with 1N HCl and the aq. layer was extracted with $CH_2Cl_2$ (20 mL). The combined org. extracts were dried over $MgSO_4$, filtered, and the solvents were removed under reduced pressure to give the title compound as a green oil. LC-MS-conditions 02: $t_R$=0.72 min.

1-[5-(4-Nitro-pyrazol-1-ylmethyl)-isoxazol-3-yl]-ethanone

In a flame dried round-bottomed flask equipped with a magnetic stir bar and under inert atmosphere ($N_2$), a solution of 1-[5-(4-nitro-pyrazol-1-ylmethyl)-isoxazol-3-yl]-ethanol (435 mg, 1.83 mmol) in $CH_2Cl_2$ (8.0 mL) was treated at rt with $MnO_2$ (1.32 g, 13.70 mmol) and the reaction mixture was stirred for 16 h at rt before being filtered through Celite. The solvent was removed under reduced pressure to give the title compound. LC-MS-conditions 02: $t_R$=0.87 min.

3-(2-Methyl-[1,3]dioxolan-2-yl)-5-(4-nitro-pyrazol-1-ylmethyl)-isoxazole

In a flame dried round-bottomed flask equipped with a magnetic stir bar and a Dean-Stark apparatus under inert atmosphere ($N_2$), a solution of 1-[5-(4-nitro-pyrazol-1-ylmethyl)-isoxazol-3-yl]-ethanone (336 mg, 1.42 mmol) in ethylene glycol (1.59 mL, 28.45 mmol) was treated with trimethylorthoformate (0.31 mL, 2.84 mmol) followed by $LiBF_4$ (27 mg, 0.29 mmol). The reaction mixture was heated at 95° C. overnight. Sat. aq. $NaHCO_3$ (10 mL) was added and the mixture was extracted with EA (10 mL). The org. extracts were washed with brine (2×20 mL), dried over $MgSO_4$, filtered, and the solvent was removed under reduced pressure. Purification of the residue by FC (20:10 hept-EA) gave the title compound as a yellow oil. TLC: rf (20:10 hept-EA)=0.19. LC-MS-conditions 02: $t_R$=0.86 min.

1-[3-(2-Methyl-[1,3]dioxolan-2-yl)-isoxazol-5-ylmethyl]-1H-pyrazol-4-ylamine

In a flame dried round-bottomed flask equipped with a magnetic stir bar and under inert atmosphere ($N_2$), a mixture of 3-(2-methyl-[1,3]dioxolan-2-yl)-5-(4-nitro-pyrazol-1-ylmethyl)-isoxazole (150 mg, 0.54 mmol), iron powder (91 mg, 1.61 mmol) and $NH_4Cl$ (145 mg, 2.68 mmol) in a mixture of EtOH (2.0 mL) and water (1.0 mL) was stirred at 85° C. for 20 min. The reaction mixture was filtered while hot and concentrated under reduced pressure. $CH_2Cl_2$ (20 mL) was added followed by water (20 mL). The aq. layer was extracted with $CH_2Cl_2$ (2×20 mL) and the combined org. extracts were dried over $MgSO_4$, filtered, and the solvents were removed under reduced pressure to give the title compound as a deep orange oil. LC-MS-conditions 02: $t_R$=0.49 min; $[M+H]^+$=251.34.

1-(6-Bromo-pyridin-2-yl)-ethanone

In a flame dried round-bottomed flask equipped with a magnetic stir bar and under inert atmosphere ($N_2$), a suspension of commercially available 2,6-dibromopyridine (2.44 g, 10.00 mmol) in ether (25.0 mL) was treated at −78° C. with n-BuLi (4.0 mL of a 2.5M solution in hexane, 10.00 mmol). The reaction mixture was stirred for 30 min before N,N-dimethylacetaminde (1.50 mL, 16.13 mmol) was added and the solution was then allowed to warm to rt over 1 h. Sat. aq. $NH_4Cl$ was then added and the aq. layer was extracted with $Et_2O$ (2×50 mL). The combined org. extracts were dried over $Na_2SO_4$, filtered, and the solvents were removed under reduced pressure. Purification of the residue by FC (20:1 hept-EA) gave the title compound as a white solid. TLC: rf (20:1 hept-EA)=0.25. LC-MS-conditions 02: $t_R$=0.98 min.

2-Bromo-6-(2-methyl-[1,3]dioxolan-2-yl)-pyridine

In a flame dried round-bottomed flask equipped with a magnetic stir bar and under inert atmosphere ($N_2$), a solution of 1-(6-bromo-pyridin-2-yl)-ethanone (1880 mg, 9.40 mmol) in ethylene glycol (10.00 mL, 179.32 mmol) was treated with trimethylorthoformate (2.10 mL, 19.16 mmol) followed by $LiBF_4$ (180 mg, 1.88 mmol). The reaction mixture was heated at 95° C. for 5 h. Sat. aq. $Na_2CO_3$ was added and the mixture was extracted twice with ether and the combined organic extracts were dried over Na$_2$SO$_4$, filtered, and the solvent was removed under reduced pressure. Purification of the residue by FC (20:1 hept-EA) gave the title compound as a pale yellow oil. TLC: rf (50:50 hept-EA)=0.57.

6-(2-Methyl-[1,3]dioxolan-2-yl)-pyridine-2-carbaldehyde

In a flame dried round-bottomed flask equipped with a magnetic stir bar and under inert atmosphere (N$_2$), to a solution of 2-bromo-6-(2-methyl-[1,3]dioxolan-2-yl)-pyridine (2.21 g, 9.05 mmol) in Et$_2$O (60.0 mL) at −78° C. was added dropwise n-BuLi (3.70 mL of a 2.5M solution in hexane, 9.25 mmol). The reaction mixture was then stirred at −78° C. for 30 min before DMF (0.85 mL, 11.00 mmol) was added dropwise. The reaction mixture was allowed to warm to rt over 1 h. 5% aq. NaHCO$_3$ was added and the mixture was extracted three times with Et$_2$O. The combined org. extracts were dried over Na$_2$SO$_4$, filtered, and the solvent was removed under reduced pressure. Purification of the residue by FC (4:1 hept-EA to pure EA) gave the title compound as a pale yellow solid.

[6-(2-Methyl-[1,3]dioxolan-2-yl)-pyridin-2-yl]-methanol

In a flame dried round-bottomed flask equipped with a magnetic stir bar and under inert atmosphere (N$_2$), to a ice-cold solution of 6-(2-methyl-[1,3]dioxolan-2-yl)-pyridine-2-carbaldehyde (713 mg, 3.69 mmol) in MeOH (10.0 mL) was added NaBH$_4$ (180 mg, 4.57 mmol in four equal portion). The reaction mixture was then stirred for 1 h at rt. Water was added and the mixture was extracted with EA followed twice with EA-MeOH 9:1. The combined org. extracts were dried over Na$_2$SO$_4$, filtered, and the solvent was removed under reduced pressure to give the title compound as a pale yellow solid. LC-MS-conditions 02: $t_R$=0.46 min; [M+H]$^+$=196.49.

Methanesulfonic acid 6-(2-methyl-[1,3]dioxolan-2-yl)-pyridin-2-ylmethyl ester In a flame dried round-bottomed flask equipped with a magnetic stir bar and under inert atmosphere (N$_2$), a solution of [6-(2-methyl-[1,3]dioxolan-2-yl)-pyridin-2-yl]-methanol (729 mg, 3.74 mmol) in dry CH$_2$Cl$_2$ (10.0 mL) was treated at 0° C. with Et$_3$N (0.67 mL, 4.83 mmol) followed by DMAP (46 mg, 0.37 mmol) and Ms-Cl (0.37 mL, 4.72 mmol). After stirring at 0° C. for 1 h, the reaction mixture was quenched with water (10 mL), extracted with CH$_2$Cl$_2$ (10 mL) and the combined org. extracts were dried over Na$_2$SO$_4$, filtered, and the solvents were removed under reduced pressure. Purification of the residue by FC (70:30 to 50:50 hept-EA) gave the title compound as a pale yellow oil. LC-MS-conditions 02: $t_R$=0.79 min; [M+H]$^+$=274.39.

2-(2-Methyl-[1,3]dioxolan-2-yl)-6-(4-nitro-pyrazol-1-ylmethyl)-pyridine

In a flame dried round-bottomed flask equipped with a magnetic stir bar and under inert atmosphere (N$_2$), a solution of methanesulfonic acid 6-(2-methyl-[1,3]dioxolan-2-yl)-pyridin-2-ylmethyl ester (273 mg, 1.00 mmol) in acetone (4.0 mL) was added, under inert atmosphere (N$_2$) to a solution of 4-nitro-1H-pyrazole (115 mg, 1.00 mmol) in acetone (4.0 mL). K$_2$CO$_3$ (698 mg, 5.00 mmol) and TBA iodide (64 mg, 0.20 mmol) were added and the reaction mixture was stirred at rt for 5 h. The solvent was removed under reduced pressure. Water (10 mL) and EA (10 mL) were added. The aq. layer was extracted with EA (10 mL) and the combined org. extracts were dried over Na$_2$SO$_4$, filtered, and the solvents were removed under reduced pressure. Purification of the residue by FC (30:10 to 50:50 hept-EA) gave the title compound as a pale yellow oil. LC-MS-conditions 02: $t_R$=0.87 min; [M+H]$^+$=291.27.

1-[6-(2-Methyl-[1,3]dioxolan-2-yl)-pyridin-2-ylmethyl]-1H-pyrazol-4-ylamine

In a flame dried round-bottomed flask equipped with a magnetic stir bar and under inert atmosphere (N$_2$), a 0.1M solution of 2-(2-methyl-[1,3]dioxolan-2-yl)-6-(4-nitro-pyrazol-1-ylmethyl)-pyridine (145 mg, 0.50 mmol), iron powder (84 mg, 1.50 mmol) and NH$_4$Cl (135 mg, 2.50 mmol) in a mixture of EtOH (2.0 mL) and water (1.0 mL) was stirred at 75° C. for 30 min. The reaction mixture was filtered while hot and concentrated under reduced pressure. CH$_2$Cl$_2$ (20 mL) was added followed by 1N NaOH (20 mL). The aq. layer was extracted with CH$_2$Cl$_2$ (2×20 mL) and the combined org. extracts were dried over MgSO$_4$, filtered, and the solvents were removed under reduced pressure to give the title compound as a deep red oil. LC-MS-conditions 02: $t_R$=0.56 min; [M+H]$^+$=261.61.

2-(2-Methyl-[1,3]dioxolan-2-yl)-6-(3-nitro-pyrazol-1-ylmethyl)-pyridine

In a flame dried round-bottomed flask equipped with a magnetic stir bar and under inert atmosphere (N$_2$), a solution of methanesulfonic acid 6-(2-methyl-[1,3]dioxolan-2-yl)-pyridin-2-ylmethyl ester (273 mg, 1.00 mmol) in acetone (4.0 mL) was added, under inert atmosphere (N$_2$) to a solution of 5-nitro-1H-pyrazole (115 mg, 1.00 mmol) in acetone (4.0 mL). K$_2$CO$_3$ (698 mg, 5.00 mmol) and TBA iodide (64 mg, 0.20 mmol) were added and the reaction mixture was stirred at rt for 5 h. The solvent was removed under reduced pressure. Water (10 mL) and EA (10 mL) were added. The aq. layer was extracted with EA (10 mL) and the combined org. extracts were dried over Na$_2$SO$_4$, filtered, and the solvents were removed under reduced pressure. Purification of the residue by FC (30:10 to 50:50 hept-EA) gave the title compound as a light brown solid. TLC: rf (50:50 hept-EA)=0.16. LC-MS-conditions 02: $t_R$=0.87 min; [M+H]$^+$=291.35.

1-[6-(2-Methyl-[1,3]dioxolan-2-yl)-pyridin-2-ylmethyl]-1H-pyrazol-3-ylamine

In a flame dried round-bottomed flask equipped with a magnetic stir bar and under inert atmosphere (N$_2$), a 0.1M solution of 2-(2-methyl-[1,3]dioxolan-2-yl)-6-(3-nitro-pyrazol-1-ylmethyl)-pyridine (270 mg, 0.93 mmol), iron powder (157 mg, 2.79 mmol) and NH$_4$Cl (251 mg, 2.79 mmol) in a mixture of EtOH (2.0 mL) and water (1.0 mL) was stirred at 75° C. for 90 min. The reaction mixture was filtered while hot and concentrated under reduced pressure. CH$_2$Cl$_2$ (20 mL) was added followed by 1N NaOH (20 mL). The aq. layer was extracted with CH$_2$Cl$_2$ (2×20 mL) and the combined org. extracts were dried over MgSO$_4$, filtered, and the solvents were removed under reduced pressure to give the title compound as a pale yellow oil. TLC: rf (EA)=0.20. LC-MS-conditions 02: $t_R$=0.59 min; [M+H]$^+$=261.40.

1-(5-Bromo-pyridin-3-yl)-ethanone

In a flame dried round-bottomed flask equipped with a magnetic stir bar and under inert atmosphere (N$_2$), a suspension of 3,5-dibromopyridine (2.39 g, 10.00 mmol) in ether (70.0 mL) was treated at −78° C. with n-BuLi (4.0 mL of a 2.5M solution in hexane, 10.00 mmol). The reaction mixture was stirred for 30 min before N,N-dimethylacetaminde (1.50 mL, 16.13 mmol) was added and the solution was then allowed to warm to rt over 1 h. Sat. aq. NH$_4$Cl was then added and the aq. layer was extracted with Et$_2$O (2×50 mL). The combined org. extracts were dried over Na$_2$SO$_4$, filtered, and the solvents were removed under reduced pressure. Purification of the residue by FC (10:1 hept-EA) gave the title compound as a white solid. TLC: rf (19:1 CH$_2$Cl$_2$-MeOH)=0.57. LC-MS-conditions 02: t$_R$=0.80 min.

3-Bromo-5-(2-methyl-[1,3]dioxolan-2-yl)-pyridine

In a flame dried round-bottomed flask equipped with a magnetic stir bar and under inert atmosphere (N$_2$), a solution of 1-(5-bromo-pyridin-3-yl)-ethanone (1800 mg, 9.00 mmol) in ethylene glycol (9.57 mL, 171.69 mmol) was treated with trimethylorthoformate (2.01 mL, 18.34 mmol) followed by LiBF$_4$ (172 mg, 1.80 mmol). The reaction mixture was heated at 95° C. overnight. Sat. aq. Na$_2$CO$_3$ was added and the mixture was extracted twice with ether. The combined organic extracts were dried over Na$_2$SO$_4$, filtered, and the solvent was removed under reduced pressure. Purification of the residue by FC (20:1 hept-EA) gave the title compound as a pale yellow oil. TLC: rf (50:50 hept-EA)=0.57. LC-MS-conditions 02: t$_R$=0.87 min.

5-(2-Methyl-[1,3]dioxolan-2-yl)-pyridine-3-carbaldehyde

In a flame dried round-bottomed flask equipped with a magnetic stir bar and under inert atmosphere (N$_2$), to a solution of 3-bromo-5-(2-methyl-[1,3]dioxolan-2-yl)-pyridine (450 mg, 1.84 mmol) in Et$_2$O (40.0 mL) at −78° C. was added dropwise n-BuLi (0.72 mL of a 2.5M solution in hexane, 1.88 mmol). The reaction mixture was then stirred at −78° C. for 30 min before DMF (0.17 mL, 2.24 mmol) was added dropwise. The reaction mixture was allowed to warm to rt over 1 h. Sat. aq NH$_4$Cl was added and the mixture was extracted three times with Et$_2$O. The combined org. extracts were dried over Na$_2$SO$_4$, filtered, and the solvent was removed under reduced pressure. Purification of the residue by FC (10:1 hept-EA to 1:2) gave the title compound as a pale yellow oil. TLC: rf (50:50 hept-EA)=0.21.

[5-(2-Methyl-[1,3]dioxolan-2-yl)-pyridin-3-yl]-methanol

In a flame dried round-bottomed flask equipped with a magnetic stir bar and under inert atmosphere (N$_2$), to a ice-cold solution of 6-(2-methyl-[1,3]dioxolan-2-yl)-pyridine-2-carbaldehyde (205 mg, 1.06 mmol) in MeOH (5.0 mL) was added NaBH$_4$ (52 mg, 1.31 mmol). The reaction mixture was then stirred at rt for 1 h. Water was added and the mixture was extracted with EA and twice with EA-MeOH 9:1. The combined org. extracts were dried over Na$_2$SO$_4$, filtered, and the solvent was removed under reduced pressure to give the title compound as a pale yellow solid. LC-MS-conditions 02: t$_R$=0.39 min; [M+H]$^+$=196.52.

Methanesulfonic acid 5-(2-methyl-[1,3]dioxolan-2-yl)-pyridin-3-ylmethyl ester In a flame dried round-bottomed flask equipped with a magnetic stir bar and under inert atmosphere (N$_2$), a solution of [5-(2-methyl-[1,3]dioxolan-2-yl)-pyridin-3-yl]-methanol (195 mg, 1.00 mmol) in dry CH$_2$Cl$_2$ (5.0 mL) was treated at 0° C. with Et$_3$N (0.18 mL, 1.29 mmol) followed by DMAP (12 mg, 0.10 mmol) and Ms-Cl (0.10 mL, 1.26 mmol). After stirring at 0° C. for 2 h, the reaction mixture was quenched with water (10 mL), extracted with CH$_2$Cl$_2$ (10 mL) and the combined org. extracts were dried over Na$_2$SO$_4$, filtered, and the solvents were removed under reduced pressure to give the title compound as a pale yellow oil. LC-MS-conditions 02: t$_R$=0.66 min; [M+H]$^+$=274.27.

3-(2-Methyl-[1,3]dioxolan-2-yl)-5-(4-nitro-pyrazol-1-ylmethyl)-pyridine

In a flame dried round-bottomed flask equipped with a magnetic stir bar and under inert atmosphere (N$_2$), a solution of methanesulfonic acid 5-(2-methyl-[1,3]dioxolan-2-yl)-pyridin-3-ylmethyl ester (271 mg, 0.99 mmol) in acetone (6.0 mL) was added, under inert atmosphere (N$_2$) to a solution of 4-nitro-1H-pyrazole (126 mg, 0.99 mmol) in acetone (6.0 mL). K$_2$CO$_3$ (691 mg, 4.95 mmol) followed by TBA iodide (64 mg, 0.20 mmol) were added to the reaction mixture, which was stirred at rt for 5 h. The solvent was removed under reduced pressure. Water (10 mL) and EA (10 mL) were added. The aq. layer was extracted with EA (10 mL) and the combined org. extracts were dried over Na$_2$SO$_4$, filtered, and the solvents were removed under reduced pressure. Purification of the residue by FC (10:1 to 2:1 hept-EA) gave the title compound as a pale yellow oil. TLC: rf (50:50 hept-EA)=0.1. LC-MS-conditions 02: t$_R$=0.74 min; [M+H]$^+$=291.11.

1-[5-(2-Methyl-[1,3]dioxolan-2-yl)-pyridin-3-ylmethyl]-1H-pyrazol-4-ylamine

In a flame dried round-bottomed flask equipped with a magnetic stir bar and under inert atmosphere (N$_2$), a 0.1M solution of 3-(2-methyl-[1,3]dioxolan-2-yl)-5-(4-nitro-pyrazol-1-ylmethyl)-pyridine (40 mg, 0.14 mmol), iron powder (23 mg, 0.41 mmol) and NH$_4$Cl (37 mg, 0.69 mmol) in a mixture of EtOH (4.0 mL) and water (2.0 mL) was stirred at 75° C. for 30 min. The reaction mixture was filtered while hot and concentrated under reduced pressure. CH$_2$Cl$_2$ (20 mL) was added followed by 1N NaOH (20 mL). The aq. layer was extracted with CH$_2$Cl$_2$ (2×20 mL) and the combined org. extracts were dried over MgSO$_4$, filtered, and the solvents were removed under reduced pressure to give the title compound as a deep red oil. TLC: rf (50:50 hept-EA)=0.1. LC-MS-conditions 02: t$_R$=0.35 min; [M+H]$^+$=261.29.

1-(3-Bromo-phenyl)-ethanone

In a flame dried round-bottomed flask equipped with a magnetic stir bar and under inert atmosphere (N$_2$), a suspension of commercially available 1,3-dibromobenzene (2.45 g, 10.07 mmol) in THF (25.0 mL) was treated at −78° C. with n-BuLi (4.0 mL of a 2.5M solution in hexane, 10.00 mmol). The reaction mixture was stirred for 30 min before N,N-dimethylacetaminde (1.50 mL, 16.13 mmol) was added and the solution was then allowed to warm to rt over 1 h. Sat. aq. NH$_4$Cl was then added and the aq. layer was extracted with Et$_2$O (3×50 mL). The combined org. extracts were dried over Na$_2$SO$_4$, filtered, and the solvents were removed under reduced pressure. Purification of the residue by FC (20:1 hept-EA) gave the title compound as a white solid. TLC: rf (10:1 hept-EA)=0.28. LC-MS-conditions 02: t$_R$=0.95 min.

2-(3-Bromo-phenyl)-2-methyl-[1,3]dioxolane

In a flame dried round-bottomed flask equipped with a magnetic stir bar and under inert atmosphere (N$_2$), a solution of 1-(3-bromo-phenyl)-ethanone (1360 mg, 6.83 mmol) in ethylene glycol (8.00 mL, 143.46 mmol) was treated with trimethylorthoformate (1.50 mL, 13.68 mmol) followed by LiBF$_4$ (131 mg, 1.37 mmol). The reaction mixture was heated at 95° C. for 15 h. Sat. aq. Na$_2$CO$_3$ was added and the mixture was extracted twice with ether and the combined organic extracts were dried over Na$_2$SO$_4$, filtered, and the solvent was removed under reduced pressure. Purification of the residue by FC (20:1 hept-EA) gave the title compound as a pale yellow oil. TLC: rf (10:1 hept-EA)=0.34. LC-MS-conditions 02: $t_R$=1.01 min.

3-(2-Methyl-[1,3]dioxolan-2-yl)-benzaldehyde

In a flame dried round-bottomed flask equipped with a magnetic stir bar and under inert atmosphere (N$_2$), to a solution of 2-(3-bromo-phenyl)-2-methyl-[1,3]dioxolane (944 mg, 3.88 mmol) in THF (20.0 mL) at −78° C. was added dropwise n-BuLi (1.60 mL of a 2.5M solution in hexane, 4.00 mmol). The reaction mixture was then stirred at −78° C. for 30 min before DMF (0.40 mL, 5.17 mmol) was added dropwise. The reaction mixture was allowed to warm to rt over 1 h. Sat. aq. NH$_4$Cl was added and the mixture was extracted three times with Et$_2$O. The combined org. extracts were dried over Na$_2$SO$_4$, filtered, and the solvent was removed under reduced pressure to give the crude title compound as a pale yellow oil. LC-MS-conditions 02: $t_R$=0.87 min.

[3-(2-Methyl-[1,3]dioxolan-2-yl)-phenyl]-methanol

In a flame dried round-bottomed flask equipped with a magnetic stir bar and under inert atmosphere (N$_2$), to a ice-cold solution of 3-(2-methyl-[1,3]dioxolan-2-yl)-benzaldehyde (896 mg, 4.66 mmol) in MeOH (10.0 mL) was added NaBH$_4$ (228 mg, 5.79 mmol in four equal portions). The reaction mixture was then stirred at rt for 1 h. Water was added and the mixture was extracted twice with EA. The combined org. extracts were washed with brine, dried over Na$_2$SO$_4$, filtered, and the solvent was removed under reduced pressure to give the title compound as a colorless oil. TLC: rf (50:50 hept-EA)=0.28. LC-MS-conditions 02: $t_R$=0.74 min; [M+H]$^+$=195.71.

Methanesulfonic acid 3-(2-methyl-[1,3]dioxolan-2-yl)-benzyl ester

In a flame dried round-bottomed flask equipped with a magnetic stir bar and under inert atmosphere (N$_2$), a solution of [3-(2-methyl-[1,3]dioxolan-2-yl)-phenyl]-methanol (786 mg, 4.05 mmol) in dry CH$_2$Cl$_2$ (10.0 mL) was treated at 0° C. with Et$_3$N (0.75 mL, 5.33 mmol) followed by DMAP (49 mg, 0.41 mmol) and Ms-Cl (0.40 mL, 5.15 mmol). After stirring at 0° C. for 1 h, the reaction mixture was quenched with water (10 mL), extracted with CH$_2$Cl$_2$ (10 mL) and the combined org. extracts were dried over Na$_2$SO$_4$, filtered, and the solvents were removed under reduced pressure. Purification of the residue by FC (80:20 to 20:10 hept-EA) gave the title compound as a white solid. LC-MS-conditions 02: $t_R$=0.91 min.

1-[3-(2-Methyl-[1,3]dioxolan-2-yl)-benzyl]-4-nitro-1H-pyrazole

In a flame dried round-bottomed flask equipped with a magnetic stir bar and under inert atmosphere (N$_2$), a solution of methanesulfonic acid 3-(2-methyl-[1,3]dioxolan-2-yl)-benzyl ester (220 mg, 0.81 mmol) and 4-nitro-1H-pyrazole (103 mg, 0.81 mmol) in acetone (8.0 mL) was treated with K$_2$CO$_3$ (564 mg, 4.04 mmol) followed by TBA bromide (48 mg, 0.15 mmol). The reaction mixture was stirred at rt for 16 h. The solvent was removed under reduced pressure. Water (10 mL) and EA (10 mL) were added. The aq. layer was extracted with EA (10 mL) and the combined org. extracts were dried over Na$_2$SO$_4$, filtered, and the solvents were removed under reduced pressure. Purification of the residue by FC (80:20 hept-EA) gave the title compound as a pale yellow solid. TLC: rf (50:50 hept-EA)=0.5. LC-MS-conditions 02: $t_R$=0.97 min.

1-[3-(2-Methyl-[1,3]dioxolan-2-yl)-benzyl]-1H-pyrazol-4-ylamine

In a flame dried round-bottomed flask equipped with a magnetic stir bar and under inert atmosphere (N$_2$), a solution of 1-[3-(2-methyl-[1,3]dioxolan-2-yl)-benzyl]-4-nitro-1H-pyrazole (148 mg, 0.51 mmol), iron powder (87 mg, 1.54 mmol) and NH$_4$Cl (138 mg, 2.56 mmol) in a mixture of EtOH (2.0 mL) and water (1.0 mL) was stirred at 75° C. for 2 h. The reaction mixture was filtered while hot and concentrated under reduced pressure. CH$_2$Cl$_2$ (20 mL) was added followed by 1N NaOH (20 mL). The aq. layer was extracted with CH$_2$Cl$_2$ (2×20 mL) and the combined org. extracts were dried over Na$_2$SO$_4$, filtered, and the solvents were removed under reduced pressure to give the title compound as a deep red oil. LC-MS-conditions 02: $t_R$=0.65 min; [M+H]$^+$=260.25.

5-[3-(2-Methoxy-ethyl)-phenyl]-oxazole-4-carboxylic acid methyl ester

In a flame dried round-bottomed flask equipped with a magnetic stir bar and under inert atmosphere (N$_2$), a solution of 5-[3-(2-hydroxy-ethyl)-phenyl]-oxazole-4-carboxylic acid (100 mg, 0.43 mmol) in DMF (1.0 mL) was treated at 0° C. with NaH (56 mg, 1.29 mmol) and the resulting mixture was stirred for 45 min at 0° C. Methyl iodide (0.14 mL, 2.14 mmol) was then added and the reaction mixture was stirred at rt for 45 min. The reaction mixture was quenched with sat. aq. NH$_4$Cl (20 mL), extracted with EA (2×20 mL) and the combined org. extracts were washed with water (2×20 mL) dried over MgSO$_4$, filtered, and the solvents were removed under reduced pressure to give the title compound. LC-MS-conditions 02: $t_R$=0.92 min; [M+H]$^+$=262.38.

5-[3-(2-Isopropoxy-ethyl)-phenyl]-oxazole-4-carboxylic acid isopropyl ester

In a flame dried round-bottomed flask equipped with a magnetic stir bar and under inert atmosphere (N$_2$), a solution of 5-[3-(2-hydroxy-ethyl)-phenyl]-oxazole-4-carboxylic acid (200 mg, 0.86 mmol) in DMF (2.0 mL) was treated at 0° C. with NaH (112 mg, 2.57 mmol) and the resulting mixture was stirred for 45 min at 0° C. 2-Iodopropane (0.44 mL, 4.28 mmol) was then added and the reaction mixture was stirred at rt until completion. The reaction mixture was quenched with sat. aq. NH$_4$Cl (20 mL), extracted with EA (2×20 mL) and the combined org. extracts were washed with water (2×20 mL) dried over MgSO$_4$, filtered, and the solvents were removed under reduced pressure. Purification of the residue by FC (1:1 hept-EA) gave the title compound as a white solid. TLC: rf (1:1 hept-EA)=0.49 to give the title compound as a yellow oil. LC-MS-conditions 02: $t_R$=1.06 min; [M+H]$^+$=317.16.

3-(2-Hydroxy-ethyl)-benzoic acid

In a flame dried round-bottomed flask equipped with a magnetic stir bar and under inert atmosphere (N$_2$), to a solution of 3-bromophenethyl alcohol (2.34 g, 11.29 mmol) and N,N,N',N'-tetramethylethylendiamine (3.24 mL, 22.58 mmol) in $Et_2O$ (29.0 mL) at −78° C. was added dropwise n-BuLi (14.0 mL of a 1.6M solution in hexane, 22.59 mmol), maintaining the temperature at −78° C. The reaction mixture was then stirred at −20° C. for 2 h. Dry carbon dioxide gas was then bubbled for 10 min through the reaction mixture at −78° C. The cooling bath was removed and the reaction mixture was stirred for 1 h. The reaction mixture was extracted with water (50 mL). The aqueous layer was acidified to pH=1 with 2N HCl and extracted with EA (2×75 mL). The combined org. extracts were dried over $MgSO_4$, filtered, and the solvents were removed under reduced pressure to give the title compound as a beige solid. LC-MS-conditions 02: $t_R$=0.67 min.

1-(2-Bromo-pyridin-4-yl)-ethanone

In a flame dried round-bottomed flask equipped with a magnetic stir bar and under inert atmosphere ($N_2$), a suspension of commercially available 2,4-dibromo-pyridine (3.30 g, 13.9 mmol) in dry $Et_2O$ (75 mL) was treated with n-BuLi (5.85 mL of a 2.5M solution in hexanes, 14.6 mmol) at −78° C. The reaction mixture was stirred at this temperature for 30 min. N,N-Dimethyl-acetamide (2.6 mL, 27.9 mmol) was then added and the mixture allowed to warm to rt over a period of 1 h and stirred at this temperature for 30 min. The reaction was quenched by the addition of sat. aq. $NH_4Cl$ (50 mL). The layers were separated and the aq. layer extracted with $Et_2O$ (2×50 mL). The combined org. extracts were dried over $Na_2SO_4$, filtered, and the solvent was removed under reduced pressure. Purification of the residue by FC (20:1 to 5:1 hept-EA) gave the title compound as a white solid. TLC: rf (1:1 hept-EA)=0.41. LC-MS-conditions 02: $t_R$=0.81 min; $[M+H]^+$=200.61.

2-Bromo-4-(2-methyl-[1,3]dioxolan-2-yl)-pyridine

In a flame dried round-bottomed flask equipped with a magnetic stir bar and under inert atmosphere ($N_2$), a mixture of 1-(2-bromo-pyridin-4-yl)-ethanone (490 mg, 2.45 mmol) in ethylene glycol (2.6 mL) was treated with trimethylorthoformate (0.55 mL, 5.00 mmol) followed by $LiBF_4$ (47 mg, 0.50 mmol). The reaction mixture was heated at 95° C. overnight. Sat. aq. $Na_2CO_3$ (5 mL) was added and the mixture was extracted with $Et_2O$ (2×20 mL). The org. extracts were dried over $Na_2SO_4$, filtered, and the solvent was removed under reduced pressure. Purification of the residue by FC (20:1 to 10:1 hept-EA) gave the title compound as a yellow oil. TLC: rf (1:1 hept-EA)=0.57. LC-MS-conditions 02: $t_R$=0.88 min; $[M+AcCN+H]^+$=285.22.

4-(2-Methyl-[1,3]dioxolan-2-yl)-pyridine-2-carbaldehyde

In a flame dried round-bottomed flask equipped with a magnetic stir bar and under inert atmosphere ($N_2$), to a solution of 2-bromo-4-(2-methyl-[1,3]dioxolan-2-yl)-pyridine (520 mg, 2.13 mmol) in dry $Et_2O$ (15 mL) was added n-BuLi (0.85 mL of a 2.5M solution in hexanes, 2.13 mmol) at −78° C. The reaction mixture was then stirred for 30 min at −78° C. before DMF (0.2 mL, 2.58 mmol) was added dropwise. The reaction mixture was allowed to warm up to rt and stirred at this temperature for 10 min. Sat. aq. $NH_4Cl$ (10 mL) was added, the layers separated and the aq. layer extracted with $Et_2O$ (3×10 mL). The combined org. extracts were dried over $Na_2SO_4$, filtered, and the solvent was removed under reduced pressure. Purification of the residue by FC (10:1 to 2:1 hept-EA) gave the title compound as a pale yellow oil. TLC: rf (1:1 hept-EA)=0.30.

[4-(2-Methyl-[1,3]dioxolan-2-yl)-pyridin-2-yl]-methanol

In a flame dried round-bottomed flask equipped with a magnetic stir bar and under inert atmosphere ($N_2$), 4-(2-methyl-[1,3]dioxolan-2-yl)-pyridine-2-carbaldehyde (195 mg, 1.01 mmol) was dissolved in MeOH (5 mL). $NaBH_4$ (49 mg, 1.25 mmol) was added portionwise at 0° C. and the reaction mixture was stirred at rt for 1 h. Water was added and the mixture extracted with EA (3×10 mL). The combined org. extracts were dried over $Na_2SO_4$, filtered, and the solvents were removed under reduced pressure to give the title compound as a yellow oil. LC-MS-conditions 02: $t_R$=0.41 min; $[M+H]^+$=196.51.

4-(2-Methyl-[1,3]dioxolan-2-yl)-2-(4-nitro-pyrazol-1-ylmethyl)-pyridine

In a flame dried round-bottomed flask equipped with a magnetic stir bar and under inert atmosphere ($N_2$), a solution of [4-(2-methyl-[1,3]dioxolan-2-yl)-pyridin-2-yl]-methanol (177 mg, 0.91 mmol) in dry $CH_2Cl_2$ (5 mL) was treated at 0° C. with $Et_3N$ (0.16 mL, 1.17 mmol) followed by DMAP (11 mg, 0.09 mmol) and Ms-Cl (0.09 mL, 1.14 mmol). After stirring at rt for 2 h, the reaction was quenched with water (5 mL). The org. layer was dried over $MgSO_4$, filtered, and the solvent was removed under reduced pressure to give crude methanesulfonic acid 4-(2-methyl-[1,3]dioxolan-2-yl)-pyridin-2-ylmethyl ester as a red oil. The crude material (246 mg) was dissolved in acetone (12 mL) under inert atmosphere ($N_2$). 4-Nitro-1H-pyrazole (114 mg, 0.90 mmol) was added followed by $K_2CO_3$ (628 mg, 4.50 mmol) and TBA bromide (58 mg, 0.18 mmol). The reaction mixture was stirred overnight at rt and concentrated to dryness. The residue was partitioned between water (5 mL) and EA (10 mL). The layers were separated and the aq. layer extracted with EA (2×10 mL). The combined org. extracts were dried over $MgSO_4$, filtered, and the solvent removed under reduced pressure. Purification of the residue by FC (10:1 to 2:1 hept-EA) gave the title compound as a pale yellow solid. TLC: rf (1:1 hept-EA)=0.10. LC-MS-conditions 02: $t_R$=0.85 min, $[M+H]^+$=291.31.

1-[4-(2-Methyl-[1,3]dioxolan-2-yl)-pyridin-2-ylmethyl]-1H-pyrazol-4-ylamine

In a flame dried round-bottomed flask equipped with a magnetic stir bar and under inert atmosphere ($N_2$), a mixture of 4-(2-methyl-[1,3]dioxolan-2-yl)-2-(4-nitro-pyrazol-1-ylmethyl)-pyridine (174 mg, 0.60 mmol), iron powder (101 mg, 1.80 mmol) and $NH_4Cl$ (162 mg, 3.00 mmol) in a mixture of EtOH (4.0 mL) and water (2.0 mL) was stirred at 75° C. for 1 h. The reaction mixture was filtered while hot and the filter cake rinsed with EtOH. The filtrate was concentrated under reduced pressure and the residue partitioned between $CH_2Cl_2$ (10 mL) and aq. 1M NaOH (10 mL). The aq. layer was extracted with $CH_2Cl_2$ (2×10 mL). The combined org. extracts were dried over $MgSO_4$, filtered, and the solvent removed under reduced pressure to give the title compound as a red oil. LC-MS-conditions 02: $t_R$=0.55 min, $[M+H]^+$=261.39.

2-Bromo-pyridine-4-carbaldehyde

In a flame dried round-bottomed flask equipped with a magnetic stir bar and under inert atmosphere ($N_2$), a suspension of commercially available 2,4-dibromo-pyridine (1.90 g, 8.02 mmol) in dry Et$_2$O (40 mL) was treated with n-BuLi (3.36 mL of a 2.5M solution in hexanes, 8.42 mmol) at −78° C. The reaction mixture was stirred at this temperature for 30 min. N,N-Dimethyl-formamide (0.78 mL, 10.03 mmol) was then added and the mixture allowed to warm to rt over a period of 1 h and stirred at this temperature for 20 min. The reaction was quenched by the addition of sat. aq. NH$_4$Cl (30 mL). The layers were separated and the aq. layer extracted with Et$_2$O (3×50 mL). The combined org. extracts were dried over Na$_2$SO$_4$, filtered, and the solvent removed under reduced pressure. Purification of the residue by FC (10:1 to 2:1 hept-EA) gave the title compound as a white solid. TLC: rf (1:1 hept-EA)=0.44.

(2-Bromo-pyridin-4-yl)-methanol

In a flame dried round-bottomed flask equipped with a magnetic stir bar and under inert atmosphere (N$_2$), 2-bromo-pyridine-4-carbaldehyde (904 mg, 4.86 mmol) was dissolved in MeOH (10 mL). NaBH$_4$ (236 mg, 5.99 mmol) was added portionwise at 0° C. and the reaction mixture stirred at rt for 1 h. Water (10 mL) was added and the reaction extracted with EA (3×20 mL). The combined org. extracts were dried over Na$_2$SO$_4$, filtered, and the solvents were removed under reduced pressure to give the title compound as a white solid. TLC: rf (1:1 hept-EA)=0.22. LC-MS-conditions 02: $t_R$=0.63 min; [M+H]$^+$=190.33.

2-Bromo-4-(tert-butyl-dimethyl-silanyloxymethyl)-pyridine

In a flame dried round-bottomed flask equipped with a magnetic stir bar and under inert atmosphere (N$_2$), (2-bromo-pyridin-4-yl)-methanol (780 mg, 4.15 mmol) was dissolved in dry CH$_2$Cl$_2$ (21 mL). tert-Butyldimethylsilyl chloride (688 mg, 4.56 mmol) was added at 0° C. followed by imidazole (579 mg, 8.50 mmol). The reaction mixture was stirred at rt for 2 h. 10% Aq. K$_2$CO$_3$ (10 mL) was added, the layers separated and the aq. layer extracted with CH$_2$Cl$_2$ (2×20 mL). The combined org. extracts were dried over MgSO$_4$, filtered, and the solvent removed under reduced pressure to give the title compound as a colorless oil. TLC: rf (1:1 hept-EA)=0.80. LC-MS-conditions 02: $t_R$=1.17 min; [M+H]$^+$=302.29.

1-[4-(tert-Butyl-dimethyl-silanyloxymethyl)-pyridin-2-yl]-ethanone

In a flame dried round-bottomed flask equipped with a magnetic stir bar and under inert atmosphere (N$_2$), to a solution of 2-bromo-4-(tert-butyl-dimethyl-silanyloxymethyl)-pyridine (1.04 g, 3.44 mmol) in dry Et$_2$O (50 mL) was added n-BuLi (1.60 mL of a 2.5M solution in hexanes, 3.96 mmol) at −78° C. The reaction mixture was then stirred for 1 h at −78° C. before N,N-dimethylacetamide (0.64 mL, 6.88 mmol) was added dropwise. The reaction mixture was allowed to warm up to rt and stirred at this temperature for 10 min. Sat. aq. NH$_4$Cl (20 mL) was added, the layers separated and the aq. layer extracted with Et$_2$O (3×30 mL). The combined org. extracts were dried over Na$_2$SO$_4$, filtered, and the solvent was removed under reduced pressure. Purification of the residue by FC (20:1 to 5:1 hept-EA) gave the title compound as a pale yellow oil. TLC: rf (1:2 hept-EA)=0.64. LC-MS-conditions 02: $t_R$=1.12 min; [M+H]$^+$=265.84.

1-(4-Hydroxymethyl-pyridin-2-yl)-ethanone

In a flame dried round-bottomed flask equipped with a magnetic stir bar and under inert atmosphere (N$_2$), a solution of 1-[4-(tert-butyl-dimethyl-silanyloxymethyl)-pyridin-2-yl]-ethanone (340 mg, 1.28 mmol) in dry THF (5 mL) was treated at 0° C. with TBAF (1.9 mL of a 1M solution in THF, 1.90 mmol). The reaction mixture was stirred at 0° C. for 5 min and at rt for 1 h30. The mixture was then diluted with EA (10 mL), washed with brine (3×10 mL), dried over MgSO$_4$, filtered and concentrated under reduced pressure. Purification of the residue by FC (5:1 to 1:3 hept-EA) gave the title compound as a yellow oil. TLC: rf (1:2 hept-EA)=0.10. LC-MS-conditions 02: $t_R$=0.40 min; [M+H]$^+$=152.24.

1-[4-(4-Nitro-pyrazol-1-ylmethyl)-pyridin-2-yl]-ethanone

In a flame dried round-bottomed flask equipped with a magnetic stir bar and under inert atmosphere (N$_2$), a solution of 1-(4-hydroxymethyl-pyridin-2-yl)-ethanone (165 mg, 1.09 mmol) in dry CH$_2$Cl$_2$ (5 mL) was treated at 0° C. with Et$_3$N (0.20 mL, 1.43 mmol) followed by DMAP (13 mg, 0.10 mmol) and Ms-Cl (0.11 mL, 1.39 mmol). After stirring at 0° C. for 1 h30, the reaction was quenched with water (5 mL). The org. layer was dried over MgSO$_4$, filtered, and the solvent was removed under reduced pressure to give crude methanesulfonic acid 2-acetyl-pyridin-4-ylmethyl ester as a brown oil. The crude material (250 mg) was dissolved in acetone (8 mL) under inert atmosphere (N$_2$). 4-Nitro-1H-pyrazole (139 mg, 1.09 mmol) was added followed by K$_2$CO$_3$ (761 mg, 5.45 mmol) and TBA bromide (70 mg, 0.22 mmol). The reaction mixture was stirred at rt for 2 h and concentrated to dryness. The residue was partitioned between water (5 mL) and EA (10 mL). The layers were separated and the aq. layer extracted with EA (2×10 mL). The combined org. extracts were dried over MgSO$_4$, filtered, and the solvent removed under reduced pressure. Purification of the residue by FC (10:1 to 2:1 hept-EA) gave the title compound as a yellow oil. TLC: rf (1:2 hept-EA)=0.41. LC-MS-conditions 02: $t_R$=0.84 min, [M+H]$^+$=247.33.

1-[4-(4-Amino-pyrazol-1-ylmethyl)-pyridin-2-yl]-ethanone

In a flame dried round-bottomed flask equipped with a magnetic stir bar and under inert atmosphere (N$_2$), a mixture of 1-[4-(4-nitro-pyrazol-1-ylmethyl)-pyridin-2-yl]-ethanone (250 mg, 1.01 mmol), iron powder (172 mg, 3.05 mmol) and NH$_4$Cl (274 mg, 5.08 mmol) in a mixture of EtOH (4.0 mL) and water (2.0 mL) was stirred at 75° C. for 5 h. The reaction mixture was filtered while hot and the filter cake rinsed with EtOH. The filtrate was concentrated under reduced pressure and the residue partitioned between CH$_2$Cl$_2$ (10 mL) and aq. 1M NaOH (10 mL). The aq. layer was extracted with CH$_2$Cl$_2$ (2×10 mL). The combined org. extracts were dried over MgSO$_4$, filtered, and the solvent removed under reduced pressure to give the title compound as a brown oil. TLC: rf (1:2 hept-EA)=0.05. LC-MS-conditions 02: $t_R$=0.50 min, [M+H]$^+$=217.47.

4-Bromo-thiazole-2-carbaldehyde

In a flame dried round-bottomed flask equipped with a magnetic stir bar and under inert atmosphere (N$_2$), a solution of commercially available 2,4-dibromo-thiazole (3.50 g, 14.41 mmol) in dry Et$_2$O (120 mL) was treated with n-BuLi (5.9 mL of a 2.5M solution in hexanes, 14.72 mmol) at −78° C. The reaction mixture was stirred at this temperature for 30 min. N,N-Dimethylformamide (1.35 mL, 14.47 mmol) was then added and the mixture allowed to warm to rt over a period of 1 h. The reaction was quenched by the addition of sat. aq. NH$_4$Cl (50 mL). The layers were separated and the aq. layer extracted with Et$_2$O (3×50 mL). The combined org. extracts dried over Na$_2$SO$_4$, filtered, and the solvents were removed under reduced pressure. Purification of the residue by FC (10:1 to 3:1 hept-EA) gave the title compound as a pale yellow solid. TLC: rf (1:1 hept-EA)=0.21. LC-MS-conditions 02: t$_R$=0.81 min.

(4-Bromo-thiazol-2-yl)-methanol

In a flame dried round-bottomed flask equipped with a magnetic stir bar and under inert atmosphere (N$_2$), 4-bromothiazole-2-carbaldehyde (1.68 g, 8.75 mmol) was dissolved in MeOH (10 mL). NaBH$_4$ (428 mg, 10.86 mmol) was added portionwise at 0° C. and the reaction mixture stirred at rt for 1 h. Water (10 mL) was added and the mixture extracted with EA (3×20 mL). The combined org. extracts were dried over Na$_2$SO$_4$, filtered, and the solvents were removed under reduced pressure. Purification of the residue by FC (6:1 to 2:1 hept-EA) gave the title compound as a pale yellow solid. TLC: rf (1:1 hept-EA)=0.31. LC-MS-conditions 02: t$_R$=0.62 min; [M+H]$^+$=194.63.

4-Bromo-2-(tert-butyl-dimethyl-silanyloxymethyl)-thiazole

In a flame dried round-bottomed flask equipped with a magnetic stir bar and under inert atmosphere (N$_2$), (4-bromothiazol-2-yl)-methanol (1.37 g, 7.06 mmol) was dissolved in dry CH$_2$Cl$_2$ (21 mL). tert-Butyldimethylsilyl chloride (1.17 g, 7.77 mmol) was added at 0° C. followed by imidazole (985 mg, 14.47 mmol). The reaction mixture was stirred at rt for 2 h. 10% Aq. K$_2$CO$_3$ (10 mL) was added, the layers separated and the aq. layer extracted with CH$_2$Cl$_2$ (2×20 mL). The combined org. extracts were dried over MgSO$_4$, filtered, and the solvent removed under reduced pressure to give the title compound as a colorless oil. TLC: rf (1:1 hept-EA)=0.80.

1-[2-(tert-Butyl-dimethyl-silanyloxymethyl)-thiazol-4-yl]-ethanone

In a flame dried round-bottomed flask equipped with a magnetic stir bar and under inert atmosphere (N$_2$), to a solution of 4-bromo-2-(tert-butyl-dimethyl-silanyloxymethyl)-thiazole (1.94 g, 6.29 mmol) in dry Et$_2$O (50 mL) was added n-BuLi (2.76 mL of a 2.5M solution in hexanes, 6.92 mmol) at −78° C. The reaction mixture was then stirred for 30 min at −78° C. before N,N-dimethylacetamide (1.17 mL, 12.58 mmol) was added dropwise. The reaction mixture was allowed to warm up to rt over a period of 1 h and stirred at this temperature for 20 min. Sat. aq. NH$_4$Cl (20 mL) was added, the layers separated and the aq. layer extracted with Et$_2$O (3×30 mL). The combined org. extracts were dried over Na$_2$SO$_4$, filtered, and the solvent was removed under reduced pressure. Purification of the residue by FC (20:1 to 5:1 hept-EA) gave the title compound as a yellow solid. TLC: rf (1:1 hept-EA)=0.51. LC-MS-conditions 02: t$_R$=1.11 min; [M+H]$^+$=272.39.

2-(tert-Butyl-dimethyl-silanyloxymethyl)-4-(2-methyl-[1,3]dioxolan-2-yl)-thiazole In a flame dried round-bottomed flask equipped with a magnetic stir bar and under inert atmosphere (N$_2$), a solution of 1-[2-(tert-butyl-dimethyl-silanyloxymethyl)-thiazol-4-yl]-ethanone (1.77 g, 6.52 mmol) in ethylene glycol (7 mL) was treated with trimethylorthoformate (1.46 mL, 13.29 mmol) followed by LiBF$_4$ (125 mg, 1.30 mmol). The reaction mixture was heated at 95° C. for 4 h. Sat. aq. Na$_2$CO$_3$ (5 mL) was added and the mixture was extracted with Et$_2$O (2×20 mL). The org. extracts were dried over Na$_2$SO$_4$, filtered, and the solvent was removed under reduced pressure. Purification of the residue by FC (20:1 to 3:1 hept-EA) gave the title compound as a brown oil. TLC: rf (1:1 hept-EA)=0.56. LC-MS-conditions 02: t$_R$=1.11 min; [M+H]$^+$=316.36.

[4-(2-Methyl-[1,3]dioxolan-2-yl)-thiazol-2-yl]-methanol

In a flame dried round-bottomed flask equipped with a magnetic stir bar and under inert atmosphere (N$_2$), a solution of 2-(tert-butyl-dimethyl-silanyloxymethyl)-4-(2-methyl-[1,3]dioxolan-2-yl)-thiazole (1.30 g, 4.12 mmol) in dry THF (10 mL) was treated at 0° C. with TBAF (6.2 mL of a 1M solution in THF, 6.20 mmol). The reaction mixture was stirred at 0° C. for 5 min and at rt for 1 h30. The mixture was then diluted with EA (10 mL), washed with brine (3×10 mL), dried over MgSO$_4$, filtered and concentrated under reduced pressure. Purification of the residue by FC (5:1 to 1:3 hept-EA) gave the title compound as a yellow oil. TLC: rf (1:2 hept-EA)=0.20. LC-MS-conditions 02: t$_R$=0.59 min; [M+H]$^+$=202.48.

4-(2-Methyl-[1,3]dioxolan-2-yl)-2-(4-nitro-pyrazol-1-ylmethyl)-thiazole

In a flame dried round-bottomed flask equipped with a magnetic stir bar and under inert atmosphere (N$_2$), a solution of [4-(2-methyl-[1,3]dioxolan-2-yl)-thiazol-2-yl]-methanol (745 mg, 3.70 mmol) in dry CH$_2$Cl$_2$ (5 mL) was treated at 0° C. with Et$_3$N (0.67 mL, 4.79 mmol) followed by DMAP (46 mg, 0.37 mmol) and Ms-Cl (0.37 mL, 4.67 mmol). After stirring at 0° C. for 1 h30, the reaction was quenched with water (5 mL). The org. layer was dried over MgSO$_4$, filtered, and the solvents were removed under reduced pressure to give crude methanesulfonic acid 4-(2-methyl-[1,3]dioxolan-2-yl)-thiazol-2-ylmethyl ester as a yellow oil. The crude material (580 mg) was dissolved in acetone (12 mL) under inert atmosphere (N$_2$). 4-Nitro-1H-pyrazole (264 mg, 2.08 mmol) was added followed by K$_2$CO$_3$ (1.45 g, 10.38 mmol) and TBA bromide (134 mg, 0.41 mmol). The reaction mixture was stirred overnight at rt and concentrated to dryness. The residue was partitioned between water (10 mL) and EA (20 mL). The layers were separated and the aq. layer extracted with EA (2×30 mL). The combined org. extracts were dried over MgSO$_4$, filtered, and the solvent removed under reduced pressure. Purification of the residue by FC (10:1 to 2:1 hept-EA) gave the title compound as a yellow oil. TLC: rf (1:2 hept-EA)=0.41. LC-MS-conditions 02: t$_R$=0.86 min, [M+H]$^+$= 297.35.

1-[4-(2-Methyl-[1,3]dioxolan-2-yl)-thiazol-2-ylmethyl]-1H-pyrazol-4-ylamine

In a flame dried round-bottomed flask equipped with a magnetic stir bar and under inert atmosphere (N$_2$), a mixture of 4-(2-methyl-[1,3]dioxolan-2-yl)-2-(4-nitro-pyrazol-1-ylmethyl)-thiazole (595 mg, 2.01 mmol), iron powder (340 mg, 6.02 mmol) and NH$_4$Cl (542 mg, 10.04 mmol) in a mixture of EtOH (10.0 mL) and water (5.0 mL) was stirred at 75° C. for 1 h. The reaction mixture was filtered while hot and the filter cake rinsed with EtOH. The filtrate was concentrated under reduced pressure and the residue partitioned between CH$_2$Cl$_2$ (10 mL) and aq. 1M NaOH (10 mL). The aq. layer was extracted with CH$_2$Cl$_2$ (2×10 mL). The combined org. extracts were dried over MgSO$_4$, filtered, and the solvent removed under reduced pressure to give the title compound as a red oil. TLC: rf (1:2 hept-EA)=0.10. LC-MS-conditions 02: t$_R$=0.51 min, [M+H]$^+$=267.18.

5-{3-[2-(tert-Butyl-dimethyl-silanyloxy)-ethyl]-phenyl}-oxazole-4-carboxylic acid methyl ester In a flame dried round-bottomed flask equipped with a magnetic stir bar and under inert atmosphere (N$_2$), 5-[3-(2-hydroxy-ethyl)-phenyl]-oxazole-4-carboxylic acid methyl ester (200 mg, 0.81 mmol) was dissolved in dry THF (5.0 mL). tert-Butyldimethylsilyl chloride (124 mg, 0.83 mmol) was added at 0° C. followed by imidazole (61 mg, 0.89 mmol). The reaction mixture was stirred at rt for 2 days. Sat. aq. NH$_4$Cl (10 mL) and EA (10 mL) were added, the layers separated and the aq. layer extracted with EA (2×10 mL). The combined org. extracts were dried over MgSO$_4$, filtered, and the solvent removed under reduced pressure. Purification of the residue by FC (20:80 hept-EA) gave the title compound as a colorless oil. TLC: rf (20:80 hept-EA)=0.21. LC-MS-conditions 02: t$_R$=1.19 min, [M+H]$^+$=362.50.

5-{3-[2-(tert-Butyl-dimethyl-silanyloxy)-ethyl]-phenyl}-oxazole-4-carboxylic acid In a flame dried round-bottomed flask equipped with a magnetic stir bar and under inert atmosphere (N$_2$), a solution of 5-{3-[2-(tert-butyl-dimethyl-silanyloxy)-ethyl]-phenyl}-oxazole-4-carboxylic acid methyl ester (110 mg, 0.30 mmol) in THF (0.5 mL) and H$_2$O (0.5 mL) was treated with LiOH (18 mg, 0.43 mmol). The reaction mixture was stirred at rt for 2.5 h, extracted with EA (2×5 mL), the organic layer was washed with 1N HCl (2 mL) dried over MgSO$_4$, filtered, and the solvent removed under reduced pressure to give the title compound as a white solid. LC-MS-conditions 02: t$_R$=1.08 min, [M+H]$^+$=348.40.

5-{3-[2-(tert-Butyl-dimethyl-silanyloxy)-ethyl]-phenyl}-oxazole-4-carboxylic acid {1-[5-(2-methyl-[1,3]dioxolan-2-yl)-furan-2-ylmethyl]-1H-pyrazol-3-yl}-amide In a flame dried round-bottomed flask equipped with a magnetic stir bar and under inert atmosphere (N$_2$), a solution of 5-{3-[2-(tert-butyl-dimethyl-silanyloxy)-ethyl]-phenyl}-oxazole-4-carboxylic acid (130 mg, 0.37 mmol) in CH$_2$Cl$_2$ (2.7 mL) was treated sequentially with DMAP (11 mg, 0.09 mmol), HOBt (60 mg, 0.45 mmol), EDC (179 mg, 0.94 mmol) and DIPEA (0.25 mL, 1.50 mmol) and the reaction mixture was stirred at rt for 1 h. A solution of 1-[5-(2-methyl-[1,3]dioxolan-2-yl)-furan-2-ylmethyl]-1H-pyrazol-3-ylamine (93 mg, 0.37 mmol) in CH$_2$Cl$_2$ (1.0 mL) was then added and the reaction mixture was stirred at rt for 48 h. CH$_2$Cl$_2$ (10 mL) was added followed by water (10 mL). The organic layer was dried over MgSO$_4$, filtered, and the solvent removed under reduced pressure. Purification of the residue by FC (1:2 hept-EA) gave the title compound as a colorless oil. TLC: rf (1:2 hept-EA)=0.26. LC-MS-conditions 02: t$_R$=1.22 min, [M+H]$^+$=579.74.

5-(3-tert-Butoxycarbonyl-phenyl)-oxazole-4-carboxylic acid methyl ester

In a flame dried round-bottomed flask equipped with a magnetic stir bar and under inert atmosphere (N$_2$), a suspension of isophthalic acid mono-tert-butyl ester (4.00 g, 18.00 mmol) and potassium carbonate sesquihydrate (6.03 g, 43.20 mmol) in DMF (36.0 mL) was treated with a solution of methyl isocyanoacetate (3.45 mL, 36.00 mmol) in DMF (6.0 mL). After 5 min, the reaction mixture was cooled to 0° C. and a solution of DPPA (4.01 mL, 18.00 mmol) in DMF (6 mL) was added dropwise. The resulting mixture was stirred at 0° C. for 2 h and then overnight at rt. A 1:1 mixture of toluene:EA (400 mL) was added and the organic layer was washed with water (150 mL), 10% aq. citric acid solution (150 mL) and sat. aq. NaHCO$_3$ (150 mL). The organic layer was dried over MgSO$_4$, filtered, and the solvent removed under reduced pressure. Purification of the residue by FC (60:40 hept-EA) gave the title compound as a white solid. TLC: rf (60:40 hept-EA)=0.27. LC-MS-conditions 02: t$_R$=1.04 min, [M+H]$^+$= 304.32.

5-(3-Carboxy-phenyl)-oxazole-4-carboxylic acid methyl ester

In a flame dried round-bottomed flask equipped with a magnetic stir bar and under inert atmosphere (N$_2$), a solution of 5-(3-tert-butoxycarbonyl-phenyl)-oxazole-4-carboxylic acid methyl ester (1.00 g, 3.30 mmol) in TFA (13.3 mL) was stirred at rt for 45 min. The TFA was removed under reduced pressure and the residue was triturate in Et$_2$O, filtered and washed with Et$_2$O to give the title compound as a white powder. LC-MS-conditions 02: t$_R$=0.79 min, [M+H]$^+$=248.20.

5-(3-Hydroxymethyl-phenyl)-oxazole-4-carboxylic acid methyl ester

In a flame dried round-bottomed flask equipped with a magnetic stir bar and under inert atmosphere (N$_2$), a suspension of 5-(3-carboxy-phenyl)-oxazole-4-carboxylic acid methyl ester (500 mg, 2.02 mmol) in THF (14.0 mL) at 0° C. was treated dropwise with a BH$_3$ (10.1 mL of a 1M solution in THF, 10.11 mmol). The resulting mixture was stirred at 0° C. for 4 h. MeOH (14 mL) was then added dropwise. After 30 min, the solvent was removed under reduced pressure. EA (20 mL) was added and the organic phase was washed with 1N NaOH (10 mL), water (10 mL) and brine (10 mL). The organic layer was dried over MgSO$_4$, filtered, and the solvent removed under reduced pressure. Purification of the residue by FC (93:7 CH$_2$Cl$_2$-MeOH) gave the title compound as a white solid. TLC: rf (93:7 CH$_2$Cl$_2$-MeOH)=0.32. LC-MS-conditions 02: t$_R$=0.76 min, [M+H]$^+$=234.39.

5-(3-Hydroxymethyl-phenyl)-oxazole-4-carboxylic acid

In a flame dried round-bottomed flask equipped with a magnetic stir bar and under inert atmosphere (N$_2$), a solution of 5-(3-hydroxymethyl-phenyl)-oxazole-4-carboxylic acid methyl ester (265 mg, 1.13 mmol) in THF (11.0 mL) was treated with a 1N NaOH (5.5 mL). The resulting mixture was stirred for 1.5 h then acidified with 1N HCl, extracted twice with EA (2×25 mL) and the combined organic phases were washed with brine (10 mL). The organic layer was dried over MgSO$_4$, filtered, and the solvent removed under reduced pressure to give the title compound as a white solid. LC-MS-conditions 02: t$_R$=0.67 min, [M+AcCN+H]$^+$=261.29.

5-(3-Methoxymethyl-phenyl)-oxazole-4-carboxylic acid methyl ester

In a flame dried round-bottomed flask equipped with a magnetic stir bar and under inert atmosphere (N$_2$), a solution of 5-(3-hydroxymethyl-phenyl)-oxazole-4-carboxylic acid (100 mg, 0.43 mmol) at 0° C. in DMF (1.0 mL) was treated with NaH (56 mg, 1.29 mmol) and the resulting mixture was stirred at 0° C. for 45 min. MeI (0.14 mL, 2.14 mmol) was added and the reaction mixture was stirred at rt for 1.5 h. Sat. aq. NH$_4$Cl (20 mL) was added and the aqueous layer extracted twice with EA (2×20 mL). The combined organic layers were washed with water (2×10 mL), dried over MgSO$_4$, filtered, and the solvent removed under reduced pressure to give the title compound as a yellow oil. LC-MS-conditions 02: $t_R$=0.89 min, [M+H]$^+$=248.36.

5-(3-Methoxymethyl-phenyl)-oxazole-4-carboxylic acid

In a flame dried round-bottomed flask equipped with a magnetic stir bar and under inert atmosphere (N$_2$), a solution of 5-(3-methoxymethyl-phenyl)-oxazole-4-carboxylic acid methyl ester (280 mg, 1.13 mmol) in THF (11.0 mL) was treated with a 1N NaOH (5.5 mL). The resulting mixture was stirred for 1.5 h then acidified with 1N HCl, extracted twice with EA (2×20 mL) and the combined organic phases were washed with brine (20 mL). The organic layer was dried over MgSO$_4$, filtered, and the solvent removed under reduced pressure to give the title compound as a white solid. LC-MS-conditions 02: $t_R$=0.77 min, [M+AcCN+H]$^+$=275.35.

5-(3-Isopropoxymethyl-phenyl)-oxazole-4-carboxylic acid isopropyl ester

In a flame dried round-bottomed flask equipped with a magnetic stir bar and under inert atmosphere (N$_2$), a solution of 5-(3-hydroxymethyl-phenyl)-oxazole-4-carboxylic acid (200 mg, 0.912 mmol) at 0° C. in DMF (2.5 mL) was treated with NaH (239 mg, 5.48 mmol) and the resulting mixture was stirred at 0° C. for 45 min. 2-iodopropane (0.14 mL, 2.14 mmol) was added and the reaction mixture was stirred at rt until completion. Sat. aq. NH$_4$Cl (20 mL) was added and the aqueous layer extracted twice with EA (2×20 mL). The combined organic layers were washed with water (2×10 mL), dried over MgSO$_4$, filtered, and the solvent removed under reduced pressure. Purification of the residue by FC (1:1 Hept-EA) gave the title compound as a yellow oil. TLC: rf (1:1 Hept-EA)=0.45 to give the title compound as a yellow oil. LC-MS-conditions 02: $t_R$=1.05 min, [M+H]$^+$=304.28.

5-(3-Isopropoxymethyl-phenyl)-oxazole-4-carboxylic acid

In a flame dried round-bottomed flask equipped with a magnetic stir bar and under inert atmosphere (N$_2$), a solution of 5-(3-isopropoxymethyl-phenyl)-oxazole-4-carboxylic acid isopropyl ester (78 mg, 0.26 mmol) in THF (2.5 mL) was treated with a 1N NaOH (1.3 mL). The resulting mixture was stirred for 1.5 h then acidified with 1N HCl, extracted twice with EA (2×20 mL) and the combined organic phases were washed with brine (20 mL). The organic layer was dried over MgSO$_4$, filtered, and the solvent removed under reduced pressure to give the title compound as a yellow oil. LC-MS-conditions 02: $t_R$=0.87 min, [M+AcCN+H]$^+$=303.18.

5-[3-(tert-Butyl-dimethyl-silanyloxymethyl)-phenyl]-oxazole-4-carboxylic acid methyl ester In a flame dried round-bottomed flask equipped with a magnetic stir bar and under inert atmosphere (N$_2$), a solution of 5-(3-hydroxymethyl-phenyl)-oxazole-4-carboxylic acid methyl ester (512 mg, 2.20 mmol) in THF (12.0 mL) was treated with imidazole (209 mg, 3.07 mmol) followed by TBDMS-Cl (397 mg, 2.63 mmol). The resulting mixture was stirred at rt overnight. EA (40 mL) was added and the organic phase was washed with sat. aq. NH$_4$Cl (30 mL). The organic layer was dried over MgSO$_4$, filtered, and the solvent removed under reduced pressure. Purification of the residue by FC (70:30 Hept-EA) gave the title compound as a colorless oil. TLC: rf (70:30 Hept-EA)=0.35. LC-MS-conditions 02: $t_R$=1.18 min, [M+H]$^+$=348.43.

5-[3-(tert-Butyl-dimethyl-silanyloxymethyl)-phenyl]-oxazole-4-carboxylic acid In a flame dried round-bottomed flask equipped with a magnetic stir bar and under inert atmosphere (N$_2$), a solution of 5-[3-(tert-butyl-dimethyl-silanyloxymethyl)-phenyl]-oxazole-4-carboxylic acid methyl ester (673 mg, 1.94 mmol) in 1:1 THF:H$_2$O (6.4 mL) was treated with lithium hydroxide monohydrate (115 mg, 2.71 mmol). The resulting mixture was stirred for 2.5 h. EA (20 mL) was added and the organic phase was washed with 1N HCl (10 mL), dried over MgSO$_4$, filtered, and the solvent removed under reduced pressure to give the title compound as a white solid. LC-MS-conditions 02: $t_R$=1.07 min, [M+H]$^+$=334.13.

2-Amino-3-hydroxy-3-phenyl-propionic acid methyl ester

In a flame dried round-bottomed flask equipped with a magnetic stir bar and under inert atmosphere (N$_2$), a solution of 3-phenylserine (15.00 g, 82.79 mmol) in MeOH (78.0 mL) was treated at 0° C. with thionylchloride (6.23 mL, 91.06 mmol). The resulting mixture was then stirred at rt overnight. The volatiles were removed under reduced pressure and the residue was triturated in EA and filtered to give the title compound as a white solid. LC-MS-conditions 02: $t_R$=0.40 min, [M+AcCN+H]$^+$=237.46.

2-(2-tert-Butoxycarbonylamino-acetylamino)-3-hydroxy-3-phenyl-propionic acid methyl ester In a flame dried round-bottomed flask equipped with a magnetic stir bar and under inert atmosphere (N$_2$), a solution of tert-butoxycarbonylamino-acetic acid (906 mg, 5.12 mmol) in CH$_2$Cl$_2$ (27.0 mL) was treated at 0° C. with HOBt (777 mg, 5.64 mmol), DCC (1.17 g, 5.64 mmol) N-methylmorpholine (0.85 mL, 7.68 mmol) and 2-amino-3-hydroxy-3-phenyl-propionic acid methyl ester (1.00 g, 5.12 mmol). The resulting mixture was stirred at rt for 2 h, poured in 5% KHSO$_4$ (100 mL), stirred for 15 min, filtered and washed with CH$_2$Cl$_2$. The aqueous phase was extracted with CH$_2$Cl$_2$ and the combined organic phases were washed with sat. aq. NaHCO$_3$, brine, dried over MgSO$_4$, filtered, and the solvent removed under reduced pressure. Purification of the residue by FC(CH$_2$Cl$_2$ to 99:1 CH$_2$Cl$_2$-MeOH) gave the title compound as a white solid. TLC: rf (90:10 CH$_2$Cl$_2$-MeOH)=0.48. LC-MS-conditions 02: $t_R$=0.85 min, [M+H]$^+$=353.05.

2-(tert-Butoxycarbonylamino-methyl)-5-phenyl-oxazole-4-carboxylic acid methyl ester In a flame dried round-bottomed flask equipped with a magnetic stir bar and under inert atmosphere (N$_2$), a solution of 2-(2-tert-butoxycarbonylamino-acetylamino)-3-hydroxy-3-phenyl-propionic acid methyl ester (620 mg, 1.76 mmol) in CH$_2$Cl$_2$ (20.0 mL) was treated at 0° C. with Dess-Martin periodinane (923 mg, 2.11 mmol). The resulting mixture was stirred at rt for 1 h and filtered through a short plug of basic alumina (activity I) and sand into a flask containing a freshly prepared solution of triphenylphosphine (946 mg, 3.55 mmol), $I_2$ (902 mg, 3.52 mmol) and $Et_3N$ (0.98 ml, 7.04 mmol) in $CH_2Cl_2$ (22.0 mL). The filter cake was washed with $CH_2Cl_2$. After 15 min, the reaction mixture was transferred to a separatory funnel, treated with sat. aq. $Na_2S_2O_3$ (150 mL) and extracted with $CH_2Cl_2$ (2×150 mL). The organic layer was washed with sat. aq. $NaHCO_3$ (150 mL), filtered, and the solvent was removed under reduced pressure. Purification of the residue by FC (50:50 $CH_2Cl_2$-MeOH) gave the title compound as a white solid. TLC: rf (50:50 $CH_2Cl_2$-MeOH)=0.33. LC-MS-conditions 02: $t_R$=0.99 min, $[M+H]^+$=333.39.

2-(tert-Butoxycarbonylamino-methyl)-5-phenyl-oxazole-4-carboxylic acid

In a flame dried round-bottomed flask equipped with a magnetic stir bar and under inert atmosphere ($N_2$), a solution of 2-(tert-butoxycarbonylamino-methyl)-5-phenyl-oxazole-4-carboxylic acid methyl ester (200 mg, 0.60 mmol) in dioxane (2.0 mL) was treated with 1N LiOH (2.0 mL). The resulting mixture was stirred for 1 h. EA (10 mL) was added and the organic phase was washed with 1N HCl (3 mL), dried over $MgSO_4$, filtered, and the solvent removed under reduced pressure to give the title compound as a white solid. LC-MS-conditions 02: $t_R$=0.89 min, $[M+H]^+$=319.17.

2-(4-Bromo-thiophen-2-yl)-2-methyl-[1,3]dioxolane

In a flame dried round-bottomed flask equipped with a magnetic stir bar and under inert atmosphere ($N_2$), a solution of commercially available 1-(4-bromo-2-thienyl)ethan-1-one (2.00 g, 9.75 mmol) in ethylene glycol (10.7 mL) was treated with trimethylorthoformate (2.14 mL, 19.51 mmol) followed by $LiBF_4$ (150 mg, 1.60 mmol). The reaction mixture was heated at 95° C. overnight. Sat. aq. $NaHCO_3$ (20 mL) was added and the mixture was extracted with EA (20 mL). The org. extracts were washed with brine (2×20 mL), dried over $MgSO_4$, filtered, and the solvent was removed under reduced pressure. Purification of the residue by FC (20:80 EA-Hept) gave the title compound as a white solid. TLC: rf (20:80 EA-Hept)=0.50. LC-MS-conditions 02: $t_R$=0.99 min.

[5-(2-Methyl-[1,3]dioxolan-2-yl)-thiophen-3-yl]-methanol

In a flame dried round-bottomed flask equipped with a magnetic stir bar and under inert atmosphere ($N_2$), to a solution of 2-(4-bromo-thiophen-2-yl)-2-methyl-[1,3]dioxolane (1.00 g, 4.01 mmol) in $Et_2O$ (36.0 mL) at −78° C. was added dropwise n-BuLi (2.5 mL of a 1.6M solution in hexane, 4.00 mmol) over 15 min. The reaction mixture was then stirred at −78° C. for 15 min before DMF (3.1 mL, 40.14 mmol) was added dropwise. The cooling bath was removed and the reaction mixture was stirred for 10 min. Sat. aq. $NaH_4Cl$ (40 mL) was added and the aqueous layer was extracted with EA (2×100 mL). The combined org. extracts were dried over $MgSO_4$, filtered, and the solvent was removed under reduced pressure to give crude 5-(2-methyl-[1,3]dioxolan-2-yl)-thiophene-3-carbaldehyde as an yellow oil. LC-MS-conditions 02: $t_R$=0.84 min. The crude material was dissolved, under inert atmosphere ($N_2$) in MeOH (9.98 mL) and treated at 0° C., portionwise with $NaBH_4$ (284 mg, 7.21 mmol). The reaction mixture was stirred at rt for 2 h. The reaction mixture was poured in water (16 mL) and the aq. layer was extracted with EA (2×100 mL). The combined org. extracts were dried over $MgSO_4$, filtered, and the solvents were removed under reduced pressure. Purification of the residue by FC (50:50 hept-EA) gave the title compound as a yellow oil. TLC: rf (50:50 EA-Hept)=0.21. LC-MS-conditions 02: $t_R$=0.71 min; $[M+H]^+$=201.49.

1-[5-(2-Methyl-[1,3]dioxolan-2-yl)-thiophen-3-ylmethyl]-4-nitro-1H-pyrazole

In a flame dried round-bottomed flask equipped with a magnetic stir bar and under inert atmosphere ($N_2$), a solution of [5-(2-methyl-[1,3]dioxolan-2-yl)-thiophen-3-yl]-methanol (280 mg, 1.40 mmol) in dry $CH_2Cl_2$ (2.58 mL) was treated at 0° C. with $Et_3N$ (0.25 mL, 1.82 mmol) followed by DMAP (17 mg, 0.14 mmol) and Ms-Cl (0.13 mL, 1.68 mmol). The reaction mixture was stirred at rt for 2 h before being quenched with water (5 mL), extracted with $CH_2Cl_2$ (20 mL) and the combined org. extracts were dried over $MgSO_4$, filtered, and the solvents were removed under reduced pressure to give crude 2-(4-chloromethyl-thiophen-2-yl)-2-methyl-[1,3]dioxolane as a yellow oil. A solution of the crude material in acetone (3.5 mL) was treated, under inert atmosphere ($N_2$) with $K_2CO_3$ (588 mg, 4.25 mmol) followed by 4-nitro-1H-pyrazole (181 mg, 1.42 mmol) and TBA bromide (91 mg, 0.28 mmol). The resulting mixture was stirred overnight at rt and then the solvent was removed under reduced pressure. Water (10 mL) and EA (20 mL) were added. The aq. layer was extracted with EA (80 mL) and the combined org. extracts were dried over $MgSO_4$, filtered, and the solvents were removed under reduced pressure. Purification of the residue by FC (50:50 hept-EA) gave the title compound as a yellow solid. TLC: rf (50:50 hept-EA)=0.45. LC-MS-conditions 02: $t_R$=0.96 min; $[M+H]^+$=296.04.

1-[5-(2-Methyl-[1,3]dioxolan-2-yl)-thiophen-3-ylmethyl]-1H-pyrazol-4-ylamine

In a flame dried round-bottomed flask equipped with a magnetic stir bar and under inert atmosphere ($N_2$), a mixture of 1-[5-(2-methyl-[1,3]dioxolan-2-yl)-thiophen-3-ylmethyl]-4-nitro-1H-pyrazole (220 mg, 0.75 mmol), iron powder (126 mg, 2.24 mmol) and $NH_4Cl$ (201 mg, 3.73 mmol) in a mixture of EtOH (4.0 mL) and water (2.0 mL) was stirred at 75° C. for 30 min. The reaction mixture was filtered while hot and concentrated under reduced pressure. $CH_2Cl_2$ (25 mL) was added followed by 1M NaOH (25 mL). The aq. layer was extracted with $CH_2Cl_2$ (2×25 mL) and the combined org. extracts were dried over $MgSO_4$, filtered, and the solvents were removed under reduced pressure to give the title compound as a red oil. LC-MS-conditions 02: $t_R$=0.63 min; $[M+H]^+$=266.09.

Amino-thioxo-acetic acid ethyl ester

In a flame dried round-bottomed flask equipped with a magnetic stir bar and under inert atmosphere ($N_2$), a solution of commercially available oxalamic acid ethyl ester (43.429 g, 370.86 mmol) and Lawesson's reagent (150.00 g, 370.86 mmol) in toluene (550.0 mL) was stirred at 80° C. for 2 h. The resulting mixture was cooled to rt and $CH_2Cl_2$ (300 mL) was added. The mixture was filtered and the solvents were removed under reduced pressure. Purification of the residue by FC($CH_2Cl_2$) gave the title compound as an orange solid.

4-Chloromethyl-thiazole-2-carboxylic acid ethyl ester

In a flame dried round-bottomed flask equipped with a magnetic stir bar and under inert atmosphere ($N_2$), a solution of amino-thioxo-acetic acid ethyl ester (2.03 g. 15.27 mmol) in toluene (16.7 mL) was treated with 1,3-dichloroacetone (2.22 g, 17.50 mmol). The resulting mixture was stirred at reflux for 2 h. EA (20 mL) was added and the org. layer was washed with sat. aq. NaHCO$_3$, brine, dried over MgSO$_4$, filtered, and the solvents were removed under reduced pressure. Purification of the residue by FC (70:30 hept-EA) gave the title compound as an orange oil. TLC: rf (70:30 hept-EA)= 0.40. LC-MS-conditions 02: $t_R$=0.88 min; [M+H]$^+$ =206.37.

4-(4-Nitro-pyrazol-1-ylmethyl)-thiazole-2-carboxylic acid ethyl ester

In a flame dried round-bottomed flask equipped with a magnetic stir bar and under inert atmosphere (N$_2$), a solution of 4-chloromethyl-thiazole-2-carboxylic acid ethyl ester (1.84 g, 8.93 mmol) in acetone (20.0 mL) was treated, under inert atmosphere (N$_2$) with K$_2$CO$_3$ (6.23 g, 44.66 mmol) followed by 4-nitro-1H-pyrazole (1.00 g, 8.93 mmol) and TBA bromide (576 mg, 1.79 mmol). The resulting mixture was stirred at rt overnight. Water (40 mL), followed by EA (50 mL) were added. The aq. layer was extracted with EA (50 mL) and the combined org. extracts were dried over MgSO$_4$, filtered, and the solvents were removed under reduced pressure. Purification of the residue by FC (50:50 hept-EA) gave the title compound as a yellow oil. TLC: rf (50:50 hept-EA)= 0.30. LC-MS-conditions 02: $t_R$=0.90 min; [M+H]$^+$=283.25.

4-(4-Amino-pyrazol-1-ylmethyl)-thiazole-2-carboxylic acid ethyl ester

In a flame dried round-bottomed flask equipped with a magnetic stir bar and under inert atmosphere (N$_2$), a mixture of 4-(4-nitro-pyrazol-1-ylmethyl)-thiazole-2-carboxylic acid ethyl ester (1.77 g, 6.27 mmol), iron powder (1.06 g, 18.81 mmol) and NH$_4$Cl (1.69 g, 31.35 mmol) in a mixture of EtOH (30.0 mL) and water (15.0 mL) was stirred at reflux for 40 min. The reaction mixture was filtered while hot and concentrated under reduced pressure. CH$_2$Cl$_2$ (60 mL) was added followed by 1M NaOH (50 mL). The aq. layer was extracted with CH$_2$Cl$_2$ (2×30 mL) and the combined org. extracts were dried over MgSO$_4$, filtered, and the solvents were removed under reduced pressure to give the title compound as a brown oil. LC-MS-conditions 02: $t_R$=0.56 min; [M+H]$^+$=253.36.

4-[4-(2-Chloro-benzyloxycarbonylamino)-pyrazol-1-ylmethyl]-thiazole-2-carboxylic acid ethyl ester In a flame dried round-bottomed flask equipped with a magnetic stir bar and under inert atmosphere (N$_2$), a solution of 4-(4-amino-pyrazol-1-ylmethyl)-thiazole-2-carboxylic acid ethyl ester (1.43 g, 5.65 mmol) in CH$_2$Cl$_2$ (56.0 mL) was treated with DIPEA (1.15 mL, 8.47 mmol) followed by 2-chlorobenzylchloroformate (1.04 mL, 6.78 mmol). The reaction mixture was stirred at rt for 1 h before being quenched with water (50 mL), extracted with CH$_2$Cl$_2$ (3×40 mL). The combined org. extracts were dried over MgSO$_4$, filtered, and the solvent was removed under reduced pressure. Purification of the residue by FC (96:4 CH$_2$Cl$_2$-MeOH) gave the title compound as a pink foam. TLC: rf (96:4 CH$_2$Cl$_2$-MeOH)=0.28. LC-MS-conditions 02: $t_R$=0.99 min; [M+H]$^+$= 421.14.

[1-(2-Hydroxymethyl-thiazol-4-ylmethyl)-1H-pyrazol-4-yl]-carbamic acid 2-chloro-benzyl ester In a flame dried round-bottomed flask equipped with a magnetic stir bar and under inert atmosphere (N$_2$), a solution of 4-[4-(2-chloro-benzyloxycarbonylamino)-pyrazol-1-ylmethyl]-thiazole-2-carboxylic acid ethyl ester (912 mg, 2.17 mmol) in THF (20.0 mL) at −78° C. was treated with DiBAL (8.70 mL of a 1M solution in toluene, 8.70 mmol). The reaction mixture was stirred at −78° C. for 1 h, then allowed to reach rt before being quenched with Rochelle's salt (100 mL). The resulting mixture was stirred for 2 h at rt, extracted with EA (2×50 mL). The combined org. extracts were dried over MgSO$_4$, filtered, and the solvents were removed under reduced pressure. Purification of the residue by FC (19:1 CH$_2$Cl$_2$-MeOH) gave the title compound as a yellow foam. TLC: rf (19:1 CH$_2$Cl$_2$-MeOH)=0.11. LC-MS-conditions 02: $t_R$=0.83 min; [M+H]$^+$=379.04.

[1-(2-Formyl-thiazol-4-ylmethyl)-1H-pyrazol-4-yl]-carbamic acid 2-chloro-benzyl ester In a flame dried round-bottomed flask equipped with a magnetic stir bar and under inert atmosphere (N$_2$), a solution of [1-(2-hydroxymethyl-thiazol-4-ylmethyl)-1H-pyrazol-4-yl]-carbamic acid 2-chloro-benzyl ester (230 mg, 0.61 mmol) in AcCN (6.0 mL) was treated at rt with MnO$_2$ (293 mg, 3.04 mmol). The reaction mixture was stirred at rt overnight before being filtered through Celite and the solvent was removed under reduced pressure to give the title compound as a white solid. LC-MS-conditions 02: $t_R$=0.96 min; [M+H]$^+$=377.08.

{1-[2-(1-Hydroxy-ethyl)-thiazol-4-ylmethyl]-1H-pyrazol-4-yl}-carbamic acid 2-chloro-benzyl ester In a flame dried round-bottomed flask equipped with a magnetic stir bar and under inert atmosphere (N$_2$), a solution of [1-(2-formyl-thiazol-4-ylmethyl)-1H-pyrazol-4-yl]-carbamic acid 2-chloro-benzyl ester (155 mg, 0.41 mmol) in THF (4.0 mL) was treated at −78° C. with methylmagnesium bromide (0.41 mL of a 1M solution in THF, 0.41 mmol). The reaction mixture was stirred at −78° C. for 4.5 h then poured in sat. aq. NH$_4$Cl (25 mL) and extracted with EA (2×25 mL). The combined org. extracts were dried over MgSO$_4$, filtered, and the solvents were removed under reduced pressure. Purification of the residue by FC (90:10 CH$_2$Cl$_2$-MeOH) gave the title compound as a yellow oil. TLC: rf (90:10 CH$_2$Cl$_2$-MeOH)=0.28. LC-MS-conditions 02: $t_R$=0.88 min; [M+H]$^+$ =393.11.

2-Bromo-pyridine-4-carbaldehyde

In a flame dried round-bottomed flask equipped with a magnetic stir bar and under inert atmosphere (N$_2$), a suspension of commercially available 2,4-dibromo-pyridine (1.90 g, 8.02 mmol) in dry Et$_2$O (40 mL) was treated with n-BuLi (3.36 mL of a 2.5M solution in hexanes, 8.42 mmol) at −78° C. The reaction mixture was stirred at this temperature for 30 min. N,N-Dimethyl-formamide (0.78 mL, 10.03 mmol) was then added and the mixture allowed to warm to rt over a period of 1 h and stirred at this temperature for 20 min. The reaction was quenched by the addition of sat. aq. NH$_4$Cl (30 mL). The layers were separated and the aq. layer extracted with Et$_2$O (3×50 mL). The combined org. extracts were dried over Na$_2$SO$_4$, filtered, and the solvent removed under reduced pressure. Purification of the residue by FC (10:1 to 2:1 hept-EA) gave the title compound as a white solid. TLC: rf (1:1 hept-EA)=0.44.

(2-Bromo-pyridin-4-yl)-methanol

In a flame dried round-bottomed flask equipped with a magnetic stir bar and under inert atmosphere (N$_2$), 2-bromopyridine-4-carbaldehyde (904 mg, 4.86 mmol) was dissolved in MeOH (10 mL). NaBH$_4$ (236 mg, 5.99 mmol) was added portionwise at 0° C. and the reaction mixture stirred at rt for 1 h. Water (10 mL) was added and the mixture extracted with EA (3×20 mL). The combined org. extracts were dried over Na$_2$SO$_4$, filtered, and the solvents were removed under reduced pressure to give the title compound as a white solid. TLC: rf (1:1 hept-EA)=0.22. LC-MS-conditions 02: $t_R$=0.63 min; [M+H]$^+$=188.33.

2-Bromo-4-(tert-butyl-dimethyl-silanyloxymethyl)-pyridine

In a flame dried round-bottomed flask equipped with a magnetic stir bar and under inert atmosphere (N$_2$), (2-bromo-pyridin-4-yl)-methanol (780 mg, 4.15 mmol) was dissolved in dry CH$_2$Cl$_2$ (21 mL). tert-Butyldimethylsilyl chloride (688 mg, 4.56 mmol) was added at 0° C. followed by imidazole (579 mg, 8.50 mmol). The reaction mixture was stirred at rt for 2 h. 10% Aq. K$_2$CO$_3$ (10 mL) was added, the layers separated and the aq. layer extracted with CH$_2$Cl$_2$ (2×20 mL). The combined org. extracts were dried over MgSO$_4$, filtered, and the solvent removed under reduced pressure to give the title compound as a colorless oil. TLC: rf (1:1 hept-EA)=0.80. LC-MS-conditions 02: $t_R$=1.17 min; [M+H]$^+$=302.29.

1-[4-(tert-Butyl-dimethyl-silanyloxymethyl)-pyridin-2-yl]-ethanone

In a flame dried round-bottomed flask equipped with a magnetic stir bar and under inert atmosphere (N$_2$), to a solution of 2-bromo-4-(tert-butyl-dimethyl-silanyloxymethyl)-pyridine (1.04 g, 3.44 mmol) in dry Et$_2$O (50 mL) was added n-BuLi (1.60 mL of a 2.5M solution in hexanes, 3.96 mmol) at −78° C. The reaction mixture was then stirred for 1 h at −78° C. before N,N-dimethylacetamide (0.64 mL, 6.88 mmol) was added dropwise. The reaction mixture was allowed to warm up to rt and stirred at this temperature for 10 min. Sat. aq. NH$_4$Cl (20 mL) was added, the layers separated and the aq. layer extracted with Et$_2$O (3×30 mL). The combined org. extracts were dried over Na$_2$SO$_4$, filtered, and the solvent was removed under reduced pressure. Purification of the residue by FC (20:1 to 5:1 hept-EA) gave the title compound as a pale yellow oil. TLC: rf (1:2 hept-EA)=0.64. LC-MS-conditions 02: $t_R$=1.12 min; [M+H]$^+$=265.84.

4-(tert-Butyl-dimethyl-silanyloxymethyl)-2-(2-methyl-[1,3]dioxolan-2-yl)-pyridine In a flame dried round-bottomed flask equipped with a magnetic stir bar and a condenser under inert atmosphere (N$_2$), a solution of 1-[4-(tert-butyl-dimethyl-silanyloxymethyl)-pyridin-2-yl]-ethanone (1.78 g, 6.71 mmol) in ethylene glycol (7.14 mL, 127.95 mmol) was treated with trimethylorthoformate (1.50 mL, 13.67 mmol) followed by LiBF$_4$ (128 mg, 1.34 mmol). The reaction mixture was heated at 95° C. overnight. Sat. aq. NaHCO$_3$ (50 mL) was added and the mixture was extracted with EA (50 mL). The org. extracts were washed with brine (2×50 mL), dried over MgSO$_4$, filtered, and the solvent was removed under reduced pressure. Purification of the residue by FC (20:1 to 1:1 hept-EA) gave the title compound as a yellow oil. TLC: rf (1:1 hept-EA)= 0.50. LC-MS-conditions 02: $t_R$=0.91 min, [M+H]$^+$=310.40.

[2-(2-Methyl-[1,3]dioxolan-2-yl)-pyridin-4-yl]-methanol

In a flame dried round-bottomed flask equipped with a magnetic stir bar and under inert atmosphere (N$_2$), a solution of 4-(tert-butyl-dimethyl-silanyloxymethyl)-2-(2-methyl-[1,3]dioxolan-2-yl)-pyridine (840 mg, 2.71 mmol) in dry THF (15 mL) was treated at 0° C. with TBAF (4.70 mL of a 1M solution in THF, 4.70 mmol). The reaction mixture was stirred at 0° C. for 5 min and at rt for 1.5 h. The mixture was then diluted with EA (10 mL), washed with brine (3×10 mL), dried over MgSO$_4$, filtered and concentrated under reduced pressure. Purification of the residue by FC (5:1 to 1:3 hept-EA) gave the title compound as a yellow oil. TLC: rf (1:2 hept-EA)=0.10. LC-MS-conditions 02: $t_R$=0.33 min; [M+H]$^+$=196.54.

Methanesulfonic acid 2-(2-methyl-[1,3]dioxolan-2-yl)-pyridin-4-ylmethyl ester In a flame dried round-bottomed flask equipped with a magnetic stir bar and under inert atmosphere (N$_2$), a solution of [2-(2-methyl-[1,3]dioxolan-2-yl)-pyridin-4-yl]-methanol (530 mg, 2.72 mmol) in dry CH$_2$Cl$_2$ (5 mL) was treated at 0° C. with Et$_3$N (0.50 mL, 3.56 mmol) followed by DMAP (34 mg, 0.27 mmol) and Ms-Cl (0.27 mL, 3.46 mmol). After stirring at rt for 2 h, the reaction was quenched with water (5 mL). The org. layer was dried over MgSO$_4$, filtered, and the solvent was removed under reduced pressure. Purification of the residue by FC (5:1 to 2:1 hept-EA) gave the title compound as a light brown oil. TLC: rf (1:2 hept-EA)=0.36.

Amino-thioxo-acetic acid ethyl ester

In a flame dried round-bottomed flask equipped with a magnetic stir bar and under inert atmosphere (N$_2$), a solution of commercially available oxalamic acid ethyl ester (43.429 g, 370.86 mmol) and Lawesson's reagent (150.00 g, 370.86 mmol) in toluene (550.0 mL) was stirred at 80° C. for 2 h. The resulting mixture was cooled to rt and CH$_2$Cl$_2$ (300 mL) was added. The mixture was filtered and the solvents were removed under reduced pressure. Purification of the residue by FC(CH$_2$Cl$_2$) gave the title compound as an orange solid.

4-Chloromethyl-thiazole-2-carboxylic acid ethyl ester

In a flame dried round-bottomed flask equipped with a magnetic stir bar and under inert atmosphere (N$_2$), a mixture of amino-thioxo-acetic acid ethyl ester (2.50 g, 18.77 mmol) and 1,3-dichloro-propan-2-one (2.88 g, 21.59 mmol) in toluene (20.0 mL) was stirred for 2 h at reflux. EtOAc (20 mL) was added at rt and the mixture was washed with sat. aq. NaHCO$_3$ (10 mL) followed by brine (20 mL). The organic layer was dried over MgSO$_4$, filtered, and the solvent removed under reduced pressure. Purification of the residue by FC (4:1 hept-EA) gave the title compound as a light yellow oil. TLC: rf (4:1 hept-EA)=0.26. LC-MS-conditions 02: $t_R$=0.89 min, [M+H]$^+$=206.40.

(4-Chloromethyl-thiazol-2-yl)-methanol

In a flame dried round-bottomed flask equipped with a magnetic stir bar and under inert atmosphere (N$_2$), a solution of 4-chloromethyl-thiazole-2-carboxylic acid ethyl ester (2.47 g, 12.03 mmol) in THF (120.0 mL) was treated at −78° C. with DiBAL (36.09 mL of a 1M sol in THF, 36.09 mmol) and the reaction mixture was stirred for 1 h at −78° C. and then allowed to warm to rt over 1 h. The reaction mixture was poured into a sat. aq. Rochelle's salt sol. and stirred for 1 h at rt. The aq. layer was extracted with EtOAc (2×150 mL) and the combined org. layer was washed with brine (200 mL). The organic layer was dried over MgSO$_4$, filtered, and the solvent removed under reduced pressure. Purification of the residue by FC (1:1 hept-EA) gave the title compound as a light yellow oil. TLC: rf (1:1 hept-EA)=0.30. LC-MS-conditions 02: t$_R$=0.59 min, [M+H]$^+$=164.07.

4-Chloromethyl-thiazole-2-carbaldehyde

In a flame dried round-bottomed flask equipped with a magnetic stir bar and under inert atmosphere (N$_2$), a solution of (4-chloromethyl-thiazol-2-yl)-methanol (1.60 g, 9.80 mmol) in AcCN (98.0 mL) was treated at rt with MnO$_2$ (4.73 g, 49.01 mmol). The reaction mixture was stirred at rt overnight before being filtered through Celite and the solvent was removed under reduced pressure. Purification of the residue by FC (4:1 hept-EA) gave the title compound as a colorless oil. TLC: rf (4:1 hept-EA)=0.37. LC-MS-conditions 02: t$_R$=0.77 min.

1-(4-Chloromethyl-thiazol-2-yl)ethanol

In a flame dried round-bottomed flask equipped with a magnetic stir bar and under inert atmosphere (N$_2$), a solution of 4-chloromethyl-thiazole-2-carbaldehyde (1.05 g, 6.49 mmol) in CH$_2$Cl$_2$ (65.0 mL) was treated at 0° C. with trimethylaluminum (32.45 mL of a 1M solution in heptane, 32.45 mmol). The reaction mixture was then stirred at 0° C. for 45 min. CH$_2$Cl$_2$ (100.0 mL) followed by sat. aq. NH$_4$Cl (80 mL) was then added. The mixture was then treated with 1N HCl (100 mL) and the aq. layer was extracted with CH$_2$Cl$_2$ (100 mL). The combined org. extracts were dried over MgSO$_4$, filtered, and the solvents were removed under reduced pressure to give the title compound as a yellow oil. LC-MS-conditions 02: t$_R$=0.66 min, [M+H]$^+$=178.50.

1-(4-Chloromethyl-thiazol-2-yl)ethanone

In a flame dried round-bottomed flask equipped with a magnetic stir bar and under inert atmosphere (N$_2$), a solution of 1-(4-chloromethyl-thiazol-2-yl)-ethanol (1.09 g, 6.15 mmol) in AcCN (61.0 mL) was treated at rt with MnO$_2$ (2.97 g, 30.76 mmol) and the reaction mixture was stirred for 16 h at rt before being filtered through Celite. The solvent was removed under reduced pressure to give the title compound as a yellow oil. LC-MS-conditions 02: t$_R$=0.84 min, [M+H]$^+$=176.41.

4-Chloromethyl-2-(2-methyl-[1,3]dioxolan-2-yl)-thiazole

In a flame dried round-bottomed flask equipped with a magnetic stir bar and a condenser under inert atmosphere (N$_2$), a solution of 1-(4-chloromethyl-thiazol-2-yl)-ethanone (992 mg, 5.65 mmol) in ethylene glycol (6.30 mL, 112.96 mmol) was treated with trimethylorthoformate (1.24 mL, 11.30 mmol) followed by LiBF$_4$ (106 mg, 1.13 mmol). The reaction mixture was heated at 95° C. for 2 h. Sat. aq. NaHCO$_3$ (50 mL) was added and the mixture was extracted with EA (50 mL). The org. extracts were washed with brine (2×50 mL), dried over MgSO$_4$, and the solvent was removed under reduced pressure. Purification of the residue by FC (4:1 hept-EA) gave the title compound as a yellow oil. TLC: rf (4:1 hept-EA)=0.30. LC-MS-conditions 02: t$_R$=0.84 min, [M+H]$^+$=220.36.

2-(2-Methyl-[1,3]dioxolan-2-yl)-4-(3-nitro-pyrazol-1-ylmethyl)-thiazole

In a flame dried round-bottomed flask equipped with a magnetic stir bar and under inert atmosphere (N$_2$), a solution of 4-chloromethyl-2-(2-methyl-[1,3]dioxolan-2-yl)-thiazole (174 mg, 0.79 mmol) in acetone (2.0 mL) was added to a solution of 5-nitro-1H-pyrazole (90 mg, 0.79 mmol) in acetone (2.0 mL). K$_2$CO$_3$ (330 mg, 2.38 mmol) followed by TBA bromide (51 mg, 0.16 mmol) were added and the reaction mixture was stirred at rt overnight. Water (10 mL) and EA (10 mL) were added. The aq. layer was extracted with EA (10 mL) and the combined org. extracts were dried over MgSO$_4$, filtered, and the solvents were removed under reduced pressure. Purification of the residue by FC (1:1 hept-EA) gave the title compound as a pale yellow oil. TLC: rf (1:1 hept-EA)=0.29. LC-MS-conditions 02: t$_R$=0.89 min, [M+H]$^+$=297.23.

1-[2-(2-Methyl-[1,3]dioxolan-2-yl)-thiazol-4-ylmethyl]-1H-pyrazol-3-ylamine

In a flame dried round-bottomed flask equipped with a magnetic stir bar and under inert atmosphere (N$_2$), a 0.1M solution of 2-(2-methyl-[1,3]dioxolan-2-yl)-4-(3-nitro-pyrazol-1-ylmethyl)-thiazole (160 mg, 0.54 mmol), iron powder (91 mg, 1.62 mmol) and NH$_4$Cl (146 mg, 2.70 mmol) in a mixture of EtOH (2.0 mL) and water (1.0 mL) was stirred at 85° C. for 30 min. The reaction mixture was filtered while hot and concentrated under reduced pressure. CH$_2$Cl$_2$ (10 mL) was added followed by 1N NaOH (10 mL). The aq. layer was extracted with CH$_2$Cl$_2$ (2×10 mL) and the combined org. extracts were dried over MgSO$_4$, filtered, and the solvents were removed under reduced pressure to give the title compound as an oil. LC-MS-conditions 02: t$_R$=0.60 min; [M+H]$^+$=267.30.

Methanesulfonic acid 4-(2-methyl-[1,3]dioxolan-2-yl)-thiazol-2-ylmethyl ester

In a flame dried round-bottomed flask equipped with a magnetic stir bar and under inert atmosphere (N$_2$), a solution of [4-(2-methyl-[1,3]dioxolan-2-yl)-thiazol-2-yl]-methanol (925 mg, 4.60 mmol) in dry CH$_2$Cl$_2$ (20 mL) was treated at 0° C. with Et$_3$N (0.83 mL, 5.94 mmol) followed by DMAP (57 mg, 0.46 mmol) and Ms-Cl (0.46 mL, 5.80 mmol). After stirring at 0° C. for 1 h, the reaction was quenched with water (10 mL). The org. layer was dried over MgSO$_4$, filtered, and the solvents were removed under reduced pressure. Purification of the residue by FC (1:2 hept-EA) gave the title compound as a yellow oil. LC-MS-conditions 01: t$_R$=0.73 min, [M+H]$^+$=280.19.

4-(2-Methyl-[1,3]dioxolan-2-yl)-2-(3-nitro-pyrazol-1-ylmethyl)-thiazole

In a flame dried round-bottomed flask equipped with a magnetic stir bar and under inert atmosphere (N$_2$), a solution of methanesulfonic acid 4-(2-methyl-[1,3]dioxolan-2-yl)-thiazol-2-ylmethyl ester (320 mg, 1.15 mmol) in acetone (6.0 mL) was added to a solution of 5-nitro-1H-pyrazole (136 mg, 1.20 mmol) in acetone (6.0 mL). K$_2$CO$_3$ (800 mg, 5.73 mmol) followed by TBA bromide (741 mg, 0.23 mmol) were added and the reaction mixture was stirred at rt overnight. Water (10 mL) and EA (10 mL) were added. The aq. layer was extracted with EA (10 mL) and the combined org. extracts were dried over MgSO$_4$, filtered, and the solvents were removed under reduced pressure. Purification of the residue by FC (2:1 hept-EA) gave the title compound as a yellow oil. TLC: rf (2:1 hept-EA)=0.10. LC-MS-conditions 01: $t_R$=0.81 min, $[M+H]^+$= 296.90.

1-[4-(2-Methyl-[1,3]dioxolan-2-yl)-thiazol-2-ylmethyl]-1H-pyrazol-3-ylamine

In a flame dried round-bottomed flask equipped with a magnetic stir bar and under inert atmosphere ($N_2$), a 0.1M solution of 4-(2-methyl-[1,3]dioxolan-2-yl)-2-(3-nitro-pyrazol-1-ylmethyl)-thiazole (320 mg, 1.08 mmol), iron powder (183 mg, 3.24 mmol) and $NH_4Cl$ (292 mg, 5.40 mmol) in a mixture of EtOH (2.0 mL) and water (1.0 mL) was stirred at 75° C. for 60 min. The reaction mixture was filtered while hot and concentrated under reduced pressure. $CH_2Cl_2$ (10 mL) was added followed by 1N NaOH (10 mL). The aq. layer was extracted with $CH_2Cl_2$ (2×10 mL) and the combined org. extracts were dried over $MgSO_4$, filtered, and the solvents were removed under reduced pressure to give the title compound as a brown oil. LC-MS-conditions 01: $t_R$=0.54 min; $[M+H]^+$=266.97.

1-(2-Bromo-thiazol-5-yl)-ethanol

In a flame dried round-bottomed flask equipped with a magnetic stir bar and under inert atmosphere ($N_2$), a solution of commercially available 2-bromo-thiazole-5-carbaldehyde (1.80 g, 9.37 mmol) in $CH_2Cl_2$ (70.0 mL) was treated at 0° C. with trimethylaluminum (46.0 mL of a 1M solution in heptane, 46 mmol). The reaction mixture was then stirred at 0° C. for 45 min. $CH_2Cl_2$ (100.0 mL) followed by sat. aq. $NH_4Cl$ (100 mL) was then added. The mixture was then treated with 1N HCl (50 mL) and the aq. layer was extracted with $CH_2Cl_2$ (150 mL). The combined org. extracts were dried over $MgSO_4$, filtered, and the solvents were removed under reduced pressure to give the title compound as a yellow oil. TLC: rf (1:2 hept-EA)=0.40. LC-MS-conditions 02: $t_R$=0.70 min, $[M+H]^+$=249.17.

1-(2-Bromo-thiazol-5-yl)-ethanone

In a flame dried round-bottomed flask equipped with a magnetic stir bar and under inert atmosphere ($N_2$), a solution of 1-(2-bromo-thiazol-5-yl)-ethanol (1.95 g, 9.37 mmol) in AcCN (90.0 mL) was treated at rt with $MnO_2$ (4.53 g, 46.85 mmol) and the reaction mixture was stirred for 16 h at rt before being filtered through Celite. The solvent was removed under reduced pressure to give the title compound as a yellow solid. LC-MS-conditions 02: $t_R$=0.80 min.

2-Bromo-5-(2-methyl-[1,3]dioxolan-2-yl)-thiazole

In a flame dried round-bottomed flask equipped with a magnetic stir bar and a condenser under inert atmosphere ($N_2$), a solution of 1-(2-bromo-thiazol-5-yl)-ethanone (2.20 g, 10.68 mmol) in ethylene glycol (11.46 mL, 205.53 mmol) was treated with trimethylorthoformate (2.39 mL, 21.76 mmol) followed by $LiBF_4$ (204 mg, 2.14 mmol). The reaction mixture was heated at 95° C. for 2 days. Sat. aq. $NaHCO_3$ (50 mL) was added and the mixture was extracted with EA (50 mL). The org. extracts were washed with brine (2×50 mL), dried over $MgSO_4$, filtered, and the solvent was removed under reduced pressure. Purification of the residue by FC (4:1 hept-EA) gave the title compound as a yellow oil. TLC: rf (3:1 hept-EA)=0.80. LC-MS-conditions 01: $t_R$=0.84 min, $[M+H]^+$= 251.85.

5-(2-Methyl-[1,3]dioxolan-2-yl)-thiazole-2-carbaldehyde

In a flame dried round-bottomed flask equipped with a magnetic stir bar and under inert atmosphere ($N_2$), a solution of 2-bromo-5-(2-methyl-[1,3]dioxolan-2-yl)-thiazole (780 mg, 3.12 mmol) in dry $Et_2O$ (10 mL) was added to a n-BuLi (1.25 mL of a 2.5M solution in hexanes, 3.13 mmol) solution in $Et_2O$ (10 mL) at −78° C. The reaction mixture was then stirred for 30 min at −78° C. before DMF (0.29 mL, 3.78 mmol) was added dropwise. The reaction mixture was allowed to warm up to −20° C. and stirred at this temperature for 20 min. Sat. aq. $NH_4Cl$ (10 mL) was added, the layers separated and the aq. layer extracted with $Et_2O$ (3×10 mL). The combined org. extracts were dried over $Na_2SO_4$, filtered, and the solvent was removed under reduced pressure. Purification of the residue by FC (10:1 to 3:1 hept-EA) gave the title compound as a yellow oil. TLC: rf (1:1 hept-EA)=0.50. LC-MS-conditions 01: $t_R$=0.78 min, $[M+H]^+$=199.93.

[5-(2-Methyl-[1,3]dioxolan-2-yl)-thiazol-2-yl]-methanol

In a flame dried round-bottomed flask equipped with a magnetic stir bar and under inert atmosphere ($N_2$), 5-(2-methyl-[1,3]dioxolan-2-yl)-thiazole-2-carbaldehyde (555 mg, 2.79 mmol) was dissolved in MeOH (5 mL). $NaBH_4$ (136 mg, 3.46 mmol) was added portionwise at 0° C. and the reaction mixture stirred at rt for 1 h. Water (10 mL) was added and the mixture extracted with EA (3×20 mL). The combined org. extracts were dried over $Na_2SO_4$, filtered, and the solvents were removed under reduced pressure to give the title compound as a yellow oil. TLC: rf (1:1 hept-EA)=0.25. LC-MS-conditions 02: $t_R$=0.64 min $[M+H]^+$=202.48.

Methanesulfonic acid 5-(2-methyl-[1,3]dioxolan-2-yl)-thiazol-2-ylmethyl ester

In a flame dried round-bottomed flask equipped with a magnetic stir bar and under inert atmosphere ($N_2$), a solution of [5-(2-methyl-[1,3]dioxolan-2-yl)-thiazol-2-yl]-methanol (560 mg, 2.78 mmol) in dry $CH_2Cl_2$ (5.0 mL) was treated at 0° C. with $Et_3N$ (0.50 mL, 3.60 mmol) followed by DMAP (34 mg, 0.28 mmol) and Ms-Cl (0.28 mL, 3.51 mmol). After stirring at 0° C. for 1 h, the reaction mixture was quenched with water (10 mL), extracted with $CH_2Cl_2$ (10 mL) and the combined org. extracts were dried over $Na_2SO_4$, filtered, and the solvents were removed under reduced pressure. Purification of the residue by FC (5:1 to 2:1 hept-EA) gave the title compound as a brown oil. LC-MS-conditions 01: $t_R$=0.77 min; $[M+H]^+$=279.88.

5-(2-Methyl-[1,3]dioxolan-2-yl)-2-(4-nitro-pyrazol-1-ylmethyl)-thiazole

In a flame dried round-bottomed flask equipped with a magnetic stir bar and under inert atmosphere ($N_2$), a solution of methanesulfonic acid 5-(2-methyl-[1,3]dioxolan-2-yl)-thiazol-2-ylmethyl ester (520 mg, 1.86 mmol) in acetone (15.0 mL) was added to a solution of 4-nitro-1H-pyrazole (221 mg, 1.96 mmol) in acetone (15.0 mL). $K_2CO_3$ (1.300 g, 9.31 mmol) followed by TBA bromide (120 mg, 0.37 mmol) were added and the reaction mixture was stirred at rt overnight. Water (10 mL) and EA (10 mL) were added. The aq. layer was extracted with EA (10 mL) and the combined org. extracts were dried over $MgSO_4$, filtered, and the solvents were removed under reduced pressure. Purification of the residue by FC (10:1 to 2:1 hept-EA) gave the title compound as a yellow oil. TLC: rf (1:2 hept-EA)=0.15. LC-MS-conditions 01: $t_R$=0.83 min, $[M+H]^+$=296.90.

1-[5-(2-Methyl-[1,3]dioxolan-2-yl)-thiazol-2-ylmethyl]-1H-pyrazol-4-ylamine

In a flame dried round-bottomed flask equipped with a magnetic stir bar and under inert atmosphere ($N_2$), a solution of 5-(2-methyl-[1,3]dioxolan-2-yl)-2-(4-nitro-pyrazol-1-ylmethyl)-thiazole (490 mg, 1.65 mmol), iron powder (280 mg, 4.96 mmol) and $NH_4Cl$ (447 mg, 8.27 mmol) in a mixture of EtOH (3.0 mL) and water (1.5 mL) was stirred at 75° C. for 60 min. The reaction mixture was filtered while hot and concentrated under reduced pressure. $CH_2Cl_2$ (10 mL) was added followed by 1N NaOH (10 mL). The aq. layer was extracted with $CH_2Cl_2$ (2×10 mL) and the combined org. extracts were dried over $MgSO_4$, filtered, and the solvents were removed under reduced pressure to give the title compound as a brown oil. TLC: rf (19:1 $CH_2Cl_2$-MeOH)=0.20. LC-MS-conditions 02: $t_R$=0.56 min; $[M+H]^+$=267.29.

(2-Bromo-thiazol-5-yl)-methanol

In a flame dried round-bottomed flask equipped with a magnetic stir bar and under inert atmosphere ($N_2$), commercially available 2-bromo-thiazole-5-carbaldehyde (2.100 g, 10.94 mmol) was dissolved in MeOH (50 mL). $NaBH_4$ (535 mg, 13.58 mmol) was added portionwise at 0° C. and the reaction mixture stirred at rt for 1 h. Water (50 mL) was added and the mixture extracted with EA (3×50 mL). The combined org. extracts were dried over $Na_2SO_4$, filtered, and the solvents were removed under reduced pressure to give the title compound as a yellow solid. TLC: rf (1:1 hept-EA)=0.31. LC-MS-conditions 01: $t_R$=0.56 min $[M+CH_3CN+H]^+$=234.84.

2-Bromo-5-(tert-butyl-dimethyl-silanyloxymethyl)-thiazole

In a flame dried round-bottomed flask equipped with a magnetic stir bar and under inert atmosphere ($N_2$), (2-bromo-thiazol-5-yl)-methanol (2.17 g, 11.18 mmol) was dissolved in dry $CH_2Cl_2$ (30 mL). tert-Butyldimethylsilyl chloride (1.85 g, 12.30 mmol) was added at 0° C. followed by imidazole (1.56 g, 22.92 mmol). The reaction mixture was stirred at rt for 16 h. 10% Aq. $K_2CO_3$ (10 mL) was added, the layers separated and the aq. layer extracted with $CH_2Cl_2$ (2×20 mL). The combined org. extracts were dried over $MgSO_4$, filtered, and the solvent removed under reduced pressure. Purification of the residue by FC (hept to 10:1 hept-EA) gave the title compound as a yellow oil. TLC: rf (2:1 hept-EA)=0.80. LC-MS-conditions 02: $t_R$=1.13 min, $[M+H]^+$=307.90.

1-[5-(tert-Butyl-dimethyl-silanyloxymethyl)-thiazol-2-yl]-ethanone

In a flame dried round-bottomed flask equipped with a magnetic stir bar and under inert atmosphere ($N_2$), a solution of 2-bromo-5-(tert-butyl-dimethyl-silanyloxymethyl)-thiazole (3.00 g, 9.73 mmol) in dry $Et_2O$ (20 mL) was added to a n-BuLi (4.30 mL of a 2.5M solution in hexanes, 10.70 mmol) solution in $Et_2O$ (50 mL) at −78° C. The reaction mixture was then stirred for 40 min at −78° C. before N,N-dimethylacetamide (1.81 mL, 19.46 mmol) was added dropwise. The reaction mixture was allowed to warm up to −50° C. and stirred at this temperature for 20 min. Sat. aq. $NH_4Cl$ (20 mL) was added, the layers separated and the aq. layer extracted with $Et_2O$ (3×20 mL). The combined org. extracts were dried over $Na_2SO_4$, filtered, and the solvent was removed under reduced pressure to give the title compound as a yellow oil. TLC: rf (1:2 hept-EA)=0.80. LC-MS-conditions 01: $t_R$=1.09 min, $[M+H]^+$=271.98.

[2-(2-Methyl-[1,3]dioxolan-2-yl)-thiazol-5-yl]-methanol

In a flame dried round-bottomed flask equipped with a magnetic stir bar and a condenser under inert atmosphere ($N_2$), a solution of 1-[5-(tert-butyl-dimethyl-silanyloxymethyl)-thiazol-2-yl]-ethanone (2.70 g, 9.95 mmol) in ethylene glycol (10.68 mL, 191.48 mmol) was treated with trimethylorthoformate (2.22 mL, 20.27 mmol) followed by $LiBF_4$ (190 mg, 1.99 mmol). The reaction mixture was heated at 95° C. for 4 days. Sat. aq. $Na_2CO_3$ (50 mL) was added and the mixture was extracted with $Et_2O$ (2×50 mL), dried over $MgSO_4$, filtered, and the solvent was removed under reduced pressure to give 3.12 g of a brown oil as a mixture of 5-(tert-butyl-dimethyl-silanyloxymethyl)-2-(2-methyl-[1,3]dioxolan-2-yl)-thiazole (TLC: rf (1:1 hept-EA)=0.41, LC-MS-conditions 02: $t_R$=1.11 min, $[M+H]^+$=316.38) along with [2-(2-methyl-[1,3]dioxolan-2-yl)-thiazol-5-yl]-methanol (TLC: rf (1:1 hept-EA)=0.13, LC-MS-conditions 02: $t_R$=0.61 min, $[M+H]^+$=202.47). A solution of this mixture in dry THF (15 mL) was treated at 0° C. with TBAF (3.0 mL of a 1M solution in THF, 3.00 mmol). The reaction mixture was stirred at 0° C. for 5 min and at rt for 3 h. The mixture was then diluted with EA (10 mL), washed with brine (3×10 mL), dried over $MgSO_4$, filtered and concentrated under reduced pressure. Purification of the residue by FC (5:1->1:3 hept-EA) gave the title compound as a yellow oil. TLC: rf (1:2 hept-EA)=0.20. LC-MS-conditions 01: $t_R$=0.56 min; $[M+H]^+$=201.92.

5-Chloromethyl-2-(2-methyl-[1,3]dioxolan-2-yl)-thiazole

In a flame dried round-bottomed flask equipped with a magnetic stir bar and under inert atmosphere ($N_2$), a solution of [2-(2-methyl-[1,3]dioxolan-2-yl)-thiazol-5-yl]-methanol (560 mg, 2.78 mmol) in dry $CH_2Cl_2$ (5.0 mL) was treated at 0° C. with $Et_3N$ (0.50 mL, 3.60 mmol) followed by DMAP (34 mg, 0.28 mmol) and Ms-Cl (0.28 mL, 3.51 mmol). After stirring at 0° C. for 1 h, the reaction mixture was quenched with water (10 mL), extracted with $CH_2Cl_2$ (10 mL) and the combined org. extracts were dried over $Na_2SO_4$, filtered, and the solvents were removed under reduced pressure. Purification of the residue by FC (5:1 to 2:1 hept-EA) gave the title compound as a pale yellow oil. LC-MS-conditions 01: $t_R$=0.81 min; $[M+H]^+$=219.89.

2-(2-Methyl-[1,3]dioxolan-2-yl)-5-(4-nitro-pyrazol-1-ylmethyl)-thiazole

In a flame dried round-bottomed flask equipped with a magnetic stir bar and under inert atmosphere ($N_2$), a solution of 5-chloromethyl-2-(2-methyl-[1,3]dioxolan-2-yl)-thiazole (495 mg, 2.25 mmol) in acetone (1.0 mL) was added to a solution of 4-nitro-1H-pyrazole (268 mg, 2.37 mmol) in acetone (1.0 mL). $K_2CO_3$ (1.57 g, 11.27 mmol) followed by TBA bromide (145 mg, 0.45 mmol) were added and the reaction mixture was stirred at rt until completion. The solvent was removed under reduced pressure and water (10 mL) followed by EA (10 mL) were added. The aq. layer was extracted with EA (10 mL) and the combined org. extracts were dried over MgSO$_4$, filtered, and the solvents were removed under reduced pressure. Purification of the residue by FC (10:1 to 2:1 hept-EA) gave the title compound as a yellow oil. TLC: rf (1:2 hept-EA)=0.24. LC-MS-conditions 01: t$_R$=0.82 min, [M+H]$^+$=296.93.

1-[2-(2-Methyl-[1,3]dioxolan-2-yl)-thiazol-5-ylmethyl]-1H-pyrazol-4-ylamine

In a flame dried round-bottomed flask equipped with a magnetic stir bar and under inert atmosphere (N$_2$), a solution of 2-(2-methyl-[1,3]dioxolan-2-yl)-5-(4-nitro-pyrazol-1-ylmethyl)-thiazole (460 mg, 1.55 mmol), iron powder (263 mg, 4.66 mmol) and NH$_4$Cl (419 mg, 7.76 mmol) in a mixture of EtOH (3.0 mL) and water (1.5 mL) was stirred at 75° C. for 60 min. The reaction mixture was filtered while hot and concentrated under reduced pressure. CH$_2$Cl$_2$ (10 mL) was added followed by 1N NaOH (10 mL). The aq. layer was extracted with CH$_2$Cl$_2$ (2×10 mL) and the combined org. extracts were dried over MgSO$_4$, filtered, and the solvents were removed under reduced pressure to give the title compound as a red oil. TLC: rf (19:1 CH$_2$Cl$_2$-MeOH)=0.20. LC-MS-conditions 02: t$_R$=0.54 min; [M+H]$^+$=266.93.

1-Oxazol-2-yl-ethanone

In a flame dried round-bottomed flask equipped with a magnetic stir bar and under inert atmosphere (N$_2$), a solution of commercially available oxazole (3.25 mL, 48.49 mmol) in dry THF (34 mL) at −15° C. was treated over 30 min with isopropylmagnesium chloride (24.2 mL of a 2.0M solution in THF, 48.49 mmol) while keeping the temperature below −10° C. The reaction mixture was then stirred for 40 min at −15° C. before N-methoxy-N-methylacetamide (4.12 mL, 38.79 mmol) in THF (10 mL) was added dropwise. The reaction mixture was allowed to warm up to rt and stirred overnight at rt. 20% NH$_4$Cl (150 mL) was added, the layers separated and the aq. layer extracted with Et$_2$O (3×100 mL). The combined org. extracts were dried over MgSO$_4$, filtered, and the solvent was removed under reduced pressure. Purification of the residue by FC (4:6 Et$_2$O-hexane) gave the title compound as an orange oil. TLC: rf (4:6 Et$_2$O-hexane)=0.27. LC-MS-conditions 02: t$_R$=0.47 min.

1-Oxazol-2-yl-ethanol

In a flame dried round-bottomed flask equipped with a magnetic stir bar and under inert atmosphere (N$_2$), 1-oxazol-2-yl-ethanone (446 mg, 4.01 mmol) was dissolved in MeOH (8.0 mL). NaBH$_4$ (206 mg, 5.22 mmol) was added portionwise at 0° C. and the reaction mixture stirred at rt for 30 min. Water (16 mL) was added and the mixture extracted with EA (3×20 mL). The combined org. extracts were dried over MgSO$_4$, filtered, and the solvents were removed under reduced pressure to give the title compound as a colorless oil. LC-MS-conditions 02: t$_R$=0.33 min.

2-[1-(tert-Butyl-dimethyl-silanyloxy)-ethyl]-oxazole

In a flame dried round-bottomed flask equipped with a magnetic stir bar and under inert atmosphere (N$_2$), 1-oxazol-2-yl-ethanol (348 mg, 3.08 mmol) was dissolved in dry THF (15 mL). tert-Butyldimethylsilyl chloride (580 mg, 3.85 mmol) was added at rt followed by imidazole (262 mg, 3.85 mmol). The reaction mixture was stirred at rt for 16 h. Sat. aq. NH$_4$Cl (20 mL) was added, the layers separated and the aq. layer extracted with EA (2×20 mL). The combined org. extracts were dried over MgSO$_4$, filtered, and the solvent removed under reduced pressure. Purification of the residue by FC (1:4 Et$_2$O-hexane) gave the title compound as a colorless oil. TLC: rf (1:4 Et$_2$O-hexane)=0.39. LC-MS-conditions 02: t$_R$=1.08 min, [M+H]$^+$=228.48.

2-[1-(tert-Butyl-dimethyl-silanyloxy)-ethyl]-oxazole-5-carbaldehyde

In a flame dried round-bottomed flask equipped with a magnetic stir bar and under inert atmosphere (N$_2$), a solution of 2-[1-(tert-butyl-dimethyl-silanyloxy)-ethyl]-oxazole (733 mg, 3.22 mmol) in dry THF (16 mL) at −78° C. was treated with t-butyllithium (2.62 mL of a 1.6M solution in pentane, 4.19 mmol) while keeping the temperature below −70° C. The reaction mixture was then stirred for 1 h at −40° C. DMF (0.50 mL, 6.45 mmol) was added dropwise at −78° C. The reaction mixture was allowed to warm up to rt and stirred for 2 h at rt. Water (30 mL) was added followed by sat. aq. NH$_4$Cl (20 mL) and EA (20 mL), the layers separated and the aq. layer extracted with EA (2×30 mL). The combined org. extracts were dried over MgSO$_4$, filtered, and the solvent was removed under reduced pressure. Purification of the residue by FC (1:4 EA-Hept) gave the title compound as a colorless oil. TLC: rf (1:4 EA-Hept)=0.33. LC-MS-conditions 02: t$_R$=1.08 min, [M+H]$^+$=256.38.

{2-[1-(tert-Butyl-dimethyl-silanyloxy)-ethyl]-oxazol-5-yl}-methanol

In a flame dried round-bottomed flask equipped with a magnetic stir bar and under inert atmosphere (N$_2$), 2-[1-(tert-butyl-dimethyl-silanyloxy)-ethyl]-oxazole-5-carbaldehyde (457 mg, 1.79 mmol) was dissolved in MeOH (8.0 mL). NaBH$_4$ (92 mg, 2.33 mmol) was added portionwise at 0° C. and the reaction mixture stirred at rt for 20 min. Water (16 mL) was added and the mixture extracted with EA (3×20 mL). The combined org. extracts were dried over MgSO$_4$, filtered, and the solvents were removed under reduced pressure to give the title compound as a colorless oil. LC-MS-conditions 02: t$_R$=0.97 min, [M+H]$^+$=258.32.

2-[1-(tert-Butyl-dimethyl-silanyloxy)-ethyl]-5-chloromethyl-oxazole

In a flame dried round-bottomed flask equipped with a magnetic stir bar and under inert atmosphere (N$_2$), a solution of {2-[1-(tert-butyl-dimethyl-silanyloxy)-ethyl]-oxazol-5-yl}-methanol (455 mg, 1.77 mmol) in dry CH$_2$Cl$_2$ (4.5 mL) was treated at 0° C. with Et$_3$N (0.32 mL, 2.30 mmol) followed by DMAP (22 mg, 0.18 mmol) and Ms-Cl (0.17 mL, 2.12 mmol). After stirring at rt for 2 h, the reaction mixture was quenched with water (10 mL), extracted with CH$_2$Cl$_2$ (10 mL) and the combined org. extracts were dried over Na$_2$SO$_4$, filtered, and the solvents were removed under reduced pressure to give in a 2:1 ratio the title compound (LC-MS-conditions 02: t$_R$=1.13 min, [M+H]$^+$=276.06) along with methanesulfonic acid 2-[1-(tert-butyl-dimethyl-silanyloxy)-ethyl]-oxazol-5-ylmethyl ester (LC-MS-conditions 02: t$_R$=1.07 min, [M+H]$^+$=336.45) as a pale yellow oil.

2-[1-(tert-Butyl-dimethyl-silanyloxy)-ethyl]-5-(3-nitro-pyrazol-1-ylmethyl)-oxazole In a flame dried round-bottomed flask equipped with a magnetic stir bar and under inert atmosphere (N$_2$), a solution of 2-[1-(tert-butyl-dimethyl-silanyloxy)-ethyl]-5-chloromethyl-oxazole (243 mg, 0.88 mmol), 5-nitro-1H-pyrazole (100 mg, 0.88 mmol) and TBA bromide (57 mg, 0.18 mmol) in acetone (2.0 mL) was treated with $K_2CO_3$ (365 mg, 2.64 mmol) and the reaction mixture was stirred at rt until completion. The solvent was removed under reduced pressure and water (10 mL) followed by EA (10 mL) were added. The aq. layer was extracted with EA (10 mL) and the combined org. extracts were dried over $MgSO_4$, filtered, and the solvents were removed under reduced pressure. Purification of the residue by FC (6:4 hept-EA) gave the title compound as a yellow oil. TLC: rf (6:4 hept-EA)=0.20. LC-MS-conditions 01: $t_R$=1.09 min, $[M+H]^+$=353.02.

1-{2-[1-(tert-Butyl-dimethyl-silanyloxy)-ethyl]-oxazol-5-ylmethyl}-1H-pyrazol-3-ylamine In a flame dried round-bottomed flask equipped with a magnetic stir bar and under inert atmosphere ($N_2$), a solution of 2-[1-(tert-butyl-dimethyl-silanyloxy)-ethyl]-5-(3-nitro-pyrazol-1-ylmethyl)-oxazole (219 mg, 0.62 mmol), iron powder (105 mg, 1.86 mmol) and $NH_4Cl$ (168 mg, 3.11 mmol) in a mixture of EtOH (2.0 mL) and water (1.0 mL) was stirred at 85° C. for 15 min. The reaction mixture was filtered while hot and concentrated under reduced pressure. $CH_2Cl_2$ (10 mL) was added followed by water (10 mL). The aq. layer was extracted with $CH_2Cl_2$ (2×10 mL) and the combined org. extracts were dried over $MgSO_4$, filtered, and the solvents were removed under reduced pressure to give the title compound as a yellow oil. LC-MS-conditions 02: $t_R$=0.89 min; $[M+H]^+$=323.42.

5-Phenyl-oxazole-4-carboxylic acid (1-{2-[1-(tert-butyl-dimethyl-silanyloxy)-ethyl]-oxazol-5-ylmethyl}-1H-pyrazol-3-yl)-amide In a flame dried round-bottomed flask equipped with a magnetic stir bar and under inert atmosphere ($N_2$), a solution of 5-phenyl-oxazole-4-carboxylic acid (114 mg, 0.60 mmol) in $CH_2Cl_2$ (3.0 mL) was treated at rt with HOBt (98 mg, 0.72 mmol), EDC (289 mg, 1.51 mmol) DMAP (18 mg, 0.15 mmol) and the resulting mixture was stirred at rt for 30 min. 1-{2-[1-(tert-Butyl-dimethyl-silanyloxy)-ethyl]-oxazol-5-ylmethyl}-1H-pyrazol-3-ylamine (297 mg, 0.60 mmol) in $CH_2Cl_2$ (3.0 mL) was then added and the resulting mixture was stirred at rt for 16 h. $CH_2Cl_2$ (20 mL) followed by water (15 mL) were added and the aqueous phase was extracted with $CH_2Cl_2$. The combined organic phases were washed with water, brine, dried over $MgSO_4$, filtered, and the solvent removed under reduced pressure to give the title compound as a yellow oil. LC-MS-conditions 02: $t_R$=1.17 min, $[M+H]^+$=494.56.

5-Phenyl-oxazole-4-carboxylic acid {1-[2-(1-hydroxy-ethyl)-oxazol-5-ylmethyl]-1H-pyrazol-3-yl}-amide In a flame dried round-bottomed flask equipped with a magnetic stir bar and under inert atmosphere ($N_2$), a solution of 5-phenyl-oxazole-4-carboxylic acid (1-{2-[1-(tert-butyl-dimethyl-silanyloxy)-ethyl]-oxazol-5-ylmethyl}-1H-pyrazol-3-yl)-amide (271 mg, 0.55 mmol) in dry THF (5.5 mL) was treated at 0° C. with TBAF (1.1 mL of a 1M solution in THF, 1.1 mmol). The reaction mixture was stirred at 0° C. for 30 min. The mixture was then diluted with EA (10 mL), washed with $NaHCO_3$ (10 mL) followed by brine (3×10 mL), dried over $MgSO_4$, filtered and concentrated under reduced pressure. Purification of the residue by FC (EA) gave the title compound as a white foam. TLC: rf (EA)=0.18. LC-MS-conditions 02: $t_R$=0.87 min; $[M+H]^+$=380.34.

(4-Bromo-thiophen-2-yl)-methanol

In a flame dried round-bottomed flask equipped with a magnetic stir bar and under inert atmosphere ($N_2$), commercially available 4-bromo-thiophene-2-carbaldehyde (3.93 g, 20.57 mmol) was dissolved in THF (60.0 mL). $NaBH_4$ (892 mg, 22.63 mmol) was added portionwise at 0° C. and the reaction mixture stirred at rt for 30 min. Sat. aq. $NaHCO_3$ was added and the mixture extracted with $Et_2O$. The combined org. extracts were dried over $Na_2SO_4$, filtered, and the solvents were removed under reduced pressure to give the title compound as a colorless oil. TLC: rf (2:1 hept-EA)=0.38.

(4-Bromo-thiophen-2-ylmethoxy)-tert-butyl-dimethyl-silane

In a flame dried round-bottomed flask equipped with a magnetic stir bar and under inert atmosphere ($N_2$), (4-bromo-thiophen-2-yl)-methanol (3.97 g, 20.57 mmol) was dissolved in dry $CH_2Cl_2$ (50 mL). tert-Butyldimethylsilyl chloride (3.59 g, 22.63 mmol) was added at rt followed by imidazole (1.56 g, 22.63 mmol). The reaction mixture was stirred at rt for 1 h. Water was added, the layers were separated and the org. layer was dried over $MgSO_4$, filtered, and the solvent removed under reduced pressure. Purification of the residue by FC (hept) gave the title compound as a colorless oil. TLC: rf (100:1 hept-EA)=0.44. LC-MS-conditions 02: $t_R$=1.21 min.

1-[5-(tert-Butyl-dimethyl-silanyloxymethyl)-thiophen-3-yl]-ethanone

In a flame dried round-bottomed flask equipped with a magnetic stir bar and under inert atmosphere ($N_2$), a solution of (4-bromo-thiophen-2-ylmethoxy)-tert-butyl-dimethyl-silane (3.07 g, 10.00 mmol) in dry $Et_2O$ (10 mL) was added to a solution of n-butyllithium (4.10 mL of a 2.5M solution in hexane, 10.25 mmol) in $Et_2O$ (40 mL) at −78° C. while keeping the temperature below −70° C. The reaction mixture was then stirred for 30 min at −78° C. N,N-Dimethyl-acetamide (1.20 mL, 12.91 mmol) was added dropwise at −78° C. The reaction mixture was then stirred for 1 h at −78° C. followed by 1 h at rt. Sat. aq. $NH_4Cl$ was added, the layers separated and the aq. layer extracted with $Et_2O$ (3×50 mL). The combined org. extracts were dried over $Na_2SO_4$, filtered, and the solvent was removed under reduced pressure. Purification of the residue by FC (0:100 to 10:90 EA-Hept) gave the title compound as a yellow solid. TLC: rf (1:9 EA-Hept)=0.30. LC-MS-conditions 02: $t_R$=1.15 min.

tert-Butyl-dimethyl-[4-(2-methyl-[1,3]dioxolan-2-yl)-thiophen-2-ylmethoxy]-silane In a flame dried round-bottomed flask equipped with a magnetic stir bar and a condenser under inert atmosphere ($N_2$), a solution of 1-[5-(tert-butyl-dimethyl-silanyloxymethyl)-thiophen-3-yl]-ethanone (811 mg, 3.00 mmol) in ethylene glycol (3.5 mL, 62.76 mmol) was treated with trimethylorthoformate (0.66 mL, 6.02 mmol) followed by $LiBF_4$ (57 mg, 0.60 mmol). The reaction mixture was heated at 95° C. for 2 h. Sat. aq. $Na_2CO_3$ (50 mL) was added and the mixture was extracted with $Et_2O$ (2×50 mL), dried over $MgSO_4$, filtered, and the solvent was removed under reduced pressure.

Purification of the residue by FC (1:20 EA-Hept) gave the title compound as a yellow oil. TLC: rf (1:10 EA-Hept)=0.34. LC-MS-conditions 02: $t_R$=1.17 min; $[M+H]^+$=315.22.

[4-(2-Methyl-[1,3]dioxolan-2-yl)-thiophen-2-yl]-methanol

In a flame dried round-bottomed flask equipped with a magnetic stir bar and under inert atmosphere ($N_2$), a solution of tert-butyl-dimethyl-[4-(2-methyl-[1,3]dioxolan-2-yl)-thiophen-2-ylmethoxy]-silane (545 mg, 1.73 mmol) in dry THF (5.0 mL) was treated at 0° C. with TBAF (2.6 mL of a 1M solution in THF, 2.60 mmol). The reaction mixture was stirred at 0° C. for 2 h. The mixture was then diluted with EA (10 mL), washed with brine (3×20 mL), dried over $MgSO_4$, filtered and concentrated under reduced pressure. Purification of the residue by FC (1:5 EA-Hept) gave the title compound as a colorless oil. TLC: rf (1:1 EA-Hept)=0.36. LC-MS-conditions 02: $t_R$=0.70 min.

1-[4-(2-Methyl-[1,3]dioxolan-2-yl)-thiophen-2-ylmethyl]-4-nitro-1H-pyrazole

In a flame dried round-bottomed flask equipped with a magnetic stir bar and under inert atmosphere ($N_2$), a solution of [4-(2-methyl-[1,3]dioxolan-2-yl)-thiophen-2-yl]-methanol (100 mg, 0.50 mmol) in dry $CH_2Cl_2$ (3.0 mL) was treated at 0° C. with $Et_3N$ (0.10 mL, 0.71 mmol) followed by DMAP (6 mg, 0.05 mmol) and Ms-Cl (0.05 mL, 0.64 mmol). After stirring at 0° C. for 30 min and at rt for 1 h, the reaction mixture was quenched with water (10 mL), extracted with $CH_2Cl_2$ (10 mL) and the combined org. extracts were dried over $Na_2SO_4$, filtered, and the solvents were removed under reduced pressure to give crude methanesulfonic acid 4-(2-methyl-[1,3]dioxolan-2-yl)-thiophen-2-ylmethyl ester which was dissolved in acetone (5.0 mL) and treated with $K_2CO_3$ (349 mg, 2.50 mmol) followed by 4-nitro-1H-pyrazole (63 mg, 0.50 mmol) and TBA bromide (32 mg, 0.10 mmol). The reaction mixture was stirred at rt until completion. The solvent was removed under reduced pressure and water (10 mL) followed by EA (10 mL) were added. The aq. layer was extracted with EA (10 mL) and the combined org. extracts were dried over $MgSO_4$, filtered, and the solvents were removed under reduced pressure. Purification of the residue by FC (9:1 hept-EA) gave the title compound as a pale yellow oil. TLC: rf (1:1 hept-EA)=0.49. LC-MS-conditions 02: $t_R$=0.95 min.

1-[4-(2-Methyl-[1,3]dioxolan-2-yl)-thiophen-2-ylmethyl]-1H-pyrazol-4-ylamine In a flame dried round-bottomed flask equipped with a magnetic stir bar and under inert atmosphere ($N_2$), a solution of 1-[4-(2-methyl-[1,3]dioxolan-2-yl)-thiophen-2-ylmethyl]-4-nitro-1H-pyrazole (110 mg, 0.37 mmol), iron powder (63 mg, 1.12 mmol) and $NH_4Cl$ (102 mg, 1.89 mmol) in a mixture of EtOH (3.0 mL) and water (1.5 mL) was stirred at 75° C. for 60 min. The reaction mixture was filtered while hot and concentrated under reduced pressure. $CH_2Cl_2$ (10 mL) was added followed by water (10 mL). The aq. layer was extracted with $CH_2Cl_2$ (2×10 mL) and the combined org. extracts were dried over $MgSO_4$, filtered, and the solvents were removed under reduced pressure to give the title compound as a red oil. TLC: rf (EA)=0.47. LC-MS-conditions 02: $t_R$=0.62 min; $[M+H]^+$=266.01.

2-Styryl-oxazole-4-carboxylic acid ethyl ester

In a flame dried round-bottomed flask equipped with a magnetic stir bar and under inert atmosphere ($N_2$), a suspension of 3-phenyl-acrylamide (10.31 g, 67.95 mmol) and $NaHCO_3$ (28.47 g, 339.73 mmol) in THF (260 mL) was treated with 3-bromo-2-oxo-propionic acid ethyl ester (13.04 mL, 88.33 mmol) and the reaction mixture was heated at reflux for 15 h. 3-Bromo-2-oxo-propionic acid ethyl ester (13.04 mL, 88.33 mmol) was added again and the reaction mixture was stirred at reflux for 15 h. The reaction mixture was then filtered over celite and the solvents were evaporated under reduced pressure. The residue was dissolved in THF (30 mL) and treated at 0° C., dropwise, with trifluoroacetic anhydride (30.0 mL, 215.83 mmol). The reaction mixture was then stirred at rt overnight. Sat. aq. $Na_2CO_3$ was added and the mixture was extracted with EA (3×150 mL), dried over $MgSO_4$, filtered, and the solvent was removed under reduced pressure. Purification of the residue by FC (1:9 EA-Hept) gave the title compound as a yellow solid. TLC: rf (1:9 EA-Hept)=0.1. LC-MS-conditions 02: $t_R$=1.01 min; $[M+H]^+$=244.48.

2-Formyl-oxazole-4-carboxylic acid ethyl ester

In a flame dried round-bottomed flask equipped with a magnetic stir bar and under inert atmosphere ($N_2$), a solution of NaIO4 (3.21 g, 15.00 mmol) in water (26.0) mL was slowly added to a vigorously stirred suspension of silica gel (15.0 g) in acetone (60.0 mL). The mixture was then concentrated under reduced pressure and the lumpy solid slurried in $CH_2Cl_2$ and the solvent was evaporated under reduced pressure. $CH_2Cl_2$ (40.0 mL) was added and the reaction mixture was treated at rt with 2-styryl-oxazole-4-carboxylic acid ethyl ester (1.22 g, 5.00 mmol) and $RuCl_3$ hydrate (82 mg, 0.15 mmol). The reaction mixture was stirred at rt in the dark for 30 min, filtered and concentrated under reduced pressure. Purification of the residue by FC (1:9 to 1:2 EA-Hept) gave the title compound as a yellow solid. TLC: rf (3:2 EA-Hept)= 0.21. LC-MS-conditions 02: $t_R$=0.51 min; $[M+H_2O+H]^+$=188.50.

2-Hydroxymethyl-oxazole-4-carboxylic acid ethyl ester

In a flame dried round-bottomed flask equipped with a magnetic stir bar and under inert atmosphere ($N_2$), 2-formyl-oxazole-4-carboxylic acid ethyl ester (272 mg, 1.61 mmol) was dissolved in EtOH (5.0 mL). $NaBH_4$ (112 mg, 2.84 mmol) was added portionwise at 0° C. and the reaction mixture stirred at 0° C. for 1 h. Sat. aq. $NH_4Cl$ was added and the mixture extracted with EA (5×10 mL). The combined org. extracts were dried over $Na_2SO_4$, filtered, and the solvents were removed under reduced pressure to give the title compound as a yellow oil. TLC: rf (EA)=0.50. LC-MS-conditions 02: $t_R$=0.58 min; $[M+H]^+$=172.03.

2-(tert-Butyl-dimethyl-silanyloxymethyl)-oxazole-4-carboxylic acid ethyl ester In a flame dried round-bottomed flask equipped with a magnetic stir bar and under inert atmosphere ($N_2$), 2-hydroxymethyl-oxazole-4-carboxylic acid ethyl ester (275 mg, 1.61 mmol) was dissolved in dry $CH_2Cl_2$ (5.0 mL). tert-Butyldimethylsilyl chloride (510 mg, 3.22 mmol) was added at rt followed by imidazole (221 mg, 3.22 mmol). The reaction mixture was stirred at rt for 30 min. Water was added, the layers were separated and the org. layer was dried over $Na_2SO_4$, filtered, and the solvent removed under reduced pressure. Purification of the residue by FC (1:20 to 1:9 EA- Hept) gave the title compound as a colorless oil. TLC: rf (9:1 hept-EA)=0.15. LC-MS-conditions 02: $t_R$=1.10 min; $[M+H]^+$=286.38.

2-(tert-Butyl-dimethyl-silanyloxymethyl)-oxazole-4-carbaldehyde

In a flame dried round-bottomed flask equipped with a magnetic stir bar and under inert atmosphere ($N_2$), a solution of 2-(tert-butyl-dimethyl-silanyloxymethyl)-oxazole-4-carboxylic acid ethyl ester (283 mg, 0.99 mmol) in $CH_2Cl_2$ (5.0 mL) was treated at −78° C. with DiBAL (1.85 mL of a 1M sol in toluene, 1.85 mmol) and the reaction mixture was stirred for 1 h at −78° C. MeOH (70 μL) and $H_2O$ (100 μL) were added and the reaction mixture was allowed to warm to rt. The reaction mixture was filtered, and the solvent removed under reduced pressure to give the title compound as a colorless oil. TLC: rf (1:1 hept-EA)=0.61. LC-MS-conditions 02: $t_R$=1.03 min; $[M+H_2O+H]^+$=260.50.

1-[2-(tert-Butyl-dimethyl-silanyloxymethyl)-oxazol-4-yl]-ethanol

In a flame dried round-bottomed flask equipped with a magnetic stir bar and under inert atmosphere ($N_2$), a solution of 2-(tert-butyl-dimethyl-silanyloxymethyl)-oxazole-4-carbaldehyde (223 mg, 0.92 mmol) in $CH_2Cl_2$ (8.0 mL) was treated at 0° C. with trimethylaluminum (2.50 mL of a 2M solution in toluene, 5.00 mmol). The reaction mixture was then stirred at 0° C. for 45 min. Sat. aq. $NH_4Cl$ was then added and the aq. layer was extracted twice with $CH_2Cl_2$ and twice with EA. The combined org. extracts were dried over $Na_2SO_4$, filtered, and the solvents were removed under reduced pressure to give the title compound as a colorless oil. TLC: rf (1:1 hept-EA)=0.32. LC-MS-conditions 02: $t_R$=0.97 min, $[M+H]^+$=258.30.

1-[2-(tert-Butyl-dimethyl-silanyloxymethyl)-oxazol-4-yl]-ethanone

In a flame dried round-bottomed flask equipped with a magnetic stir bar and under inert atmosphere ($N_2$), a solution of 1-[2-(tert-butyl-dimethyl-silanyloxymethyl)-oxazol-4-yl]-ethanol (193 mg, 0.75 mmol) in AcCN (5.0 mL) was treated at rt with $MnO_2$ (362 mg, 3.75 mmol). The reaction mixture was stirred for 16 h at rt before being filtered through Celite. The solvent was removed under reduced pressure to give the title compound as a white solid. TLC: rf (1:1 hept-EA)=0.69. LC-MS-conditions 02: $t_R$=1.04 min, $[M+H]^+$=255.84.

1-(2-Hydroxymethyl-oxazol-4-yl)ethanone

In a flame dried round-bottomed flask equipped with a magnetic stir bar and under inert atmosphere ($N_2$), a solution of 1-[2-(tert-butyl-dimethyl-silanyloxymethyl)-oxazol-4-yl]-ethanone (192 mg, 0.75 mmol) in dry THF (5.0 mL) was treated at rt with TBAF (1.1 mL of a 1M solution in THF, 1.10 mmol). The reaction mixture was stirred at rt for 1.5 h. The mixture was then diluted with EA (10 mL), washed with brine (3×10 mL), dried over $Na_2SO_4$, filtered and concentrated under reduced pressure. Purification of the residue by FC (1:1 to 2:1 EA-Hept) gave the title compound as a pale yellow solid. TLC: rf (EA)=0.37. LC-MS-conditions 02: $t_R$=0.34 min, $[M+H]^+$=142.46.

Methanesulfonic acid 4-acetyl-oxazol-2-ylmethyl ester

In a flame dried round-bottomed flask equipped with a magnetic stir bar and under inert atmosphere ($N_2$), a solution of 1-(2-hydroxymethyl-oxazol-4-yl)-ethanone (45 mg, 0.32 mmol) in dry $CH_2Cl_2$ (5.0 mL) was treated at 0° C. with $Et_3N$ (0.06 mL, 0.41 mmol) followed by DMAP (3.9 mg, 0.03 mmol) and Ms-Cl (0.03 mL, 0.40 mmol). After stirring at 0° C. for 30 min, the reaction mixture was quenched with water (10 mL), extracted with $CH_2Cl_2$ (10 mL) and the combined org. extracts were dried over $Na_2SO_4$, filtered, and the solvents were removed under reduced pressure to give the title compound as a yellow oil. TLC: rf (EA)=0.63. LC-MS-conditions 02: $t_R$=0.64 min; $[M+H]^+$=220.22.

1-[2-(3-Nitro-pyrazol-1-ylmethyl)-oxazol-4-yl]-ethanone

In a flame dried round-bottomed flask equipped with a magnetic stir bar and under inert atmosphere ($N_2$), a solution of methanesulfonic acid 4-acetyl-oxazol-2-ylmethyl ester (70 mg, 0.32 mmol) in acetone (5.0 mL) was treated with $K_2CO_3$ (223 mg, 1.60 mmol) followed by 5-nitro-1H-pyrazole (37 mg, 0.32 mmol) and TBA bromide (21 mg, 0.06 mmol). The reaction mixture was stirred at rt until completion. The solvent was removed under reduced pressure and water (10 mL) followed by EA (10 mL) were added. The aq. layer was extracted with EA (10 mL) and the combined org. extracts were dried over $Na_2SO_4$, filtered, and the solvents were removed under reduced pressure. Purification of the residue by FC (1:1 hept-EA) gave the title compound as a yellow solid. TLC: rf (EA)=0.50. LC-MS-conditions 02: $t_R$=0.74 min; $[M+H]^+$=237.31.

1-[2-(3-Amino-pyrazol-1-ylmethyl)-oxazol-4-yl]-ethanone

In a flame dried round-bottomed flask equipped with a magnetic stir bar and under inert atmosphere ($N_2$), a solution of 1-[2-(3-nitro-pyrazol-1-ylmethyl)-oxazol-4-yl]-ethanone (48 mg, 0.20 mmol), iron powder (34 mg, 0.61 mmol) and $NH_4Cl$ (56 mg, 1.03 mmol) in a mixture of EtOH (2.0 mL) and water (1.0 mL) was stirred at 75° C. for 60 min. The reaction mixture was filtered while hot and concentrated under reduced pressure. $CH_2Cl_2$ (10 mL) was added followed by water (10 mL). The aq. layer was extracted with $CH_2Cl_2$ (2×10 mL) and the combined org. extracts were dried over $Na_2SO_4$, filtered, and the solvents were removed under reduced pressure to give the title compound as a yellow oil. TLC: rf (EA)=0.13. LC-MS-conditions 02: $t_R$=0.38 min; $[M+H]^+$=207.40.

1-[2-(3-Nitro-pyrazol-1-ylmethyl)-thiazol-4-yl]-ethanone

In a flame dried round-bottomed flask equipped with a magnetic stir bar and under inert atmosphere ($N_2$), a solution of 4-(2-methyl-[1,3]dioxolan-2-yl)-2-(3-nitro-pyrazol-1-ylmethyl)-thiazole (250 mg, 0.84 mmol) in THF (10.0 mL) was treated at 0° C. with HCl (2.5 mL of a 1M solution in water, 2.50 mmol). The reaction mixture was stirred at rt for 6 h. Water (10 mL) was added and the aqueous layer was set to pH 9-10 using 1M NaOH. The aq. layer was extracted with EA (2×10 mL) and the combined org. extracts were dried over $MgSO_4$, filtered, and the solvents were removed under reduced pressure to give the title compound as a yellow solid.

TLC: rf (19:1 CH$_2$Cl$_2$-MeOH)=0.25. LC-MS-conditions 02: t$_R$=0.81 min; [M+H]$^+$=253.06.

4-(1,1-Difluoro-ethyl)-2-(3-nitro-pyrazol-1-ylmethyl)-thiazole

In a flame dried round-bottomed flask equipped with a magnetic stir bar and under inert atmosphere (N$_2$), a solution of 1-[2-(3-nitro-pyrazol-1-ylmethyl)-thiazol-4-yl]-ethanone (210 mg, 0.83 mmol) in CH$_2$Cl$_2$ (5 mL) was treated at rt with (diethylamino)sulphur trifluoride (671 mg, 4.16 mmol) and the reaction mixture was stirred under reflux for 72 h. The reaction mixture was poured onto ice (20 mL) and the mixture was extracted with CH$_2$Cl$_2$ (2×20 mL), washed with water (30 mL), brine (30 mL), dried over MgSO$_4$, filtered, and the solvents were removed under reduced pressure. Purification of the residue by FC (2:1 hept-EA) gave the title compound as a brown oil. TLC: rf (2:1 hept-EA)=0.3. LC-MS-conditions 02: t$_R$=0.81 min.

1-[4-(1,1-Difluoro-ethyl)-thiazol-2-ylmethyl]-1H-pyrazol-3-ylamine

In a flame dried round-bottomed flask equipped with a magnetic stir bar and under inert atmosphere (N$_2$), a solution of 4-(1,1-difluoro-ethyl)-2-(3-nitro-pyrazol-1-ylmethyl)-thiazole (95 mg, 0.35 mmol), iron powder (59 mg, 1.04 mmol) and NH$_4$Cl (94 mg, 1.73 mmol) in a mixture of EtOH (3.0 mL) and water (1.5 mL) was stirred at 75° C. for 2.5 h. The reaction mixture was filtered while hot and concentrated under reduced pressure. CH$_2$Cl$_2$ (10 mL) was added followed by 1N NaOH (10 mL). The aq. layer was extracted with CH$_2$Cl$_2$ (2×10 mL) and the combined org. extracts were dried over Na$_2$SO$_4$, filtered, and the solvents were removed under reduced pressure to give the title compound as a brown oil. TLC: rf (19:1 CH$_2$Cl$_2$-MeOH)=0.2. LC-MS-conditions 02: t$_R$=0.7 min.

Oxazole-2-carbaldehyde

In a flame dried round-bottomed flask equipped with a magnetic stir bar and under inert atmosphere (N$_2$), a solution of commercially available oxazole (2.00 g, 28.96 mmol) in dry THF (87.0 mL) was treated at −78° C. with a solution of n-butyllithium (18.0 mL of a 1.6M solution in hexane, 28.96 mmol) while keeping the temperature below −70° C. The reaction mixture was then stirred for 20 min at −78° C. N,N-Dimethyl-formamide (2.23 mL, 28.96 mmol) in THF (18.0 mL) was added dropwise at −78° C. and the reaction mixture was allowed to warm to rt over a 24 h period. Methanol moistened Dowex 50×2-200 resin (58 mL, conditioned by washing consecutively with 2H HCl, distilled water and methanol) was added to the reaction mixture with additional methanol (20 mL) to complete the transfer. The resulting slurry was stirred at room temperature for 30 min and the resine was removed by filtration and rinsing with ether. The combined filtrates and washings were dried over MgSO$_4$, filtered, and the solvents were removed under reduced pressure. Purification of the residue by FC (98:2 CH$_2$Cl$_2$-Et$_2$O) gave the title compound as a yellow oil. TLC: rf (98:2 CH$_2$Cl$_2$-Et$_2$O)=0.37.

Oxazol-2-yl-methanol

In a flame dried round-bottomed flask equipped with a magnetic stir bar and under inert atmosphere (N$_2$), oxazole-2-carbaldehyde (1.033 g, 10.64 mmol) was dissolved in MeOH (50.0 mL). NaBH$_4$ (545 mg, 13.83 mmol) was added portionwise at 0° C. and the reaction mixture stirred at 0° C. for 1 h. The reaction mixture was poured into water (100 mL) and the methanol was removed under reduced pressure. The aq. layer was extracted with EA (2×100 mL). The combined org. extracts were dried over MgSO$_4$, filtered, and the solvents were removed under reduced pressure to give the title compound as a colorless oil.

2-(tert-Butyl-dimethyl-silanyloxymethyl)-oxazole

In a flame dried round-bottomed flask equipped with a magnetic stir bar and under inert atmosphere (N$_2$), oxazol-2-yl-methanol (503 mg, 5.08 mmol) was dissolved in dry THF (25.0 mL). tert-Butyldimethylsilyl chloride (1.53 g, 10.15 mmol) was added at rt followed by imidazole (691 mg, 10.15 mmol). The reaction mixture was stirred at rt for 2 days. Sat. aq. NH$_4$Cl (20 mL) and EA (20 mL) were added. The aqueous layer was extracted with EA (20 mL). The combined org. extracts were dried over MgSO$_4$, filtered, and the solvent removed under reduced pressure. Purification of the residue by FC (1:9 EA-Hept) gave the title compound as a colorless oil. TLC: rf (9:1 hept-EA)=0.33. LC-MS-conditions 02: t$_R$=1.04 min; [M+H]$^+$=214.56.

1-[2-(tert-Butyl-dimethyl-silanyloxymethyl)-oxazol-5-yl]-ethanone

In a flame dried round-bottomed flask equipped with a magnetic stir bar and under inert atmosphere (N$_2$), a solution of 2-(tert-butyl-dimethyl-silanyloxymethyl)-oxazole (480 mg, 2.25 mmol) in dry THF (11.0 mL) was treated at −78° C. with a solution of t-butyllithium (1.83 mL of a 1.6M solution in pentane, 2.93 mmol) while keeping the temperature below −70° C. The reaction mixture was then stirred for 1 h at −40° C. N,N-Dimethyl-acetamide (0.42 mL, 4.50 mmol) was added dropwise to the reaction mixture at −78° C. and the reaction mixture was allowed to warm to rt and stirred for 2 h at rt. Water (20 mL) followed by sat. aq. NH$_4$Cl (15 mL) were added. The aq. layer was extracted with EA (2×20 mL) and the combined org. extracts were washed with brine, dried over MgSO$_4$, filtered, and the solvents were removed under reduced pressure. Purification of the residue by FC (4:1 hept-EA) gave the title compound as a yellow oil. TLC: rf (4:1 hept-EA)=0.25. LC-MS-conditions 02: t$_R$=1.05 min; [M+H]$^+$=256.47.

[5-(2-Methyl-[1,3]dioxolan-2-yl)-oxazol-2-yl]-methanol

In a flame dried round-bottomed flask equipped with a magnetic stir bar and a condenser under inert atmosphere (N$_2$), a solution of 1-[2-(tert-butyl-dimethyl-silanyloxymethyl)-oxazol-5-yl]-ethanone (105 mg, 0.41 mmol) in ethylene glycol (0.46 mL, 8.22 mmol) was treated with trimethylorthoformate (0.09 mL, 0.82 mmol) followed by LiBF$_4$ (8 mg, 0.08 mmol). The reaction mixture was heated at 95° C. until reaction completion. Sat. aq. NaHCO$_3$ (10 mL) was added and the mixture was extracted with EA (2×10 mL). The combined org. extracts were washed with brine (20 mL), dried over MgSO$_4$, filtered, and the solvent was removed under reduced pressure. Purification of the residue by FC (4:1 EA-Hept) gave the title compound as a yellow oil. TLC: rf (4:1 EA-Hept)=0.25. LC-MS-conditions 02: t$_R$=0.56 min; [M+H]$^+$=186.55.

5-(2-Methyl-[1,3]dioxolan-2-yl)-2-(3-nitro-pyrazol-1-ylmethyl)-oxazole

In a flame dried round-bottomed flask equipped with a magnetic stir bar and under inert atmosphere ($N_2$), a solution of [5-(2-methyl-[1,3]dioxolan-2-yl)-oxazol-2-yl]-methanol (35 mg, 0.19 mmol) in dry $CH_2Cl_2$ (1.0 mL) was treated at 0° C. with $Et_3N$ (0.03 mL, 0.25 mmol) followed by DMAP (2.3 mg, 0.02 mmol) and Ms-Cl (0.02 mL, 0.23 mmol). After stirring at rt for 30 min, the reaction mixture was quenched with water (10 mL), extracted with $CH_2Cl_2$ (10 mL) and the combined org. extracts were dried over $Na_2SO_4$, filtered, and the solvents were removed under reduced pressure to give crude 2-chloromethyl-5-(2-methyl-[1,3]dioxolan-2-yl)-oxazole as a yellow oil. A solution of this crude 2-chloromethyl-5-(2-methyl-[1,3]dioxolan-2-yl)-oxazole (38 mg, 0.19 mmol) in acetone (1.0 mL) was treated with 5-nitro-1H-pyrazole (21 mg, 0.19 mmol) and TBA bromide (12 mg, 0.04 mmol) followed by $K_2CO_3$ (77 mg, 0.56 mmol). The reaction mixture was stirred at rt until completion. The solvent was removed under reduced pressure and water (10 mL) followed by EA (10 mL) were added. The aq. layer was extracted with EA (10 mL) and the combined org. extracts were dried over $MgSO_4$, filtered, and the solvents were removed under reduced pressure. Purification of the residue by FC (4:6 hept-EA) gave the title compound as a colorless oil. TLC: rf (4:6 hept-EA)=0.15. LC-MS-conditions 02: $t_R$=0.83 min; $[M+H]^+$=281.05.

1-[5-(2-Methyl-[1,3]dioxolan-2-yl)-oxazol-2-ylmethyl]-1H-pyrazol-3-ylamine

In a flame dried round-bottomed flask equipped with a magnetic stir bar and under inert atmosphere ($N_2$), a solution of 5-(2-methyl-[1,3]dioxolan-2-yl)-2-(3-nitro-pyrazol-1-ylmethyl)-oxazole (23 mg, 0.08 mmol), iron powder (14 mg, 0.25 mmol) and $NH_4Cl$ (22 mg, 0.41 mmol) in a mixture of EtOH (1.0 mL) and water (0.5 mL) was stirred at 85° C. for 15 min. The reaction mixture was filtered while hot, dried over $MgSO_4$, filtered, and the solvents were removed under reduced pressure to give the title compound as a yellow oil. LC-MS-conditions 02: $t_R$=0.56 min; $[M+H]^+$=251.38.

[2-(tert-Butyl-dimethyl-silanyloxymethyl)-oxazol-4-yl]-methanol

In a flame dried round-bottomed flask equipped with a magnetic stir bar and under inert atmosphere ($N_2$), a solution of 2-(tert-butyl-dimethyl-silanyloxymethyl)-oxazole-4-carboxylic acid ethyl ester (410 mg, 1.43 mmol) in THF (10.0 mL) was treated at 0° C. with DiBAL (5.70 mL of a 1M sol in toluene, 5.70 mmol) and the reaction mixture was stirred for 45 min at 0° C. The reaction mixture was then diluted with EA (5.0 mL), sat. aq. Rochelle's salt (20.0 mL) was added and the mixture stirred at rt for 2 h. The layers were separated and the aq. layer extracted with EA (3×20 mL). The combined org. extracts were dried over $Na_2SO_4$, filtered, and the solvents were removed under reduced pressure to give the title compound as a yellow solid. TLC: rf (EA)=0.59. LC-MS-conditions 02: $t_R$=0.94 min; $[M+H]^+$=244.46.

Methanesulfonic acid 2-(tert-Butyl-dimethyl-silanyloxymethyl)-oxazol-4-ylmethyl ester In a flame dried round-bottomed flask equipped with a magnetic stir bar and under inert atmosphere ($N_2$), a solution of [2-(tert-butyl-dimethyl-silanyloxymethyl)-oxazol-4-yl]-methanol (326 mg, 1.33 mmol) in dry $CH_2Cl_2$ (8.0 mL) was treated at 0° C. with $Et_3N$ (0.24 mL, 1.70 mmol) followed by DMAP (16 mg, 0.13 mmol) and Ms-Cl (0.13 mL, 1.67 mmol). After stirring at 0° C. for 30 min, the reaction mixture was quenched with water (10 mL), extracted with $CH_2Cl_2$ (10 mL) and the combined org. extracts were dried over $Na_2SO_4$, filtered, and the solvents were removed under reduced pressure to give the title compound as a yellow oil. TLC: rf (1:1 hept-EA)=0.50. LC-MS-conditions 02: $t_R$=1.05 min; $[M+H]^+$=322.25.

2-(tert-Butyl-dimethyl-silanyloxymethyl)-4-(4-nitro-pyrazol-1-ylmethyl)-oxazole In a flame dried round-bottomed flask equipped with a magnetic stir bar and under inert atmosphere ($N_2$), a solution of methanesulfonic acid 2-(tert-butyl-dimethyl-silanyloxymethyl)-oxazol-4-ylmethyl ester (430 mg, 1.33 mmol), 4-nitro-1H-pyrazole (172 mg, 1.33 mmol) and TBA bromide (86 mg, 0.26 mmol) in acetone (15.0 mL) was treated with $K_2CO_3$ (935 mg, 6.69 mmol) and the reaction mixture was stirred at rt until completion. The solvent was removed under reduced pressure and water (10 mL) and EA (10 mL) were added. The aq. layer was extracted with EA (10 mL) and the combined org. extracts were dried over $Na_2SO_4$, filtered, and the solvents were removed under reduced pressure. Purification of the residue by FC (1:0 to 17:3 hept-EA) gave the title compound as a pale yellow solid. TLC: rf (1:1 hept-EA)=0.46. LC-MS-conditions 02: $t_R$=1.09 min; $[M+H]^+$=339.44.

1-[2-(tert-Butyl-dimethyl-silanyloxymethyl)-oxazol-4-ylmethyl]-1H-pyrazol-4-ylamine In a flame dried round-bottomed flask equipped with a magnetic stir bar and under inert atmosphere ($N_2$), a solution of 2-(tert-butyl-dimethyl-silanyloxymethyl)-4-(4-nitro-pyrazol-1-ylmethyl)-oxazole (408 mg, 1.20 mmol), iron powder (204 mg, 3.62 mmol) and $NH_4Cl$ (326 mg, 6.03 mmol) in a mixture of EtOH (6.0 mL) and water (3.0 mL) was stirred at 75° C. for 45 min. The reaction mixture was filtered while hot and concentrated under reduced pressure. The residue was redissolved in $CH_2Cl_2$ (20 mL), dried over $Na_2SO_4$, filtered, and the solvents were removed under reduced pressure to give the title compound as an orange oil. TLC: rf (EA)=0.20. LC-MS-conditions 02: $t_R$=0.81 min; $[M+H]^+$=309.07.

{1-[2-(tert-Butyl-dimethyl-silanyloxymethyl)-oxazol-4-ylmethyl]-1H-pyrazol-4-yl}-carbamic acid 2-chloro-benzyl ester In a flame dried round-bottomed flask equipped with a magnetic stir bar and under inert atmosphere ($N_2$), a solution of 1-[2-(tert-butyl-dimethyl-silanyloxymethyl)-oxazol-4-ylmethyl]-1H-pyrazol-4-ylamine (347 mg, 1.12 mmol) in $CH_2Cl_2$ (5.0 mL) was treated with DIPEA (0.31 mL, 1.78 mmol) followed by 2-chlorobenzylchloroformate (0.23 mL, 1.45 mmol) at 0° C. The reaction mixture was stirred at 0° C. for 1 h and water (5.0 mL) was added. The layers were separated and the aq. layer extracted with $CH_2Cl_2$ (2×10 mL). The combined org. extracts were dried over $Na_2SO_4$, filtered, and the solvent was removed under reduced pressure. Purification of the residue by FC (9:1 to 1:1 hept-EA) gave the title compound as an orange oil. TLC: rf (1:1 hept-EA)=0.27. LC-MS-conditions 02: $t_R$=1.13 min; $[M+H]^+$=476.95.

[1-(2-Hydroxymethyl-oxazol-4-ylmethyl)-1H-pyrazol-4-yl]-carbamic acid 2-chloro-benzyl ester In a flame dried round-bottomed flask equipped with a magnetic stir bar and under inert atmosphere ($N_2$), a solution of {1-[2-(tert-butyl-dimethyl-silanyloxymethyl)-oxazol-4-ylmethyl]-1H-pyrazol-4-yl}-carbamic acid 2-chloro-benzyl ester (313 mg, 0.65 mmol) in dry THF (5.0 mL) was treated at 0° C. with TBAF (1.0 mL of a 1M solution in THF, 1.00 mmol). The reaction mixture was stirred at 0° C. for 30 min. Sat. aq. NH$_4$Cl (10 mL) was added, the layers separated and the aq. layer extracted with EA (3×10 mL). The combined organic extracts were dried over Na$_2$SO$_4$, filtered and concentrated under reduced pressure. Purification of the residue by FC (EA) gave the title compound as a pale yellow oil. TLC: rf (EA)=0.28. LC-MS-conditions 02: $t_R$=0.84 min; [M+H]$^+$=363.22.

[1-(2-Dihydroxymethyl-oxazol-4-ylmethyl)-1H-pyrazol-4-yl]-carbamic acid 2-chloro-benzyl ester In a flame dried round-bottomed flask equipped with a magnetic stir bar and under inert atmosphere (N$_2$), a solution of [1-(2-hydroxymethyl-oxazol-4-ylmethyl)-1H-pyrazol-4-yl]-carbamic acid 2-chloro-benzyl ester (238 mg, 0.65 mmol) in AcCN (5.0 mL) was treated at rt with MnO$_2$ (317 mg, 3.28 mmol) and the reaction mixture was stirred at 55° C. for 4 h before being filtered through Celite. The solvent was removed under reduced pressure to give the title compound as a brown oil. TLC: rf (EA)=0.48. LC-MS-conditions 02: $t_R$=0.81 min; [M+H]$^+$=379.22.

{1-[2-(1-Hydroxy-ethyl)-oxazol-4-ylmethyl]-1H-pyrazol-4-yl}-carbamic acid 2-chloro-benzyl ester In a flame dried round-bottomed flask equipped with a magnetic stir bar and under inert atmosphere (N$_2$), a solution of [1-(2-dihydroxymethyl-oxazol-4-ylmethyl)-1H-pyrazol-4-yl]-carbamic acid 2-chloro-benzyl ester (212 mg, 0.56 mmol) in CH$_2$Cl$_2$ (4.0 mL) was treated at 0° C. with trimethylaluminum (1.40 mL of a 2M solution in toluene, 2.80 mmol). The reaction mixture was then stirred at 0° C. for 1 h and at rt for 16 h. Sat. aq. NH$_4$Cl was then added and the aq. layer was extracted with CH$_2$Cl$_2$ (3×10 mL). The combined org. extracts were dried over Na$_2$SO$_4$, filtered, and the solvents were removed under reduced pressure to give the title compound as a pale yellow oil. TLC: rf (1:1 hept-EA)=0.28. LC-MS-conditions 02: $t_R$=0.86 min, [M+H]$^+$=377.17.

5-(3-Methoxy-phenyl)-oxazole-4-carboxylic acid

Prepared starting from 3-(3-methoxy-phenyl)-3-oxo-propionic acid ethyl ester following sequentially general procedures R, Q, P and J. LC-MS-conditions 02: $t_R$=0.80 min; [M+H]$^+$=220.13.

5-m-Tolyl-oxazole-4-carboxylic acid

Prepared starting from 3-oxo-3-m-tolyl-propionic acid ethyl ester following sequentially general procedures R, Q, P and J. LC-MS-conditions 02: $t_R$=0.83 min; [M+H]$^+$=204.17.

5-(2-Fluoro-phenyl)-thiazole-4-carboxylic acid

Prepared starting from 2-fluoro-benzaldehyde following sequentially general procedures E, O, N, M and J. LC-MS-conditions 02: $t_R$=0.79 min; [M+H]$^+$=224.07.

5-(3-Chloro-phenyl)thiazole-4-carboxylic acid

Prepared starting from 3-chloro-benzaldehyde following sequentially general procedures E, O, N, M and J. LC-MS-conditions 02: $t_R$=0.85 min; [M+H]$^+$=239.95.

5-(3-Methoxy-phenyl)-thiazole-4-carboxylic acid

Prepared starting from 3-methoxy-benzaldehyde following sequentially general procedures E, O, N, M and J. LC-MS-conditions 02: $t_R$=0.81 min; [M+H]$^+$=236.02.

5-(3-Trifluoromethyl-phenyl)-thiazole-4-carboxylic acid

Prepared starting from 3-trifluoromethyl-benzaldehyde following sequentially general procedures E, O, N, M and J. LC-MS-conditions 02: $t_R$=0.89 min; [M+H]$^+$=274.0.

2-Methyl-5-phenyl-thiazole-4-carboxylic acid

Prepared starting from benzaldehyde following sequentially general procedures E, F and J. LC-MS-conditions 02: $t_R$=0.77 min; [M+H]$^+$=220.29.

2-Methyl-5-m-tolyl-thiazole-4-carboxylic acid

Prepared starting from 3-methyl-benzaldehyde following sequentially general procedures E, F and J. LC-MS-conditions 01: $t_R$=0.83 min; [M+H]$^+$=234.01.

2-Methyl-5-phenyl-oxazole-4-carboxylic acid

Prepared starting from 3-oxo-3-phenyl-propionic acid ethyl ester following sequentially general procedures K, L and J. LC-MS-conditions 01: $t_R$=0.76 min; [M+H]$^+$=204.03.

2-Methyl-5-m-tolyl-oxazole-4-carboxylic acid

Prepared starting from 3-oxo-3-m-tolyl-propionic acid ethyl ester following sequentially general procedures K, L and J. LC-MS-conditions 02: $t_R$=0.85 min; [M+H]$^+$=218.46.

5-(4-Methoxy-phenyl)-2-methyl-oxazole-4-carboxylic acid

Prepared starting from 3-(4-methoxy-phenyl)-3-oxo-propionic acid ethyl ester following sequentially general procedures K, L and J. LC-MS-conditions 02: $t_R$=0.82 min; [M+H]$^+$=234.09.

2-Methyl-5-o-tolyl-oxazole-4-carboxylic acid

Prepared starting from 3-oxo-3-o-tolyl-propionic acid ethyl ester following sequentially general procedures K, L and J. LC-MS-conditions 02: $t_R$=0.83 min; [M+H]$^+$=218.16.

2-Methyl-5-p-tolyl-oxazole-4-carboxylic acid

Prepared starting from 3-oxo-3-p-tolyl-propionic acid ethyl ester following sequentially general procedures K, L and J. LC-MS-conditions 02: $t_R$=0.86 min; [M+H]$^+$=218.18.

5-(3-Methoxy-phenyl)-2-methyl-oxazole-4-carboxylic acid

Prepared starting from 3-(3-methoxy-phenyl)-3-oxo-propionic acid ethyl ester following sequentially general procedures K, L and J. LC-MS-conditions 02: $t_R$=0.82 min; [M+H]$^+$=234.10.

5-(3,5-Dimethyl-phenyl)-2-methyl-oxazole-4-carboxylic acid

Prepared starting from 3-(3,5-dimethyl-phenyl)-3-oxo-propionic acid ethyl ester following sequentially general procedures K, L and J. LC-MS-conditions 02: $t_R$=0.89 min; [M+H]$^+$=232.12.

5-(3-Fluoro-phenyl)-2-methyl-oxazole-4-carboxylic acid

Prepared starting from 3-(3-fluoro-phenyl)-3-oxo-propionic acid ethyl ester following sequentially general procedures K, L and J. LC-MS-conditions 02: $t_R$=0.83 min; [M+H]$^+$=222.14.

2-Methyl-5-(3-trifluoromethoxy-phenyl)-oxazole-4-carboxylic acid

Prepared starting from 3-trifluoromethoxy-benzoic acid following sequentially general procedures S, K, L and J. LC-MS-conditions 02: $t_R$=0.93 min; [M+H]$^+$=288.06.

5-(3,4-Dimethyl-phenyl)-oxazole-4-carboxylic acid

Prepared starting from 3,4-dimethyl-benzoic acid following sequentially general procedures S, R, Q, P and J. LC-MS-conditions 02: $t_R$=0.87 min; [M+H]$^+$=218.16.

2-Methyl-5-(3-trifluoromethyl-phenyl)-oxazole-4-carboxylic acid

Prepared starting from 3-trifluoromethyl-benzoic acid following sequentially general procedures S, K, L and J. LC-MS-conditions 02: $t_R$=0.91 min; [M+H]$^+$=272.05.

5-(3-Chloro-phenyl)-2-methyl-oxazole-4-carboxylic acid

Prepared starting from 3-chloro-benzoic acid following sequentially general procedures S, K, L and J. LC-MS-conditions 02: $t_R$=0.87 min; [M+H]$^+$=238.06.

5-Biphenyl-3-yl-2-methyl-oxazole-4-carboxylic acid

Prepared starting from biphenyl-3-carboxylic acid following sequentially general procedures S, K, L and J. LC-MS-conditions 02: $t_R$=0.96 min; [M+H]$^+$=280.10.

5-p-Tolyl-oxazole-4-carboxylic acid

Prepared starting from 4-methyl-benzoic acid following sequentially general procedures S, R, Q, P and J. LC-MS-conditions 02: $t_R$=0.83 min; [M+H]$^+$=204.22.

5-(4-Trifluoromethyl-phenyl)-oxazole-4-carboxylic acid

Prepared starting from 4-trifluoromethyl-benzoic acid following sequentially general procedures S, R, Q, P and J. LC-MS-conditions 02: $t_R$=0.89 min.

5-(3-Trifluoromethyl-phenyl)-oxazole-4-carboxylic acid

Prepared starting from 3-trifluoromethyl-benzoic acid following sequentially general procedures S, R, Q, P and J. LC-MS-conditions 02: $t_R$=0.89 min; [M+AcCN+H]$^+$=298.92.

5-(3-Fluoro-phenyl)-oxazole-4-carboxylic acid

Prepared starting from 3-fluoro-benzoic acid following sequentially general procedures S, R, Q, P and J. LC-MS-conditions 02: $t_R$=0.80 min; [M+AcCN+H]$^+$=249.09.

5-(4-Chloro-phenyl)-oxazole-4-carboxylic acid

Prepared starting from 4-chloro-benzoic acid following sequentially general procedures S, R, Q, P and J. LC-MS-conditions 02: $t_R$=0.85 min; [M+AcCN+H]$^+$=264.87.

5-(4-Fluoro-phenyl)-oxazole-4-carboxylic acid

Prepared starting from 4-fluoro-benzoic acid following sequentially general procedures S, R, Q, P and J. LC-MS-conditions 02: $t_R$=0.80 min; [M+AcCN+H]$^+$=249.04.

5-(4-Trifluoromethoxy-phenyl)-oxazole-4-carboxylic acid

Prepared starting from 4-trifluoromethoxy-benzoic acid following sequentially general procedures S, R, Q, P and J. LC-MS-conditions 02: $t_R$=0.91 min; [M+AcCN+H]$^+$=314.99.

5-(3-Chloro-phenyl)-oxazole-4-carboxylic acid

Prepared starting from 3-chloro-benzoic acid following sequentially general procedures S, R, Q, P and J. LC-MS-conditions 02: $t_R$=0.85 min; [M+AcCN+H]$^+$=265.23.

5-Biphenyl-3-yl-oxazole-4-carboxylic acid

Prepared starting from biphenyl-3-carboxylic acid following sequentially general procedures S, R, Q, P and J. LC-MS-conditions 02: $t_R$=0.94 min; [M+H]$^+$=266.10.

5-(3-Trifluoromethoxy-phenyl)-oxazole-4-carboxylic acid

Prepared starting from 3-trifluoromethoxy-benzoic acid following sequentially general procedures S, R, Q, P and J. LC-MS-conditions 02: $t_R$=0.91 min; [M+AcCN+H]$^+$=314.98.

2-Cyclopropyl-5-phenyl-oxazole-4-carboxylic acid

Prepared starting from 3-oxo-3-phenyl-propionic acid ethyl ester following sequentially general procedures R, Q, P and J. LC-MS-conditions 02: $t_R$=0.87 min; [M+H]$^+$=230.17.

2-Ethyl-5-phenyl-oxazole-4-carboxylic acid

Prepared starting from 3-oxo-3-phenyl-propionic acid ethyl ester following sequentially general procedures R, Q, P and J. LC-MS-conditions 02: $t_R$=0.85 min; [M+H]$^+$=218.19.

5-(4-Chloro-phenyl)-2-methyl-oxazole-4-carboxylic acid

Prepared starting from 3-(4-chloro-phenyl)-3-oxo-propionic acid ethyl ester following sequentially general procedures K, L and J. LC-MS-conditions 02: $t_R$=0.87 min; [M+H]$^+$=238.06.

5-(2,5-Dimethyl-phenyl)-2-methyl-oxazole-4-carboxylic acid

Prepared starting from 3-(2,5-dimethyl-phenyl)-3-oxo-propionic acid ethyl ester following sequentially general procedures K, L and J. LC-MS-conditions 02: $t_R$=0.87 min; [M+H]$^+$=232.09.

5-(2-Methoxy-phenyl)-2-methyl-oxazole-4-carboxylic acid

Prepared starting from 3-(2-methoxy-phenyl)-3-oxo-propionic acid ethyl ester following sequentially general procedures K, L and J. LC-MS-conditions 02: $t_R$=0.78 min; [M+H]$^+$=234.09.

5-(4-Fluoro-phenyl)-thiazole-4-carboxylic acid

Prepared starting from 4-fluoro-benzaldehyde following sequentially general procedures E, O, N, M and J. LC-MS-conditions 02: $t_R$=0.80 min; [M+H]$^+$=224.08.

5-Pyridin-2-yl-oxazole-4-carboxylic acid

Prepared starting from pyridine-2-carboxylic acid following sequentially general procedures U and J. LC-MS-conditions 02: $t_R$=0.57 min; [M+H]$^+$=191.44.

5-(3-Cyano-phenyl)-oxazole-4-carboxylic acid

Prepared starting from 3-cyano-benzoic acid following sequentially general procedures U and J. LC-MS-conditions 02: $t_R$=0.77 min; [M+AcCN+H]$^+$=256.09.

5-(3-Dimethylamino-phenyl)-oxazole-4-carboxylic acid

Prepared starting from 3-dimethylamino-benzoic acid following sequentially general procedures U and J. LC-MS-conditions 02: $t_R$=0.60 min; [M+H]$^+$=233.36.

5-[3-(2-Methoxy-ethyl)-phenyl]-oxazole-4-carboxylic acid

Prepared starting from 5-[3-(2-methoxy-ethyl)-phenyl]-oxazole-4-carboxylic acid methyl ester following general procedure J. LC-MS-conditions 02: $t_R$=0.81 min; [M+H]$^+$=248.37.

5-[3-(2-Isopropoxy-ethyl)-phenyl]-oxazole-4-carboxylic acid

Prepared starting from 5-[3-(2-isopropoxy-ethyl)-phenyl]-oxazole-4-carboxylic acid isopropyl ester following general procedure J. LC-MS-conditions 02: $t_R$=0.89 min; [M+H]$^+$=275.6.

5-[3-(2-Hydroxy-ethyl)-phenyl]-oxazole-4-carboxylic acid

Prepared starting from 3-(2-hydroxy-ethyl)-benzoic acid following sequentially general procedures U and J. LC-MS-conditions 02: $t_R$=0.71 min; [M+H]$^+$=234.36.

5-[3-(2-Hydroxy-ethyl)-phenyl]-oxazole-4-carboxylic acid methyl ester

Prepared starting from 3-(2-hydroxy-ethyl)-benzoic acid following sequentially general procedure U. LC-MS-conditions 02: $t_R$=0.78 min; [M+H]$^+$=248.33.

5-(3-tert-Butoxycarbonyl-phenyl)-oxazole-4-carboxylic acid

Prepared starting from isophthalic acid mono-tert-butyl ester following sequentially general procedures U and V. LC-MS-conditions 02: $t_R$=0.94 min.

5-(2-Fluoro-pyridin-4-yl)-oxazole-4-carboxylic acid

Prepared starting from 2-fluoro-isonicotinic acid following sequentially general procedures U and V. LC-MS-conditions 02: $t_R$=0.69 min; [M+AcCN+H]$^+$=250.10.

5-Pyridin-4-yl-oxazole-4-carboxylic acid (lithium salt of) Prepared starting from isonicotinic acid following sequentially general procedures U and V. LC-MS-conditions 02: $t_R$=0.31 min; [M+AcCN+H]$^+$=191.48.

2-Methoxymethyl-5-phenyl-oxazole-4-carboxylic acid

Prepared starting from DL-3-phenylserine hydrate following sequentially general procedures Y, Z with methoxyacetic acid, Z1 and Z2. LC-MS-conditions 02: $t_R$=0.81 min; [M+H]$^+$=234.45.

2-(2-Methoxy-ethyl)-5-phenyl-oxazole-4-carboxylic acid

Prepared starting from DL-3-phenylserine hydrate following sequentially general procedures Y, Z with 3-methoxy-propionic acid, Z1 and Z2. LC-MS-conditions 02: $t_R$=0.77 min; [M+H]$^+$=247.96.

2-Isopropyl-5-phenyl-oxazole-4-carboxylic acid

Prepared starting from DL-3-phenylserine hydrate following sequentially general procedures Y, Z with isobutyric acid, Z1 and Z2. LC-MS-conditions 02: $t_R$=0.90 min; [M+H]$^+$=232.51.

2-Butyl-5-phenyl-oxazole-4-carboxylic acid

Prepared starting from DL-3-phenylserine hydrate following sequentially general procedures Y, Z with pentanoic acid, Z1 and Z2. LC-MS-conditions 02: $t_R$=0.95 min; [M+H]$^+$=246.45.

2-Benzyl-5-phenyl-oxazole-4-carboxylic acid

Prepared starting from DL-3-phenylserine hydrate following sequentially general procedures Y, Z with phenyl-acetic acid, Z1 and Z2. LC-MS-conditions 02: $t_R$=0.95 min; $[M+H]^+$=220.18.

2-(2-tert-Butoxycarbonyl-ethyl)-5-phenyl-oxazole-4-carboxylic acid

Prepared starting from DL-3-phenylserine hydrate following sequentially general procedures Y, Z with succinic acid mono-tert-butyl ester, Z1 and Z2. LC-MS-conditions 02: $t_R$=0.95 min; $[M+H]^+$=318.32.

5-(6-Methyl-pyridin-2-yl)-oxazole-4-carboxylic acid lithium salt

Prepared starting from 6-methyl-pyridine-2-carboxylic acid following sequentially general procedures U and V. LC-MS-conditions 02: $t_R$=0.59 min; $[M+H]^+$=205.48.

5-(6-Trifluoromethyl-pyridin-2-yl)-oxazole-4-carboxylic acid lithium salt

Prepared starting from 6-trifluoromethyl-pyridine-2-carboxylic acid following sequentially general procedures U and V. LC-MS-conditions 02: $t_R$=0.80 min; $[M+H]^+$=259.12.

5-Isoxazol-5-yl-oxazole-4-carboxylic acid lithium salt

Prepared starting from isoxazole-5-carboxylic acid following sequentially general procedures U and V. LC-MS-conditions 02: $t_R$=0.64 min.

2-Methyl-5-(3-chloro-phenyl)-oxazole-4-carboxylic acid

Prepared starting from 3-(3-chloro-phenyl)-3-oxo-propionic acid ethyl ester following sequentially general procedures K, L and J. LC-MS-conditions 02: $t_R$=0.87 min; $[M+H]^+$=238.06.

5-(3-Methyl-phenyl)-oxazole-4-carboxylic acid

Prepared starting from 3-methyl-benzoic acid following sequentially general procedures U and J. LC-MS-conditions 02: $t_R$=0.83 min; $[M+H]^+$=204.17.

5-(3-Cyano-phenyl)-oxazole-4-carboxylic acid

Prepared starting from 3-cyano-benzoic acid following sequentially general procedures U and J. LC-MS-conditions 02: $t_R$=0.77 min; $[M+AcCN+H]^+$=256.09.

5-(4-Chloro-phenyl)-2-methyl-thiazole-4-carboxylic acid

Prepared starting from 4-chloro-benzaldehyde following sequentially general procedures E, F and J. LC-MS-conditions 02: $t_R$=0.84 min; $[M+H]^+$=254.23.

5-(3-Methoxy-4-methyl-phenyl)-oxazole-4-carboxylic acid

Prepared starting from 3-methoxy-4-methyl-benzoic acid following sequentially general procedures S, R, Q, P and J. LC-MS-conditions 02: $t_R$=0.86 min; $[M+H]^+$=234.11.

EXAMPLES

Example 1

[1-(5-Acetyl-furan-2-ylmethyl)-1H-pyrazol-4-yl]-carbamic acid 2-chloro-benzyl ester Following general procedures G and H, starting from [1-(5-formyl-furan-2-ylmethyl)-1H-pyrazol-4-yl]-carbamic acid 2-chloro-benzyl ester and methylmagnesium bromide.
LC-MS-conditions 02: $t_R$=0.96 min; $[M+H]^+$=373.99.

Example 2

[1-(5-Propionyl-furan-2-ylmethyl)-1H-pyrazol-4-yl]-carbamic acid 2-chloro-benzyl ester Following general procedures G and H, starting from [1-(5-formyl-furan-2-ylmethyl)-1H-pyrazol-4-yl]-carbamic acid 2-chloro-benzyl ester and ethylmagnesium bromide.
LC-MS-conditions 02: $t_R$=0.94 min; $[M+H]^+$=388.3.

Example 3

[1-(5-Cyclopropanecarbonyl-furan-2-ylmethyl)-1H-pyrazol-4-yl]-carbamic acid 2-chloro-benzyl ester Following general procedures G and H, starting from [1-(5-formyl-furan-2-ylmethyl)-1H-pyrazol-4-yl]-carbamic acid 2-chloro-benzyl ester and cyclopropylmagnesium bromide.
LC-MS-conditions 02: $t_R$=0.95 min; $[M+H]^+$=400.3.

Example 4

[1-(5-Isobutyryl-furan-2-ylmethyl)-1H-pyrazol-4-yl]-carbamic acid 2-chloro-benzyl ester Following general procedures G and H, starting from [1-(5-formyl-furan-2-ylmethyl)-1H-pyrazol-4-yl]-carbamic acid 2-chloro-benzyl ester and isopropylmagnesium bromide.
LC-MS-conditions 02: $t_R$=0.98 min; $[M+H]^+$=402.29.

Example 5

[1-(5-Acetyl-furan-2-ylmethyl)-1H-pyrazol-3-yl]-carbamic acid benzyl ester

Following general procedure A or I followed by either C or D, starting from 1-[5-(2-methyl-[1,3]dioxolan-2-yl)-furan-2-ylmethyl]-1H-pyrazol-3-ylamine and phenyl-methanol.
LC-MS-conditions 01: $t_R$=0.89 min; $[M+H]^+$=340.05.

Example 6

[1-(5-Acetyl-furan-2-ylmethyl)-1H-pyrazol-3-yl]-carbamic acid 2-methyl-benzyl ester Following general procedure A or I followed by either C or D, starting from 1-[5-(2-methyl-[1,3]dioxolan-2-yl)-furan-2-ylmethyl]-1H-pyrazol-3-ylamine and o-tolyl-methanol
LC-MS-conditions 01: $t_R$=0.92 min; $[M+H]^+$=354.07. .

Example 7

[1-(5-Acetyl-furan-2-ylmethyl)-1H-pyrazol-3-yl]-carbamic acid 4-trifluoromethyl-benzyl ester Following general procedure A or I followed by either C or D, starting from 1-[5-(2-methyl-[1,3]dioxolan-2-yl)-furan-2-ylmethyl]-1H-pyrazol-3-ylamine and (4-trifluoromethyl-phenyl)-methanol.
LC-MS-conditions 01: $t_R$=0.96 min; $[M+H]^+$=408.04.

Example 8

[1-(5-Acetyl-furan-2-ylmethyl)-1H-pyrazol-3-yl]-carbamic acid 3-trifluoromethyl-benzyl ester Following general procedure A or I followed by either C or D, starting from 1-[5-(2-methyl-[1,3]dioxolan-2-yl)-furan-2-ylmethyl]-1H-pyrazol-3-ylamine and (3-trifluoromethyl-phenyl)-methanol.
LC-MS-conditions 01: $t_R$=0.96 min; $[M+H]^+$=408.04.

Example 9

[1-(5-Acetyl-furan-2-ylmethyl)-1H-pyrazol-3-yl]-carbamic acid 3-chloro-benzyl ester Following general procedure A or I followed by either C or D, starting from 1-[5-(2-methyl-[1,3]dioxolan-2-yl)-furan-2-ylmethyl]-1H-pyrazol-3-ylamine and (3-chloro-phenyl)-methanol.
LC-MS-conditions 01: $t_R$=0.94 min; $[M+H]^+$=374.02.

Example 10

[1-(5-Acetyl-furan-2-ylmethyl)-1H-pyrazol-3-yl]-carbamic acid 2-chloro-4-fluoro-benzyl ester Following general procedure A or I followed by either C or D, starting from 1-[5-(2-methyl-[1,3]dioxolan-2-yl)-furan-2-ylmethyl]-1H-pyrazol-3-ylamine and (2-chloro-4-fluoro-phenyl)-methanol.
LC-MS-conditions 01: $t_R$=0.95 min; $[M+H]^+$=392.0.

Example 11

[1-(5-Acetyl-furan-2-ylmethyl)-1H-pyrazol-3-yl]-carbamic acid 2-ethyl-benzyl ester Following general procedure A or I followed by either C or D, starting from 1-[5-(2-methyl-[1,3]dioxolan-2-yl)-furan-2-ylmethyl]-1H-pyrazol-3-ylamine and (2-ethyl-phenyl)-methanol.
LC-MS-conditions 01: $t_R$=0.96 min; $[M+H]^+$=368.09.

Example 12

[1-(5-Acetyl-furan-2-ylmethyl)-1H-pyrazol-3-yl]-carbamic acid 2,6-dichloro-benzyl ester Following general procedure A or I followed by either C or D, starting from 1-[5-(2-methyl-[1,3]dioxolan-2-yl)-furan-2-ylmethyl]-1H-pyrazol-3-ylamine and (2,6-dichloro-phenyl)-methanol.
LC-MS-conditions 01: $t_R$=0.96 min; $[M+H]^+$=408.0.

Example 13

[1-(5-Acetyl-furan-2-ylmethyl)-1H-pyrazol-3-yl]-carbamic acid 3,4-dimethyl-benzyl ester Following general procedure A or I followed by either C or D, starting from 1-[5-(2-methyl-[1,3]dioxolan-2-yl)-furan-2-ylmethyl]-1H-pyrazol-3-ylamine and (3,4-dimethyl-phenyl)-methanol.
LC-MS-conditions 01: $t_R$=0.96 min; $[M+H]^+$=368.1.

Example 14

[1-(5-Acetyl-furan-2-ylmethyl)-1H-pyrazol-3-yl]-carbamic acid 3,4-difluoro-benzyl ester Following general procedure A or I followed by either C or D, starting from 1-[5-(2-methyl-[1,3]dioxolan-2-yl)-furan-2-ylmethyl]-1H-pyrazol-3-ylamine and (3,4-difluoro-phenyl)-methanol.
LC-MS-conditions 01: $t_R$=0.92 min; $[M+H]^+$=376.03.

Example 15

[1-(5-Acetyl-furan-2-ylmethyl)-1H-pyrazol-3-yl]-carbamic acid 2-chloro-6-fluoro-benzyl ester Following general procedure A or I followed by either C or D, starting from 1-[5-(2-methyl-[1,3]dioxolan-2-yl)-furan-2-ylmethyl]-1H-pyrazol-3-ylamine and (2-chloro-6-fluoro-phenyl)-methanol.
LC-MS-conditions 01: $t_R$=0.93 min; $[M+H]^+$=392.0.

Example 16

[1-(5-Acetyl-furan-2-ylmethyl)-1H-pyrazol-3-yl]-carbamic acid naphthalen-1-ylmethyl ester Following general procedure A or I followed by either C or D, starting from 1-[5-(2-methyl-[1,3]dioxolan-2-yl)-furan-2-ylmethyl]-1H-pyrazol-3-ylamine and naphthalen-1-yl-methanol.
LC-MS-conditions 01: $t_R$=0.96 min; $[M+H]^+$=390.07.

Example 17

[1-(5-Acetyl-furan-2-ylmethyl)-1H-pyrazol-3-yl]-carbamic acid 2,5-dimethyl-benzyl ester Following general procedure A or I followed by either C or D, starting from 1-[5-(2-methyl-[1,3]dioxolan-2-yl)-furan-2-ylmethyl]-1H-pyrazol-3-ylamine and (2,5-dimethyl-phenyl)-methanol.
LC-MS-conditions 01: $t_R$=0.96 min; $[M+H]^+$=368.09.

Example 18

[1-(5-Acetyl-furan-2-ylmethyl)-1H-pyrazol-3-yl]-carbamic acid 2,4,6-trifluoro-benzyl ester Following general procedure A or I followed by either C or D, starting from 1-[5-(2-methyl-[1,3]dioxolan-2-yl)-furan-2-ylmethyl]-1H-pyrazol-3-ylamine and (2,4,6-trifluoro-phenyl)-methanol
LC-MS-conditions 01: $t_R$=0.92 min; $[M+H]^+$=394.03. .

Example 19

[1-(5-Acetyl-furan-2-ylmethyl)-1H-pyrazol-3-yl]-carbamic acid 2,3-difluoro-benzyl ester Following general procedure A or I followed by either C or D, starting from 1-[5-(2-methyl-[1,3]dioxolan-2-yl)-furan-2-ylmethyl]-1H-pyrazol-3-ylamine and (2,3-difluoro-phenyl)-methanol.
LC-MS-conditions 01: $t_R$=0.92 min; $[M+H]^+$=376.02.

Example 20

[1-(5-Acetyl-furan-2-ylmethyl)-1H-pyrazol-3-yl]-carbamic acid 3-chloro-2,6-difluoro-benzyl ester Following general procedure A or I followed by either C or D, starting from 1-[5-(2-methyl-[1,3]dioxolan-2-yl)-furan-2-ylmethyl]-1H-pyrazol-3-ylamine and (3-chloro-2,6-difluoro-phenyl)-methanol.
LC-MS-conditions 01: $t_R$=0.95 min; $[M+H]^+$=410.0.

Example 21

[1-(5-Acetyl-furan-2-ylmethyl)-1H-pyrazol-3-yl]-carbamic acid 6-chloro-2-fluoro-3-methyl-benzyl ester Following general procedure A or I followed by either C or D, starting from 1-[5-(2-methyl-[1,3]dioxolan-2-yl)-furan-2-ylmethyl]-1H-pyrazol-3-ylamine and (6-chloro-2-fluoro-3-methyl-phenyl)-methanol.
LC-MS-conditions 01: $t_R$=0.97 min; $[M+H]^+$=406.03.

Example 22

[1-(5-Acetyl-furan-2-ylmethyl)-1H-pyrazol-3-yl]-carbamic acid 3-chloro-2-fluoro-benzyl ester Following general procedure A or I followed by either C or D, starting from 1-[5-(2-methyl-[1,3]dioxolan-2-yl)-furan-2-ylmethyl]-1H-pyrazol-3-ylamine and (3-chloro-2-fluoro-phenyl)-methanol.
LC-MS-conditions 01: $t_R$=0.94 min; $[M+H]^+$=392.0.

Example 23

[1-(5-Acetyl-furan-2-ylmethyl)-1H-pyrazol-3-yl]-carbamic acid 2-chloro-6-fluoro-3-methyl-benzyl ester Following general procedure A or I followed by either C or D, starting from 1-[5-(2-methyl-[1,3]dioxolan-2-yl)-furan-2-ylmethyl]-1H-pyrazol-3-ylamine and (2-chloro-6-fluoro-3-methyl-phenyl)-methanol.
LC-MS-conditions 01: $t_R$=0.97 min; $[M+H]^+$=406.03.

Example 24

[1-(5-Acetyl-furan-2-ylmethyl)-1H-pyrazol-3-yl]-carbamic acid 2,4,5-trifluoro-benzyl ester Following general procedure A or I followed by either C or D, starting from 1-[5-(2-methyl-[1,3]dioxolan-2-yl)-furan-2-ylmethyl]-1H-pyrazol-3-ylamine and (2,4,5-trifluoro-phenyl)-methanol.
LC-MS-conditions 01: $t_R$=0.93 min; $[M+H]^+$=394.04.

Example 25

[1-(5-Acetyl-furan-2-ylmethyl)-1H-pyrazol-3-yl]-carbamic acid 2,3,4-trifluoro-benzyl ester Following general procedure A or I followed by either C or D, starting from 1-[5-(2-methyl-[1,3]dioxolan-2-yl)-furan-2-ylmethyl]-1H-pyrazol-3-ylamine and (2,3,4-trifluoro-phenyl)-methanol.
LC-MS-conditions 01: $t_R$=0.93 min; $[M+H]^+$=394.02.

Example 26

[1-(5-Acetyl-furan-2-ylmethyl)-1H-pyrazol-3-yl]-carbamic acid 4-bromo-benzyl ester Following general procedure A or I followed by either C or D, starting from 1-[5-(2-methyl-[1,3]dioxolan-2-yl)-furan-2-ylmethyl]-1H-pyrazol-3-ylamine and (4-bromo-phenyl)-methanol.
LC-MS-conditions 01: $t_R$=0.94 min; $[M+H]^+$=417.99.

Example 27

[1-(5-Acetyl-furan-2-ylmethyl)-1H-pyrazol-3-yl]-carbamic acid 2-trifluoromethyl-benzyl ester Following general procedure A or I followed by either C or D, starting from 1-[5-(2-methyl-[1,3]dioxolan-2-yl)-furan-2-ylmethyl]-1H-pyrazol-3-ylamine and (2-trifluoromethyl-phenyl)-methanol.
LC-MS-conditions 01: $t_R$=0.96 min; $[M+H]^+$=408.05.

Example 28

[1-(5-Acetyl-furan-2-ylmethyl)-1H-pyrazol-3-yl]-carbamic acid 2-fluoro-benzyl ester Following general procedure A or I followed by either C or D, starting from 1-[5-(2-methyl-[1,3]dioxolan-2-yl)-furan-2-ylmethyl]-1H-pyrazol-3-ylamine and (2-fluoro-phenyl)-methanol.
LC-MS-conditions 01: $t_R$=0.90 min; $[M+H]^+$=358.04.

Example 29

[1-(5-Acetyl-furan-2-ylmethyl)-1H-pyrazol-3-yl]-carbamic acid 4-chloro-benzyl ester Following general procedure A or I followed by either C or D, starting from 1-[5-(2-methyl-[1,3]dioxolan-2-yl)-furan-2-ylmethyl]-1H-pyrazol-3-ylamine and (4-chloro-phenyl)-methanol.
LC-MS-conditions 01: $t_R$=0.94 min; $[M+H]^+$=374.02.

Example 30

[1-(5-Acetyl-furan-2-ylmethyl)-1H-pyrazol-3-yl]-carbamic acid 3-methyl-benzyl ester Following general procedure A or I followed by either C or D, starting from 1-[5-(2-methyl-[1,3]dioxolan-2-yl)-furan-2-ylmethyl]-1H-pyrazol-3-ylamine and (3-methyl-phenyl)-methanol.
LC-MS-conditions 01: $t_R$=0.93 min; $[M+H]^+$=354.07.

Example 31

[1-(5-Acetyl-furan-2-ylmethyl)-1H-pyrazol-3-yl]-carbamic acid 2,6-difluoro-3-methyl-benzyl ester Following general procedure A or I followed by either C or D, starting from 1-[5-(2-methyl-[1,3]dioxolan-2-yl)-furan-2-ylmethyl]-1H-pyrazol-3-ylamine and (2,6-difluoro-3-methyl-phenyl)-methanol.
LC-MS-conditions 01: $t_R$=0.95 min; [M+H]$^+$=390.05.

Example 32

5-Phenyl-oxazole-4-carboxylic acid [1-(5-acetyl-furan-2-ylmethyl)-1H-pyrazol-3-yl]-amide Following general procedure B followed by either C or D, starting from 1-[5-(2-methyl-[1,3]dioxolan-2-yl)-furan-2-ylmethyl]-1H-pyrazol-3-ylamine and 5-phenyl-oxazole-4-carboxylic acid.
LC-MS-conditions 01: $t_R$=0.92 min; [M+H]$^+$=377.06.

Example 33

(E)-N-[1-(5-Acetyl-furan-2-ylmethyl)-1H-pyrazol-3-yl]-3-phenyl-acrylamide

Following general procedure B followed by either C or D, starting from 1-[5-(2-methyl-[1,3]dioxolan-2-yl)-furan-2-ylmethyl]-1H-pyrazol-3-ylamine and (E)-3-phenyl-acrylic acid.
LC-MS-conditions 01: $t_R$=0.87 min; [M+H]$^+$=336.10.

Example 34

(E)-N-[1-(5-Acetyl-furan-2-ylmethyl)-1H-pyrazol-3-yl]-3-(2-trifluoromethyl-phenyl)-acrylamide Following general procedure B followed by either C or D, starting from 1-[5-(2-methyl-[1,3]dioxolan-2-yl)-furan-2-ylmethyl]-1H-pyrazol-3-ylamine and (E)-3-(2-trifluoromethyl-phenyl)-acrylic acid.
LC-MS-conditions 01: $t_R$=0.95 min; [M+H]$^+$=404.07.

Example 35

(E)-N-[1-(5-Acetyl-furan-2-ylmethyl)-1H-pyrazol-3-yl]-3-(4-trifluoromethyl-phenyl)-acrylamide Following general procedure B followed by either C or D, starting from 1-[5-(2-methyl-[1,3]dioxolan-2-yl)-furan-2-ylmethyl]-1H-pyrazol-3-ylamine and (E)-3-(4-trifluoromethyl-phenyl)-acrylic acid.
LC-MS-conditions 01: $t_R$=0.96 min; [M+H]$^+$=404.08.

Example 36

(E)-N-[1-(5-Acetyl-furan-2-ylmethyl)-1H-pyrazol-3-yl]-3-(2-chloro-6-fluoro-phenyl)-acrylamide Following general procedure B followed by either C or D, starting from 1-[5-(2-methyl-[1,3]dioxolan-2-yl)-furan-2-ylmethyl]-1H-pyrazol-3-ylamine and (E)-3-(2-chloro-6-fluoro-phenyl)-acrylic acid.
LC-MS-conditions 01: $t_R$=0.93 min; [M+H]$^+$=388.03.

Example 37

(E)-N-[1-(5-Acetyl-furan-2-ylmethyl)-1H-pyrazol-3-yl]-3-(2,3-dimethoxy-phenyl)-acrylamide Following general procedure B followed by either C or D, starting from 1-[5-(2-methyl-[1,3]dioxolan-2-yl)-furan-2-ylmethyl]-1H-pyrazol-3-ylamine and (E)-3-(2,3-dimethoxy-phenyl)-acrylic acid.
LC-MS-conditions 01: $t_R$=0.88 min; [M+H]$^+$=396.11.

Example 38

(E)-N-[1-(5-Acetyl-furan-2-ylmethyl)-1H-pyrazol-3-yl]-3-(2,3-dichloro-phenyl)-acrylamide Following general procedure B followed by either C or D, starting from 1-[5-(2-methyl-[1,3]dioxolan-2-yl)-furan-2-ylmethyl]-1H-pyrazol-3-ylamine and (E)-3-(2,3-dichloro-phenyl)-acrylic acid.
LC-MS-conditions 01: $t_R$=0.96 min; [M+H]$^+$=404.01.

Example 39

(E)-N-[1-(5-Acetyl-furan-2-ylmethyl)-1H-pyrazol-3-yl]-3-(3-trifluoromethoxy-phenyl)-acrylamide Following general procedure B followed by either C or D, starting from 1-[5-(2-methyl-[1,3]dioxolan-2-yl)-furan-2-ylmethyl]-1H-pyrazol-3-ylamine and (E)-3-(3-trifluoromethoxy-phenyl)-acrylic acid.
LC-MS-conditions 01: $t_R$=0.97 min; [M+H]$^+$=420.09.

Example 40

(E)-N-[1-(5-Acetyl-furan-2-ylmethyl)-1H-pyrazol-3-yl]-3-(3-chloro-4-fluoro-phenyl)-acrylamide Following general procedure B followed by either C or D, starting from 1-[5-(2-methyl-[1,3]dioxolan-2-yl)-furan-2-ylmethyl]-1H-pyrazol-3-ylamine and (E)-3-(3-chloro-4-fluoro-phenyl)-acrylic acid.
LC-MS-conditions 01: $t_R$=0.94 min; [M+H]$^+$=388.03.

Example 41

(E)-N-[1-(5-Acetyl-furan-2-ylmethyl)-1H-pyrazol-3-yl]-3-(2-chloro-3,6-difluoro-phenyl)-acrylamide Following general procedure B followed by either C or D, starting from 1-[5-(2-methyl-[1,3]dioxolan-2-yl)-furan-2-ylmethyl]-1H-pyrazol-3-ylamine and (E)-3-(2-chloro-3,6-difluoro-phenyl)-acrylic acid.
LC-MS-conditions 01: $t_R$=0.95 min; [M+H]$^+$=406.04.

Example 42

(E)-N-[1-(5-Acetyl-furan-2-ylmethyl)-1H-pyrazol-3-yl]-3-(2,4-dichloro-phenyl)-acrylamide Following general procedure B followed by either C or D, starting from 1-[5-(2-methyl-[1,3]dioxolan-2-yl)-furan-2-ylmethyl]-1H-pyrazol-3-ylamine and (E)-3-(2,4-dichloro-phenyl)-acrylic acid.
LC-MS-conditions 01: $t_R$=0.97 min; [M+H]$^+$=404.02.

Example 43

(E)-N-[1-(5-Acetyl-furan-2-ylmethyl)-1H-pyrazol-3-yl]-3-(2-chloro-4-fluoro-phenyl)-acrylamide Following general procedure B followed by either C or D, starting from 1-[5-(2-methyl-[1,3]dioxolan-2-yl)-furan-2-yl-methyl]-1H-pyrazol-3-ylamine and (E)-3-(2-chloro-4-fluoro-phenyl)-acrylic acid.
LC-MS-conditions 01: $t_R$=0.93 min; [M+H]$^+$=388.03.

Example 44

(E)-N-[1-(5-Acetyl-furan-2-ylmethyl)-1H-pyrazol-3-yl]-3-(2-methoxy-phenyl)-acrylamide Following general procedure B followed by either C or D, starting from 1-[5-(2-methyl-[1,3]dioxolan-2-yl)-furan-2-yl-methyl]-1H-pyrazol-3-ylamine and (E)-3-(2-methoxy-phenyl)-acrylic acid.
LC-MS-conditions 01: $t_R$=0.89 min; [M+H]$^+$=366.09.

Example 45

(E)-N-[1-(5-Acetyl-furan-2-ylmethyl)-1H-pyrazol-3-yl]-3-(2-fluoro-3-trifluoromethyl-phenyl)-acrylamide Following general procedure B followed by either C or D, starting from 1-[5-(2-methyl-[1,3]dioxolan-2-yl)-furan-2-yl-methyl]-1H-pyrazol-3-ylamine and (E)-3-(2-fluoro-3-trifluoromethyl-phenyl)-acrylic acid.
LC-MS-conditions 01: $t_R$=0.97 min; [M+H]$^+$=422.09.

Example 46

(E)-N-[1-(5-Acetyl-furan-2-ylmethyl)-1H-pyrazol-3-yl]-3-o-tolyl-acrylamide

Following general procedure B followed by either C or D, starting from 1-[5-(2-methyl-[1,3]dioxolan-2-yl)-furan-2-yl-methyl]-1H-pyrazol-3-ylamine and (E)-3-o-tolyl-acrylic acid.
LC-MS-conditions 01: $t_R$=0.9 min; [M+H]$^+$=350.1.

Example 47

(E)-N-[1-(5-Acetyl-furan-2-ylmethyl)-1H-pyrazol-3-yl]-3-(3-chloro-phenyl)-acrylamide Following general procedure B followed by either C or D, starting from 1-[5-(2-methyl-[1,3]dioxolan-2-yl)-furan-2-yl-methyl]-1H-pyrazol-3-ylamine and (E)-3-(3-chloro-phenyl)-acrylic acid.
LC-MS-conditions 01: $t_R$=0.93 min; [M+H]$^+$=370.03.

Example 48

5-(4-Methoxy-phenyl)-oxazole-4-carboxylic acid [1-(5-acetyl-furan-2-ylmethyl)-1H-pyrazol-3-yl]-amide Following general procedure B followed by either C or D, starting from 1-[5-(2-methyl-[1,3]dioxolan-2-yl)-furan-2-yl-methyl]-1H-pyrazol-3-ylamine and 5-(4-methoxy-phenyl)-oxazole-4-carboxylic acid.
LC-MS-conditions 01: $t_R$=0.94 min; [M+H]$^+$=407.09.

Example 49

2-Methyl-5-m-tolyl-oxazole-4-carboxylic acid [1-(5-acetyl-furan-2-ylmethyl)-1H-pyrazol-3-yl]-amide Following general procedure B followed by either C or D, starting from 1-[5-(2-methyl-[1,3]dioxolan-2-yl)-furan-2-yl-methyl]-1H-pyrazol-3-ylamine and 2-methyl-5-m-tolyl-oxazole-4-carboxylic acid.
LC-MS-conditions 01: $t_R$=0.99 min; [M+H]$^+$=405.11.

Example 50

(E)-N-[1-(5-Acetyl-furan-2-ylmethyl)-1H-pyrazol-3-yl]-3-(3-trifluoromethyl-phenyl)-acrylamide Following general procedure B followed by either C or D, starting from 1-[5-(2-methyl-[1,3]dioxolan-2-yl)-furan-2-yl-methyl]-1H-pyrazol-3-ylamine and (E)-3-(3-trifluoromethyl-phenyl)-acrylic acid.
LC-MS-conditions 01: $t_R$=0.96 min; [M+H]$^+$=404.07.

Example 51

(E)-N-[1-(5-Acetyl-furan-2-ylmethyl)-1H-pyrazol-3-yl]-3-(4-methoxy-phenyl)-acrylamide Following general procedure B followed by either C or D, starting from 1-[5-(2-methyl-[1,3]dioxolan-2-yl)-furan-2-yl-methyl]-1H-pyrazol-3-ylamine and (E)-3-(4-methoxy-phenyl)-acrylic acid.
LC-MS-conditions 01: $t_R$=0.88 min; [M+H]$^+$=366.05.

Example 52

(E)-N-[1-(5-Acetyl-furan-2-ylmethyl)-1H-pyrazol-3-yl]-3-p-tolyl-acrylamide

Following general procedure B followed by either C or D, starting from 1-[5-(2-methyl-[1,3]dioxolan-2-yl)-furan-2-yl-methyl]-1H-pyrazol-3-ylamine and (E)-3-p-tolyl-acrylic acid.
LC-MS-conditions 01: $t_R$=0.91 min; [M+H]$^+$=350.09.

Example 53

(E)-N-[1-(5-Acetyl-furan-2-ylmethyl)-1H-pyrazol-3-yl]-3-(3-methoxy-phenyl)-acrylamide Following general procedure B followed by either C or D, starting from 1-[5-(2-methyl-[1,3]dioxolan-2-yl)-furan-2-yl-methyl]-1H-pyrazol-3-ylamine and (E)-3-(3-methoxy-phenyl)-acrylic acid.
LC-MS-conditions 01: $t_R$=0.89 min; [M+H]$^+$=366.06.

Example 54

(E)-N-[1-(5-Acetyl-furan-2-ylmethyl)-1H-pyrazol-3-yl]-3-m-tolyl-acrylamide

Following general procedure B followed by either C or D, starting from 1-[5-(2-methyl-[1,3]dioxolan-2-yl)-furan-2-yl-methyl]-1H-pyrazol-3-ylamine and (E)-3-m-tolyl-acrylic acid.
LC-MS-conditions 01: $t_R$=0.91 min; [M+H]$^+$=350.07.

Example 55

5-(3-Methoxy-phenyl)-thiazole-4-carboxylic acid [1-(5-acetyl-furan-2-ylmethyl)-1H-pyrazol-3-yl]-amide Following general procedure B followed by either C or D, starting from 1-[5-(2-methyl-[1,3]dioxolan-2-yl)-furan-2-ylmethyl]-1H-pyrazol-3-ylamine and 5-(3-methoxy-phenyl)-thiazole-4-carboxylic acid.

LC-MS-conditions 01: $t_R$=0.93 min; [M+H]$^+$=423.05.

Example 56

5-(3-Methoxy-phenyl)-oxazole-4-carboxylic acid [1-(5-acetyl-furan-2-ylmethyl)-1H-pyrazol-3-yl]-amide Following general procedure B followed by either C or D, starting from 1-[5-(2-methyl-[1,3]dioxolan-2-yl)-furan-2-ylmethyl]-1H-pyrazol-3-ylamine and 5-(3-methoxy-phenyl)-oxazole-4-carboxylic acid.

LC-MS-conditions 01: $t_R$=0.94 min; [M+H]$^+$=407.07.

Example 57

5-(4-Methoxy-phenyl)-2-methyl-oxazole-4-carboxylic acid [1-(5-acetyl-furan-2-ylmethyl)-1H-pyrazol-3-yl]-amide Following general procedure B followed by either C or D, starting from 1-[5-(2-methyl-[1,3]dioxolan-2-yl)-furan-2-ylmethyl]-1H-pyrazol-3-ylamine and 5-(4-methoxy-phenyl)-2-methyl-oxazole-4-carboxylic acid.

LC-MS-conditions 01: $t_R$=0.97 min; [M+H]$^+$=421.08.

Example 58

5-(2-Fluoro-phenyl)-thiazole-4-carboxylic acid [1-(5-acetyl-furan-2-ylmethyl)-1H-pyrazol-3-yl]-amide Following general procedure B followed by either C or D, starting from 1-[5-(2-methyl-[1,3]dioxolan-2-yl)-furan-2-ylmethyl]-1H-pyrazol-3-ylamine and 5-(2-fluoro-phenyl)-thiazole-4-carboxylic acid.

LC-MS-conditions 01: $t_R$=0.92 min; [M+H]$^+$=411.02.

Example 59

2-Methyl-5-o-tolyl-oxazole-4-carboxylic acid [1-(5-acetyl-furan-2-ylmethyl)-1H-pyrazol-3-yl]-amide Following general procedure B followed by either C or D, starting from 1-[5-(2-methyl-[1,3]dioxolan-2-yl)-furan-2-ylmethyl]-1H-pyrazol-3-ylamine and 2-methyl-5-o-tolyl-oxazole-4-carboxylic acid.

LC-MS-conditions 01: $t_R$=0.95 min; [M+H]$^+$=405.09.

Example 60

5-(3-Trifluoromethyl-phenyl)-thiazole-4-carboxylic acid [1-(5-acetyl-furan-2-ylmethyl)-1H-pyrazol-3-yl]-amide Following general procedure B followed by either C or D, starting from 1-[5-(2-methyl-[1,3]dioxolan-2-yl)-furan-2-ylmethyl]-1H-pyrazol-3-ylamine and 5-(3-trifluoromethyl-phenyl)-thiazole-4-carboxylic acid.

LC-MS-conditions 01: $t_R$=0.99 min; [M+H]$^+$=461.03.

Example 61

[1-(5-Acetyl-furan-2-ylmethyl)-1H-pyrazol-4-yl]-carbamic acid benzyl ester

Following general procedure A or I followed by either C or D, starting from 1-[5-(2-methyl-[1,3]dioxolan-2-yl)-furan-2-ylmethyl]-1H-pyrazol-4-ylamine and phenyl-methanol.

LC-MS-conditions 01: $t_R$=0.87 min; [M+H]$^+$=340.05.

Example 62

[1-(5-Acetyl-furan-2-ylmethyl)-1H-pyrazol-4-yl]-carbamic acid 2-methyl-benzyl ester Following general procedure A or I followed by either C or D, starting from 1-[5-(2-methyl-[1,3]dioxolan-2-yl)-furan-2-ylmethyl]-1H-pyrazol-4-ylamine and (2-methyl-phenyl)-methanol.

LC-MS-conditions 01: $t_R$=0.91 min; [M+H]$^+$=354.07.

Example 63

[1-(5-Acetyl-furan-2-ylmethyl)-1H-pyrazol-4-yl]-carbamic acid 4-trifluoromethyl-benzyl ester Following general procedure A or I followed by either C or D, starting from 1-[5-(2-methyl-[1,3]dioxolan-2-yl)-furan-2-ylmethyl]-1H-pyrazol-4-ylamine and (4-trifluoromethyl-phenyl)-methanol.

LC-MS-conditions 01: $t_R$=0.95 min; [M+H]$^+$=408.05.

Example 64

[1-(5-Acetyl-furan-2-ylmethyl)-1H-pyrazol-4-yl]-carbamic acid 3-trifluoromethyl-benzyl ester Following general procedure A or I followed by either C or D, starting from 1-[5-(2-methyl-[1,3]dioxolan-2-yl)-furan-2-ylmethyl]-1H-pyrazol-4-ylamine and (3-trifluoromethyl-phenyl)-methanol.

LC-MS-conditions 01: $t_R$=0.93 min; [M+H]$^+$=408.05.

Example 65

[1-(5-Acetyl-furan-2-ylmethyl)-1H-pyrazol-4-yl]-carbamic acid 3-chloro-benzyl ester Following general procedure A or I followed by either C or D, starting from 1-[5-(2-methyl-[1,3]dioxolan-2-yl)-furan-2-ylmethyl]-1H-pyrazol-4-ylamine and (3-chloro-phenyl)-methanol.

LC-MS-conditions 01: $t_R$=0.92 min; [M+H]$^+$=374.02.

Example 66

[1-(5-Acetyl-furan-2-ylmethyl)-1H-pyrazol-4-yl]-carbamic acid 2-chloro-4-fluoro-benzyl ester Following general procedure A or I followed by either C or D, starting from 1-[5-(2-methyl-[1,3]dioxolan-2-yl)-furan-2-ylmethyl]-1H-pyrazol-4-ylamine and (2-chloro-4-fluoro-phenyl)-methanol.

LC-MS-conditions 01: $t_R$=0.93 min; [M+H]$^+$=392.0.

Example 67

[1-(5-Acetyl-furan-2-ylmethyl)-1H-pyrazol-4-yl]-carbamic acid 2-ethyl-benzyl ester Following general procedure A or I followed by either C or D, starting from 1-[5-(2-methyl-[1,3]dioxolan-2-yl)-furan-2-ylmethyl]-1H-pyrazol-4-ylamine and (2-ethyl-phenyl)-methanol.
LC-MS-conditions 01: $t_R$=0.94 min; [M+H]$^+$=368.08.

Example 68

[1-(5-Acetyl-furan-2-ylmethyl)-1H-pyrazol-4-yl]-carbamic acid 2,6-dichloro-benzyl ester Following general procedure A or I followed by either C or D, starting from 1-[5-(2-methyl-[1,3]dioxolan-2-yl)-furan-2-ylmethyl]-1H-pyrazol-4-ylamine and (2,6-dichloro-phenyl)-methanol.
LC-MS-conditions 01: $t_R$=0.94 min; [M+H]$^+$=407.98.

Example 69

[1-(5-Acetyl-furan-2-ylmethyl)-1H-pyrazol-4-yl]-carbamic acid 3,4-dimethyl-benzyl ester Following general procedure A or I followed by either C or D, starting from 1-[5-(2-methyl-[1,3]dioxolan-2-yl)-furan-2-ylmethyl]-1H-pyrazol-4-ylamine and (3,4-dimethyl-phenyl)-methanol.
LC-MS-conditions 01: $t_R$=0.94 min; [M+H]$^+$=368.08.

Example 70

[1-(5-Acetyl-furan-2-ylmethyl)-1H-pyrazol-4-yl]-carbamic acid 3,4-difluoro-benzyl ester Following general procedure A or I followed by either C or D, starting from 1-[5-(2-methyl-[1,3]dioxolan-2-yl)-furan-2-ylmethyl]-1H-pyrazol-4-ylamine and (3,4-difluoro-phenyl)-methanol.
LC-MS-conditions 01: $t_R$=0.91 min; [M+H]$^+$=376.02

Example 71

[1-(5-Acetyl-furan-2-ylmethyl)-1H-pyrazol-4-yl]-carbamic acid 2-chloro-6-fluoro-benzyl ester Following general procedure A or I followed by either C or D, starting from 1-[5-(2-methyl-[1,3]dioxolan-2-yl)-furan-2-ylmethyl]-1H-pyrazol-4-ylamine and (2-chloro-6-fluoro-phenyl)-methanol.
LC-MS-conditions 01: $t_R$=0.91 min; [M+H]$^+$=392.01.

Example 72

[1-(5-Acetyl-furan-2-ylmethyl)-1H-pyrazol-4-yl]-carbamic acid naphthalen-1-ylmethyl ester Following general procedure A or I followed by either C or D, starting from 1-[5-(2-methyl-[1,3]dioxolan-2-yl)-furan-2-ylmethyl]-1H-pyrazol-4-ylamine and naphthalen-1-yl-methanol.
LC-MS-conditions 01: $t_R$=0.94 min; [M+H]$^+$=390.06.

Example 73

[1-(5-Acetyl-furan-2-ylmethyl)-1H-pyrazol-4-yl]-carbamic acid 2,5-dimethyl-benzyl ester Following general procedure A or I followed by either C or D, starting from 1-[5-(2-methyl-[1,3]dioxolan-2-yl)-furan-2-ylmethyl]-1H-pyrazol-4-ylamine and (2,5-dimethyl-phenyl)-methanol.
LC-MS-conditions 01: $t_R$=0.94 min; [M+H]$^+$=368.08.

Example 74

[1-(5-Acetyl-furan-2-ylmethyl)-1H-pyrazol-4-yl]-carbamic acid 2,4,6-trifluoro-benzyl ester Following general procedure A or I followed by either C or D, starting from 1-[5-(2-methyl-[1,3]dioxolan-2-yl)-furan-2-ylmethyl]-1H-pyrazol-4-ylamine and (2,4,6-trifluoro-phenyl)-methanol.
LC-MS-conditions 01: $t_R$=0.91 min; [M+H]$^+$=394.02.

Example 75

[1-(5-Acetyl-furan-2-ylmethyl)-1H-pyrazol-4-yl]-carbamic acid 2,3-difluoro-benzyl ester Following general procedure A or I followed by either C or D, starting from 1-[5-(2-methyl-[1,3]dioxolan-2-yl)-furan-2-ylmethyl]-1H-pyrazol-4-ylamine and (2,3-difluoro-phenyl)-methanol.
LC-MS-conditions 01: $t_R$=0.90 min; [M+H]$^+$=376.01.

Example 76

[1-(5-Acetyl-furan-2-ylmethyl)-1H-pyrazol-4-yl]-carbamic acid 3-chloro-2,6-difluoro-benzyl ester Following general procedure A or I followed by either C or D, starting from 1-[5-(2-methyl-[1,3]dioxolan-2-yl)-furan-2-ylmethyl]-1H-pyrazol-4-ylamine and (3-chloro-2,6-difluoro-phenyl)-methanol.
LC-MS-conditions 01: $t_R$=0.93 min; [M+H]$^+$=410.01.

Example 77

[1-(5-Acetyl-furan-2-ylmethyl)-1H-pyrazol-4-yl]-carbamic acid 6-chloro-2-fluoro-3-methyl-benzyl ester Following general procedure A or I followed by either C or D, starting from 1-[5-(2-methyl-[1,3]dioxolan-2-yl)-furan-2-ylmethyl]-1H-pyrazol-4-ylamine and (6-chloro-2-fluoro-3-methyl-phenyl)-methanol.
LC-MS-conditions 01: $t_R$=0.95 min; [M+H]$^+$=406.03.

Example 78

[1-(5-Acetyl-furan-2-ylmethyl)-1H-pyrazol-4-yl]-carbamic acid 3-chloro-2-fluoro-benzyl ester Following general procedure A or I followed by either C or D, starting from 1-[5-(2-methyl-[1,3]dioxolan-2-yl)-furan-2-ylmethyl]-1H-pyrazol-4-ylamine and (3-chloro-2-fluoro-phenyl)-methanol.
LC-MS-conditions 01: $t_R$=0.93 min; [M+H]$^+$=391.99.

Example 79

[1-(5-Acetyl-furan-2-ylmethyl)-1H-pyrazol-4-yl]-carbamic acid 2-chloro-6-fluoro-3-methyl-benzyl ester Following general procedure A or I followed by either C or D, starting from 1-[5-(2-methyl-[1,3]dioxolan-2-yl)-furan-2-ylmethyl]-1H-pyrazol-4-ylamine and (2-chloro-6-fluoro-3-methyl-phenyl)-methanol.
LC-MS-conditions 01: $t_R$=0.95 min; [M+H]$^+$=406.02.

Example 80

[1-(5-Acetyl-furan-2-ylmethyl)-1H-pyrazol-4-yl]-carbamic acid 2,4,5-trifluoro-benzyl ester Following general procedure A or I followed by either C or D, starting from 1-[5-(2-methyl-[1,3]dioxolan-2-yl)-furan-2-ylmethyl]-1H-pyrazol-4-ylamine and (2,4,5-trifluoro-phenyl)-methanol.
LC-MS-conditions 01: $t_R$=0.92 min; [M+H]$^+$=394.04.

Example 81

[1-(5-Acetyl-furan-2-ylmethyl)-1H-pyrazol-4-yl]-carbamic acid 2,6-difluoro-3-methyl-benzyl ester Following general procedure A or I followed by either C or D, starting from 1-[5-(2-methyl-[1,3]dioxolan-2-yl)-furan-2-ylmethyl]-1H-pyrazol-4-ylamine and (2,6-difluoro-3-methyl-phenyl)-methanol.
LC-MS-conditions 01: $t_R$=0.93 min; [M+H]$^+$=390.05.

Example 82

[1-(5-Acetyl-furan-2-ylmethyl)-1H-pyrazol-4-yl]-carbamic acid 2,3,4-trifluoro-benzyl ester Following general procedure A or I followed by either C or D, starting from 1-[5-(2-methyl-[1,3]dioxolan-2-yl)-furan-2-ylmethyl]-1H-pyrazol-4-ylamine and (2,3,4-trifluoro-phenyl)-methanol.
LC-MS-conditions 01: $t_R$=0.92 min; [M+H]$^+$=394.01.

Example 83

[1-(5-Acetyl-furan-2-ylmethyl)-1H-pyrazol-4-yl]-carbamic acid 4-bromo-benzyl ester Following general procedure A or I followed by either C or D, starting from 1-[5-(2-methyl-[1,3]dioxolan-2-yl)-furan-2-ylmethyl]-1H-pyrazol-4-ylamine and (4-bromo-phenyl)-methanol.
LC-MS-conditions 01: $t_R$=0.93 min; [M+H]$^+$=417.98.

Example 84

[1-(5-Acetyl-furan-2-ylmethyl)-1H-pyrazol-4-yl]-carbamic acid 2-trifluoromethyl-benzyl ester Following general procedure A or I followed by either C or D, starting from 1-[5-(2-methyl-[1,3]dioxolan-2-yl)-furan-2-ylmethyl]-1H-pyrazol-4-ylamine and (2-trifluoromethyl-phenyl)-methanol.
LC-MS-conditions 01: $t_R$=0.94 min; [M+H]$^+$=408.05.

Example 85

[1-(5-Acetyl-furan-2-ylmethyl)-1H-pyrazol-4-yl]-carbamic acid 2-fluoro-benzyl ester Following general procedure A or I followed by either C or D, starting from 1-[5-(2-methyl-[1,3]dioxolan-2-yl)-furan-2-ylmethyl]-1H-pyrazol-4-ylamine and (2-fluoro-phenyl)-methanol.
LC-MS-conditions 01: $t_R$=0.89 min; [M+H]$^+$=358.05.

Example 86

[1-(5-Acetyl-furan-2-ylmethyl)-1H-pyrazol-4-yl]-carbamic acid 4-chloro-benzyl ester Following general procedure A or I followed by either C or D, starting from 1-[5-(2-methyl-[1,3]dioxolan-2-yl)-furan-2-ylmethyl]-1H-pyrazol-4-ylamine and (4-chloro-phenyl)-methanol.
LC-MS-conditions 01: $t_R$=0.92 min; [M+H]$^+$=374.02.

Example 87

[1-(5-Acetyl-furan-2-ylmethyl)-1H-pyrazol-4-yl]-carbamic acid 3-methyl-benzyl ester Following general procedure A or I followed by either C or D, starting from 1-[5-(2-methyl-[1,3]dioxolan-2-yl)-furan-2-ylmethyl]-1H-pyrazol-4-ylamine and (3-methyl-phenyl)-methanol.
LC-MS-conditions 01: $t_R$=0.91 min; [M+H]$^+$=354.07.

Example 88

5-Phenyl-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 5-phenyl-oxazole-4-carboxylic acid.
LC-MS-conditions 01: $t_R$=0.9 min; [M+H]$^+$=377.07.

Example 89

(E)-N-[1-(5-Acetyl-furan-2-ylmethyl)-1H-pyrazol-4-yl]-3-phenyl-acrylamide

Following general procedure B followed by either C or D, starting from 1-[5-(2-methyl-[1,3]dioxolan-2-yl)-furan-2-ylmethyl]-1H-pyrazol-4-ylamine and (E)-3-phenyl-acrylic acid.
LC-MS-conditions 01: $t_R$=0.85 min; [M+H]$^+$=336.1.

Example 90

(E)-N-[1-(5-Acetyl-furan-2-ylmethyl)-1H-pyrazol-4-yl]-3-(2-trifluoromethyl-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(2-trifluoromethyl-phenyl)-acrylic acid.
LC-MS-conditions 01: $t_R$=0.92 min; [M+H]$^+$=404.07.

Example 91

(E)-N-[1-(5-Acetyl-furan-2-ylmethyl)-1H-pyrazol-4-yl]-3-(4-trifluoromethyl-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(4-trifluoromethyl-phenyl)-acrylic acid.
LC-MS-conditions 01: $t_R$=0.94 min; [M+H]$^+$=404.06.

Example 92

(E)-N-[1-(5-Acetyl-furan-2-ylmethyl)-1H-pyrazol-4-yl]-3-(2-chloro-6-fluoro-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(2-chloro-6-fluoro-phenyl)-acrylic acid.
LC-MS-conditions 01: $t_R$=0.91 min; [M+H]$^+$=388.04.

Example 93

(E)-N-[1-(5-Acetyl-furan-2-ylmethyl)-1H-pyrazol-4-yl]-3-(2,3-dimethoxy-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(2,3-dimethoxy-phenyl)-acrylic acid.
LC-MS-conditions 01: $t_R$=0.86 min; [M+H]$^+$=396.1.

Example 94

(E)-N-[1-(5-Acetyl-furan-2-ylmethyl)-1H-pyrazol-4-yl]-3-(2,3-dichloro-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(2,3-dichloro-phenyl)-acrylic acid.
LC-MS-conditions 01: $t_R$=0.94 min; [M+H]$^+$=404.0.

Example 95

(E)-N-[1-(5-Acetyl-furan-2-ylmethyl)-1H-pyrazol-4-yl]-3-(3-trifluoromethoxy-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(3-trifluoromethoxy-phenyl)-acrylic acid.
LC-MS-conditions 01: $t_R$=0.95 min; [M+H]$^+$=420.08.

Example 96

(E)-N-[1-(5-Acetyl-furan-2-ylmethyl)-1H-pyrazol-4-yl]-3-(3-chloro-4-fluoro-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(3-chloro-4-fluoro-phenyl)-acrylic acid.
LC-MS-conditions 01: $t_R$=0.92 min; [M+H]$^+$=388.03.

Example 97

(E)-N-[1-(5-Acetyl-furan-2-ylmethyl)-1H-pyrazol-4-yl]-3-(2-chloro-3,6-difluoro-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(2-chloro-3,6-difluoro-phenyl)-acrylic acid.
LC-MS-conditions 01: $t_R$=0.93 min; [M+H]$^+$=406.03.

Example 98

(E)-N-[1-(5-Acetyl-furan-2-ylmethyl)-1H-pyrazol-4-yl]-3-(2,4-dichloro-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(2,4-dichloro-phenyl)-acrylic acid.
LC-MS-conditions 01: $t_R$=0.95 min; [M+H]$^+$=404.01.

Example 99

(E)-N-[1-(5-Acetyl-furan-2-ylmethyl)-1H-pyrazol-4-yl]-3-(2-chloro-4-fluoro-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(2-chloro-4-fluoro-phenyl)-acrylic acid.
LC-MS-conditions 01: $t_R$=0.91 min; [M+H]$^+$=388.04.

Example 100

(E)-N-[1-(5-Acetyl-furan-2-ylmethyl)-1H-pyrazol-4-yl]-3-(2-methoxy-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(2-methoxy-phenyl)-acrylic acid.
LC-MS-conditions 01: $t_R$=0.87 min; [M+H]$^+$=366.08.

Example 101

(E)-N-[1-(5-Acetyl-furan-2-ylmethyl)-1H-pyrazol-4-yl]-3-(2-fluoro-3-trifluoromethyl-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(2-fluoro-3-trifluoromethyl-phenyl)-acrylic acid.
LC-MS-conditions 01: $t_R$=0.95 min; [M+H]$^+$=422.08.

Example 102

(E)-N-[1-(5-Acetyl-furan-2-ylmethyl)-1H-pyrazol-4-yl]-3-o-tolyl-acrylamide

Following general procedure B followed by either C or D, starting from 1-[5-(2-methyl-[1,3]dioxolan-2-yl)-furan-2-ylmethyl]-1H-pyrazol-4-ylamine and (E)-3-o-tolyl-acrylic acid.
LC-MS-conditions 01: $t_R$=0.88 min; [M+H]$^+$=350.11.

Example 103

(E)-N-[1-(5-Acetyl-furan-2-ylmethyl)-1H-pyrazol-4-yl]-3-(3-chloro-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(3-chloro-phenyl)-acrylic acid.
LC-MS-conditions 01: $t_R$=0.91 min; [M+H]$^+$=370.04.

Example 104

5-(4-Methoxy-phenyl)-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 5-(4-methoxy-phenyl)-oxazole-4-carboxylic acid.
LC-MS-conditions 01: $t_R$=0.92 min; [M+H]$^+$=407.1.

Example 105

2-Methyl-5-phenyl-thiazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 2-methyl-5-phenyl-thiazole-4-carboxylic acid.
LC-MS-conditions 01: $t_R$=0.93 min; [M+H]$^+$=407.09.

Example 106

2-Methyl-5-m-tolyl-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 2-methyl-5-m-tolyl-oxazole-4-carboxylic acid.
LC-MS-conditions 01: $t_R$=0.97 min; [M+H]$^+$=405.11.

Example 107

5-(4-Methoxy-phenyl)-2-methyl-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 5-(4-methoxy-phenyl)-2-methyl-oxazole-4-carboxylic acid.
LC-MS-conditions 02: $t_R$=0.99 min; [M+H]$^+$=421.01.

Example 108

2-Methyl-5-m-tolyl-thiazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 2-methyl-5-m-tolyl-thiazole-4-carboxylic acid.
LC-MS-conditions 01: $t_R$=0.97 min; [M+H]$^+$=421.11.

Example 109

(E)-N-[1-(5-Acetyl-furan-2-ylmethyl)-1H-pyrazol-4-yl]-3-(3-trifluoromethyl-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(3-trifluoromethyl-phenyl)-acrylic acid.
LC-MS-conditions 01: $t_R$=0.94 min; [M+H]$^+$=404.07.

Example 110

2-Methyl-5-p-tolyl-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 2-methyl-5-p-tolyl-oxazole-4-carboxylic acid.
LC-MS-conditions 01: $t_R$=0.97 min; [M+H]$^+$=405.12.

Example 111

5-(3-Methoxy-phenyl)-2-methyl-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 5-(3-methoxy-phenyl)-2-methyl-oxazole-4-carboxylic acid.
LC-MS-conditions 02: $t_R$=0.99 min; [M+H]$^+$=420.96.

Example 112

2-Methyl-5-phenyl-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 2-methyl-5-phenyl-oxazole-4-carboxylic acid.
LC-MS-conditions 02: $t_R$=1.00 min; [M+H]$^+$=390.93.

Example 113

(E)-N-[1-(5-Acetyl-furan-2-ylmethyl)-1H-pyrazol-4-yl]-3-(2-chloro-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(2-chloro-phenyl)-acrylic acid.
LC-MS-conditions 01: $t_R$=0.89 min; [M+H]$^+$=370.04.

Example 114

5-m-Tolyl-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 5-m-tolyl-oxazole-4-carboxylic acid.
LC-MS-conditions 02: $t_R$=0.98 min; [M+H]$^+$=390.93.

Example 115

(E)-N-[1-(5-Acetyl-furan-2-ylmethyl)-1H-pyrazol-4-yl]-3-p-tolyl-acrylamide

Following general procedure B followed by either C or D, starting from 1-[5-(2-methyl-[1,3]dioxolan-2-yl)-furan-2-ylmethyl]-1H-pyrazol-4-ylamine and (E)-3-p-tolyl-acrylic acid.
LC-MS-conditions 02: $t_R$=0.93 min; [M+H]$^+$=350.04.

Example 116

(E)-N-[1-(5-Acetyl-furan-2-ylmethyl)-1H-pyrazol-4-yl]-3-(3-methoxy-phenyl)-acrylamide Following general procedure B followed by either C or D, starting from 1-[5-(2-methyl-[1,3]dioxolan-2-yl)-furan-2-ylmethyl]-1H-pyrazol-4-ylamine and (E)-3-(3-methoxy-phenyl)-acrylic acid.
LC-MS-conditions 02: $t_R$=0.91 min; [M+H]$^+$=366.03.

Example 117

5-(3,5-Dimethyl-phenyl)-2-methyl-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 5-(3,5-dimethyl-phenyl)-2-methyl-oxazole-4-carboxylic acid.
LC-MS-conditions 02: $t_R$=1.04 min; [M+H]$^+$=419.05.

Example 118

5-(3-Methoxy-phenyl)-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 5-(3-methoxy-phenyl)-oxazole-4-carboxylic acid.
LC-MS-conditions 02: $t_R$=0.96 min; [M+H]$^+$=406.97.

Example 119

2-Methyl-5-o-tolyl-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 2-methyl-5-o-tolyl-oxazole-4-carboxylic acid.
LC-MS-conditions 02: $t_R$=0.97 min; [M+H]$^+$=404.98.

Example 120

5-(3-Chloro-phenyl)-thiazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 5-(3-chloro-phenyl)-thiazole-4-carboxylic acid.
LC-MS-conditions 02: $t_R$=0.99 min; [M+H]$^+$=426.85.

Example 121

5-(3-Trifluoromethyl-phenyl)-thiazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 5-(3-trifluoromethyl-phenyl)-thiazole-4-carboxylic acid.
LC-MS-conditions 02: $t_R$=1.01 min; [M+H]$^+$=460.88.

Example 122

5-(2-Fluoro-phenyl)-thiazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 5-(2-fluoro-phenyl)-thiazole-4-carboxylic acid.
LC-MS-conditions 02: $t_R$=0.94 min; [M+H]$^+$=410.89.

Example 123

[1-(5-Oxo-hexyl)-1H-pyrazol-4-yl]-carbamic acid 2-chloro-benzyl ester

Following general procedure A or I followed by either C or D, starting from 1-[4-(2-methyl-[1,3]dioxolan-2-yl)-butyl]-1H-pyrazol-4-ylamine and (2-chloro-phenyl)-methanol.
LC-MS-conditions 01: $t_R$=0.91 min; [M+H]$^+$=350.08.

Example 124

[1-(5-Oxo-hexyl)-1H-pyrazol-4-yl]-carbamic acid (RS)-1-(2-chloro-phenyl)-ethyl ester Following general procedure A or I followed by either C or D, starting from 1-[4-(2-methyl-[1,3]dioxolan-2-yl)-butyl]-1H-pyrazol-4-ylamine and (RS)-1-(2-chloro-phenyl)-ethanol.
LC-MS-conditions 01: $t_R$=0.94 min; [M+H]$^+$=364.1.

Example 125

[1-(5-Oxo-hexyl)-1H-pyrazol-4-yl]-carbamic acid (RS)-1-phenyl-ethyl ester

Following general procedure A or I followed by either C or D, starting from 1-[4-(2-methyl-[1,3]dioxolan-2-yl)-butyl]-1H-pyrazol-4-ylamine and (RS)-1-phenyl-ethanol.
LC-MS-conditions 01: $t_R$=0.9 min; [M+H]$^+$=330.14.

Example 126

[1-(5-Oxo-hexyl)-1H-pyrazol-4-yl]-carbamic acid 4-bromo-benzyl ester

Following general procedure A or I followed by either C or D, starting from 1-[4-(2-methyl-[1,3]dioxolan-2-yl)-butyl]-1H-pyrazol-4-ylamine and (4-bromo-phenyl)-methanol.
LC-MS-conditions 01: $t_R$=0.94 min; [M+H]$^+$=393.9.

Example 127

[1-(5-Oxo-hexyl)-1H-pyrazol-4-yl]-carbamic acid 2-trifluoromethyl-benzyl ester

Following general procedure A or I followed by either C or D, starting from 1-[4-(2-methyl-[1,3]dioxolan-2-yl)-butyl]-1H-pyrazol-4-ylamine and (2-trifluoromethyl-phenyl)-methanol.
LC-MS-conditions 01: $t_R$=0.94 min; [M+H]$^+$=384.09.

Example 128

[1-(5-Oxo-hexyl)-1H-pyrazol-4-yl]-carbamic acid 2-fluoro-benzyl ester

Following general procedure A or I followed by either C or D, starting from 1-[4-(2-methyl-[1,3]dioxolan-2-yl)-butyl]-1H-pyrazol-4-ylamine and (2-fluoro-phenyl)-methanol.
LC-MS-conditions 01: $t_R$=0.88 min; [M+H]$^+$=334.1.

Example 129

[1-(5-Oxo-hexyl)-1H-pyrazol-4-yl]-carbamic acid 4-chloro-benzyl ester

Following general procedure A or I followed by either C or D, starting from 1-[4-(2-methyl-[1,3]dioxolan-2-yl)-butyl]-1H-pyrazol-4-ylamine and (4-chloro-phenyl)-methanol.
LC-MS-conditions 01: $t_R$=0.92 min; [M+H]$^+$=350.07.

Example 130

[1-(5-Oxo-hexyl)-1H-pyrazol-4-yl]-carbamic acid 3-methyl-benzyl ester

Following general procedure A or I followed by either C or D, starting from 1-[4-(2-methyl-[1,3]dioxolan-2-yl)-butyl]-1H-pyrazol-4-ylamine and (3-methyl-phenyl)-methanol.
LC-MS-conditions 01: $t_R$=0.91 min; [M+H]$^+$=330.14.

Example 131

[1-(5-Oxo-hexyl)-1H-pyrazol-4-yl]-carbamic acid 4-trifluoromethyl-benzyl ester

Following general procedure A or I followed by either C or D, starting from 1-[4-(2-methyl-[1,3]dioxolan-2-yl)-butyl]-1H-pyrazol-4-ylamine and (4-trifluoromethyl-phenyl)-methanol.
LC-MS-conditions 01: $t_R$=0.95 min; [M+H]$^+$=384.1.

Example 132

[1-(5-Oxo-hexyl)-1H-pyrazol-4-yl]-carbamic acid 3-trifluoromethyl-benzyl ester

Following general procedure A or I followed by either C or D, starting from 1-[4-(2-methyl-[1,3]dioxolan-2-yl)-butyl]-1H-pyrazol-4-ylamine and (3-trifluoromethyl-phenyl)-methanol.
LC-MS-conditions 01: $t_R$=0.95 min; [M+H]$^+$=384.1.

Example 133

[1-(5-Oxo-hexyl)-1H-pyrazol-4-yl]-carbamic acid 3-chloro-benzyl ester

Following general procedure A or I followed by either C or D, starting from 1-[4-(2-methyl-[1,3]dioxolan-2-yl)-butyl]-1H-pyrazol-4-ylamine and (3-chloro-phenyl)-methanol.
LC-MS-conditions 01: $t_R$=0.92 min; [M+H]$^+$=350.06.

Example 134

[1-(5-Oxo-hexyl)-1H-pyrazol-4-yl]-carbamic acid 2-chloro-4-fluoro-benzyl ester

Following general procedure A or I followed by either C or D, starting from 1-[4-(2-methyl-[1,3]dioxolan-2-yl)-butyl]-1H-pyrazol-4-ylamine and (2-chloro-4-fluoro-phenyl)-methanol.
LC-MS-conditions 01: $t_R$=0.93 min; [M+H]$^+$=368.06.

Example 135

[1-(5-Oxo-hexyl)-1H-pyrazol-4-yl]-carbamic acid 2-ethyl-benzyl ester

Following general procedure A or I followed by either C or D, starting from 1-[4-(2-methyl-[1,3]dioxolan-2-yl)-butyl]-1H-pyrazol-4-ylamine and (2-ethyl-phenyl)-methanol.
LC-MS-conditions 01: $t_R$=0.94 min; [M+H]$^+$=344.15.

Example 136

[1-(5-Oxo-hexyl)-1H-pyrazol-4-yl]-carbamic acid 2,6-dichloro-benzyl ester

Following general procedure A or I followed by either C or D, starting from 1-[4-(2-methyl-[1,3]dioxolan-2-yl)-butyl]-1H-pyrazol-4-ylamine and (2,6-dichloro-phenyl)-methanol.
LC-MS-conditions 01: $t_R$=0.94 min; [M+H]$^+$=384.04.

Example 137

[1-(5-Oxo-hexyl)-1H-pyrazol-4-yl]-carbamic acid 3,4-dimethyl-benzyl ester

Following general procedure A or I followed by either C or D, starting from 1-[4-(2-methyl-[1,3]dioxolan-2-yl)-butyl]-1H-pyrazol-4-ylamine and (3,4-dimethyl-phenyl)-methanol.
LC-MS-conditions 01: $t_R$=0.94 min; [M+H]$^+$=344.15.

Example 138

[1-(5-Oxo-hexyl)-1H-pyrazol-4-yl]-carbamic acid 3,4-difluoro-benzyl ester

Following general procedure A or I followed by either C or D, starting from 1-[4-(2-methyl-[1,3]dioxolan-2-yl)-butyl]-1H-pyrazol-4-ylamine and (3,4-difluoro-phenyl)-methanol.
LC-MS-conditions 01: $t_R$=0.91 min; [M+H]$^+$=352.1.

Example 139

[1-(5-Oxo-hexyl)-1H-pyrazol-4-yl]-carbamic acid naphthalen-1-ylmethyl ester

Following general procedure A or I followed by either C or D, starting from 1-[4-(2-methyl-[1,3]dioxolan-2-yl)-butyl]-1H-pyrazol-4-ylamine and naphthalen-1-yl-methanol.
LC-MS-conditions 01: $t_R$=0.94 min; [M+H]$^+$=366.12.

Example 140

[1-(5-Oxo-hexyl)-1H-pyrazol-4-yl]-carbamic acid 2,5-dimethyl-benzyl ester

Following general procedure A or I followed by either C or D, starting from 1-[4-(2-methyl-[1,3]dioxolan-2-yl)-butyl]-1H-pyrazol-4-ylamine and (2,5-dimethyl-phenyl)-methanol.
LC-MS-conditions 01: $t_R$=0.94 min; [M+H]$^+$=344.15.

Example 141

[1-(5-Oxo-hexyl)-1H-pyrazol-4-yl]-carbamic acid 2,4,6-trifluoro-benzyl ester

Following general procedure A or I followed by either C or D, starting from 1-[4-(2-methyl-[1,3]dioxolan-2-yl)-butyl]-1H-pyrazol-4-ylamine and (2,4,6-trifluoro-phenyl)-methanol.
LC-MS-conditions 01: $t_R$=0.91 min; [M+H]$^+$=370.07.

Example 142

[1-(5-Oxo-hexyl)-1H-pyrazol-4-yl]-carbamic acid 2,3-difluoro-benzyl ester

Following general procedure A or I followed by either C or D, starting from 1-[4-(2-methyl-[1,3]dioxolan-2-yl)-butyl]-1H-pyrazol-4-ylamine and (2,3-difluoro-phenyl)-methanol.
LC-MS-conditions 01: $t_R$=0.9 min; [M+H]$^+$=352.09.

Example 143

[1-(5-Oxo-hexyl)-1H-pyrazol-4-yl]-carbamic acid 3-chloro-2,6-difluoro-benzyl ester Following general procedure A or I followed by either C or D, starting from 1-[4-(2-methyl-[1,3]dioxolan-2-yl)-butyl]-1H-pyrazol-4-ylamine and (3-chloro-2,6-difluoro-phenyl)-methanol.
LC-MS-conditions 01: $t_R$=0.93 min; [M+H]$^+$=386.03.

Example 144

[1-(5-Oxo-hexyl)-1H-pyrazol-4-yl]-carbamic acid 6-chloro-2-fluoro-3-methyl-benzyl ester Following general procedure A or I followed by either C or D, starting from 1-[4-(2-methyl-[1,3]dioxolan-2-yl)-butyl]-1H-pyrazol-4-ylamine and (6-chloro-2-fluoro-3-methyl-phenyl)-methanol.
LC-MS-conditions 01: $t_R$=0.95 min; [M+H]$^+$=382.07.

Example 145

[1-(5-Oxo-hexyl)-1H-pyrazol-4-yl]-carbamic acid 3-chloro-2-fluoro-benzyl ester

Following general procedure A or I followed by either C or D, starting from 1-[4-(2-methyl-[1,3]dioxolan-2-yl)-butyl]-1H-pyrazol-4-ylamine and (3-chloro-2-fluoro-phenyl)-methanol.
LC-MS-conditions 01: $t_R$=0.93 min; [M+H]$^+$=368.06.

Example 146

[1-(5-Oxo-hexyl)-1H-pyrazol-4-yl]-carbamic acid 2-chloro-6-fluoro-3-methyl-benzyl ester Following general procedure A or I followed by either C or D, starting from 1-[4-(2-methyl-[1,3]dioxolan-2-yl)-butyl]-1H-pyrazol-4-ylamine and (2-chloro-6-fluoro-3-methyl-phenyl)-methanol.
LC-MS-conditions 01: $t_R$=0.96 min; [M+H]$^+$=382.08.

Example 147

[1-(5-Oxo-hexyl)-1H-pyrazol-4-yl]-carbamic acid 2,4,5-trifluoro-benzyl ester

Following general procedure A or I followed by either C or D, starting from 1-[4-(2-methyl-[1,3]dioxolan-2-yl)-butyl]-1H-pyrazol-4-ylamine and (2,4,5-trifluoro-phenyl)-methanol.
LC-MS-conditions 01: $t_R$=0.92 min; [M+H]$^+$=370.09.

Example 148

[1-(5-Oxo-hexyl)-1H-pyrazol-4-yl]-carbamic acid 2,6-difluoro-3-methyl-benzyl ester Following general procedure A or I followed by either C or D, starting from 1-[4-(2-methyl-[1,3]dioxolan-2-yl)-butyl]-1H-pyrazol-4-ylamine and (2,6-difluoro-3-methyl-phenyl)-methanol.
LC-MS-conditions 01: $t_R$=0.93 min; [M+H]$^+$=366.1.

Example 149

[1-(5-Oxo-hexyl)-1H-pyrazol-4-yl]-carbamic acid 2-fluoro-5-trifluoromethyl-benzyl ester Following general procedure A or I followed by either C or D, starting from 1-[4-(2-methyl-[1,3]dioxolan-2-yl)-butyl]-1H-pyrazol-4-ylamine and (2-fluoro-5-trifluoromethyl-phenyl)-methanol.
LC-MS-conditions 01: $t_R$=0.96 min; [M+H]$^+$=402.1.

Example 150

[1-(5-Oxo-hexyl)-1H-pyrazol-4-yl]-carbamic acid 2,3,5-trifluoro-benzyl ester

Following general procedure A or I followed by either C or D, starting from 1-[4-(2-methyl-[1,3]dioxolan-2-yl)-butyl]-1H-pyrazol-4-ylamine and (2,3,5-trifluoro-phenyl)-methanol.
LC-MS-conditions 01: $t_R$=0.92 min; [M+H]$^+$=370.08.

Example 151

[1-(5-Oxo-hexyl)-1H-pyrazol-4-yl]-carbamic acid 2,3,4-trifluoro-benzyl ester

Following general procedure A or I followed by either C or D, starting from 1-[4-(2-methyl-[1,3]dioxolan-2-yl)-butyl]-1H-pyrazol-4-ylamine and (2,3,4-trifluoro-phenyl)-methanol.
LC-MS-conditions 01: $t_R$=0.92 min; [M+H]$^+$=370.07.

Example 152

5-Phenyl-oxazole-4-carboxylic acid [1-(5-oxo-hexyl)-1H-pyrazol-4-yl]-amide

Following general procedure B followed by either C or D, starting from 1-[4-(2-methyl-[1,3]dioxolan-2-yl)-butyl]-1H-pyrazol-4-ylamine and 5-phenyl-oxazole-4-carboxylic acid.
LC-MS-conditions 01: $t_R$=0.9 min; [M+H]$^+$=353.15.

Example 153

(E)-N-[1-(5-Oxo-hexyl)-1H-pyrazol-4-yl]-3-(2-trifluoromethyl-phenyl)-acrylamide

Following general procedure B followed by either C or D, starting from 1-[4-(2-methyl-[1,3]dioxolan-2-yl)-butyl]-1H-pyrazol-4-ylamine and (E)-3-(2-trifluoromethyl-phenyl)-acrylic acid.
LC-MS-conditions 01: $t_R$=0.92 min; [M+H]$^+$=380.13.

Example 154

(E)-N-[1-(5-Oxo-hexyl)-1H-pyrazol-4-yl]-3-(3-trifluoromethoxy-phenyl)-acrylamide Following general procedure B followed by either C or D, starting from 1-[4-(2-methyl-[1,3]dioxolan-2-yl)-butyl]-1H-pyrazol-4-ylamine and (E)-3-(3-trifluoromethoxy-phenyl)-acrylic acid.
LC-MS-conditions 01: $t_R$=0.95 min; [M+H]$^+$=396.13.

Example 155

(E)-3-(2-Chloro-4-fluoro-phenyl)-N-[1-(5-oxo-hexyl)-1H-pyrazol-4-yl]-acrylamide

Following general procedure B followed by either C or D, starting from 1-[4-(2-methyl-[1,3]dioxolan-2-yl)-butyl]-1H-pyrazol-4-ylamine and (E)-3-(2-chloro-4-fluoro-phenyl)-acrylic acid.
LC-MS-conditions 01: $t_R$=0.91 min; [M+H]$^+$=364.11.

Example 156

(E)-N-[1-(5-Oxo-hexyl)-1H-pyrazol-4-yl]-3-o-tolyl-acrylamide

Following general procedure B followed by either C or D, starting from 1-[4-(2-methyl-[1,3]dioxolan-2-yl)-butyl]-1H-pyrazol-4-ylamine and (E)-3-o-tolyl-acrylic acid.
LC-MS-conditions 01: $t_R$=0.88 min; [M+H]$^+$=326.18.

Example 157

(E)-3-(2-Chloro-phenyl)-N-[1-(5-oxo-hexyl)-1H-pyrazol-4-yl]-acrylamide

Following general procedure B followed by either C or D, starting from 1-[4-(2-methyl-[1,3]dioxolan-2-yl)-butyl]-1H-pyrazol-4-ylamine and (E)-3-(2-chloro-phenyl)-acrylic acid.
LC-MS-conditions 01: $t_R$=0.89 min; [M+H]$^+$=346.14.

Example 158

5-(4-Methoxy-phenyl)-oxazole-4-carboxylic acid [1-(5-oxo-hexyl)-1H-pyrazol-4-yl]-amide Following general procedure B followed by either C or D, starting from 1-[4-(2-methyl-[1,3]dioxolan-2-yl)-butyl]-1H-pyrazol-4-ylamine and 5-(4-methoxy-phenyl)-oxazole-4-carboxylic acid.
LC-MS-conditions 01: $t_R$=0.92 min; [M+H]$^+$=383.15.

Example 159

2-Methyl-5-m-tolyl-oxazole-4-carboxylic acid [1-(5-oxo-hexyl)-1H-pyrazol-4-yl]-amide Following general procedure B followed by either C or D, starting from 1-[4-(2-methyl-[1,3]dioxolan-2-yl)-butyl]-1H-pyrazol-4-ylamine and 2-methyl-5-m-tolyl-oxazole-4-carboxylic acid.
LC-MS-conditions 01: $t_R$=0.97 min; [M+H]$^+$=381.17.

Example 160

(E)-3-(2-Methoxy-phenyl)-N-[1-(5-oxo-hexyl)-1H-pyrazol-4-yl]-acrylamide

Following general procedure B followed by either C or D, starting from 1-[4-(2-methyl-[1,3]dioxolan-2-yl)-butyl]-1H-pyrazol-4-ylamine and (E)-3-(2-methoxy-phenyl)-acrylic acid.
LC-MS-conditions 01: $t_R$=0.97 min; [M+H]$^+$=342.14.

Example 161

[1-(5-Oxo-hexyl)-1H-pyrazol-3-yl]-carbamic acid 2-chloro-benzyl ester

Following general procedure A or I followed by either C or D, starting from 1-[4-(2-methyl-[1,3]dioxolan-2-yl)-butyl]-1H-pyrazol-3-ylamine and (2-chloro-phenyl)-methanol.
LC-MS-conditions 01: $t_R$=0.93 min; [M+H]$^+$=350.09.

Example 162

[1-(5-Oxo-hexyl)-1H-pyrazol-3-yl]-carbamic acid benzyl ester

Following general procedure A or I followed by either C or D, starting from 1-[4-(2-methyl-[1,3]dioxolan-2-yl)-butyl]-1H-pyrazol-3-ylamine and (phenyl)-methanol.
LC-MS-conditions 01: $t_R$=0.89 min; [M+H]$^+$=316.09.

Example 163

[1-(5-Oxo-hexyl)-1H-pyrazol-3-yl]-carbamic acid 2-methyl-benzyl ester

Following general procedure A or I followed by either C or D, starting from 1-[4-(2-methyl-[1,3]dioxolan-2-yl)-butyl]-1H-pyrazol-3-ylamine and (2-methyl-phenyl)-methanol.
LC-MS-conditions 01: $t_R$=0.92 min; $[M+H]^+$=330.11.

Example 164

[1-(5-Oxo-hexyl)-1H-pyrazol-3-yl]-carbamic acid 4-trifluoromethyl-benzyl ester

Following general procedure A or I followed by either C or D, starting from 1-[4-(2-methyl-[1,3]dioxolan-2-yl)-butyl]-1H-pyrazol-3-ylamine and (4-trifluoromethyl-phenyl)-methanol.
LC-MS-conditions 01: $t_R$=0.96 min; $[M+H]^+$=384.08.

Example 165

[1-(5-Oxo-hexyl)-1H-pyrazol-3-yl]-carbamic acid 3-trifluoromethyl-benzyl ester

Following general procedure A or I followed by either C or D, starting from 1-[4-(2-methyl-[1,3]dioxolan-2-yl)-butyl]-1H-pyrazol-3-ylamine and (3-trifluoromethyl phenyl)-methanol.
LC-MS-conditions 01: $t_R$=0.96 min; $[M+H]^+$=384.08.

Example 166

[1-(5-Oxo-hexyl)-1H-pyrazol-3-yl]-carbamic acid 3-chloro-benzyl ester

Following general procedure A or I followed by either C or D, starting from 1-[4-(2-methyl-[1,3]dioxolan-2-yl)-butyl]-1H-pyrazol-3-ylamine and (3-chloro-phenyl)-methanol.
LC-MS-conditions 01: $t_R$=0.94 min; $[M+H]^+$=350.05.

Example 167

[1-(5-Oxo-hexyl)-1H-pyrazol-3-yl]-carbamic acid 2-chloro-4-fluoro-benzyl ester

Following general procedure A or I followed by either C or D, starting from 1-[4-(2-methyl-[1,3]dioxolan-2-yl)-butyl]-1H-pyrazol-3-ylamine and (2-chloro-4-fluoro-phenyl)-methanol.
LC-MS-conditions 01: $t_R$=0.94 min; $[M+H]^+$=368.02.

Example 168

[1-(5-Oxo-hexyl)-1H-pyrazol-3-yl]-carbamic acid 3,4-dimethyl-benzyl ester

Following general procedure A or I followed by either C or D, starting from 1-[4-(2-methyl-[1,3]dioxolan-2-yl)-butyl]-1H-pyrazol-3-ylamine and (3,4-dimethyl-phenyl)-methanol.
LC-MS-conditions 01: $t_R$=0.96 min; $[M+H]^+$=344.12.

Example 169

[1-(5-Oxo-hexyl)-1H-pyrazol-3-yl]-carbamic acid 3,4-difluoro-benzyl ester

Following general procedure A or I followed by either C or D, starting from 1-[4-(2-methyl-[1,3]dioxolan-2-yl)-butyl]-1H-pyrazol-3-ylamine and (3,4-difluoro-phenyl)-methanol.
LC-MS-conditions 01: $t_R$=0.92 min; $[M+H]^+$=352.08.

Example 170

[1-(5-Oxo-hexyl)-1H-pyrazol-3-yl]-carbamic acid 2-chloro-6-fluoro-benzyl ester

Following general procedure A or I followed by either C or D, starting from 1-[4-(2-methyl-[1,3]dioxolan-2-yl)-butyl]-1H-pyrazol-3-ylamine and (2-chloro-6-fluoro-phenyl)-methanol.
LC-MS-conditions 01: $t_R$=0.93 min; $[M+H]^+$=368.04.

Example 171

[1-(5-Oxo-hexyl)-1H-pyrazol-3-yl]-carbamic acid naphthalen-1-ylmethyl ester

Following general procedure A or I followed by either C or D, starting from 1-[4-(2-methyl-[1,3]dioxolan-2-yl)-butyl]-1H-pyrazol-3-ylamine and naphthalen-1-yl-methanol.
LC-MS-conditions 01: $t_R$=0.96 min; $[M+H]^+$=366.11.

Example 172

[1-(5-Oxo-hexyl)-1H-pyrazol-3-yl]-carbamic acid 2,5-dimethyl-benzyl ester

Following general procedure A or I followed by either C or D, starting from 1-[4-(2-methyl-[1,3]dioxolan-2-yl)-butyl]-1H-pyrazol-3-ylamine and (2,5-dimethyl-phenyl)-methanol.
LC-MS-conditions 01: $t_R$=0.96 min; $[M+H]^+$=344.13.

Example 173

[1-(5-Oxo-hexyl)-1H-pyrazol-3-yl]-carbamic acid 2,3-difluoro-benzyl ester

Following general procedure A or I followed by either C or D, starting from 1-[4-(2-methyl-[1,3]dioxolan-2-yl)-butyl]-1H-pyrazol-3-ylamine and (2,3-difluoro-phenyl)-methanol.
LC-MS-conditions 01: $t_R$=0.92 min; $[M+H]^+$=352.08.

Example 174

[1-(5-Oxo-hexyl)-1H-pyrazol-3-yl]-carbamic acid 6-chloro-2-fluoro-3-methyl-benzyl ester Following general procedure A or I followed by either C or D, starting from 1-[4-(2-methyl-[1,3]dioxolan-2-yl)-butyl]-1H-pyrazol-3-ylamine and (6-chloro-2-fluoro-3-methyl-phenyl)-methanol.
LC-MS-conditions 01: $t_R$=0.97 min; $[M+H]^+$=382.06.

Example 175

[1-(5-Oxo-hexyl)-1H-pyrazol-3-yl]-carbamic acid 3-chloro-2-fluoro-benzyl ester

Following general procedure A or I followed by either C or D, starting from 1-[4-(2-methyl-[1,3]dioxolan-2-yl)-butyl]-1H-pyrazol-3-ylamine and (3-chloro-2-fluoro-phenyl)-methanol.
LC-MS-conditions 01: $t_R$=0.94 min; $[M+H]^+$=368.04.

Example 176

[1-(5-Oxo-hexyl)-1H-pyrazol-3-yl]-carbamic acid 2-chloro-6-fluoro-3-methyl-benzyl ester Following general procedure A or I followed by either C or D, starting from 1-[4-(2-methyl-[1,3]dioxolan-2-yl)-butyl]-1H-pyrazol-3-ylamine and (2-chloro-6-fluoro-3-methyl-phenyl)-methanol.
LC-MS-conditions 01: $t_R$=0.97 min; $[M+H]^+$=382.05.

Example 177

[1-(5-Oxo-hexyl)-1H-pyrazol-3-yl]-carbamic acid 2,6-difluoro-3-methyl-benzyl ester Following general procedure A or I followed by either C or D, starting from 1-[4-(2-methyl-[1,3]dioxolan-2-yl)-butyl]-1H-pyrazol-3-ylamine and (2,6-difluoro-3-methyl-phenyl)-methanol.
LC-MS-conditions 01: $t_R$=0.94 min; $[M+H]^+$=366.08.

Example 178

[1-(5-Oxo-hexyl)-1H-pyrazol-3-yl]-carbamic acid 2-ethyl-benzyl ester

Following general procedure A or I followed by either C or D, starting from 1-[4-(2-methyl-[1,3]dioxolan-2-yl)-butyl]-1H-pyrazol-3-ylamine and (2-ethyl-phenyl)-methanol.
LC-MS-conditions 01: $t_R$=0.96 min; $[M+H]^+$=344.13.

Example 179

5-Phenyl-oxazole-4-carboxylic acid [1-(5-oxo-hexyl)-1H-pyrazol-3-yl]-amide

Following general procedure B followed by either C or D, starting from 1-[4-(2-methyl-[1,3]dioxolan-2-yl)-butyl]-1H-pyrazol-3-ylamine and 5-phenyl-oxazole-4-carboxylic acid.
LC-MS-conditions 02: $t_R$=0.96 min; $[M+H]^+$=352.74.

Example 180

(E)-N-[1-(5-Oxo-hexyl)-1H-pyrazol-3-yl]-3-phenyl-acrylamide

Following general procedure B followed by either C or D, starting from 1-[4-(2-methyl-[1,3]dioxolan-2-yl)-butyl]-1H-pyrazol-3-ylamine and (E)-3-phenyl-acrylic acid.
LC-MS-conditions 01: $t_R$=0.88 min; $[M+H]^+$=312.13.

Example 181

(E)-N-[1-(5-Oxo-hexyl)-1H-pyrazol-3-yl]-3-(2-trifluoromethyl-phenyl)-acrylamide

Following general procedure B followed by either C or D, starting from 1-[4-(2-methyl-[1,3]dioxolan-2-yl)-butyl]-1H-pyrazol-3-ylamine and (E)-3-(2-trifluoromethyl-phenyl)-acrylic acid.
LC-MS-conditions 01: $t_R$=0.95 min; $[M+H]^+$=380.1.

Example 182

(E)-N-[1-(5-Oxo-hexyl)-1H-pyrazol-3-yl]-3-(4-trifluoromethyl-phenyl)-acrylamide

Following general procedure B followed by either C or D, starting from 1-[4-(2-methyl-[1,3]dioxolan-2-yl)-butyl]-1H-pyrazol-3-ylamine and (E)-3-(4-trifluoromethyl-phenyl)-acrylic acid.
LC-MS-conditions 01: $t_R$=0.96 min; $[M+H]^+$=380.1.

Example 183

(E)-3-(2-Chloro-6-fluoro-phenyl)-N-[1-(5-oxo-hexyl)-1H-pyrazol-3-yl]-acrylamide

Following general procedure B followed by either C or D, starting from 1-[4-(2-methyl-[1,3]dioxolan-2-yl)-butyl]-1H-pyrazol-3-ylamine and (E)-3-(2-chloro-6-fluoro-phenyl)-acrylic acid.
LC-MS-conditions 01: $t_R$=0.94 min; $[M+H]^+$=364.07.

Example 184

(E)-3-(2,3-Dimethoxy-phenyl)-N-[1-(5-oxo-hexyl)-1H-pyrazol-3-yl]-acrylamide

Following general procedure B followed by either C or D, starting from 1-[4-(2-methyl-[1,3]dioxolan-2-yl)-butyl]-1H-pyrazol-3-ylamine and (E)-3-(2,3-dimethoxy-phenyl)-acrylic acid.
LC-MS-conditions 01: $t_R$=0.88 min; $[M+H]^+$=372.14.

Example 185

(E)-3-(2,3-Dichloro-phenyl)-N-[1-(5-oxo-hexyl)-1H-pyrazol-3-yl]-acrylamide

Following general procedure B followed by either C or D, starting from 1-[4-(2-methyl-[1,3]dioxolan-2-yl)-butyl]-1H-pyrazol-3-ylamine and (E)-3-(2,3-dichloro-phenyl)-acrylic acid.
LC-MS-conditions 01: $t_R$=0.97 min; $[M+H]^+$=380.03.

Example 186

(E)-N-[1-(5-Oxo-hexyl)-1H-pyrazol-3-yl]-3-(3-trifluoromethoxy-phenyl)-acrylamide Following general procedure B followed by either C or D, starting from 1-[4-(2-methyl-[1,3]dioxolan-2-yl)-butyl]-1H-pyrazol-3-ylamine and (E)-3-(3-trifluoromethoxy-phenyl)-acrylic acid.
LC-MS-conditions 01: $t_R$=0.98 min; $[M+H]^+$=396.09.

Example 187

(E)-3-(2-Chloro-3,6-difluoro-phenyl)-N-[1-(5-oxo-hexyl)-1H-pyrazol-3-yl]-acrylamide Following general procedure B followed by either C or D, starting from 1-[4-(2-methyl-[1,3]dioxolan-2-yl)-butyl]-1H-pyrazol-3-ylamine and (E)-3-(2-chloro-3,6-difluoro-phenyl)-acrylic acid.
LC-MS-conditions 01: $t_R$=0.95 min; $[M+H]^+$=382.05.

Example 188

(E)-3-(2,4-Dichloro-phenyl)-N-[1-(5-oxo-hexyl)-1H-pyrazol-3-yl]-acrylamide

Following general procedure B followed by either C or D, starting from 1-[4-(2-methyl-[1,3]dioxolan-2-yl)-butyl]-1H-pyrazol-3-ylamine and (E)-3-(2,4-dichloro-phenyl)-acrylic acid.
LC-MS-conditions 01: $t_R$=0.98 min; $[M+H]^+$=380.04.

Example 189

(E)-3-(2-Chloro-4-fluoro-phenyl)-N-[1-(5-oxo-hexyl)-1H-pyrazol-3-yl]-acrylamide

Following general procedure B followed by either C or D, starting from 1-[4-(2-methyl-[1,3]dioxolan-2-yl)-butyl]-1H-pyrazol-3-ylamine and (E)-3-(2-chloro-4-fluoro-phenyl)-acrylic acid.
LC-MS-conditions 01: $t_R$=0.94 min; $[M+H]^+$=364.07.

Example 190

(E)-3-(2-Methoxy-phenyl)-N-[1-(5-oxo-hexyl)-1H-pyrazol-3-yl]-acrylamide

Following general procedure B followed by either C or D, starting from 1-[4-(2-methyl-[1,3]dioxolan-2-yl)-butyl]-1H-pyrazol-3-ylamine and (E)-3-(2-methoxy-phenyl)-acrylic acid.
LC-MS-conditions 01: $t_R$=0.89 min; $[M+H]^+$=342.14.

Example 191

(E)-3-(2-Fluoro-3-trifluoromethyl-phenyl)-N-[1-(5-oxo-hexyl)-1H-pyrazol-3-yl]-acrylamide Following general procedure B followed by either C or D, starting from 1-[4-(2-methyl-[1,3]dioxolan-2-yl)-butyl]-1H-pyrazol-3-ylamine and (E)-3-(2-fluoro-3-trifluoromethyl-phenyl)-acrylic acid.
LC-MS-conditions 01: $t_R$=0.97 min; $[M+H]^+$=398.11.

Example 192

(E)-N-[1-(5-Oxo-hexyl)-1H-pyrazol-3-yl]-3-o-tolyl-acrylamide

Following general procedure B followed by either C or D, starting from 1-[4-(2-methyl-[1,3]dioxolan-2-yl)-butyl]-1H-pyrazol-3-ylamine and (E)-3-o-tolyl-acrylic acid.
LC-MS-conditions 01: $t_R$=0.91 min; $[M+H]^+$=326.15.

Example 193

(E)-3-(2-Chloro-phenyl)-N-[1-(5-oxo-hexyl)-1H-pyrazol-3-yl]-acrylamide

Following general procedure B followed by either C or D, starting from 1-[4-(2-methyl-[1,3]dioxolan-2-yl)-butyl]-1H-pyrazol-3-ylamine and (E)-3-(2-chloro-phenyl)-acrylic acid.
LC-MS-conditions 01: $t_R$=0.93 min; $[M+H]^+$=346.09.

Example 194

2-Methyl-5-m-tolyl-oxazole-4-carboxylic acid [1-(5-oxo-hexyl)-1H-pyrazol-3-yl]-amide Following general procedure B followed by either C or D, starting from 1-[4-(2-methyl-[1,3]dioxolan-2-yl)-butyl]-1H-pyrazol-3-ylamine and 2-methyl-5-m-tolyl-oxazole-4-carboxylic acid.
LC-MS-conditions 01: $t_R$=1.0 min; $[M+H]^+$=381.13.

Example 195

(E)-N-[1-(5-Oxo-hexyl)-1H-pyrazol-3-yl]-3-(3-trifluoromethyl-phenyl)-acrylamide

Following general procedure B followed by either C or D, starting from 1-[4-(2-methyl-[1,3]dioxolan-2-yl)-butyl]-1H-pyrazol-3-ylamine and (E)-3-(3-trifluoromethyl-phenyl)-acrylic acid.
LC-MS-conditions 01: $t_R$=0.97 min; $[M+H]^+$=380.1.

Example 196

(E)-3-(3-Chloro-phenyl)-N-[1-(5-oxo-hexyl)-1H-pyrazol-3-yl]-acrylamide

Following general procedure B followed by either C or D, starting from 1-[4-(2-methyl-[1,3]dioxolan-2-yl)-butyl]-1H-pyrazol-3-ylamine and (E)-3-(3-chloro-phenyl)-acrylic acid.
LC-MS-conditions 01: $t_R$=0.92 min; $[M+H]^+$=346.08.

Example 197

{1-[5-(1,1-Difluoro-ethyl)-furan-2-ylmethyl]-1H-pyrazol-3-yl}-carbamic acid 2-chloro-benzyl ester Following general procedure A or I, starting from 1-[5-(1,1-difluoro-ethyl)-furan-2-ylmethyl]-1H-pyrazol-3-ylamine and (2-chloro-phenyl)-methanol.
LC-MS-conditions 02: $t_R$=1.07 min; $[M+H]^+$=395.96.

Example 198

5-Phenyl-oxazole-4-carboxylic acid {1-[5-(1,1-difluoro-ethyl)-furan-2-ylmethyl]-1H-pyrazol-3-yl}-amide Following general procedure B, starting from 1-[5-(1,1-difluoro-ethyl)-furan-2-ylmethyl]-1H-pyrazol-3-ylamine and 5-phenyl-oxazole-4-carboxylic acid.
LC-MS-conditions 02: $t_R$=1.07 min; $[M+H]^+$=398.98.

Example 199

{1-[5-(1,1-Difluoro-ethyl)-furan-2-ylmethyl]-1H-pyrazol-4-yl}-carbamic acid 2-chloro-benzyl ester Following general procedure A or I, starting from 1-[5-(1,1-difluoro-ethyl)-furan-2-ylmethyl]-1H-pyrazol-4-ylamine and (2-chloro-phenyl)-methanol.
LC-MS-conditions 02: $t_R$=1.05 min; [M+H]$^+$=395.93.

Example 200

5-Phenyl-oxazole-4-carboxylic acid {1-[5-(1,1-difluoro-ethyl)-furan-2-ylmethyl]-1H-pyrazol-4-yl}-amide Following general procedure B, starting from 1-[5-(1,1-difluoro-ethyl)-furan-2-ylmethyl]-1H-pyrazol-4-ylamine and 5-phenyl-oxazole-4-carboxylic acid.
LC-MS-conditions 02: $t_R$=1.05 min; [M+H]$^+$=399.00.

Example 201

[1-(5,5-Difluoro-hexyl)-1H-pyrazol-3-yl]-carbamic acid 2-chloro-benzyl ester

Following general procedure A or I, starting from 1-(5,5-difluoro-hexyl)-1H-pyrazol-3-ylamine and (2-chloro-phenyl)-methanol.
LC-MS-conditions 01: $t_R$=1.02 min; [M+H]$^+$=372.05.

Example 202

5-Phenyl-oxazole-4-carboxylic acid [1-(5,5-difluoro-hexyl)-1H-pyrazol-3-yl]-amide Following general procedure B, starting from 1-(5,5-difluoro-hexyl)-1H-pyrazol-3-ylamine and 5-phenyl-oxazole-4-carboxylic acid.
LC-MS-conditions 02: $t_R$=1.07 min; [M+H]$^+$=375.00.

Example 203

[1-(5,5-Difluoro-hexyl)-1H-pyrazol-4-yl]-carbamic acid 2-chloro-benzyl ester

Following general procedure A or I, starting from 1-(5,5-difluoro-hexyl)-1H-pyrazol-4-ylamine and (2-chloro-phenyl)-methanol.
LC-MS-conditions 02: $t_R$=1.05 min; [M+H]$^+$=372.00.

Example 204

5-Phenyl-oxazole-4-carboxylic acid [1-(5,5-difluoro-hexyl)-1H-pyrazol-4-yl]-amide Following general procedure B, starting from 1-(5,5-difluoro-hexyl)-1H-pyrazol-4-ylamine and 5-phenyl-oxazole-4-carboxylic acid.
LC-MS-conditions 02: $t_R$=1.05 min; [M+H]$^+$=375.08.

Example 205

2-Cyclopropyl-5-phenyl-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 2-cyclopropyl-5-phenyl-oxazole-4-carboxylic acid.
LC-MS-conditions 01: $t_R$=0.99 min; [M+H]$^+$=417.16.

Example 206

2-Ethyl-5-phenyl-oxazole-4-carboxylic acid [1-(5-acetyl-furan-2-ylmethyl)-1H-pyrazol-4-yl]-amide Following general procedure B followed by either C or D, starting from 1-[5-(2-methyl-[1,3]dioxolan-2-yl)-furan-2-ylmethyl]-1H-pyrazol-4-ylamine and 2-ethyl-5-phenyl-oxazole-4-carboxylic acid. LC-MS-conditions 01: $t_R$=0.97 min; [M+H]$^+$=405.16.

Example 207

{1-[5-(1,1-Difluoro-ethyl)-furan-2-ylmethyl]-1H-pyrazol-3-yl}-carbamic acid 6-chloro-2-fluoro-3-methyl-benzyl ester Following general procedure A or I, starting from 1-[5-(1,1-difluoro-ethyl)-furan-2-ylmethyl]-1H-pyrazol-3-ylamine and (6-chloro-2-fluoro-3-methyl-phenyl)-methanol.
LC-MS-conditions 05b: $t_R$=1.17 min; [M+H]$^+$=428.15.

Example 208

{1-[5-(1,1-Difluoro-ethyl)-furan-2-ylmethyl]-1H-pyrazol-3-yl}-carbamic acid 2-chloro-6-fluoro-3-methyl-benzyl ester Following general procedure A or I, starting from 1-[5-(1,1-difluoro-ethyl)-furan-2-ylmethyl]-1H-pyrazol-3-ylamine and (2-chloro-6-fluoro-3-methyl-phenyl)-methanol.
LC-MS-conditions 05b: $t_R$=1.17 min; [M+H]$^+$=428.11.

Example 209

[1-(5,5-Difluoro-hexyl)-1H-pyrazol-3-yl]-carbamic acid 2-chloro-6-fluoro-3-methyl-benzyl ester Following general procedure A or I, starting from 1-(5,5-difluoro-hexyl)-1H-pyrazol-3-ylamine and (2-chloro-6-fluoro-3-methyl-phenyl)-methanol. LC-MS-conditions 05b: $t_R$=1.18 min; [M+H]$^+$=404.16.

Example 210

[1-(5,5-Difluoro-hexyl)-1H-pyrazol-3-yl]-carbamic acid 6-chloro-2-fluoro-3-methyl-benzyl ester Following general procedure A or I, starting from 1-(5,5-difluoro-hexyl)-1H-pyrazol-3-ylamine and (6-chloro-2- fluoro-3-methyl-phenyl)-methanol. LC-MS-conditions 05b: $t_R$=1.18 min; [M+H]$^+$=404.19.

Example 211

2-Methyl-5-phenyl-oxazole-4-carboxylic acid [1-(5,5-difluoro-hexyl)-1H-pyrazol-4-yl]-amide Following general procedure B, starting from 1-(5,5-difluoro-hexyl)-1H-pyrazol-4-ylamine and 2-methyl-5-phenyl-oxazole-4-carboxylic acid. LC-MS-conditions 05b: $t_R$=1.14 min; [M+H]$^+$=389.28.

Example 212

2-Methyl-5-m-tolyl-oxazole-4-carboxylic acid [1-(5,5-difluoro-hexyl)-1H-pyrazol-4-yl]-amide Following general procedure B, starting from 1-(5,5-difluoro-hexyl)-1H-pyrazol-4-ylamine and 2-methyl-5-m-tolyl-oxazole-4-carboxylic acid. LC-MS-conditions 05b: $t_R$=1.18 min; [M+H]$^+$=403.28.

Example 213

5-(3-Methoxy-phenyl)-2-methyl-oxazole-4-carboxylic acid [1-(5,5-difluoro-hexyl)-1H-pyrazol-4-yl]-amide Following general procedure B, starting from 1-(5,5-difluoro-hexyl)-1H-pyrazol-4-ylamine and 5-(3-methoxy-phenyl)-2-methyl-oxazole-4-carboxylic acid. LC-MS-conditions 05b: $t_R$=1.15 min; [M+H]$^+$=419.22.

Example 214

5-(3-Methoxy-phenyl)-oxazole-4-carboxylic acid [1-(5,5-difluoro-hexyl)-1H-pyrazol-4-yl]-amide Following general procedure B, starting from 1-(5,5-difluoro-hexyl)-1H-pyrazol-4-ylamine and 5-(3-methoxy-phenyl)-oxazole-4-carboxylic acid. LC-MS-conditions 05b: $t_R$=1.12 min; [M+H]$^+$=405.24.

Example 215

(E)-N-[1-(5,5-Difluoro-hexyl)-1H-pyrazol-4-yl]-3-(2-trifluoromethyl-phenyl)-acrylamide Following general procedure B, starting from 1-(5,5-difluoro-hexyl)-1H-pyrazol-4-ylamine and (E)-3-(2-trifluoromethyl-phenyl)-acrylic acid. LC-MS-conditions 05b: $t_R$=1.12 min; [M+H]$^+$=402.11.

Example 216

(E)-N-[1-(5,5-Difluoro-hexyl)-1H-pyrazol-4-yl]-3-o-tolyl-acrylamide

Following general procedure B, starting from 1-(5,5-difluoro-hexyl)-1H-pyrazol-4-ylamine and (E)-o-tolyl-acrylic acid. LC-MS-conditions 05b: $t_R$=1.09 min; [M+H]$^+$=348.33.

Example 217

5-(4-Methoxy-phenyl)-oxazole-4-carboxylic acid [1-(5,5-difluoro-hexyl)-1H-pyrazol-4-yl]-amide Following general procedure B, starting from 1-(5,5-difluoro-hexyl)-1H-pyrazol-4-ylamine and 5-(4-methoxy-phenyl)-oxazole-4-carboxylic acid. LC-MS-conditions 05b: $t_R$=1.12 min; [M+H]$^+$=405.20.

Example 218

5-(4-Methoxy-phenyl)-2-methyl-oxazole-4-carboxylic acid [1-(5,5-difluoro-hexyl)-1H-pyrazol-4-yl]-amide Following general procedure B, starting from 1-(5,5-difluoro-hexyl)-1H-pyrazol-4-ylamine and 5-(4-methoxy-phenyl)-2-methyl-oxazole-4-carboxylic acid. LC-MS-conditions 05b: $t_R$=1.14 min; [M+H]$^+$=419.26.

Example 219

2-Methyl-5-o-tolyl-oxazole-4-carboxylic acid [1-(5,5-difluoro-hexyl)-1H-pyrazol-4-yl]-amide Following general procedure B, starting from 1-(5,5-difluoro-hexyl)-1H-pyrazol-4-ylamine and 2-methyl-5-o-tolyl-oxazole-4-carboxylic acid. LC-MS-conditions 05b: $t_R$=1.14 min; [M+H]$^+$=403.22.

Example 220

(E)-N-[1-(5,5-Difluoro-hexyl)-1H-pyrazol-3-yl]-3-(4-trifluoromethyl-phenyl)-acrylamide Following general procedure B, starting from 1-(5,5-difluoro-hexyl)-1H-pyrazol-3-ylamine and (E)-3-(4-trifluoromethyl-phenyl)-acrylic acid. LC-MS-conditions 05b: $t_R$=1.16 min; [M+H]$^+$=402.11.

Example 221

(E)-N-[1-(5,5-Difluoro-hexyl)-1H-pyrazol-3-yl]-3-(2-trifluoromethyl-phenyl)-acrylamide Following general procedure B, starting from 1-(5,5-difluoro-hexyl)-1H-pyrazol-3-ylamine and (E)-3-(2-trifluoromethyl-phenyl)-acrylic acid. LC-MS-conditions 05b: $t_R$=1.15 min; [M+H]$^+$=402.04.

Example 222

(E)-N-[1-(5,5-Difluoro-hexyl)-1H-pyrazol-3-yl]-3-p-tolyl-acrylamide

Following general procedure B, starting from 1-(5,5-difluoro-hexyl)-1H-pyrazol-3-ylamine and (E)-3-p-tolyl-acrylic acid. LC-MS-conditions 05b: $t_R$=1.12 min; [M+H]$^+$=348.31.

Example 223

(E)-N-[1-(5,5-Difluoro-hexyl)-1H-pyrazol-3-yl]-3-o-tolyl-acrylamide

Following general procedure B, starting from 1-(5,5-difluoro-hexyl)-1H-pyrazol-3-ylamine and (E)-3-o-tolyl-acrylic acid. LC-MS-conditions 05b: $t_R$=1.12 min; [M+H]$^+$=348.28.

Example 224

(E)-3-(2,3-Dichloro-phenyl)-N-[1-(5,5-difluoro-hexyl)-1H-pyrazol-3-yl]-acrylamide Following general procedure B, starting from 1-(5,5-difluoro-hexyl)-1H-pyrazol-3-ylamine and (E)-3-(2,3-dichloro-phenyl)-acrylic acid. LC-MS-conditions 05b: $t_R$=1.17 min; $[M+H]^+$=401.99.

Example 225

(E)-3-(2-Chloro-phenyl)-N-[1-(5,5-difluoro-hexyl)-1H-pyrazol-3-yl]-acrylamide

Following general procedure B, starting from 1-(5,5-difluoro-hexyl)-1H-pyrazol-3-ylamine and (E)-3-(2-chloro-phenyl)-acrylic acid. LC-MS-conditions 05b: $t_R$=1.13 min; $[M+H]^+$=368.25.

Example 226

(E)-N-[1-(5,5-Difluoro-hexyl)-1H-pyrazol-3-yl]-3-(2,3-dimethoxy-phenyl)-acrylamide Following general procedure B, starting from 1-(5,5-difluoro-hexyl)-1H-pyrazol-3-ylamine and (E)-3-(2,3-dimethoxy-phenyl)-acrylic acid. LC-MS-conditions 05b: $t_R$=1.09 min; $[M+H]^+$=394.28.

Example 227

2-Methyl-5-phenyl-oxazole-4-carboxylic acid [1-(5,5-difluoro-hexyl)-1H-pyrazol-3-yl]-amide Following general procedure B, starting from 1-(5,5-difluoro-hexyl)-1H-pyrazol-3-ylamine and 2-methyl-5-phenyl-oxazole-4-carboxylic acid. LC-MS-conditions 05b: $t_R$=1.19 min; $[M+H]^+$=389.29.

Example 228

(E)-N-[1-(5,5-Difluoro-hexyl)-1H-pyrazol-3-yl]-3-(4-methoxy-phenyl)-acrylamide

Following general procedure B, starting from 1-(5,5-difluoro-hexyl)-1H-pyrazol-3-ylamine and (E)-3-(4-methoxy-phenyl)-acrylic acid. LC-MS-conditions 05b: $t_R$=1.08 min; $[M+H]^+$=364.29.

Example 229

(E)-N-[1-(5,5-Difluoro-hexyl)-1H-pyrazol-3-yl]-3-(3-trifluoromethyl-phenyl)-acrylamide Following general procedure B, starting from 1-(5,5-difluoro-hexyl)-1H-pyrazol-3-ylamine and (E)-3-(3-trifluoromethyl-phenyl)-acrylic acid. LC-MS-conditions 05b: $t_R$=1.15 min; $[M+H]^+$=402.06.

Example 230

(E)-N-[1-(5,5-Difluoro-hexyl)-1H-pyrazol-3-yl]-3-m-tolyl-acrylamide

Following general procedure B, starting from 1-(5,5-difluoro-hexyl)-1H-pyrazol-3-ylamine and (E)-3-m-tolyl-acrylic acid. LC-MS-conditions 05b: $t_R$=1.13 min; $[M+H]^+$=348.31.

Example 231

[1-(5-Acetyl-furan-2-ylmethyl)-1H-pyrazol-3-yl]-carbamic acid 2-chloro-benzyl ester Following general procedure A or I followed by either C or D, starting from 1-[5-(2-methyl-[1,3]dioxolan-2-yl)-furan-2-ylmethyl]-1H-pyrazol-3-ylamine and (2-chloro-phenyl)-methanol. LC-MS-conditions 02: $t_R$=0.97 min; $[M+H]^+$=374.2.

Example 232

(E)-3-(2-Chloro-6-fluoro-phenyl)-N-[1-(5-oxo-hexyl)-1H-pyrazol-4-yl]-acrylamide

Following general procedure B followed by either C or D, starting from 1-[4-(2-methyl-[1,3]dioxolan-2-yl)-butyl]-1H-pyrazol-4-ylamine and (E)-3-(2-chloro-6-fluoro-phenyl)-acrylic acid. LC-MS-conditions 01: $t_R$=0.91 min; $[M+H]^+$=364.10.

Example 233

(E)-3-(2,3-Dimethoxy-phenyl)-N-[1-(5-oxo-hexyl)-1H-pyrazol-4-yl]-acrylamide

Following general procedure B followed by either C or D, starting from 1-[4-(2-methyl-[1,3]dioxolan-2-yl)-butyl]-1H-pyrazol-4-ylamine and (E)-3-(2,3-dimethoxy-phenyl)-acrylic acid. LC-MS-conditions 01: $t_R$=0.85 min; $[M+H]^+$=372.16.

Example 234

5-(4-Chloro-phenyl)-2-methyl-oxazole-4-carboxylic acid [1-(5-oxo-hexyl)-1H-pyrazol-4-yl]-amide Following general procedure B followed by either C or D, starting from 1-[4-(2-methyl-[1,3]dioxolan-2-yl)-butyl]-1H-pyrazol-4-ylamine and 5-(4-chloro-phenyl)-2-methyl-oxazole-4-carboxylic acid. LC-MS-conditions 01: $t_R$=0.99 min; $[M+H]^+$=401.13.

Example 235

2-Methyl-5-phenyl-thiazole-4-carboxylic acid [1-(5-oxo-hexyl)-1H-pyrazol-4-yl]-amide Following general procedure B followed by either C or D, starting from 1-[4-(2-methyl-[1,3]dioxolan-2-yl)-butyl]-1H-pyrazol-4-ylamine and 2-methyl-5-phenyl-thiazole-4-carboxylic acid. LC-MS-conditions 01: $t_R$=0.94 min; $[M+H]^+$=383.10.

Example 236

[1-(5-Fluoro-hexyl)-1H-pyrazol-4-yl]-carbamic acid 2-chloro-benzyl ester

Following general procedure A or I, starting from 1-(5-fluoro-hexyl)-1H-pyrazol-4-ylamine and (2-chloro-phenyl)-methanol. LC-MS-conditions 02: $t_R$=1.04 min; $[M+H]^+$=354.22.

Example 237

5-(4-Chloro-phenyl)-2-methyl-oxazole-4-carboxylic acid [1-(5-acetyl-furan-2-ylmethyl)-1H-pyrazol-3-yl]-amide Following general procedure B followed by either C or D, starting from 1-[5-(2-methyl-[1,3]dioxolan-2-yl)-furan-2-ylmethyl]-1H-pyrazol-3-ylamine and 5-(4-chloro-phenyl)-2-methyl-oxazole-4-carboxylic acid. LC-MS-conditions 01: $t_R$=1.01 min; [M+H]$^+$=426.06.

Example 238

(E)-N-[1-(5-Acetyl-furan-2-ylmethyl)-1H-pyrazol-3-yl]-3-(2-chloro-phenyl)-acrylamide Following general procedure B followed by either C or D, starting from 1-[5-(2-methyl-[1,3]dioxolan-2-yl)-furan-2-ylmethyl]-1H-pyrazol-3-ylamine and (E)-3-(2-chloro-phenyl)-acrylic acid. LC-MS-conditions 01: $t_R$=0.92 min; [M+H]$^+$=370.04.

Example 239

5-(2,5-Dimethyl-phenyl)-2-methyl-oxazole-4-carboxylic acid [1-(5-acetyl-furan-2-ylmethyl)-1H-pyrazol-4-yl]-amide Following general procedure B followed by either C or D, 1-[5-(2-methyl-[1,3]dioxolan-2-yl)-furan-2-ylmethyl]-1H-pyrazol-4-ylamine and 5-(2,5-dimethyl-phenyl)-2-methyl-oxazole-4-carboxylic acid. LC-MS-conditions 02: $t_R$=1.01 min; [M+H]$^+$=419.00.

Example 240

5-(2-Methoxy-phenyl)-2-methyl-oxazole-4-carboxylic acid [1-(5-acetyl-furan-2-ylmethyl)-1H-pyrazol-4-yl]-amide Following general procedure B followed by either C or D, 1-[5-(2-methyl-[1,3]dioxolan-2-yl)-furan-2-ylmethyl]-1H-pyrazol-4-ylamine and 5-(2-methoxy-phenyl)-2-methyl-oxazole-4-carboxylic acid. LC-MS-conditions 02: $t_R$=0.92 min; [M+H]$^+$=421.00.

Example 241

5-(4-Fluoro-phenyl)-thiazole-4-carboxylic acid [1-(5-acetyl-furan-2-ylmethyl)-1H-pyrazol-4-yl]-amide Following general procedure B followed by either C or D, 1-[5-(2-methyl-[1,3]dioxolan-2-yl)-furan-2-ylmethyl]-1H-pyrazol-4-ylamine and 5-(4-fluoro-phenyl)-thiazole-4-carboxylic acid. LC-MS-conditions 02: $t_R$=0.95 min; [M+H]$^+$=410.92.

Example 242

5-(4-Fluoro-phenyl)-thiazole-4-carboxylic acid [1-(5-acetyl-furan-2-ylmethyl)-1H-pyrazol-3-yl]-amide Following general procedure B followed by either C or D, 1-[5-(2-methyl-[1,3]dioxolan-2-yl)-furan-2-ylmethyl]-1H-pyrazol-3-ylamine and 5-(4-fluoro-phenyl)-thiazole-4-carboxylic acid. LC-MS-conditions 01: $t_R$=0.93 min; [M+H]$^+$=411.03.

Example 243

5-(2-Methoxy-phenyl)-2-methyl-oxazole-4-carboxylic acid [1-(5-acetyl-furan-2-ylmethyl)-1H-pyrazol-3-yl]-amide Following general procedure B followed by either C or D, 1-[5-(2-methyl-[1,3]dioxolan-2-yl)-furan-2-ylmethyl]-1H-pyrazol-3-ylamine and 5-(2-methoxy-phenyl)-2-methyl-oxazole-4-carboxylic acid. LC-MS-conditions 01: $t_R$=0.90 min; [M+H]$^+$=421.09.

Example 244

5-(3,5-Dimethyl-phenyl)-2-methyl-oxazole-4-carboxylic acid [1-(5-acetyl-furan-2-ylmethyl)-1H-pyrazol-3-yl]-amide Following general procedure B followed by either C or D, 1-[5-(2-methyl-[1,3]dioxolan-2-yl)-furan-2-ylmethyl]-1H-pyrazol-3-ylamine and 5-(3,5-dimethyl-phenyl)-2-methyl-oxazole-4-carboxylic acid. LC-MS-conditions 01: $t_R$=1.02 min; [M+H]$^+$=419.11.

Example 245

{1-[5-(1,1-Difluoro-ethyl)-furan-2-ylmethyl]-1H-pyrazol-4-yl}-carbamic acid 6-chloro-2-fluoro-3-methyl-benzyl ester Following general procedure A or I, starting from 1-[5-(1,1-difluoro-ethyl)-furan-2-ylmethyl]-1H-pyrazol-4-ylamine and (6-chloro-2-fluoro-3-methyl-phenyl)-methanol. LC-MS-conditions 05b: $t_R$=1.15 min; [M+H]$^+$=428.15.

Example 246

{1-[5-(1,1-Difluoro-ethyl)-furan-2-ylmethyl]-1H-pyrazol-4-yl}-carbamic acid 2-chloro-6-fluoro-3-methyl-benzyl ester Following general procedure A or I, starting from 1-[5-(1,1-difluoro-ethyl)-furan-2-ylmethyl]-1H-pyrazol-4-ylamine and (2-chloro-6-fluoro-3-methyl-phenyl)-methanol. LC-MS-conditions 05b: $t_R$=1.15 min; [M+H]$^+$=428.13.

Example 247

[1-(5,5-Difluoro-hexyl)-1H-pyrazol-4-yl]-carbamic acid 2-chloro-6-fluoro-3-methyl-benzyl ester Following general procedure A or I, starting from 1-(5,5-difluoro-hexyl)-1H-pyrazol-4-ylamine and (2-chloro-6-fluoro-3-methyl-phenyl)-methanol. LC-MS-conditions 05b: $t_R$=1.15 min; [M+H]$^+$=404.17.

Example 248

[1-(5,5-Difluoro-hexyl)-1H-pyrazol-4-yl]-carbamic acid 6-chloro-2-fluoro-3-methyl-benzyl ester Following general procedure A or I, starting from 1-(5,5-difluoro-hexyl)-1H-pyrazol-4-ylamine and (6-chloro-2- fluoro-3-methyl-phenyl)-methanol. LC-MS-conditions 05b: $t_R$=1.15 min; [M+H]$^+$=404.19.

Example 249

5-m-Tolyl-oxazole-4-carboxylic acid {1-[5-(1,1-difluoro-ethyl)-furan-2-ylmethyl]-1H-pyrazol-4-yl}-amide Following general procedure B, starting from 1-[5-(1,1-difluoro-ethyl)-furan-2-ylmethyl]-1H-pyrazol-4-ylamine and 5-m-tolyl-oxazole-4-carboxylic acid. LC-MS-conditions 05b: $t_R$=1.15 min; [M+H]$^+$=413.05.

Example 250

5-(4-Methoxy-phenyl)-oxazole-4-carboxylic acid {1-[5-(1,1-difluoro-ethyl)-furan-2-ylmethyl]-1H-pyrazol-4-yl}-amide Following general procedure B, starting from 1-[5-(1,1-difluoro-ethyl)-furan-2-ylmethyl]-1H-pyrazol-4-ylamine and 5-(4-methoxy-phenyl)-oxazole-4-carboxylic acid. LC-MS-conditions 05b: $t_R$=1.11 min; [M+H]$^+$=429.03.

Example 251

5-(4-Methoxy-phenyl)-2-methyl-oxazole-4-carboxylic acid {1-[5-(1,1-difluoro-ethyl)-furan-2-ylmethyl]-1H-pyrazol-4-yl}amide Following general procedure B, starting from 1-[5-(1,1-difluoro-ethyl)-furan-2-ylmethyl]-1H-pyrazol-4-ylamine and 5-(4-methoxy-phenyl)-2-methyl-oxazole-4-carboxylic acid. LC-MS-conditions 05b: $t_R$=1.14 min; [M+H]$^+$=442.99.

Example 252

(E)-N-{1-[5-(1,1-Difluoro-ethyl)-furan-2-ylmethyl]-1H-pyrazol-4-yl}-3-(4-trifluoromethyl-phenyl)-acrylamide Following general procedure B, starting from 1-[5-(1,1-difluoro-ethyl)-furan-2-ylmethyl]-1H-pyrazol-4-ylamine and (E)-3-(4-trifluoromethyl-phenyl)-acrylic acid. LC-MS-conditions 05b: $t_R$=1.13 min; [M+H]$^+$=426.04.

Example 253

(E)-N-{1-[5-(1,1-Difluoro-ethyl)-furan-2-ylmethyl]-1H-pyrazol-4-yl}-3-(2,3-dimethoxy-phenyl)-acrylamide Following general procedure B, starting from 1-[5-(1,1-difluoro-ethyl)-furan-2-ylmethyl]-1H-pyrazol-4-ylamine and (E)-3-(2,3-dimethoxy-phenyl)-acrylic acid. LC-MS-conditions 05b: $t_R$=1.06 min; [M+H]$^+$=418.09.

Example 254

(E)-N-{1-[5-(1,1-Difluoro-ethyl)-furan-2-ylmethyl]-1H-pyrazol-4-yl}-3-p-tolyl-acrylamide Following general procedure B, starting from 1-[5-(1,1-difluoro-ethyl)-furan-2-ylmethyl]-1H-pyrazol-4-ylamine and (E)-3-p-tolyl-acrylic acid. LC-MS-conditions 05b: $t_R$=1.10 min; [M+H]$^+$=372.18.

Example 255

5-(3-Methoxy-phenyl)-2-methyl-oxazole-4-carboxylic acid {1-[5-(1,1-difluoro-ethyl)-furan-2-ylmethyl]-1H-pyrazol-4-yl}-amide Following general procedure B, starting from 1-[5-(1,1-difluoro-ethyl)-furan-2-ylmethyl]-1H-pyrazol-4-ylamine and 5-(3-methoxy-phenyl)-2-methyl-oxazole-4-carboxylic acid. LC-MS-conditions 05b: $t_R$=1.15 min; [M+H]$^+$=443.03.

Example 256

5-(3-Chloro-phenyl)-thiazole-4-carboxylic acid {1-[5-(1,1-difluoro-ethyl)-furan-2-ylmethyl]-1H-pyrazol-4-yl}amide Following general procedure B, starting from 1-[5-(1,1-difluoro-ethyl)-furan-2-ylmethyl]-1H-pyrazol-4-ylamine and 5-(3-chloro-phenyl)-thiazole-4-carboxylic acid. LC-MS-conditions 05b: $t_R$=1.15 min; [M+H]$^+$=449.00.

Example 257

(E)-N-{1-[5-(1,1-Difluoro-ethyl)-furan-2-ylmethyl]-1H-pyrazol-4-yl}-3-(4-methoxy-phenyl)-acrylamide Following general procedure B, starting from 1-[5-(1,1-difluoro-ethyl)-furan-2-ylmethyl]-1H-pyrazol-4-ylamine and (E)-3-(4-methoxy-phenyl)-acrylic acid. LC-MS-conditions 05b: $t_R$=1.06 min; [M+H]$^+$=388.10.

Example 258

(E)-3-(2-Chloro-4-fluoro-phenyl)-N-{1-[5-(1,1-difluoro-ethyl)-furan-2-ylmethyl]-1H-pyrazol-4-yl}-acrylamide Following general procedure B, starting from 1-[5-(1,1-difluoro-ethyl)-furan-2-ylmethyl]-1H-pyrazol-4-ylamine and (E)-3-(2-chloro-4-fluoro-phenyl)-acrylic acid. LC-MS-conditions 05b: $t_R$=1.12 min; [M+H]$^+$=410.06.

Example 259

(E)-N-{1-[5-(1,1-Difluoro-ethyl)-furan-2-ylmethyl]-1H-pyrazol-3-yl}-3-(3-trifluoromethyl-phenyl)-acrylamide Following general procedure B, starting from 1-[5-(1,1-difluoro-ethyl)-furan-2-ylmethyl]-1H-pyrazol-3-ylamine and (E)-3-(3-trifluoromethyl-phenyl)-acrylic acid. LC-MS-conditions 05b: $t_R$=1.15 min; [M+H]$^+$=425.99.

Example 260

(E)-3-(2,3-Dichloro-phenyl)-N-{1-[5-(1,1-difluoro-ethyl)-furan-2-ylmethyl]-1H-pyrazol-3-yl}-acrylamide Following general procedure B, starting from 1-[5-(1,1-difluoro-ethyl)-furan-2-ylmethyl]-1H-pyrazol-3-ylamine and (E)-3-(2,3-dichloro-phenyl)-acrylic acid. LC-MS-conditions 05b: $t_R$=1.17 min; [M+H]$^+$=425.94.

Example 261

(E)-N-{1-[5-(1,1-Difluoro-ethyl)-furan-2-ylmethyl]-1H-pyrazol-3-yl}-3-(2,3-dimethoxy-phenyl)-acrylamide Following general procedure B, starting from 1-[5-(1,1-difluoro-ethyl)-furan-2-ylmethyl]-1H-pyrazol-3-ylamine and (E)-3-(2,3-dimethoxy-phenyl)-acrylic acid. LC-MS-conditions 05b: $t_R$=1.09 min; [M+H]$^+$=418.09.

Example 262

(E)-3-(2-Chloro-4-fluoro-phenyl)-N-{1-[5-(1,1-difluoro-ethyl)-furan-2-ylmethyl]-1H-pyrazol-3-yl}-acrylamide Following general procedure B, starting from 1-[5-(1,1-difluoro-ethyl)-furan-2-ylmethyl]-1H-pyrazol-3-ylamine and (E)-3-(2-chloro-4-fluoro-phenyl)-acrylic acid. LC-MS-conditions 05b: $t_R$=1.14 min; [M+H]$^+$=410.03.

Example 263

(E)-N-{1-[5-(1,1-Difluoro-ethyl)-furan-2-ylmethyl]-1H-pyrazol-3-yl}-3-p-tolyl-acrylamide Following general procedure B, starting from 1-[5-(1,1-difluoro-ethyl)-furan-2-ylmethyl]-1H-pyrazol-3-ylamine and (E)-3-p-tolyl-acrylic acid. LC-MS-conditions 05b: $t_R$=1.12 min; [M+H]$^+$=372.16.

Example 264

(E)-3-(2,4-Dichloro-phenyl)-N-{1-[5-(1,1-difluoro-ethyl)-furan-2-ylmethyl]-1H-pyrazol-3-yl}-acrylamide Following general procedure B, starting from 1-[5-(1,1-difluoro-ethyl)-furan-2-ylmethyl]-1H-pyrazol-3-ylamine and (E)-3-(2,4-dichloro-phenyl)-acrylic acid. LC-MS-conditions 05b: $t_R$=1.18 min; [M+H]$^+$=425.96.

Example 265

(E)-3-(2-Chloro-6-fluoro-phenyl)-N-{1-[5-(1,1-difluoro-ethyl)-furan-2-ylmethyl]-1H-pyrazol-3-yl}-acrylamide Following general procedure B, starting from 1-[5-(1,1-difluoro-ethyl)-furan-2-ylmethyl]-1H-pyrazol-3-ylamine and (E)-3-(2-chloro-6-fluoro-phenyl)-acrylic acid. LC-MS-conditions 05b: $t_R$=1.14 min; [M+H]$^+$=410.0.

Example 266

(E)-3-(2-Chloro-3,6-difluoro-phenyl)-N-{1-[5-(1,1-difluoro-ethyl)-furan-2-ylmethyl]-1H-pyrazol-3-yl}-acrylamide Following general procedure B, starting from 1-[5-(1,1-difluoro-ethyl)-furan-2-ylmethyl]-1H-pyrazol-3-ylamine and (E)-3-(2-chloro-3,6-difluoro-phenyl)-acrylic acid. LC-MS-conditions 05b: $t_R$=1.14 min; [M+H]$^+$=427.98.

Example 267

(E)-3-(3-Chloro-phenyl)-N-{1-[5-(1,1-difluoro-ethyl)-furan-2-ylmethyl]-1H-pyrazol-3-yl}-acrylamide Following general procedure B, starting from 1-[5-(1,1-difluoro-ethyl)-furan-2-ylmethyl]-1H-pyrazol-3-ylamine and (E)-3-(3-chloro-phenyl)-acrylic acid. LC-MS-conditions 05b: $t_R$=1.14 min; [M+H]$^+$=392.14.

Example 268

(E)-N-{1-[5-(1,1-Difluoro-ethyl)-furan-2-ylmethyl]-1H-pyrazol-3-yl}-3-(2-fluoro-3-trifluoromethyl-phenyl)-acrylamide Following general procedure B, starting from 1-[5-(1,1-difluoro-ethyl)-furan-2-ylmethyl]-1H-pyrazol-3-ylamine and (E)-3-(2-fluoro-3-trifluoromethyl-phenyl)-acrylic acid. LC-MS-conditions 05b: $t_R$=1.16 min; [M+H]$^+$=443.98.

Example 269

(E)-N-{1-[5-(1,1-Difluoro-ethyl)-furan-2-ylmethyl]-1H-pyrazol-3-yl}-3-m-tolyl-acrylamide Following general procedure B, starting from 1-[5-(1,1-difluoro-ethyl)-furan-2-ylmethyl]-1H-pyrazol-3-ylamine and (E)-3-m-tolyl-acrylic acid. LC-MS-conditions 05b: $t_R$=1.13 min; [M+H]$^+$=372.16.

Example 270

(E)-N-{1-[5-(1,1-Difluoro-ethyl)-furan-2-ylmethyl]-1H-pyrazol-3-yl}-3-(3-methoxy-phenyl)-acrylamide Following general procedure B, starting from 1-[5-(1,1-difluoro-ethyl)-furan-2-ylmethyl]-1H-pyrazol-3-ylamine and (E)-3-(3-methoxy-phenyl)-acrylic acid. LC-MS-conditions 05b: $t_R$=1.09 min; [M+H]$^+$=388.21.

Example 271

(E)-N-{1-[5-(1,1-Difluoro-ethyl)-furan-2-ylmethyl]-1H-pyrazol-3-yl}-3-(4-methoxy-phenyl)-acrylamide Following general procedure B, starting from 1-[5-(1,1-difluoro-ethyl)-furan-2-ylmethyl]-1H-pyrazol-3-ylamine and (E)-3-(4-methoxy-phenyl)-acrylic acid. LC-MS-conditions 05b: $t_R$=1.08 min; [M+H]$^+$=388.12.

Example 272

2-Methyl-5-phenyl-oxazole-4-carboxylic acid {1-[5-(1,1-difluoro-ethyl)-furan-2-ylmethyl]-1H-pyrazol-4-yl}-amide Following general procedure B, starting from 1-[5-(1,1-difluoro-ethyl)-furan-2-ylmethyl]-1H-pyrazol-4-ylamine and 2-methyl-5-phenyl-oxazole-4-carboxylic acid. LC-MS-conditions 05b: $t_R$=1.14 min; [M+H]$^+$=413.07.

Example 273

2-Methyl-5-m-tolyl-oxazole-4-carboxylic acid {1-[5-(1,1-difluoro-ethyl)-furan-2-ylmethyl]-1H-pyrazol-4-yl}-amide Following general procedure B, starting from 1-[5-(1,1-difluoro-ethyl)-furan-2-ylmethyl]-1H-pyrazol-4-ylamine and 2-methyl-5-m-tolyl-oxazole-4-carboxylic acid. LC-MS-conditions 05b: $t_R$=1.17 min; $[M+H]^+$=427.12.

Example 274

2-Methyl-5-m-tolyl-oxazole-4-carboxylic acid {1-[5-(1,1-difluoro-ethyl)-furan-2-ylmethyl]-1H-pyrazol-3-yl}-amide Following general procedure B, starting from 1-[5-(1,1-difluoro-ethyl)-furan-2-ylmethyl]-1H-pyrazol-3-ylamine and 2-methyl-5-m-tolyl-oxazole-4-carboxylic acid. LC-MS-conditions 05b: $t_R$=1.21 min; $[M+H]^+$=427.09.

Example 275

5-(3-Methoxy-phenyl)-2-methyl-oxazole-4-carboxylic acid {1-[5-(1,1-difluoro-ethyl)-furan-2-ylmethyl]-1H-pyrazol-3-yl}-amide Following general procedure B, starting from 1-[5-(1,1-difluoro-ethyl)-furan-2-ylmethyl]-1H-pyrazol-3-ylamine and 5-(3-methoxy-phenyl)-2-methyl-oxazole-4-carboxylic acid. LC-MS-conditions 05b: $t_R$=1.18 min; $[M+H]^+$=443.0.

Example 276

5-(3-Methoxy-phenyl)-oxazole-4-carboxylic acid {1-[5-(1,1-difluoro-ethyl)-furan-2-ylmethyl]-1H-pyrazol-4-yl}-amide Following general procedure B, starting from 1-[5-(1,1-difluoro-ethyl)-furan-2-ylmethyl]-1H-pyrazol-4-ylamine and 5-(3-methoxy-phenyl)-oxazole-4-carboxylic acid. LC-MS-conditions 05b: $t_R$=1.12 min; $[M+H]^+$=429.04.

Example 277

5-(3-Methoxy-phenyl)-oxazole-4-carboxylic acid {1-[5-(1,1-difluoro-ethyl)-furan-2-ylmethyl]-1H-pyrazol-3-yl}-amide Following general procedure B, starting from 1-[5-(1,1-difluoro-ethyl)-furan-2-ylmethyl]-1H-pyrazol-3-ylamine and 5-(3-methoxy-phenyl)-oxazole-4-carboxylic acid. LC-MS-conditions 05b: $t_R$=1.15 min; $[M+H]^+$=429.13.

Example 278

5-(4-Methoxy-phenyl)-oxazole-4-carboxylic acid {1-[5-(1,1-difluoro-ethyl)-furan-2-ylmethyl]-1H-pyrazol-3-yl}-amide Following general procedure B, starting from 1-[5-(1,1-difluoro-ethyl)-furan-2-ylmethyl]-1H-pyrazol-3-ylamine and 5-(4-methoxy-phenyl)-oxazole-4-carboxylic acid. LC-MS-conditions 05b: $t_R$=1.15 min; $[M+H]^+$=429.03.

Example 279

{1-[5-(1,1-Difluoro-ethyl)-furan-2-ylmethyl]-1H-pyrazol-4-yl}-carbamic acid 3-chloro-2-fluoro-benzyl ester Following general procedure I, starting from 1-[5-(1,1-difluoro-ethyl)-furan-2-ylmethyl]-1H-pyrazol-4-ylamine and (3-chloro-2-fluoro-phenyl)-methanol. LC-MS-conditions 05b: $t_R$=1.13 min; $[M+H]^+$=414.04.

Example 280

{1-[5-(1,1-Difluoro-ethyl)-furan-2-ylmethyl]-1H-pyrazol-3-yl}-carbamic acid 3-trifluoromethyl-benzyl ester Following general procedure I, starting from 1-[5-(1,1-difluoro-ethyl)-furan-2-ylmethyl]-1H-pyrazol-3-ylamine and (3-trifluoromethyl-phenyl)-methanol. LC-MS-conditions 05b: $t_R$=1.16 min; $[M+H]^+$=430.05.

Example 281

{1-[5-(1,1-Difluoro-ethyl)-furan-2-ylmethyl]-1H-pyrazol-4-yl}-carbamic acid 2-chloro-4-fluoro-benzyl ester Following general procedure I, starting from 1-[5-(1,1-difluoro-ethyl)-furan-2-ylmethyl]-1H-pyrazol-4-ylamine and (2-chloro-4-fluoro-phenyl)-methanol. LC-MS-conditions 05b: $t_R$=1.13 min; $[M+H]^+$=414.06.

Example 282

[1-(5,5-Difluoro-hexyl)-1H-pyrazol-3-yl]-carbamic acid 2,6-difluoro-3-methyl-benzyl ester Following general procedure I, starting from 1-(5,5-difluoro-hexyl)-1H-pyrazol-3-ylamine and (2,6-difluoro-3-methyl-phenyl)-methanol. LC-MS-conditions 05b: $t_R$=1.15 min; $[M+H]^+$=388.13.

Example 283

{1-[5-(1,1-Difluoro-ethyl)-furan-2-ylmethyl]-1H-pyrazol-4-yl}-carbamic acid 2-chloro-6-fluoro-benzyl ester Following general procedure I, starting from 1-[5-(1,1-difluoro-ethyl)-furan-2-ylmethyl]-1H-pyrazol-4-ylamine and (2-chloro-6-fluoro-phenyl)-methanol. LC-MS-conditions 05b: $t_R$=1.11 min; $[M+H]^+$=414.05.

Example 284

{1-[5-(1,1-Difluoro-ethyl)-furan-2-ylmethyl]-1H-pyrazol-3-yl}-carbamic acid 2-fluoro-benzyl ester Following general procedure I, starting from 1-[5-(1,1-difluoro-ethyl)-furan-2-ylmethyl]-1H-pyrazol-3-ylamine

Example 285

[1-(5,5-Difluoro-hexyl)-1H-pyrazol-3-yl]-carbamic acid 3-trifluoromethyl-benzyl ester Following general procedure I, starting from 1-(5,5-difluoro-hexyl)-1H-pyrazol-3-ylamine and (3-trifluoromethyl-phenyl)-methanol. LC-MS-conditions 05b: $t_R$=1.16 min; [M+H]$^+$=406.14.

Example 286

{1-[5-(1,1-Difluoro-ethyl)-furan-2-ylmethyl]-1H-pyrazol-3-yl}-carbamic acid 3-chloro-benzyl ester Following general procedure I, starting from 1-[5-(1,1-difluoro-ethyl)-furan-2-ylmethyl]-1H-pyrazol-3-ylamine and (3-chloro-phenyl)-methanol. LC-MS-conditions 05b: $t_R$=1.15 min; [M+H]$^+$=396.08.

Example 287

[1-(5,5-Difluoro-hexyl)-1H-pyrazol-4-yl]-carbamic acid 3-trifluoromethyl-benzyl ester Following general procedure I, starting from 1-(5,5-difluoro-hexyl)-1H-pyrazol-4-ylamine and (3-trifluoromethyl-phenyl)-methanol. LC-MS-conditions 05b: $t_R$=1.14 min; [M+H]$^+$=406.15.

Example 288

{1-[5-(1,1-Difluoro-ethyl)-furan-2-ylmethyl]-1H-pyrazol-4-yl}-carbamic acid 2,6-difluoro-3-methyl-benzyl ester Following general procedure I, starting from 1-[5-(1,1-difluoro-ethyl)-furan-2-ylmethyl]-1H-pyrazol-4-ylamine and (2,6-difluoro-3-methyl-phenyl)-methanol. LC-MS-conditions 05b: $t_R$=1.13 min; [M+H]$^+$=412.12.

Example 289

{1-[5-(1,1-Difluoro-ethyl)-furan-2-ylmethyl]-1H-pyrazol-4-yl}-carbamic acid 2-fluoro-benzyl ester Following general procedure I, starting from 1-[5-(1,1-difluoro-ethyl)-furan-2-ylmethyl]-1H-pyrazol-4-ylamine and (2-fluorol-phenyl)-methanol. LC-MS-conditions 05b: $t_R$=1.09 min; [M+H]$^+$=380.12.

Example 290

[1-(5,5-Difluoro-hexyl)-1H-pyrazol-3-yl]-carbamic acid 2-fluoro-benzyl ester

Following general procedure I, starting from 1-(5,5-difluoro-hexyl)-1H-pyrazol-3-ylamine and (2-fluoro-phenyl)-methanol. LC-MS-conditions 05b: $t_R$=1.12 min; [M+H]$^+$=356.19.

Example 291

{1-[5-(1,1-Difluoro-ethyl)-furan-2-ylmethyl]-1H-pyrazol-3-yl}-carbamic acid benzyl ester Following general procedure I, starting from 1-[5-(1,1-difluoro-ethyl)-furan-2-ylmethyl]-1H-pyrazol-3-ylamine and phenyl-methanol. LC-MS-conditions 05b: $t_R$=1.11 min; [M+H]$^+$=362.14.

Example 292

{1-[5-(1,1-Difluoro-ethyl)-furan-2-ylmethyl]-1H-pyrazol-4-yl}-carbamic acid 3-trifluoromethyl-benzyl ester Following general procedure I, starting from 1-[5-(1,1-difluoro-ethyl)-furan-2-ylmethyl]-1H-pyrazol-4-ylamine and (3-trifluoromethyl-phenyl)-methanol. LC-MS-conditions 05b: $t_R$=1.14 min; [M+H]$^+$=430.07.

Example 293

[1-(5,5-Difluoro-hexyl)-1H-pyrazol-4-yl]-carbamic acid 2-fluoro-benzyl ester

Following general procedure I, starting from 1-(5,5-difluoro-hexyl)-1H-pyrazol-4-ylamine and (2-fluoro-phenyl)-methanol. LC-MS-conditions 05b: $t_R$=1.09 min; [M+H]$^+$=356.22.

Example 294

[1-(5,5-Difluoro-hexyl)-1H-pyrazol-3-yl]-carbamic acid 3-chloro-benzyl ester

Following general procedure I, starting from 1-(5,5-difluoro-hexyl)-1H-pyrazol-3-ylamine and (3-chloro-phenyl)-methanol. LC-MS-conditions 05b: $t_R$=1.15 min; [M+H]$^+$=371.82.

Example 295

[1-(5,5-Difluoro-hexyl)-1H-pyrazol-3-yl]-carbamic acid 3,4-dimethyl-benzyl ester Following general procedure I, starting from 1-(5,5-difluoro-hexyl)-1H-pyrazol-3-ylamine and (3,4-dimethyl-phenyl)-methanol. LC-MS-conditions 05b: $t_R$=1.17 min; [M+H]$^+$=366.21.

Example 296

[1-(5,5-Difluoro-hexyl)-1H-pyrazol-3-yl]-carbamic acid 2-ethyl-benzyl ester

Following general procedure I, starting from 1-(5,5-difluoro-hexyl)-1H-pyrazol-3-ylamine and (2-ethyl-phenyl)-methanol. LC-MS-conditions 05b: $t_R$=1.17 min; [M+H]$^+$=366.22.

Example 297

{1-[5-(1,1-Difluoro-ethyl)-furan-2-ylmethyl]-1H-pyrazol-3-yl}-carbamic acid 3-methyl-benzyl ester Following general procedure I, starting from 1-[5-(1,1-difluoro-ethyl)-furan-2-ylmethyl]-1H-pyrazol-3-ylamine and (3-methyl-phenyl)-methanol. LC-MS-conditions 05b: $t_R$=1.13 min; [M+H]$^+$=376.16.

Example 298

[1-(5,5-Difluoro-hexyl)-1H-pyrazol-4-yl]-carbamic acid 3-chloro-benzyl ester

Following general procedure I, starting from 1-(5,5-difluoro-hexyl)-1H-pyrazol-4-ylamine and (3-chloro-phenyl)-methanol. LC-MS-conditions 05b: $t_R$=1.13 min; [M+H]$^+$=371.86.

Example 299

{1-[5-(1,1-Difluoro-ethyl)-furan-2-ylmethyl]-1H-pyrazol-3-yl}-carbamic acid 2-ethyl-benzyl ester Following general procedure I, starting from 1-[5-(1,1-difluoro-ethyl)-furan-2-ylmethyl]-1H-pyrazol-3-ylamine and (2-ethyl-phenyl)-methanol. LC-MS-conditions 05b: $t_R$=1.17 min; [M+H]$^+$=390.19.

Example 300

{1-[5-(1,1-Difluoro-ethyl)-furan-2-ylmethyl]-1H-pyrazol-4-yl}-carbamic acid benzylester Following general procedure I, starting from 1-[5-(1,1-difluoro-ethyl)-furan-2-ylmethyl]-1H-pyrazol-4-ylamine and phenyl-methanol. LC-MS-conditions 05b: $t_R$=1.08 min; [M+H]$^+$=362.16.

Example 301

[1-(5,5-Difluoro-hexyl)-1H-pyrazol-3-yl]-carbamic acid benzyl ester

Following general procedure I, starting from 1-(5,5-difluoro-hexyl)-1H-pyrazol-3-ylamine and phenyl-methanol. LC-MS-conditions 05b: $t_R$=1.11 min; [M+H]$^+$=338.46.

Example 302

[1-(5,5-Difluoro-hexyl)-1H-pyrazol-4-yl]-carbamic acid 3,4-dimethyl-benzyl ester Following general procedure I, starting from 1-(5,5-difluoro-hexyl)-1H-pyrazol-4-ylamine and (3,4-dimethyl-phenyl)-methanol. LC-MS-conditions 05b: $t_R$=1.15 min; [M+H]$^+$=366.2.

Example 303

{1-[5-(1,1-Difluoro-ethyl)-furan-2-ylmethyl]-1H-pyrazol-4-yl}-carbamic acid 2-methyl-benzyl ester Following general procedure I, starting from 1-[5-(1,1-difluoro-ethyl)-furan-2-ylmethyl]-1H-pyrazol-4-ylamine and (2-methyl-phenyl)-methanol. LC-MS-conditions 05b: $t_R$=1.12 min; [M+H]$^+$=376.2.

Example 304

{1-[5-(1,1-Difluoro-ethyl)-furan-2-ylmethyl]-1H-pyrazol-4-yl}-carbamic acid 3-chloro-benzyl ester Following general procedure I, starting from 1-[5-(1,1-difluoro-ethyl)-furan-2-ylmethyl]-1H-pyrazol-4-ylamine and (3-chloro-phenyl)-methanol. LC-MS-conditions 05b: $t_R$=1.13 min; [M+H]$^+$=396.09.

Example 305

[1-(5,5-Difluoro-hexyl)-1H-pyrazol-3-yl]-carbamic acid 2-methyl-benzyl ester

Following general procedure I, starting from 1-(5,5-difluoro-hexyl)-1H-pyrazol-3-ylamine and (2-methyl-phenyl)-methanol. LC-MS-conditions 05b: $t_R$=1.14 min; [M+H]$^+$=352.21.

Example 306

{1-[5-(1,1-Difluoro-ethyl)-furan-2-ylmethyl]-1H-pyrazol-4-yl}-carbamic acid 3,4-dimethyl-benzyl ester Following general procedure I, starting from 1-[5-(1,1-difluoro-ethyl)-furan-2-ylmethyl]-1H-pyrazol-4-ylamine and (3,4-dimethyl-phenyl)-methanol. LC-MS-conditions 05b: $t_R$=1.15 min; [M+H]$^+$=390.15.

Example 307

[1-(5,5-Difluoro-hexyl)-1H-pyrazol-4-yl]-carbamic acid benzyl ester

Following general procedure I, starting from 1-(5,5-difluoro-hexyl)-1H-pyrazol-4-ylamine and phenyl-methanol. LC-MS-conditions 05b: $t_R$=1.08 min; [M+H]$^+$=338.47.

Example 308

[1-(5,5-Difluoro-hexyl)-1H-pyrazol-3-yl]-carbamic acid 2,5-dimethyl-benzyl ester Following general procedure I, starting from 1-(5,5-difluoro-hexyl)-1H-pyrazol-3-ylamine and (2,5-dimethyl-phenyl)-methanol. LC-MS-conditions 05b: $t_R$=1.17 min; [M+H]$^+$=366.23.

Example 309

[1-(5,5-Difluoro-hexyl)-1H-pyrazol-3-yl]-carbamic acid 3-methyl-benzyl ester

Following general procedure I, starting from 1-(5,5-difluoro-hexyl)-1H-pyrazol-3-ylamine and (3-methyl-phenyl)-methanol. LC-MS-conditions 05b: $t_R$=1.13 min; [M+H]$^+$=352.23.

Example 310

[1-(5,5-Difluoro-hexyl)-1H-pyrazol-4-yl]-carbamic acid 2-ethyl-benzyl ester

Following general procedure I, starting from 1-(5,5-difluoro-hexyl)-1H-pyrazol-4-ylamine and (2-ethyl-phenyl)-methanol. LC-MS-conditions 05b: $t_R$=1.15 min; [M+H]$^+$=366.23.

Example 311

[1-(5,5-Difluoro-hexyl)-1H-pyrazol-4-yl]-carbamic acid 2-methyl-benzyl ester

Following general procedure I, starting from 1-(5,5-difluoro-hexyl)-1H-pyrazol-4-ylamine and (2-methyl-phenyl)-methanol. LC-MS-conditions 05b: $t_R$=1.12 min; [M+H]$^+$=352.23.

Example 312

[1-(5,5-Difluoro-hexyl)-1H-pyrazol-4-yl]-carbamic acid 3-methyl-benzyl ester

Following general procedure I, starting from 1-(5,5-difluoro-hexyl)-1H-pyrazol-4-ylamine and (3-methyl-phenyl)-methanol. LC-MS-conditions 05b: $t_R$=1.12 min; [M+H]$^+$=352.21.

Example 313

[1-(5,5-Difluoro-hexyl)-1H-pyrazol-4-yl]-carbamic acid 2,5-dimethyl-benzyl ester Following general procedure I, starting from 1-(5,5-difluoro-hexyl)-1H-pyrazol-4-ylamine and (2,5-dimethyl-phenyl)-methanol. LC-MS-conditions 05b: $t_R$=1.15 min; [M+H]$^+$=366.22.

Example 314

{1-[5-(1,1-Difluoro-ethyl)-furan-2-ylmethyl]-1H-pyrazol-4-yl}-carbamic acid 2-ethyl-benzyl ester Following general procedure I, starting from 1-[5-(1,1-difluoro-ethyl)-furan-2-ylmethyl]-1H-pyrazol-4-ylamine and (2-ethyl-phenyl)-methanol. LC-MS-conditions 05b: $t_R$=1.14 min; [M+H]$^+$=390.24.

Example 315

{1-[5-(1,1-Difluoro-ethyl)-furan-2-ylmethyl]-1H-pyrazol-4-yl}-carbamic acid 3-methyl-benzyl ester Following general procedure I, starting from 1-[5-(1,1-difluoro-ethyl)-furan-2-ylmethyl]-1H-pyrazol-4-ylamine and (3-methyl-phenyl)-methanol. LC-MS-conditions 05b: $t_R$=1.12 min; [M+H]$^+$=376.13.

Example 316

{1-[5-(1,1-Difluoro-ethyl)-furan-2-ylmethyl]-1H-pyrazol-4-yl}-carbamic acid 2,5-dimethyl-benzyl ester Following general procedure I, starting from 1-[5-(1,1-difluoro-ethyl)-furan-2-ylmethyl]-1H-pyrazol-4-ylamine and (2,5-dimethyl-phenyl)-methanol. LC-MS-conditions 05b: $t_R$=1.15 min; [M+H]$^+$=390.16.

Example 317

(E)-N-[1-(5-Acetyl-furan-2-ylmethyl)-1H-pyrazol-3-yl]-3-(2,4-dimethoxy-phenyl)-acrylamide Following general procedure B followed by T, starting from 1-[5-(2-methyl-[1,3]dioxolan-2-yl)-furan-2-ylmethyl]-1H-pyrazol-3-ylamine and (E)-3-(2,4-dimethoxy-phenyl)-acrylic acid. LC-MS-conditions 05b: $t_R$=0.97 min; [M+H]$^+$=396.15.

Example 318

5-(3-Fluoro-phenyl)-2-methyl-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 5-(3-fluoro-phenyl)-2-methyl-oxazole-4-carboxylic acid. LC-MS-conditions 05b: $t_R$=1.09 min; [M+H]$^+$=409.11.

Example 319

(E)-N-[1-(5-Acetyl-furan-2-ylmethyl)-1H-pyrazol-3-yl]-3-(4-chloro-phenyl)-acrylamide Following general procedure B followed by T, starting from 1-[5-(2-methyl-[1,3]dioxolan-2-yl)-furan-2-ylmethyl]-1H-pyrazol-3-ylamine and (E)-3-(4-chloro-phenyl)-acrylic acid. LC-MS-conditions 05b: $t_R$=1.03 min; [M+H]$^+$=371.8.

Example 320

2-Methyl-5-(3-trifluoromethoxy-phenyl)-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 2-methyl-5-(3-trifluoromethoxy-phenyl)-oxazole-4-carboxylic acid. LC-MS-conditions 05b: $t_R$=1.16 min; [M+H]$^+$=475.07.

Example 321

5-(3,4-Dimethyl-phenyl)-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 5-(3,4-dimethyl-phenyl)-oxazole-4-carboxylic acid. LC-MS-conditions 05b: $t_R$=1.08 min; [M+H]$^+$=405.12.

Example 322

(E)-N-[1-(5-Acetyl-furan-2-ylmethyl)-1H-pyrazol-4-yl]-3-(2,4-dimethoxy-phenyl)-acrylamide Following general procedure B followed by T, starting from 1-[5-(2-methyl-[1,3]dioxolan-2-yl)-furan-2-ylmethyl]-1H-pyrazol-4-ylamine and (E)-3-(2,4-dimethoxy-phenyl)-acrylic acid. LC-MS-conditions 05b: $t_R$=0.93 min; [M+H]$^+$=396.15.

Example 323

5-(3,4-Dimethyl-phenyl)-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-

1H-pyrazol-3-ylamine and 5-(3,4-dimethyl-phenyl)-oxazole-4-carboxylic acid. LC-MS-conditions 05b: $t_R$=1.11 min; $[M+H]^+$=405.09.

Example 324

5-(3-Fluoro-phenyl)-2-methyl-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 5-(3-fluoro-phenyl)-2-methyl-oxazole-4-carboxylic acid. LC-MS-conditions 05b: $t_R$=1.06 min; $[M+H]^+$=409.11.

Example 325

(E)-N-[1-(5-Acetyl-furan-2-ylmethyl)-1H-pyrazol-4-yl]-3-(4-methoxy-phenyl)-acrylamide Following general procedure B followed by T, starting from 1-[5-(2-methyl-[1,3]dioxolan-2-yl)-furan-2-ylmethyl]-1H-pyrazol-4-ylamine and (E)-3-(4-methoxy-phenyl)-acrylic acid. LC-MS-conditions 05b: $t_R$=0.89 min; $[M+H]^+$=366.19.

Example 326

2-Methyl-5-(3-trifluoromethyl-phenyl)-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 2-methyl-5-(3-trifluoromethyl-phenyl)-oxazole-4-carboxylic acid. LC-MS-conditions 05b: $t_R$=1.12 min; $[M+H]^+$=459.1.

Example 327

(E)-N-[1-(5-Acetyl-furan-2-ylmethyl)-1H-pyrazol-4-yl]-3-(4-chloro-phenyl)-acrylamide Following general procedure B followed by T, starting from 1-[5-(2-methyl-[1,3]dioxolan-2-yl)-furan-2-ylmethyl]-1H-pyrazol-4-ylamine and (E)-3-(4-chloro-phenyl)-acrylic acid. LC-MS-conditions 05b: $t_R$=1.0 min; $[M+H]^+$=371.85.

Example 328

5-(3-Chloro-phenyl)-2-methyl-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 2-methyl-5-(3-chloro-phenyl)-oxazole-4-carboxylic acid. LC-MS-conditions 05b: $t_R$=1.10 min; $[M+H]^+$=425.02.

Example 329

2-Methyl-5-(3-trifluoromethoxy-phenyl)-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 2-methyl-5-(3-trifluoromethoxy-phenyl)-oxazole-4-carboxylic acid. LC-MS-conditions 05b: $t_R$=1.13 min; $[M+H]^+$=475.08.

Example 330

5-Biphenyl-3-yl-2-methyl-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 5-biphenyl-3-yl-2-methyl-oxazole-4-carboxylic acid. LC-MS-conditions 05b: $t_R$=1.16 min; $[M+H]^+$=466.33.

Example 331

5-p-Tolyl-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 5-p-tolyl-oxazole-4-carboxylic acid. LC-MS-conditions 05b: $t_R$=1.04 min; $[M+H]^+$=391.15.

Example 332

5-p-Tolyl-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 5-p-tolyl-oxazole-4-carboxylic acid. LC-MS-conditions 05b: $t_R$=1.08 min; $[M+H]^+$=391.12.

Example 333

2-Methyl-5-(3-trifluoromethyl-phenyl)-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 2-methyl-5-(3-trifluoromethyl-phenyl)-oxazole-4-carboxylic acid. LC-MS-conditions 05b: $t_R$=1.15 min; $[M+H]^+$=459.09.

Example 334

[1-(5-Acetyl-furan-2-ylmethyl)-1H-pyrazol-3-yl]-carbamic acid 4-fluoro-benzyl ester Following general procedure I followed by T, starting from 1-[5-(1,1-difluoro-ethyl)-furan-2-ylmethyl]-1H-pyrazol-3-ylamine and (4-fluoro-phenyl)-methanol. LC-MS-conditions 05b: $t_R$=0.98 min; $[M+H]^+$=358.22.

Example 335

[1-(5-Acetyl-furan-2-ylmethyl)-1H-pyrazol-3-yl]-carbamic acid 3-bromo-benzyl ester Following general procedure I followed by T, starting from 1-[5-(1,1-difluoro-ethyl)-furan-2-ylmethyl]-1H-pyrazol-3-

Example 336

[1-(5-Acetyl-furan-2-ylmethyl)-1H-pyrazol-4-yl]-carbamic acid 4-fluoro-benzyl ester Following general procedure I followed by T, starting from 1-[5-(1,1-difluoro-ethyl)-furan-2-ylmethyl]-1H-pyrazol-4-ylamine and (4-fluoro-phenyl)-methanol. LC-MS-conditions 05b: $t_R$=0.94 min; $[M+H]^+$=358.18.

Example 337

[1-(5-Acetyl-furan-2-ylmethyl)-1H-pyrazol-4-yl]-carbamic acid 3-bromo-benzyl ester Following general procedure I followed by T, starting from 1-[5-(1,1-difluoro-ethyl)-furan-2-ylmethyl]-1H-pyrazol-4-ylamine and (3-bromo-phenyl)-methanol. LC-MS-conditions 05b: $t_R$=1.03 min; $[M+H]^+$=418.03.

Example 338

(E)-N-[1-(5-Acetyl-furan-2-ylmethyl)-1H-pyrazol-4-yl]-3-(2,3-difluoro-4-trifluoromethyl-phenyl)-acrylamide Following general procedure B followed by T, starting from 1-[5-(2-methyl-[1,3]dioxolan-2-yl)-furan-2-ylmethyl]-1H-pyrazol-4-ylamine and (E)-3-(2,3-difluoro-4-trifluoromethyl-phenyl)-acrylic acid. LC-MS-conditions 01b: $t_R$=0.97 min; $[M+H]^+$=440.1.

Example 339

(E)-N-[1-(5-Acetyl-furan-2-ylmethyl)-1H-pyrazol-4-yl]-3-(2,5-difluoro-4-methoxy-phenyl)-acrylamide Following general procedure B followed by T, starting from 1-[5-(2-methyl-[1,3]dioxolan-2-yl)-furan-2-ylmethyl]-1H-pyrazol-4-ylamine and (E)-3-(2,5-difluoro-4-methoxy-phenyl)-acrylic acid. LC-MS-conditions 01b: $t_R$=0.86 min; $[M+H]^+$=402.17.

Example 340

5-(4-Trifluoromethyl-phenyl)-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 5-(4-trifluoromethyl-phenyl)-oxazole-4-carboxylic acid. LC-MS-conditions 01b: $t_R$=1.03 min; $[M+H]^+$=445.11.

Example 341

5-(3-Trifluoromethyl-phenyl)-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 5-(3-trifluoromethyl-phenyl)-oxazole-4-carboxylic acid. LC-MS-conditions 01b: $t_R$=1.02 min; $[M+H]^+$=445.14.

Example 342

5-(3-Fluoro-phenyl)-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 5-(3-fluoro-phenyl)-oxazole-4-carboxylic acid. LC-MS-conditions 01b: $t_R$=0.95 min; $[M+H]^+$=395.14.

Example 343

5-(4-Chloro-phenyl)-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 5-(4-chloro-phenyl)-oxazole-4-carboxylic acid. LC-MS-conditions 01b: $t_R$=1.01 min; $[M+H]^+$=411.11.

Example 344

5-(4-Fluoro-phenyl)-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 5-(4-fluoro-phenyl)-oxazole-4-carboxylic acid. LC-MS-conditions 01b: $t_R$=0.94 min; $[M+H]^+$=395.16.

Example 345

5-(4-Trifluoromethoxy-phenyl)-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 5-(4-trifluoromethoxy-phenyl)-oxazole-4-carboxylic acid. LC-MS-conditions 01b: $t_R$=1.04 min; $[M+H]^+$=461.10.

Example 346

5-(4-Trifluoromethoxy-phenyl)-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 5-(4-trifluoromethoxy-phenyl)-oxazole-4-carboxylic acid. LC-MS-conditions 01b: $t_R$=1.01 min; $[M+H]^+$=461.11.

Example 347

5-(3-Trifluoromethyl-phenyl)-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-

1H-pyrazol-4-ylamine and 5-(3-trifluoromethyl-phenyl)-oxazole-4-carboxylic acid. LC-MS-conditions 01b: $t_R$=0.98 min; [M+H]$^+$=445.13.

Example 348

(E)-N-[1-(5-Acetyl-furan-2-ylmethyl)-1H-pyrazol-3-yl]-3-(4-chloro-3,5-difluoro-phenyl)-acrylamide Following general procedure B followed by T, starting from 1-[5-(2-methyl-[1,3]dioxolan-2-yl)-furan-2-ylmethyl]-1H-pyrazol-3-ylamine and (E)-3-(4-chloro-3,5-difluoro-phenyl)-acrylic acid. LC-MS-conditions 01b: $t_R$=0.97 min; [M+H]$^+$=406.11.

Example 349

(E)-N-[1-(5-Acetyl-furan-2-ylmethyl)-1H-pyrazol-4-yl]-3-(2,5-difluoro-4-trifluoromethyl-phenyl)-acrylamide Following general procedure B followed by T, starting from 1-[5-(2-methyl-[1,3]dioxolan-2-yl)-furan-2-ylmethyl]-1H-pyrazol-4-ylamine and (E)-3-(2,5-difluoro-4-trifluoromethyl-phenyl)-acrylic acid. LC-MS-conditions 01b: $t_R$=0.97 min; [M+H]$^+$=440.1.

Example 350

5-(4-Chloro-phenyl)-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 5-(4-chloro-phenyl)-oxazole-4-carboxylic acid. LC-MS-conditions 01b: $t_R$=0.96 min; [M+H]$^+$=411.11.

Example 351

5-(3-Chloro-phenyl)-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 5-(3-chloro-phenyl)-oxazole-4-carboxylic acid. LC-MS-conditions 01b: $t_R$=0.96 min; [M+H]$^+$=411.11.

Example 352

5-(3-Chloro-phenyl)-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 5-(3-chloro-phenyl)-oxazole-4-carboxylic acid. LC-MS-conditions 01b: $t_R$=1.0 min; [M+H]$^+$=411.11.

Example 353

5-(3-Fluoro-phenyl)-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 5-(3-fluoro-phenyl)-oxazole-4-carboxylic acid. LC-MS-conditions 01b: $t_R$=0.91 min; [M+H]$^+$=395.12.

Example 354

5-Biphenyl-3-yl-2-methyl-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 5-biphenyl-3-yl-2-methyl-oxazole-4-carboxylic acid. LC-MS-conditions 02: $t_R$=1.11 min; [M+H]$^+$=467.31.

Example 355

5-(3-Chloro-phenyl)-2-methyl-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 2-methyl-5-(3-chloro-phenyl)-oxazole-4-carboxylic acid. LC-MS-conditions 05b (with gradient: 5% B→95% B over 1 min): $t_R$=0.79 min; [M+H]$^+$=425.14.

Example 356

5-Biphenyl-3-yl-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 5-biphenyl-3-yl-oxazole-4-carboxylic acid. LC-MS-conditions 02: $t_R$=1.08 min; [M+H]$^+$=453.3.

Example 357

5-Biphenyl-3-yl-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 5-biphenyl-3-yl-oxazole-4-carboxylic acid. LC-MS-conditions 01b: $t_R$=1.04 min; [M+H]$^+$=453.15.

Example 358

5-(3-Methoxy-phenyl)-2-methyl-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 2-methyl-5-(3-methoxy-phenyl)-oxazole-4-carboxylic acid. LC-MS-conditions 02: $t_R$=1.01 min; [M+H]$^+$=421.41.

Example 359

5-m-Tolyl-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-

1H-pyrazol-3-ylamine and 5-(3-methyl-phenyl)-oxazole-4-carboxylic acid. LC-MS-conditions 02: $t_R$=1.01 min; [M+H]$^+$=391.5.

Example 360

2-Methyl-5-phenyl-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-1H-pyrazol-3-ylamine and 2-methyl-5-phenyl-oxazole-4-carboxylic acid. LC-MS-conditions 02: $t_R$=1.0 min; [M+H]$^+$= 391.44.

Example 361

[1-(5-Acetyl-thiophen-2-ylmethyl)-1H-pyrazol-4-yl]-carbamic acid 2-chloro-benzyl ester Following general procedure I followed by C, 1-[5-(2-methyl-[1,3]dioxolan-2-yl)-thiophen-2-ylmethyl]-1H-pyrazol-4-ylamine and (2-chloro-phenyl)-methanol. LC-MS-conditions 02: $t_R$=1.00 min; [M+H]$^+$=390.24.

Example 362

5-Phenyl-oxazole-4-carboxylic acid [1-(3-acetyl-isoxazol-5-ylmethyl)-1H-pyrazol-4-yl]-amide Following general procedure B followed by T, starting from 1-[3-(2-methyl-[1,3]dioxolan-2-yl)-isoxazol-5-ylmethyl]-1H-pyrazol-4-ylamine and 5-phenyl-oxazole-4-carboxylic acid. LC-MS-conditions 02: $t_R$=0.97 min; [M+H]$^+$= 378.36.

Example 363

[1-(6-Acetyl-pyridin-2-ylmethyl)-1H-pyrazol-4-yl]-carbamic acid 2-chloro-benzyl ester Following general procedure I followed by C, 1-[6-(2-methyl-[1,3]dioxolan-2-yl)-pyridin-2-ylmethyl]-1H-pyrazol-4-ylamine and (2-chloro-phenyl)-methanol. LC-MS-conditions 05: $t_R$=0.87 min; [M+H]$^+$=385.2.

Example 364

5-Phenyl-oxazole-4-carboxylic acid [1-(6-acetyl-pyridin-2-ylmethyl)-1H-pyrazol-4-yl]-amide Following general procedure B followed by C, starting from 1-[6-(2-methyl-[1,3]dioxolan-2-yl)-pyridin-2-ylmethyl]-1H-pyrazol-4-ylamine and 5-phenyl-oxazole-4-carboxylic acid. LC-MS-conditions 02: $t_R$=0.99 min; [M+H]$^+$= 388.43.

Example 365

(E)-N-[1-(6-Acetyl-pyridin-2-ylmethyl)-1H-pyrazol-4-yl]-3-(4-trifluoromethyl-phenyl)-acrylamide Following general procedure B followed by C, starting from 1-[6-(2-methyl-[1,3]dioxolan-2-yl)-pyridin-2-ylmethyl]-1H-pyrazol-4-ylamine and (E)-3-(4-trifluoromethyl-phenyl)-acrylic acid. LC-MS-conditions 02: $t_R$=1.02 min; [M+H]$^+$=414.95.

Example 366

[1-(3-Acetyl-benzyl)-1H-pyrazol-4-yl]-carbamic acid 2-chloro-benzyl ester

Following general procedure I followed by C, 1-[3-(2-methyl-[1,3]dioxolan-2-yl)-benzyl]-1H-pyrazol-4-ylamine and (2-chloro-phenyl)-methanol. LC-MS-conditions 02: $t_R$=1.01 min; [M+H]$^+$=383.63.

Example 367

5-Phenyl-oxazole-4-carboxylic acid [1-(3-acetyl-benzyl)-1H-pyrazol-4-yl]-amide

Following general procedure B followed by C, starting from 1-[3-(2-methyl-[1,3]dioxolan-2-yl)-benzyl]-1H-pyrazol-4-ylamine and 5-phenyl-oxazole-4-carboxylic acid. LC-MS-conditions 02: $t_R$=1.00 min; [M+H]$^+$=387.06.

Example 368

5-Pyridin-2-yl-oxazole-4-carboxylic acid [1-(5-acetyl-furan-2-ylmethyl)-1H-pyrazol-4-yl]-amide Following general procedure B followed by C, starting from 1-[5-(2-methyl-[1,3]dioxolan-2-yl)-furan-2-ylmethyl]-1H-pyrazol-4-ylamine and 5-pyridin-2-yl-oxazole-4-carboxylic acid. LC-MS-conditions 05: $t_R$=0.56 min; [M+H]$^+$= 378.14.

Example 369

5-Phenyl-oxazole-4-carboxylic acid [1-(5-acetyl-thiophen-2-ylmethyl)-1H-pyrazol-4-yl]-amide Following general procedure B followed by C, starting from 1-[5-(2-methyl-[1,3]dioxolan-2-yl)-thiophen-2-ylmethyl]-1H-pyrazol-4-ylamine and 5-phenyl-oxazole-4-carboxylic acid. LC-MS-conditions 02: $t_R$=0.99 min; [M+H]$^+$= 393.41.

Example 370

(E)-N-[1-(5-Acetyl-thiophen-2-ylmethyl)-1H-pyrazol-4-yl]-3-(4-trifluoromethyl-phenyl)-acrylamide Following general procedure B followed by C, starting from 1-[5-(2-methyl-[1,3]dioxolan-2-yl)-thiophen-2-ylmethyl]-1H-pyrazol-4-ylamine and (E)-3-(4-trifluoromethyl-phenyl)-acrylic acid. LC-MS-conditions 02: $t_R$=1.02 min; [M+H]$^+$=420.12.

Example 371

5-(3-Trifluoromethoxy-phenyl)-oxazole-4-carboxylic acid [1-(5-acetyl-furan-2-ylmethyl)-1H-pyrazol-3-yl]-amide Following general procedure B followed by T, starting from 1-[5-(2-methyl-[1,3]dioxolan-2-yl)-furan-2-ylmethyl]-

Example 372

5-(3-Trifluoromethoxy-phenyl)-oxazole-4-carboxylic acid [1-(5-acetyl-furan-2-ylmethyl)-1H-pyrazol-4-yl]-amide Following general procedure B followed by T, starting from 1-[5-(2-methyl-[1,3]dioxolan-2-yl)-furan-2-ylmethyl]-1H-pyrazol-4-ylamine and 5-(3-trifluoromethoxy-phenyl)-oxazole-4-carboxylic acid. LC-MS-conditions 01b: $t_R$=1.00 min; [M+H]$^+$=461.09.

Example 373

5-(3-Cyano-phenyl)-oxazole-4-carboxylic acid [1-(5-acetyl-furan-2-ylmethyl)-1H-pyrazol-4-yl]-amide Following general procedure B followed by C, starting from 1-[5-(2-methyl-[1,3]dioxolan-2-yl)-furan-2-ylmethyl]-1H-pyrazol-4-ylamine and 5-(3-cyano-phenyl)-oxazole-4-carboxylic acid. LC-MS-conditions 02: $t_R$=0.95 min; [M+H]$^+$=402.40.

Example 374

5-(3-Carbamoyl-phenyl)-oxazole-4-carboxylic acid [1-(5-acetyl-furan-2-ylmethyl)-1H-pyrazol-4-yl]-amide 5-(3-Cyano-phenyl)-oxazole-4-carboxylic acid [1-(5-acetyl-furan-2-ylmethyl)-1H-pyrazol-4-yl]-amide (50 mg, 0.112 mmol) in 97% sulfuric acid (0.17 mL) was stirred at rt overnight. The reaction mixture was then poured onto crushed ice, adjusted to pH 9 with NH$_4$OH, and then strongly acidified with HCl 25%. The precipitate was filtered and washed with water until neutral pH. After drying, the title compound was obtained as a beige solid. LC-MS-conditions 02: $t_R$=0.81 min; [M+H]$^+$=420.12.

Example 375

5-(3-Dimethylamino-phenyl)-oxazole-4-carboxylic acid [1-(5-acetyl-furan-2-ylmethyl)-1H-pyrazol-4-yl]-amide Following general procedure B followed by C, starting from 1-[5-(2-methyl-[1,3]dioxolan-2-yl)-furan-2-ylmethyl]-1H-pyrazol-4-ylamine and 5-(3-dimethylamino-phenyl)-oxazole-4-carboxylic acid. LC-MS-conditions 02: $t_R$=0.79 min; [M+H]$^+$=420.50.

Example 376

5-Phenyl-oxazole-4-carboxylic acid [1-(5-acetyl-thiophen-2-ylmethyl)-1H-pyrazol-3-yl]-amide Following general procedure B followed by C, starting from 1-[5-(2-methyl-[1,3]dioxolan-2-yl)-thiophen-2-ylmethyl]-1H-pyrazol-3-ylamine and 5-phenyl-oxazole-4-carboxylic acid. LC-MS-conditions 02: $t_R$=1.02 min; [M+H]$^+$=393.34.

Example 377

(E)-N-[1-(5-Acetyl-thiophen-2-ylmethyl)-1H-pyrazol-3-yl]-3-(4-trifluoromethyl-phenyl)-acrylamide Following general procedure B followed by C, starting from 1-[5-(2-methyl-[1,3]dioxolan-2-yl)-thiophen-2-ylmethyl]-1H-pyrazol-3-ylamine and (E)-3-(4-trifluoromethyl-phenyl)-acrylic acid. LC-MS-conditions 02: $t_R$=1.04 min; [M+H]$^+$=420.19.

Example 378

[1-(5-Acetyl-thiophen-2-ylmethyl)-1H-pyrazol-3-yl]-carbamic acid 2-chloro-benzyl ester Following general procedure I followed by C, 1-[5-(2-methyl-[1,3]dioxolan-2-yl)-thiophen-2-ylmethyl]-1H-pyrazol-3-ylamine and (2-chloro-phenyl)-methanol. LC-MS-conditions 02: $t_R$=1.02 min; [M+H]$^+$=390.28.

Example 379

5-[3-(2-Methoxy-ethyl)-phenyl]-oxazole-4-carboxylic acid [1-(5-acetyl-furan-2-ylmethyl)-1H-pyrazol-3-yl]-amide Following general procedure B followed by C, 1-[5-(2-methyl-[1,3]dioxolan-2-yl)-furan-2-ylmethyl]-1H-pyrazol-3-ylamine and 5-[3-(2-methoxy-ethyl)-phenyl]-oxazole-4-carboxylic acid. LC-MS-conditions 02: $t_R$=0.98 min; [M+H]$^+$=435.45.

Example 380

5-(3-Cyano-phenyl)-oxazole-4-carboxylic acid [1-(5-acetyl-furan-2-ylmethyl)-1H-pyrazol-3-yl]-amide Following general procedure B followed by C, starting from 1-[5-(2-methyl-[1,3]dioxolan-2-yl)-furan-2-ylmethyl]-1H-pyrazol-3-ylamine and 5-(3-cyano-phenyl)-oxazole-4-carboxylic acid. LC-MS-conditions 02: $t_R$=0.97 min; [M+H]$^+$=402.37.

Example 381

3-{4-[1-(5-Acetyl-furan-2-ylmethyl)-1H-pyrazol-3-ylcarbamoyl]-oxazol-5-yl}-benzoic acid tert-butyl ester Following general procedure B followed by C, starting from 1-[5-(2-methyl-[1,3]dioxolan-2-yl)-furan-2-ylmethyl]-1H-pyrazol-3-ylamine and 5-(3-tert-butoxycarbonyl-phenyl)-oxazole-4-carboxylic acid. LC-MS-conditions 02: $t_R$=1.09 min; [M+H]$^+$=477.45.

Example 382

[1-(5-Acetyl-pyridin-3-ylmethyl)-1H-pyrazol-4-yl]-carbamic acid 2-chloro-benzyl ester Following general procedure I followed by C, starting from 1-[5-(2-methyl-[1,3]dioxolan-2-yl)-pyridin-3-ylmethyl]-1H-pyrazol-4-ylamine and (2-chloro-phenyl)-methanol. LC-MS-conditions 05: $t_R$=0.47 min; [M+H]$^+$=385.14.

Example 383

5-[3-(2-Hydroxy-ethyl)-phenyl]-oxazole-4-carboxylic acid [1-(5-acetyl-furan-2-ylmethyl)-1H-pyrazol-3-yl]-amide Following general procedure C starting from 5-{3-[2-(tert-Butyl-dimethyl-silanyloxy)-ethyl]-phenyl}-oxazole-4-carboxylic acid {1-[5-(2-methyl-[1,3]dioxolan-2-yl)-furan-2-ylmethyl]-1H-pyrazol-3-yl}-amide. LC-MS-conditions 02: $t_R$=0.88 min; [M+H]$^+$=421.15.

Example 384

5-(3-Methoxymethyl-phenyl)-oxazole-4-carboxylic acid [1-(5-acetyl-furan-2-ylmethyl)-1H-pyrazol-3-yl]-amide Following general procedure B followed by C starting from 1-[5-(2-methyl-[1,3]dioxolan-2-yl)-furan-2-ylmethyl]-1H-pyrazol-3-ylamine and 5-(3-methoxymethyl-phenyl)-oxazole-4-carboxylic acid. LC-MS-conditions 02: $t_R$=0.96 min; [M+H]$^+$=421.17.

Example 385

[1-(4-Acetyl-pyridin-2-ylmethyl)-1H-pyrazol-4-yl] carbamic acid 2-chloro-benzyl ester Following general procedure A followed by C (at 60° C.) starting from 1-[4-(2-methyl-[1,3]dioxolan-2-yl)-pyridin-2-ylmethyl]-1H-pyrazol-4-ylamine and (2-chloro-phenyl)-methanol. LC-MS-conditions 02: $t_R$=0.95 min; [M+H]$^+$=384.65.

Example 386

{4-[1-(5-Acetyl-furan-2-ylmethyl)-1H-pyrazol-3-ylcarbamoyl]-5-phenyl-oxazol-2-yl methyl}-carbamic acid tert-butyl ester Following general procedure B followed by C starting from 1-[5-(2-methyl-[1,3]dioxolan-2-yl)-furan-2-ylmethyl]-1H-pyrazol-3-ylamine and 2-(tert-butoxycarbonylaminomethyl)-5-phenyl-oxazole-4-carboxylic acid. LC-MS-conditions 02: $t_R$=1.03 min; [M+H]$^+$=506.46.

Example 387

[1-(4-Acetyl-thiazol-2-ylmethyl)-1H-pyrazol-4-yl]-carbamic acid 2-chloro-benzyl ester Following general procedure A followed by C starting from 1-[4-(2-methyl-[1,3]dioxolan-2-yl)-thiazol-2-ylmethyl]-1H-pyrazol-4-ylamine and (2-chloro-phenyl)-methanol. LC-MS-conditions 02: $t_R$=0.95 min; [M+H]$^+$=391.14.

Example 388

5-Phenyl-oxazole-4-carboxylic acid [1-(4-acetyl-thiazol-2-ylmethyl)-1H-pyrazol-4-yl]-amide Following general procedure B followed by C starting from 1-[4-(2-methyl-[1,3]dioxolan-2-yl)-thiazol-2-ylmethyl]-1H-pyrazol-4-ylamine and 5-phenyl-1,3-oxazole-4-carboxylic acid. LC-MS-conditions 02: $t_R$=0.93 min; [M+H]$^+$=394.01.

Example 389

(E)-N-[1-(4-Acetyl-thiazol-2-ylmethyl)-1H-pyrazol-4-yl]-3-(4-trifluoromethyl-phenyl)-acrylamide Following general procedure B followed by C starting from 1-[4-(2-methyl-[1,3]dioxolan-2-yl)-thiazol-2-ylmethyl]-1H-pyrazol-4-ylamine and (E)-3-(4-trifluoromethyl-phenyl)-acrylic acid. LC-MS-conditions 02: $t_R$=0.98 min; [M+H]$^+$=421.22.

Example 390

2-Aminomethyl-5-phenyl-oxazole-4-carboxylic acid [1-(5-acetyl-furan-2-ylmethyl)-1H-pyrazol-3-yl]-amide Following general procedure W starting from {4-[1-(5-acetyl-furan-2-ylmethyl)-1H-pyrazol-3-ylcarbamoyl]-5-phenyl-oxazol-2-ylmethyl}-carbamic acid tert-butyl ester. LC-MS-conditions 02: $t_R$=0.76 min; [M+H]$^+$=406.43.

Example 391

2-Methyl-5-(3-trifluoromethoxy-phenyl)-oxazole-4-carboxylic acid [1-(5-acetyl-thiophen-2-ylmethyl)-1H-pyrazol-4-yl]-amide Following general procedure X followed by C, starting from 1-[5-(2-methyl-[1,3]dioxolan-2-yl)-thiophen-2-ylmethyl]-1H-pyrazol-4-ylamine and 2-methyl-5-(3-trifluoromethoxy-phenyl)-oxazole-4-carboxylic acid. LC-MS-conditions 05c: $t_R$=0.81 min; [M+H]$^+$=492.2.

Example 392

2-Methyl-5-(3-trifluoromethoxy-phenyl)-oxazole-4-carboxylic acid [1-(5-acetyl-thiophen-2-ylmethyl)-1H-pyrazol-3-yl]-amide Following general procedure X followed by C, starting from 1-[5-(2-methyl-[1,3]dioxolan-2-yl)-thiophen-2-ylmethyl]-1H-pyrazol-3-ylamine and 2-methyl-5-(3-trifluoromethoxy-phenyl)-oxazole-4-carboxylic acid. LC-MS-conditions 05c: $t_R$=0.83 min; [M+H]$^+$=492.2.

Example 393

5-m-Tolyl-oxazole-4-carboxylic acid [1-(5-acetyl-thiophen-2-ylmethyl)-1H-pyrazol-4-yl]-amide Following general procedure X followed by C, starting from 1-[5-(2-methyl-[1,3]dioxolan-2-yl)-thiophen-2-ylmethyl]-1H-pyrazol-4-ylamine and 5-m-tolyl-oxazole-4-carboxylic acid. LC-MS-conditions 05c: $t_R$=0.72 min; [M+H]$^+$=407.20.

Example 394

5-m-Tolyl-oxazole-4-carboxylic acid [1-(5-acetyl-thiophen-2-ylmethyl)-1H-pyrazol-3-yl]-amide Following general procedure X followed by C, starting from 1-[5-(2-methyl-[1,3]dioxolan-2-yl)-thiophen-2-ylmethyl]-1H-pyrazol-3-ylamine and 5-m-tolyl-oxazole-4-carboxylic acid. LC-MS-conditions 05c: $t_R$=0.75 min; [M+H]$^+$=407.22.

Example 395

2-Methyl-5-m-tolyl-thiazole-4-carboxylic acid [1-(5-acetyl-thiophen-2-ylmethyl)-1H-pyrazol-4-yl]-amide Following general procedure X followed by C, starting from 1-[5-(2-methyl-[1,3]dioxolan-2-yl)-thiophen-2-ylmethyl]-1H-pyrazol-4-ylamine and 2-methyl-5-m-tolyl-thiazole-4-carboxylic acid. LC-MS-conditions 05c: $t_R$=0.75 min; $[M+H]^+$=437.22.

Example 396

5-(4-Chloro-phenyl)-2-methyl-thiazole-4-carboxylic acid [1-(5-acetyl-thiophen-2-ylmethyl)-1H-pyrazol-4-yl]-amide Following general procedure X followed by C, starting from 1-[5-(2-methyl-[1,3]dioxolan-2-yl)-thiophen-2-ylmethyl]-1H-pyrazol-4-ylamine and 5-(4-chloro-phenyl)-2-methyl-thiazole-4-carboxylic acid. LC-MS-conditions 05c: $t_R$=0.77 min; $[M+H]^+$=457.15.

Example 397

5-(3-Cyano-phenyl)-oxazole-4-carboxylic acid [1-(5-acetyl-thiophen-2-ylmethyl)-1H-pyrazol-4-yl]-amide Following general procedure X followed by C, starting from 1-[5-(2-methyl-[1,3]dioxolan-2-yl)-thiophen-2-ylmethyl]-1H-pyrazol-4-ylamine and 5-(3-cyano-phenyl)-oxazole-4-carboxylic acid. LC-MS-conditions 05c: $t_R$=0.69 min; $[M+H]^+$=417.76.

Example 398

5-(3-Cyano-phenyl)-oxazole-4-carboxylic acid [1-(5-acetyl-thiophen-2-ylmethyl)-1H-pyrazol-3-yl]-amide Following general procedure X followed by C, starting from 1-[5-(2-methyl-[1,3]dioxolan-2-yl)-thiophen-2-ylmethyl]-1H-pyrazol-3-ylamine and 5-(3-cyano-phenyl)-oxazole-4-carboxylic acid. LC-MS-conditions 05c: $t_R$=0.70 min; $[M+H]^+$=417.70.

Example 399

5-(3-Dimethylamino-phenyl)-oxazole-4-carboxylic acid [1-(5-acetyl-thiophen-2-ylmethyl)-1H-pyrazol-4-yl]-amide Following general procedure X followed by C, starting from 1-[5-(2-methyl-[1,3]dioxolan-2-yl)-thiophen-2-ylmethyl]-1H-pyrazol-4-ylamine and 5-(3-dimethylamino-phenyl)-oxazole-4-carboxylic acid. LC-MS-conditions 05c: $t_R$=0.58 min; $[M+H]^+$=436.28.

Example 400

5-(3-Dimethylamino-phenyl)-oxazole-4-carboxylic acid [1-(5-acetyl-thiophen-2-ylmethyl)-1H-pyrazol-3-yl]-amide Following general procedure X followed by C, starting from 1-[5-(2-methyl-[1,3]dioxolan-2-yl)-thiophen-2-ylmethyl]-1H-pyrazol-3-ylamine and 5-(3-dimethylamino-phenyl)-oxazole-4-carboxylic acid. LC-MS-conditions 05c: $t_R$=0.59 min; $[M+H]^+$=436.27.

Example 401

2-Cyclopropyl-5-phenyl-oxazole-4-carboxylic acid [1-(5-acetyl-thiophen-2-ylmethyl)-1H-pyrazol-4-yl]-amide Following general procedure X followed by C, starting from 1-[5-(2-methyl-[1,3]dioxolan-2-yl)-thiophen-2-ylmethyl]-1H-pyrazol-4-ylamine and 2-cyclopropyl-5-phenyl-oxazole-4-carboxylic acid. LC-MS-conditions 05c: $t_R$=0.77 min; $[M+H]^+$=433.25.

Example 402

2-Cyclopropyl-5-phenyl-oxazole-4-carboxylic acid [1-(5-acetyl-thiophen-2-ylmethyl)-1H-pyrazol-3-yl]-amide Following general procedure X followed by C, starting from 1-[5-(2-methyl-[1,3]dioxolan-2-yl)-thiophen-2-ylmethyl]-1H-pyrazol-3-ylamine and 2-cyclopropyl-5-phenyl-oxazole-4-carboxylic acid. LC-MS-conditions 05c: $t_R$=0.80 min; $[M+H]^+$=433.17.

Example 403

5-(3-Methoxy-4-methyl-phenyl)-oxazole-4-carboxylic acid [1-(5-acetyl-thiophen-2-ylmethyl)-1H-pyrazol-4-yl]-amide Following general procedure X followed by C, starting from 1-[5-(2-methyl-[1,3]dioxolan-2-yl)-thiophen-2-ylmethyl]-1H-pyrazol-4-ylamine and 5-(3-methoxy-4-methyl-phenyl)-oxazole-4-carboxylic acid. LC-MS-conditions 05c: $t_R$=0.75 min; $[M+H]^+$=437.25.

Example 404

5-(3-Hydroxymethyl-phenyl)-oxazole-4-carboxylic acid [1-(5-acetyl-furan-2-ylmethyl)-1H-pyrazol-3-yl]-amide Following general procedure B followed by C, starting from 1-[5-(2-methyl-[1,3]dioxolan-2-yl)-furan-2-ylmethyl]-1H-pyrazol-3-ylamine and 5-[3-(tert-butyl-dimethyl-silanyloxymethyl)-phenyl]-oxazole-4-carboxylic acid. LC-MS-conditions 02: $t_R$=0.86 min; $[M+H]^+$=407.37.

Example 405

5-[3-(2-Dimethylamino-ethyl)-phenyl]-oxazole-4-carboxylic acid [1-(5-acetyl-furan-2-ylmethyl)-1H-pyrazol-3-yl]-amide In a flame dried round-bottomed flask equipped with a magnetic stir bar and under inert atmosphere ($N_2$), a solution of 5-[3-(2-hydroxy-ethyl)-phenyl]-oxazole-4-carboxylic acid [1-(5-acetyl-furan-2-ylmethyl)-1H-pyrazol-3-yl]-amide (51 mg, 0.12 mmol) in $CH_2Cl_2$ (1.0 mL) was treated with DIPEA (0.03 mL, 0.18 mmol) followed by methanesulfonyl chloride (0.01 mL, 0.15 mmol). The reaction mixture was stirred at rt for 2.5 h before dimethylamine (0.9 mL of a 2N solution in THF, 1.8 mmol) was and the reaction mixture was further stirred at rt for 2 h. EA (10 mL) and sat. aq. $NaHCO_3$ (10 mL) were added and the aqueous layer was extracted with EA (10 mL). The combined organic extracts were dried over MgSO$_4$, filtered, and the solvents were removed under reduced pressure. Purification of the residue by HPLC gave the title compound as a pale yellow oil. LC-MS-conditions 02: $t_R$=0.76 min; [M+H]$^+$=448.25.

Example 406

5-(3-Dimethylaminomethyl-phenyl)-oxazole-4-carboxylic acid [1-(5-acetyl-furan-2-ylmethyl)-1H-pyrazol-3-yl]-amide In a flame dried round-bottomed flask equipped with a magnetic stir bar and under inert atmosphere (N$_2$), a solution of 5-(3-hydroxymethyl-phenyl)-oxazole-4-carboxylic acid [1-(5-acetyl-furan-2-ylmethyl)-1H-pyrazol-3-yl]-amide (75 mg, 0.19 mmol) in CH$_2$Cl$_2$ (2.0 mL) was treated with DIPEA (0.05 mL, 0.28 mmol) followed by methanesulfonyl chloride (0.02 mL, 0.22 mmol). The reaction mixture was stirred for at rt 2.5 h before dimethylamine (0.9 mL of a 2N solution in THF, 1.8 mmol) was added and the reaction mixture was further stirred at rt for 8 h. EA (10 mL) and sat. aq. NaHCO$_3$ (10 mL) were added and the aqueous layer was extracted with EA (10 mL). The combined organic extracts were dried over MgSO$_4$, filtered, and the solvents were removed under reduced pressure. Purification of the residue by FC (93:7 CH$_2$Cl$_2$-MeOH) gave the title compound as a pale yellow oil. TLC: rf (93:7 CH$_2$Cl$_2$-MeOH)=0.27. LC-MS-conditions 02: $t_R$=0.74 min; [M+H]$^+$=434.14.

Example 407

[1-(2-Acetyl-pyridin-4-ylmethyl)-1H-pyrazol-4-yl]-carbamic acid 2-chloro-benzyl ester Following general procedure A followed by C, starting from 1-[4-(4-amino-pyrazol-1-ylmethyl)-pyridin-2-yl]-ethanone and (2-chloro-phenyl)-methanol. LC-MS-conditions 01: $t_R$=0.92 min; [M+H]$^+$=384.98.

Example 408

5-Phenyl-oxazole-4-carboxylic acid [1-(5-acetyl-thiophen-3-ylmethyl)-1H-pyrazol-4-yl]-amide Following general procedure B followed by C, starting from 1-[5-(2-methyl-[1,3]dioxolan-2-yl)-thiophen-3-ylmethyl]-1H-pyrazol-4-ylamine and 5-phenyl-oxazole-4-carboxylic acid. LC-MS-conditions 02: $t_R$=0.98 min; [M+H]$^+$=393.24.

Example 409

[1-(2-Acetyl-thiazol-4-ylmethyl)-1H-pyrazol-4-yl]-carbamic acid 2-chloro-benzyl ester In a flame dried round-bottomed flask equipped with a magnetic stir bar and under inert atmosphere (N$_2$), a solution of {1-[2-(1-hydroxy-ethyl)-thiazol-4-ylmethyl]-1H-pyrazol-4-yl}-carbamic acid 2-chloro-benzyl ester in AcCN (1.0 mL) was treated at rt with MnO$_2$ (49.2 mg, 0.51 mmol) and the reaction mixture was stirred at rt overnight before being filtered through Celite to give the title compound as a brown foam. LC-MS-conditions 02: $t_R$=0.98 min; [M+H]$^+$=390.98.

Example 410

(E)-N-[1-(6-Acetyl-pyridin-2-ylmethyl)-1H-pyrazol-3-yl]-3-(4-trifluoromethyl-phenyl)-acrylamide Following general procedure B followed by C, starting from 1-[6-(2-methyl-[1,3]dioxolan-2-yl)-pyridin-2-ylmethyl]-1H-pyrazol-3-ylamine and (E)-3-(4-trifluoromethyl-phenyl)-acrylic acid. LC-MS-conditions 02: $t_R$=1.04 min; [M+H]$^+$=414.93.

Example 411

[1-(6-Acetyl-pyridin-2-ylmethyl)-1H-pyrazol-3-yl]-carbamic acid 2-chloro-benzyl ester Following general procedure A followed by C, starting from 1-[6-(2-methyl-[1,3]dioxolan-2-yl)-pyridin-2-ylmethyl]-1H-pyrazol-3-ylamine and (2-chloro-phenyl)-methanol. LC-MS-conditions 01: $t_R$=0.97 min; [M+H]$^+$=385.34.

Example 412

5-(2-Fluoro-pyridin-4-yl)-oxazole-4-carboxylic acid [1-(5-acetyl-furan-2-ylmethyl)-1H-pyrazol-4-yl]-amide Following general procedure B followed by C, starting from 1-[5-(2-methyl-[1,3]dioxolan-2-yl)-furan-2-ylmethyl]-1H-pyrazol-4-ylamine and 5-(2-fluoro-pyridin-4-yl)-oxazole-4-carboxylic acid. LC-MS-conditions 02: $t_R$=0.90 min; [M+H]$^+$=395.98.

Example 413

5-Phenyl-oxazole-4-carboxylic acid [1-(5-methanesulfonyl-furan-2-ylmethyl)-1H-pyrazol-4-yl]-amide Following general procedure B followed by C, starting from 1-(5-methanesulfonyl-furan-2-ylmethyl)-1H-pyrazol-4-ylamine and 5-phenyl-oxazole-4-carboxylic acid. LC-MS-conditions 02: $t_R$=0.94 min; [M+H]$^+$=413.29.

Example 414

5-Pyridin-4-yl-oxazole-4-carboxylic acid [1-(5-acetyl-furan-2-ylmethyl)-1H-pyrazol-4-yl]-amide Following general procedure Z3 followed by C, starting from 1-[5-(2-methyl-[1,3]dioxolan-2-yl)-furan-2-ylmethyl]-1H-pyrazol-4-ylamine and 5-pyridin-4-yl-oxazole-4-carboxylic acid lithium salt. LC-MS-conditions 02: $t_R$=0.70 min; [M+H]$^+$=378.15.

Example 415

5-(6-Methyl-pyridin-2-yl)-oxazole-4-carboxylic acid [1-(5-acetyl-furan-2-ylmethyl)-1H-pyrazol-4-yl]-amide Following general procedure Z3 followed by C, starting from 1-[5-(2-methyl-[1,3]dioxolan-2-yl)-furan-2-ylmethyl]-1H-pyrazol-4-ylamine and 5-(6-methyl-pyridin-2-yl)-oxazole-4-carboxylic acid lithium salt. LC-MS-conditions 02: $t_R$=0.75 min; [M+H]$^+$=392.31.

Example 416

2-Methoxymethyl-5-phenyl-oxazole-4-carboxylic acid [1-(5-acetyl-furan-2-ylmethyl)-1H-pyrazol-4-yl]-amide Following general procedure B followed by C, starting from 1-[5-(2-methyl-[1,3]dioxolan-2-yl)-furan-2-ylmethyl]-1H-pyrazol-4-ylamine and 2-methoxymethyl-5-phenyl-oxazole-4-carboxylic acid. LC-MS-conditions 02: $t_R$=0.96 min; [M+H]$^+$=421.6.

Example 417

2-Methoxymethyl-5-phenyl-oxazole-4-carboxylic acid [1-(5-acetyl-furan-2-ylmethyl)-1H-pyrazol-3-yl]-amide Following general procedure B followed by C, starting from 1-[5-(2-methyl-[1,3]dioxolan-2-yl)-furan-2-ylmethyl]-1H-pyrazol-3-ylamine and 2-methoxymethyl-5-phenyl-oxazole-4-carboxylic acid. LC-MS-conditions 02: $t_R$=0.99 min; [M+H]$^+$=421.61.

Example 418

{4-[1-(5-Acetyl-furan-2-ylmethyl)-1H-pyrazol-4-ylcarbamoyl]-5-phenyl-oxazol-2-yl methyl}-carbamic acid tert-butyl ester Following general procedure B, starting from 1-[5-(2-methyl-[1,3]dioxolan-2-yl)-furan-2-ylmethyl]-1H-pyrazol-4-ylamine and 2-(tert-butoxycarbonylamino-methyl)-5-phenyl-oxazole-4-carboxylic acid. LC-MS-conditions 02: $t_R$=1.01 min; [M+H]$^+$=506.44.

Example 419

5-(6-Trifluoromethyl-pyridin-2-yl)-oxazole-4-carboxylic acid [1-(5-acetyl-furan-2-ylmethyl)-1H-pyrazol-4-yl]-amide Following general procedure Z3 followed by C, starting from 1-[5-(2-methyl-[1,3]dioxolan-2-yl)-furan-2-ylmethyl]-1H-pyrazol-4-ylamine and 5-(6-trifluoromethyl-pyridin-2-yl)-oxazole-4-carboxylic acid lithium salt. LC-MS-conditions 02: $t_R$=0.92 min; [M+H]$^+$=446.24.

Example 420

5-Isoxazol-5-yl-oxazole-4-carboxylic acid [1-(5-acetyl-furan-2-ylmethyl)-1H-pyrazol-4-yl]-amide Following general procedure Z3 followed by C, starting from 1-[5-(2-methyl-[1,3]dioxolan-2-yl)-furan-2-ylmethyl]-1H-pyrazol-4-ylamine and 5-isoxazol-5-yl-oxazole-4-carboxylic acid lithium salt. LC-MS-conditions 01: $t_R$=0.81 min; [M+H]$^+$=367.95.

Example 421

5-Phenyl-oxazole-4-carboxylic acid [1-(2-acetyl-thiazol-4-ylmethyl)-1H-pyrazol-3-yl]-amide Following general procedure B followed by C, starting from 1-[2-(2-methyl-[1,3]dioxolan-2-yl)-thiazol-4-ylmethyl]-1H-pyrazol-3-ylamine and 5-phenyl-oxazole-4-carboxylic acid. LC-MS-conditions 02: $t_R$=1.0 min; [M+H]$^+$=394.25.

Example 422

2-(2-Methoxy-ethyl)-5-phenyl-oxazole-4-carboxylic acid [1-(5-acetyl-furan-2-ylmethyl)-1H-pyrazol-4-yl]-amide Following general procedure B followed by C, starting from 1-[5-(2-methyl-[1,3]dioxolan-2-yl)-furan-2-ylmethyl]-1H-pyrazol-4-ylamine and 2-(2-methoxy-ethyl)-5-phenyl-oxazole-4-carboxylic acid. LC-MS-conditions 02: $t_R$=0.97 min; [M+H]$^+$=435.13.

Example 423

2-(2-Methoxy-ethyl)-5-phenyl-oxazole-4-carboxylic acid [1-(5-acetyl-furan-2-ylmethyl)-1H-pyrazol-3-yl]-amide Following general procedure B followed by C, starting from 1-[5-(2-methyl-[1,3]dioxolan-2-yl)-furan-2-ylmethyl]-1H-pyrazol-3-ylamine and 2-(2-methoxy-ethyl)-5-phenyl-oxazole-4-carboxylic acid. LC-MS-conditions 02: $t_R$=1.0 min; [M+H]$^+$=435.31.

Example 424

2-Isopropyl-5-phenyl-oxazole-4-carboxylic acid [1-(5-acetyl-furan-2-ylmethyl)-1H-pyrazol-4-yl]-amide Following general procedure B followed by C, starting from 1-[5-(2-methyl-[1,3]dioxolan-2-yl)-furan-2-ylmethyl]-1H-pyrazol-4-ylamine and 2-isopropyl-5-phenyl-oxazole-4-carboxylic acid. LC-MS-conditions 02: $t_R$=1.05 min; [M+H]$^+$=418.95.

Example 425

2-Butyl-5-phenyl-oxazole-4-carboxylic acid [1-(5-acetyl-furan-2-ylmethyl)-1H-pyrazol-4-yl]-amide Following general procedure B followed by C, starting from 1-[5-(2-methyl-[1,3]dioxolan-2-yl)-furan-2-ylmethyl]-1H-pyrazol-4-ylamine and 2-butyl-5-phenyl-oxazole-4-carboxylic acid. LC-MS-conditions 02: $t_R$=1.08 min; [M+H]$^+$=433.69.

Example 426

2-Isopropyl-5-phenyl-oxazole-4-carboxylic acid [1-(5-acetyl-furan-2-ylmethyl)-1H-pyrazol-3-yl]-amide Following general procedure B followed by C, starting from 1-[5-(2-methyl-[1,3]dioxolan-2-yl)-furan-2-ylmethyl]-1H-pyrazol-3-ylamine and 2-isopropyl-5-phenyl-oxazole-4-carboxylic acid. LC-MS-conditions 02: $t_R$=1.08 min; [M+H]$^+$=419.3.

Example 427

2-Butyl-5-phenyl-oxazole-4-carboxylic acid [1-(5-acetyl-furan-2-ylmethyl)-1H-pyrazol-3-yl]-amide Following general procedure B followed by C, starting from 1-[5-(2-methyl-[1,3]dioxolan-2-yl)-furan-2-ylmethyl]-

1H-pyrazol-3-ylamine and 2-butyl-5-phenyl-oxazole-4-carboxylic acid. LC-MS-conditions 02: $t_R$=1.11 min; [M+H]$^+$=433.37.

Example 428

5-(3-Isopropoxymethyl-phenyl)-oxazole-4-carboxylic acid [1-(5-acetyl-furan-2-ylmethyl)-1H-pyrazol-3-yl]-amide Following general procedure B followed by C, starting from 1-[5-(2-methyl-[1,3]dioxolan-2-yl)-furan-2-ylmethyl]-1H-pyrazol-3-ylamine and 5-(3-isopropoxymethyl-phenyl)-oxazole-4-carboxylic acid. LC-MS-conditions 02: $t_R$=1.03 min; [M+H]$^+$=449.63.

Example 429

5-[3-(2-Isopropoxy-ethyl)-phenyl]-oxazole-4-carboxylic acid [1-(5-acetyl-furan-2-ylmethyl)-1H-pyrazol-3-yl]-amide Following general procedure B followed by C, starting from 1-[5-(2-methyl-[1,3]dioxolan-2-yl)-furan-2-ylmethyl]-1H-pyrazol-3-ylamine and 5-[3-(2-isopropoxy-ethyl)-phenyl]-oxazole-4-carboxylic acid. LC-MS-conditions 02: $t_R$=1.04 min; [M+H]$^+$=463.35.

Example 430

[1-(4-Acetyl-thiazol-2-ylmethyl)-1H-pyrazol-3-yl]-carbamic acid 2-chloro-benzyl ester Following general procedure I followed by C, starting from 1-[4-(2-methyl-[1,3]dioxolan-2-yl)-thiazol-2-ylmethyl]-1H-pyrazol-3-ylamine and (2-chloro-phenyl)-methanol. LC-MS-conditions 01: $t_R$=0.92 min; [M+H]$^+$=390.9.

Example 431

5-Phenyl-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 5-phenyl-oxazole-4-carboxylic acid. LC-MS-conditions 01: $t_R$=0.92 min; [M+H]$^+$=393.99.

Example 432

2-Benzyl-5-phenyl-oxazole-4-carboxylic acid [1-(5-acetyl-furan-2-ylmethyl)-1H-pyrazol-4-yl]-amide Following general procedure B followed by C, starting from 1-[5-(2-methyl-[1,3]dioxolan-2-yl)-furan-2-ylmethyl]-1H-pyrazol-4-ylamine and 2-benzyl-5-phenyl-oxazole-4-carboxylic acid. LC-MS-conditions 02: $t_R$=1.06 min; [M+H]$^+$=467.69.

Example 433

2-Benzyl-5-phenyl-oxazole-4-carboxylic acid [1-(5-acetyl-furan-2-ylmethyl)-1H-pyrazol-3-yl]-amide Following general procedure B followed by C, starting from 1-[5-(2-methyl-[1,3]dioxolan-2-yl)-furan-2-ylmethyl]-1H-pyrazol-3-ylamine and 2-benzyl-5-phenyl-oxazole-4-carboxylic acid. LC-MS-conditions 02: $t_R$=1.09 min; [M+H]$^+$=467.25.

Example 434

3-{4-[1-(5-Acetyl-furan-2-ylmethyl)-1H-pyrazol-3-ylcarbamoyl]-5-phenyl-oxazol-2-yl}-propionic acid tert-butyl ester Following general procedure B followed by C, starting from 1-[5-(2-methyl-[1,3]dioxolan-2-yl)-furan-2-ylmethyl]-1H-pyrazol-3-ylamine and 2-(2-tert-butoxycarbonyl-ethyl)-5-phenyl-oxazole-4-carboxylic acid. LC-MS-conditions 02: $t_R$=1.09 min; [M+H]$^+$=505.42.

Example 435

5-Phenyl-oxazole-4-carboxylic acid [1-(5-acetyl-thiazol-2-ylmethyl)-1H-pyrazol-4-yl]-amide Following general procedure B followed by C, starting from 1-[5-(2-methyl-[1,3]dioxolan-2-yl)-thiazol-2-ylmethyl]-1H-pyrazol-4-ylamine and 5-phenyl-oxazole-4-carboxylic acid. LC-MS-conditions 01: $t_R$=0.9 min; [M+H]$^+$=393.96.

Example 436

[1-(5-Acetyl-thiazol-2-ylmethyl)-1H-pyrazol-4-yl]-carbamic acid 2-chloro-benzyl ester Following general procedure I followed by C, starting from 1-[5-(2-methyl-[1,3]dioxolan-2-yl)-thiazol-2-ylmethyl]-1H-pyrazol-4-ylamine and (2-chloro-phenyl)-methanol. LC-MS-conditions 01: $t_R$=0.91 min; [M+H]$^+$=390.93.

Example 437

5-Phenyl-oxazole-4-carboxylic acid [1-(2-acetyl-thiazol-5-ylmethyl)-1H-pyrazol-4-yl]-amide Following general procedure B followed by C, starting from 1-[2-(2-methyl-[1,3]dioxolan-2-yl)-thiazol-5-ylmethyl]-1H-pyrazol-4-ylamine and 5-phenyl-oxazole-4-carboxylic acid. LC-MS-conditions 02: $t_R$=0.98 min; [M+H]$^+$=393.91.

Example 438

(E)-N-[1-(2-Acetyl-thiazol-5-ylmethyl)-1H-pyrazol-4-yl]-3-(4-trifluoromethyl-phenyl)-acrylamide Following general procedure B followed by C, starting from 1-[2-(2-methyl-[1,3]dioxolan-2-yl)-thiazol-5-ylmethyl]-1H-pyrazol-4-ylamine and (E)-3-(4-trifluoromethyl-phenyl)-acrylic acid. LC-MS-conditions 02: $t_R$=1.01 min; [M+H]$^+$=420.83.

Example 439

[1-(2-Acetyl-thiazol-5-ylmethyl)-1H-pyrazol-4-yl]-carbamic acid 2-chloro-benzyl ester Following general procedure I followed by C, starting from 1-[2-(2-methyl-[1,3]dioxolan-2-yl)-thiazol-5-ylmethyl]-1H- pyrazol-4-ylamine and (2-chloro-phenyl)-methanol. LC-MS-conditions 02: $t_R$=0.98 min; [M+H]$^+$=390.93.

Example 440

5-Phenyl-oxazole-4-carboxylic acid [1-(2-acetyl-oxazol-5-ylmethyl)-1H-pyrazol-3-yl]-amide In a flame dried round-bottomed flask equipped with a magnetic stir bar and under inert atmosphere (N$_2$), a solution of 5-phenyl-oxazole-4-carboxylic acid {1-[2-(1-hydroxy-ethyl)-oxazol-5-ylmethyl]-1H-pyrazol-3-yl}-amide (140 mg, 0.37 mmol) in AcCN (4.0 mL) was treated at rt with MnO$_2$ (267 mg, 2.77 mmol) and the reaction mixture was stirred at rt overnight before being filtered through Celite. Purification of the residue by FC (3:7 hept-EA) gave the title compound as a white foam. TLC: rf (3:7 hept-EA)=0.28. LC-MS-conditions 02: $t_R$=0.95 min; [M+H]$^+$=378.21.

Example 441

5-Phenyl-oxazole-4-carboxylic acid [1-(4-acetyl-thiophen-2-ylmethyl)-1H-pyrazol-4-yl]-amide Following general procedure B followed by C, starting from 1-[4-(2-methyl-[1,3]dioxolan-2-yl)-thiophen-2-ylmethyl]-1H-pyrazol-4-ylamine and 5-phenyl-oxazole-4-carboxylic acid. LC-MS-conditions 01: $t_R$=0.95 min; [M+H]$^+$=392.94.

Example 442

[1-(4-Acetyl-thiophen-2-ylmethyl)-1H-pyrazol-4-yl]-carbamic acid 2-chloro-benzyl ester Following general procedure I followed by C, starting from 1-[4-(2-methyl-[1,3]dioxolan-2-yl)-thiophen-2-ylmethyl]-1H-pyrazol-4-ylamine and (2-chloro-phenyl)-methanol. LC-MS-conditions 01: $t_R$=0.95 min; [M+H]$^+$=389.93.

Example 443

2-Methyl-5-m-tolyl-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 2-methyl-5-m-tolyl-oxazole-4-carboxylic acid. LC-MS-conditions 05: $t_R$=0.92 min; [M+H]$^+$=422.07.

Example 444

5-(3-Chloro-phenyl)-2-methyl-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 5-(3-chloro-phenyl)-2-methyl-oxazole-4-carboxylic acid. LC-MS-conditions 05: $t_R$=0.95 min; [M+H]$^+$=442.07.

Example 445

5-m-Tolyl-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 5-m-tolyl-oxazole-4-carboxylic acid. LC-MS-conditions 05: $t_R$=0.87 min; [M+H]$^+$=408.05.

Example 446

2-Methyl-5-phenyl-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 2-methyl-5-phenyl-oxazole-4-carboxylic acid. LC-MS-conditions 05: $t_R$=0.87 min; [M+H]$^+$=408.12.

Example 447

2-Methyl-5-(3-trifluoromethyl-phenyl)-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 2-methyl-5-(3-trifluoromethyl-phenyl)-oxazole-4-carboxylic acid. LC-MS-conditions 05: $t_R$=0.96 min; [M+H]$^+$=476.03.

Example 448

5-(3-Fluoro-phenyl)-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 5-(3-fluoro-phenyl)-oxazole-4-carboxylic acid. LC-MS-conditions 05: $t_R$=0.84 min; [M+H]$^+$=412.07.

Example 449

5-(3-Dimethylamino-phenyl)-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 5-(3-dimethylamino-phenyl)-oxazole-4-carboxylic acid. LC-MS-conditions 05: $t_R$=0.68 min; [M+H]$^+$=437.04.

Example 450

5-(3-Chloro-phenyl)-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 5-(3-chloro-phenyl)-oxazole-4-carboxylic acid. LC-MS-conditions 05: $t_R$=0.89 min; [M+H]$^+$=428.02.

Example 451

2-Methyl-5-(3-trifluoromethoxy-phenyl)-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 2-methyl-5-(3-trifluoromethoxy-phenyl)-oxazole-4-carboxylic acid. LC-MS-conditions 05: $t_R$=0.98 min; [M+H]$^+$=492.06.

Example 452

5-(3-Trifluoromethoxy-phenyl)-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 5-(3-trifluoromethoxy-phenyl)-oxazole-4-carboxylic acid. LC-MS-conditions 05: $t_R$=0.94 min; [M+H]$^+$=478.03.

Example 453

5-(3-Methoxy-phenyl)-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 5-(3-methoxy-phenyl)-oxazole-4-carboxylic acid. LC-MS-conditions 05: $t_R$=0.83 min; [M+H]$^+$=424.07.

Example 454

(E)-N-[1-(4-Acetyl-thiazol-2-ylmethyl)-1H-pyrazol-3-yl]-3-(4-trifluoromethyl-phenyl)-acrylamide Following general procedure B followed by C, starting from 1-[4-(2-methyl-[1,3]dioxolan-2-yl)-thiazol-2-ylmethyl]-1H-pyrazol-3-ylamine and (E)-3-(4-trifluoromethyl-phenyl)-acrylic acid. LC-MS-conditions 05: $t_R$=0.86 min; [M+H]$^+$=420.88.

Example 455

(E)-N-[1-(4-Acetyl-thiazol-2-ylmethyl)-1H-pyrazol-3-yl]-3-(2-trifluoromethyl-phenyl)-acrylamide Following general procedure B followed by C, starting from 1-[4-(2-methyl-[1,3]dioxolan-2-yl)-thiazol-2-ylmethyl]-1H-pyrazol-3-ylamine and (E)-3-(2-trifluoromethyl-phenyl)-acrylic acid. LC-MS-conditions 05: $t_R$=0.85 min; [M+H]$^+$=420.84.

Example 456

(E)-N-[1-(4-Acetyl-thiazol-2-ylmethyl)-1H-pyrazol-3-yl]-3-(3-trifluoromethoxy-phenyl)-acrylamide Following general procedure B followed by C, starting from 1-[4-(2-methyl-[1,3]dioxolan-2-yl)-thiazol-2-ylmethyl]-1H-pyrazol-3-ylamine and (E)-3-(3-trifluoromethoxy-phenyl)-acrylic acid. LC-MS-conditions 05: $t_R$=0.87 min; [M+H]$^+$=436.88.

Example 457

(E)-N-[1-(4-Acetyl-thiazol-2-ylmethyl)-1H-pyrazol-3-yl]-3-(2-chloro-4-fluoro-phenyl)-acrylamide Following general procedure B followed by C, starting from 1-[4-(2-methyl-[1,3]dioxolan-2-yl)-thiazol-2-ylmethyl]-1H-pyrazol-3-ylamine and (E)-3-(2-chloro-4-fluoro-phenyl)-acrylic acid. LC-MS-conditions 05: $t_R$=0.83 min; [M+H]$^+$=404.9.

Example 458

5-(3-Methoxy-phenyl)-2-methyl-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 5-(3-methoxy-phenyl)-2-methyl-oxazole-4-carboxylic acid. LC-MS-conditions 05: $t_R$=0.87 min; [M+H]$^+$=438.02.

Example 459

5-(3-Fluoro-phenyl)-2-methyl-oxazole-4-carboxylic acid [1-(4-acetyl-thiazol-2-ylmethyl)-1H-pyrazol-3-yl]-amide Following general procedure B followed by C, starting from 1-[4-(2-methyl-[1,3]dioxolan-2-yl)-thiazol-2-ylmethyl]-1H-pyrazol-3-ylamine and 5-(3-fluoro-phenyl)-2-methyl-oxazole-4-carboxylic acid. LC-MS-conditions 05: $t_R$=0.89 min; [M+H]$^+$=426.04.

Example 460

5-Phenyl-oxazole-4-carboxylic acid [1-(4-acetyl-oxazol-2-ylmethyl)-1H-pyrazol-3-yl]-amide Following general procedure B, starting from 1-[2-(3-amino-pyrazol-1-ylmethyl)-oxazol-4-yl]-ethanone and 5-phenyl-oxazole-4-carboxylic acid. LC-MS-conditions 01: $t_R$=0.88 min; [M+H]$^+$=377.95.

Example 461

5-Phenyl-oxazole-4-carboxylic acid {1-[4-(1,1-difluoro-ethyl)-thiazol-2-ylmethyl]-1H-pyrazol-3-yl}-amide Following general procedure B, 1-[4-(1,1-difluoro-ethyl)-thiazol-2-ylmethyl]-1H-pyrazol-3-ylamine and 5-phenyl-oxazole-4-carboxylic acid. LC-MS-conditions 02: $t_R$=1.04 min; [M+H]$^+$=415.86.

Example 462

[1-(5-Oxo-hexyl)-1H-pyrazol-4-yl]-carbamic acid benzothiazol-2-ylmethyl ester

Following general procedure A or I followed by either C or D, starting from 1-[4-(2-methyl-[1,3]dioxolan-2-yl)-butyl]-

1H-pyrazol-4-ylamine and benzothiazol-2-yl-methanol. LC-MS-conditions 01: $t_R$=0.87 min; [M+H]$^+$=373.07.

Example 463

5-(6-Trifluoromethyl-pyridin-2-yl)-oxazole-4-carboxylic acid [1-(5-acetyl-furan-2-ylmethyl)-1H-pyrazol-3-yl]-amide Following general procedure Z3 followed by C, starting from 1-[5-(2-methyl-[1,3]dioxolan-2-yl)-furan-2-ylmethyl]-1H-pyrazol-3-ylamine and 5-(6-trifluoromethyl-pyridin-2-yl)-oxazole-4-carboxylic acid lithium salt. LC-MS-conditions 01: $t_R$=0.90 min; [M+H]$^+$=445.99.

Example 464

(E)-N-[1-(5-Acetyl-furan-2-ylmethyl)-1H-pyrazol-4-yl]-3-(1H-indol-3-yl)-acrylamide Following general procedure B followed by C, starting from 1-[5-(2-methyl-[1,3]dioxolan-2-yl)-furan-2-ylmethyl]-1H-pyrazol-4-ylamine and (E)-3-(1H-indol-3-yl)-acrylic acid. LC-MS-conditions 05b: $t_R$=0.84 min; [M+H]$^+$=375.31.

Example 465

5-Phenyl-oxazole-4-carboxylic acid [1-(5-acetyl-oxazol-2-ylmethyl)-1H-pyrazol-3-yl]-amide Following general procedure B followed by C, starting from 1-[5-(2-methyl-[1,3]dioxolan-2-yl)-oxazol-2-ylmethyl]-1H-pyrazol-3-ylamine and 5-phenyl-oxazole-4-carboxylic acid. LC-MS-conditions 02: $t_R$=0.92 min; [M+H]$^+$=378.55.

Example 466

[1-(2-Acetyl-oxazol-4-ylmethyl)-1H-pyrazol-4-yl]-carbamic acid 2-chloro-benzyl ester In a flame dried round-bottomed flask equipped with a magnetic stir bar and under inert atmosphere ($N_2$), a solution of {1-[2-(1-hydroxy-ethyl)-oxazol-4-ylmethyl]-1H-pyrazol-4-yl}-carbamic acid 2-chloro-benzyl ester (211 mg, 0.56 mmol) in AcCN (5.0 mL) was treated at rt with $MnO_2$ (270 mg, 2.80 mmol) and the reaction mixture was stirred at 55° C. for 3 h before being filtered through Celite. Purification of the residue by FC (2:1 to 1:2 hept-EA) gave the title compound as a pale yellow oil. TLC: rf (EA)=0.60. LC-MS-conditions 02: $t_R$=0.94 min; [M+H]$^+$=375.16.

II. Biological Assays

In Vitro Assay

The ALX receptor agonistic activity of the compounds of formula (I) is determined in accordance with the following experimental method.

Experimental Method:

Intracellular Calcium Measurements:

Cells expressing recombinant human ALX receptor and the G-protein Gα16 (HEK293-hALXR-Gα16) were grown to 80% confluency in Growing Medium (GM). Cells were detached from culture dishes with a cell dissociation buffer (Invitrogen, 13151-014), and collected by centrifugation at 1'000 rpm at RT for 5 min in Assay Buffer (AB) (equal parts of Hank's BSS (Gibco, 14065-049) and DMEM without Phemol Red (Gibco, 11880-028)). After 60 min incubation at 37° C. under 5% $CO_2$ in AB supplemented with 1 μM Fluo-4 (AM) (TEFLABS.COM, 0152), 0.04% (v/v) Pluronic F-127 (Molecular Probes, P6866), and 20 mM HEPES (Gibco, 15630-056), the cells were washed and resuspended in AB. They were then seeded onto 384-well FLIPR assay plates (Greiner, 781091) at 50'000 cells in 70 μl per well and sedimented by centrifugation at 1'000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. A FLIPR384 instrument (Molecular Devices) was operated according to the manufacturer's standard instructions, adding 4 μl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (WKYMVm compound, 10 nM final concentration) after subtraction of the base line value (AB addition). The program XLlfit 3.0 (IDBS) was used to fit the data to a single site dose response curve of the equation $(A+((B-A)/(1+((C/x)^D))))$ and to calculate the $EC_{50}$ values.

Agonistic activities ($EC_{50}$ values) of all exemplified compounds are in the range of 1-2830 nM with an average of 274 nM with respect to ALX receptor. Agonistic activities of selected compounds are displayed in Table 1.

TABLE 1

| Compound | $EC_{50}$ [nM] |
| --- | --- |
| [1-(5-Cyclopropanecarbonyl-furan-2-ylmethyl)-1H-pyrazol-4-yl]-carbamic acid 2-chloro-benzyl ester (Example 3) | 205 |
| [1-(5-Acetyl-furan-2-ylmethyl)-1H-pyrazol-3-yl]-carbamic acid 2,4,5-trifluoro-benzyl ester (Example 24) | 33 |
| (E)—N-[1-(5-Acetyl-furan-2-ylmethyl)-1H-pyrazol-3-yl]-3-(2-fluoro-3-trifluoromethyl-phenyl)-acrylamide (Example 45) | 95 |
| 5-(4-Methoxy-phenyl)-oxazole-4-carboxylic acid [1-(5-acetyl-furan-2-ylmethyl)-1H-pyrazol-3-yl]-amide (Example 48) | 198 |
| [1-(5-Acetyl-furan-2-ylmethyl)-1H-pyrazol-4-yl]-carbamic acid 4-trifluoromethyl-benzyl ester (Example 63) | 53 |
| (E)—N-[1-(5-Acetyl-furan-2-ylmethyl)-1H-pyrazol-4-yl]-3-(2,3-dimethoxy-phenyl)-acrylamide (Example 93) | 210 |
| 5-(3-Chloro-phenyl)-thiazole-4-carboxylic acid [1-(5-acetyl-furan-2-ylmethyl)-1H-pyrazol-4-yl]-amide (Example 120) | 202 |
| [1-(5-Oxo-hexyl)-1H-pyrazol-4-yl]-carbamic acid (RS)-1-phenyl-ethyl ester (Example 125) | 69 |

TABLE 1-continued

| Compound | EC$_{50}$ [nM] |
|---|---|
| 5-Phenyl-oxazole-4-carboxylic acid [1-(5-oxo-hexyl)-1H-pyrazol-4-yl]-amide (Example 152) | 191 |
| (E)-3-(2-Chloro-phenyl)-N-[1-(5-oxo-hexyl)-1H-pyrazol-4-yl]-acrylamide (Example 157) | 330 |
| [1-(5-Oxo-hexyl)-1H-pyrazol-3-yl]-carbamic acid 3,4-difluoro-benzyl ester (Example 169) | 363 |
| 5-Phenyl-oxazole-4-carboxylic acid [1-(5-oxo-hexyl)-1H-pyrazol-3-yl]-amide (Example 179) | 955 |
| (E)—N-[1-(5-Oxo-hexyl)-1H-pyrazol-3-yl]-3-(2-trifluoromethyl-phenyl)-acrylamide (Example 181) | 67 |
| {1-[5-(1,1-Difluoro-ethyl)-furan-2-ylmethyl]-1H-pyrazol-3-yl}-carbamic acid 2-chloro-benzyl ester (Example 197) | 29 |
| 5-Phenyl-oxazole-4-carboxylic acid {1-[5-(1,1-difluoro-ethyl)-furan-2-ylmethyl]-1H-pyrazol-3-yl}-amide (Example 198) | 310 |
| {1-[5-(1,1-Difluoro-ethyl)-furan-2-ylmethyl]-1H-pyrazol-4-yl}-carbamic acid 2-chloro-benzyl ester (Example 199) | 33 |
| 5-Phenyl-oxazole-4-carboxylic acid {1-[5-(1,1-difluoro-ethyl)-furan-2-ylmethyl]-1H-pyrazol-4-yl}-amide (Example 200) | 46 |
| [1-(5,5-Difluoro-hexyl)-1H-pyrazol-3-yl]-carbamic acid 2-chloro-benzyl ester (Example 201) | 154 |
| 5-Phenyl-oxazole-4-carboxylic acid [1-(5,5-difluoro-hexyl)-1H-pyrazol-3-yl]-amide (Example 202) | 899 |
| [1-(5,5-Difluoro-hexyl)-1H-pyrazol-4-yl]-carbamic acid 2-chloro-benzyl ester (Example 203) | 28 |
| 5-Phenyl-oxazole-4-carboxylic acid [1-(5,5-difluoro-hexyl)-1H-pyrazol-4-yl]-amide (Example 204) | 195 |
| [1-(5-Fluoro-hexyl)-1H-pyrazol-4-yl]-carbamic acid 2-chloro-benzyl ester (Example 236) | 118 |
| {1-[5-(1,1-Difluoro-ethyl)-furan-2-ylmethyl]-1H-pyrazol-3-yl}-carbamic acid 3-trifluoromethyl-benzyl ester (example 280) | 27 |
| [1-(5,5-Difluoro-hexyl)-1H-pyrazol-4-yl]-carbamic acid 2,6-difluoro-3-methyl-benzyl ester (example 282) | 25 |
| {1-[5-(1,1-Difluoro-ethyl)-furan-2-ylmethyl]-1H-pyrazol-4-yl}-carbamic acid 2-ethyl-benzyl ester (example 314) | 27 |
| 5-p-Tolyl-oxazole-4-carboxylic acid [1-(5-acetyl-furan-2-ylmethyl)-1H-pyrazol-4-yl]-amide (example 331) | 85 |
| 5-Biphenyl-3-yl-2-methyl-oxazole-4-carboxylic acid [1-(5-acetyl-furan-2-ylmethyl)-1H-pyrazol-3-yl]-amide (example 354) | 60 |
| 5-Biphenyl-3-yl-oxazole-4-carboxylic acid [1-(5-acetyl-furan-2-ylmethyl)-1H-pyrazol-3-yl]-amide (example 356) | 29 |
| 5-Phenyl-oxazole-4-carboxylic acid [1-(3-acetyl-isoxazol-5-ylmethyl)-1H-pyrazol-4-yl]-amide (example 362) | 1472 |
| 5-Phenyl-oxazole-4-carboxylic acid [1-(6-acetyl-pyridin-2-ylmethyl)-1H-pyrazol-4-yl]-amide (example 364) | 809 |
| [1-(3-Acetyl-benzyl)-1H-pyrazol-4-yl]-carbamic acid 2-chloro-benzyl ester (example 366) | 56 |
| 5-Phenyl-oxazole-4-carboxylic acid [1-(5-acetyl-thiophen-2-ylmethyl)-1H-pyrazol-3-yl]-amide (example 376) | 74 |
| 5-[3-(2-Methoxy-ethyl)-phenyl]-oxazole-4-carboxylic acid [1-(5-acetyl-furan-2-ylmethyl)-1H-pyrazol-3-yl]-amide (example 379) | 18 |
| 3-{4-[1-(5-Acetyl-furan-2-ylmethyl)-1H-pyrazol-3-ylcarbamoyl]-oxazol-5-yl}-benzoic acid tert-butyl ester (example 381) | 35 |
| [1-(5-Acetyl-pyridin-3-ylmethyl)-1H-pyrazol-4-yl]-carbamic acid 2-chloro-benzyl ester (example 382) | 401 |
| (E)—N-[1-(4-Acetyl-thiazol-2-ylmethyl)-1H-pyrazol-4-yl]-3-(4-trifluoromethyl-phenyl)-acrylamide (example 389) | 79 |
| 2-Aminomethyl-5-phenyl-oxazole-4-carboxylic acid [1-(5-acetyl-furan-2-ylmethyl)-1H-pyrazol-3-yl]-amide (example 390) | 727 |
| 2-Methyl-5-(3-trifluoromethoxy-phenyl)-oxazole-4-carboxylic acid [1-(5-acetyl-thiophen-2-ylmethyl)-1H-pyrazol-3-yl]-amide (example 392) | 237 |
| 2-Methyl-5-m-tolyl-thiazole-4-carboxylic acid [1-(5-acetyl-thiophen-2-ylmethyl)-1H-pyrazol-4-yl]-amide (example 395) | 170 |
| 5-(3-Cyano-phenyl)-oxazole-4-carboxylic acid [1-(5-acetyl-thiophen-2-ylmethyl)-1H-pyrazol-4-yl]-amide (example 397) | 23 |
| 2-Cyclopropyl-5-phenyl-oxazole-4-carboxylic acid [1-(5-acetyl-thiophen-2-ylmethyl)-1H-pyrazol-4-yl]-amide (example 401) | 49 |
| [1-(2-Acetyl-pyridin-4-ylmethyl)-1H-pyrazol-4-yl]-carbamic acid 2-chloro-benzyl ester (example 407) | 58 |
| 5-Phenyl-oxazole-4-carboxylic acid [1-(5-acetyl-thiophen-3-ylmethyl)-1H-pyrazol-4-yl]-amide (example 408) | 83 |
| [1-(2-Acetyl-thiazol-4-ylmethyl)-1H-pyrazol-4-yl]-carbamic acid 2-chloro-benzyl ester (example 409) | 805 |
| 5-(2-Fluoro-pyridin-4-yl)-oxazole-4-carboxylic acid [1-(5-acetyl-furan-2-ylmethyl)-1H-pyrazol-4-yl]-amide (example 412) | 179 |
| 5-Phenyl-oxazole-4-carboxylic acid [1-(5-methanesulfonyl-furan-2-ylmethyl)-1H-pyrazol-4-yl]-amide (example 413) | 486 |

TABLE 1-continued

| Compound | EC$_{50}$ [nM] |
|---|---|
| 2-Methoxymethyl-5-phenyl-oxazole-4-carboxylic acid [1-(5-acetyl-furan-2-ylmethyl)-1H-pyrazol-4-yl]-amide (example 416) | 61 |
| 5-(6-Trifluoromethyl-pyridin-2-yl)-oxazole-4-carboxylic acid [1-(5-acetyl-furan-2-ylmethyl)-1H-pyrazol-4-yl]-amide (example 419) | 66 |
| 5-Isoxazol-5-yl-oxazole-4-carboxylic acid [1-(5-acetyl-furan-2-ylmethyl)-1H-pyrazol-4-yl]-amide (example 420) | 388 |
| 2-Isopropyl-5-phenyl-oxazole-4-carboxylic acid [1-(5-acetyl-furan-2-ylmethyl)-1H-pyrazol-4-yl]-amide (example 424) | 114 |
| 2-Benzyl-5-phenyl-oxazole-4-carboxylic acid [1-(5-acetyl-furan-2-ylmethyl)-1H-pyrazol-4-yl]-amide (example 432) | 200 |
| 5-Phenyl-oxazole-4-carboxylic acid [1-(5-acetyl-thiazol-2-ylmethyl)-1H-pyrazol-4-yl]-amide (example 435) | 445 |
| 5-Phenyl-oxazole-4-carboxylic acid [1-(2-acetyl-thiazol-5-ylmethyl)-1H-pyrazol-4-yl]-amide (example 437) | 99 |
| 5-Phenyl-oxazole-4-carboxylic acid [1-(2-acetyl-oxazol-5-ylmethyl)-1H-pyrazol-3-yl]-amide (example 440) | 143 |
| [1-(4-Acetyl-thiophen-2-ylmethyl)-1H-pyrazol-4-yl]-carbamic acid 2-chloro-benzyl ester (example 442) | 94 |
| 5-(3-Dimethylamino-phenyl)-oxazole-4-carboxylic acid [1-(4-acetyl-thiazol-2-ylmethyl)-1H-pyrazol-3-yl]-amide (example 449) | 182 |
| 5-Phenyl-oxazole-4-carboxylic acid [1-(4-acetyl-oxazol-2-ylmethyl)-1H-pyrazol-3-yl]-amide (example 460) | 10 |
| 5-Phenyl-oxazole-4-carboxylic acid {1-[4-(1,1-difluoro-ethyl)-thiazol-2-ylmethyl]-1H-pyrazol-3-yl}-amide (example 461) | 1090 |
| [1-(5-Oxo-hexyl)-1H-pyrazol-4-yl]-carbamic acid benzothiazol-2-ylmethyl ester (example 462) | 43 |
| 5-Phenyl-oxazole-4-carboxylic acid [1-(5-acetyl-oxazol-2-ylmethyl)-1H-pyrazol-3-yl]-amide (example 465) | 73 |
| [1-(2-Acetyl-oxazol-4-ylmethyl)-1H-pyrazol-4-yl]-carbamic acid 2-chloro-benzyl ester (example 466) | 34 |

The invention claimed is:

1. A compound of formula (I),

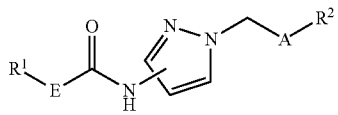
(I)

wherein

A represents a phenyl- or a monocyclic heterocyclyl-group, wherein the phenyl- or monocyclic heterocyclyl-group is substituted in a 1,3-arrangement; or A represents propan-1,3-diyl;

E represents *-(C$_1$-C$_4$)alkyl-O—, —CH=CH— or

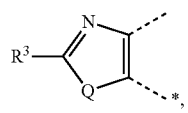

wherein the asterisks indicate the bond which is linked to R$^1$;

Q represents O, or S;

R$^3$ represents hydrogen, (C$_1$-C$_4$)alkyl, cyclopropyl, (C$_1$-C$_4$)alkoxy-(C$_1$-C$_2$)alkyl, —CH$_2$NH$_2$, —CH$_2$NHBoc, —CH$_2$CH$_2$C(O)OtBu or benzyl;

R$^1$ represents a heterocyclyl- or an aryl-group, which group is unsubstituted, mono-, di- or tri-substituted, with halogen, (C$_1$-C$_4$)alkyl, (C$_1$-C$_4$)alkoxy, (C$_1$-C$_4$)fluoroalkyl, (C$_1$-C$_4$)fluoroalkoxy, phenyl, cyano, di-[(C$_1$-C$_3$)alkyl]-amino, —C(O)—NH$_2$, —C(O)OtBu, (C$_1$-C$_4$)alkoxy-(C$_1$-C$_2$)alkyl, hydroxy-(C$_1$-C$_2$)alkyl or dimethylamino-(C$_1$-C$_2$)alkyl; and R$^2$ represents —CO—(C$_1$-C$_3$)alkyl, —CO-cyclopropyl, —CF$_2$—(C$_1$-C$_3$)alkyl, —CHF—(C$_1$-C$_3$)alkyl or —SO$_2$—(C$_1$-C$_3$)alkyl;

or a salt thereof.

2. The compound of claim 1, wherein A represents furan-2,5-diyl, oxazol-2,4-diyl, oxazol-2,5-diyl, thiophen-2,4-diyl, thiophen-2,5-diyl, thiazol-2,4-diyl or pyridin-2,4-diyl;

or a salt thereof.

3. The compound of claim 1, wherein A represents propan-1,3-diyl;

or a salt thereof.

4. The compound of claim 1, wherein E represents

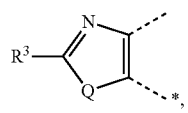

or a salt thereof.

5. The compound of claim 1, wherein E represents *-(C$_1$-C$_4$)alkyl-O— or —CH=CH—;

or a salt thereof.

6. The compound of claim 4, wherein Q represents O; or a salt thereof.

7. The compound of claim 1, wherein R$^3$ represents hydrogen or methyl;

or a salt thereof.

8. The compound of claim 1, wherein R$^1$ represents phenyl, which is unsubstituted, mono-, di- or tri-substituted with halogen, (C$_1$-C$_4$)alkyl, (C$_1$-C$_4$)alkoxy, (C$_1$-C$_4$)fluoroalkyl, (C$_1$-C$_4$)fluoroalkoxy, phenyl, cyano, dimethylamino, —C(O)OtBu or (C$_1$-C$_4$)alkoxy-(C$_1$-C$_2$)alkyl;

or a salt thereof.

9. The compound of claim 1, wherein R² represents —CO—(C₁-C₃)alkyl or —CF₂—(C₁-C₃)alkyl; or a salt thereof.

10. The compound of claim 1, wherein the compound is:
[1-(5-Acetyl-furan-2-ylmethyl)-1H-pyrazol-4-yl]-carbamic acid 2-chloro-benzyl ester;
[1-(5-Propionyl-furan-2-ylmethyl)-1H-pyrazol-4-yl]-carbamic acid 2-chloro-benzyl ester;
[1-(5-Cyclopropanecarbonyl-furan-2-ylmethyl)-1H-pyrazol-4-yl]-carbamic acid 2-chloro-benzyl ester;
[1-(5-Acetyl-furan-2-ylmethyl)-1H-pyrazol-3-yl]-carbamic acid benzyl ester;
[1-(5-Acetyl-furan-2-ylmethyl)-1H-pyrazol-3-yl]-carbamic acid 2-methyl-benzyl ester;
[1-(5-Acetyl-furan-2-ylmethyl)-1H-pyrazol-3-yl]-carbamic acid 4-trifluoromethyl-benzyl ester;
[1-(5-Acetyl-furan-2-ylmethyl)-1H-pyrazol-3-yl]-carbamic acid 3-trifluoromethyl-benzyl ester;
[1-(5-Acetyl-furan-2-ylmethyl)-1H-pyrazol-3-yl]-carbamic acid 3-chloro-benzyl ester;
[1-(5-Acetyl-furan-2-ylmethyl)-1H-pyrazol-3-yl]-carbamic acid 2-chloro-4-fluoro-benzyl ester;
[1-(5-Acetyl-furan-2-ylmethyl)-1H-pyrazol-3-yl]-carbamic acid 2-ethyl-benzyl ester;
[1-(5-Acetyl-furan-2-ylmethyl)-1H-pyrazol-3-yl]-carbamic acid 2,6-dichloro-benzyl ester;
[1-(5-Acetyl-furan-2-ylmethyl)-1H-pyrazol-3-yl]-carbamic acid 3,4-dimethyl-benzyl ester;
[1-(5-Acetyl-furan-2-ylmethyl)-1H-pyrazol-3-yl]-carbamic acid 3,4-difluoro-benzyl ester;
[1-(5-Acetyl-furan-2-ylmethyl)-1H-pyrazol-3-yl]-carbamic acid 2-chloro-6-fluoro-benzyl ester;
[1-(5-Acetyl-furan-2-ylmethyl)-1H-pyrazol-3-yl]-carbamic acid naphthalen-1-ylmethyl ester;
[1-(5-Acetyl-furan-2-ylmethyl)-1H-pyrazol-3-yl]-carbamic acid 2,5-dimethyl-benzyl ester;
[1-(5-Acetyl-furan-2-ylmethyl)-1H-pyrazol-3-yl]-carbamic acid 2,4,6-trifluoro-benzyl ester;
[1-(5-Acetyl-furan-2-ylmethyl)-1H-pyrazol-3-yl]-carbamic acid 2,3-difluoro-benzyl ester;
[1-(5-Acetyl-furan-2-ylmethyl)-1H-pyrazol-3-yl]-carbamic acid 3-chloro-2,6-difluoro-benzyl ester;
[1-(5-Acetyl-furan-2-ylmethyl)-1H-pyrazol-3-yl]-carbamic acid 6-chloro-2-fluoro-3-methyl-benzyl ester;
[1-(5-Acetyl-furan-2-ylmethyl)-1H-pyrazol-3-yl]-carbamic acid 3-chloro-2-fluoro-benzyl ester;
[1-(5-Acetyl-furan-2-ylmethyl)-1H-pyrazol-3-yl]-carbamic acid 2-chloro-6-fluoro-3-methyl-benzyl ester;
[1-(5-Acetyl-furan-2-ylmethyl)-1H-pyrazol-3-yl]-carbamic acid 2,4,5-trifluoro-benzyl ester;
[1-(5-Acetyl-furan-2-ylmethyl)-1H-pyrazol-3-yl]-carbamic acid 2,3,4-trifluoro-benzyl ester;
[1-(5-Acetyl-furan-2-ylmethyl)-1H-pyrazol-3-yl]-carbamic acid 4-bromo-benzyl ester;
[1-(5-Acetyl-furan-2-ylmethyl)-1H-pyrazol-3-yl]-carbamic acid 2-trifluoromethyl-benzyl ester;
[1-(5-Acetyl-furan-2-ylmethyl)-1H-pyrazol-3-yl]-carbamic acid 2-fluoro-benzyl ester;
[1-(5-Acetyl-furan-2-ylmethyl)-1H-pyrazol-3-yl]-carbamic acid 4-chloro-benzyl ester;
[1-(5-Acetyl-furan-2-ylmethyl)-1H-pyrazol-3-yl]-carbamic acid 3-methyl-benzyl ester;
[1-(5-Acetyl-furan-2-ylmethyl)-1H-pyrazol-3-yl]-carbamic acid 2,6-difluoro-3-methyl-benzyl ester;
5-Phenyl-oxazole-4-carboxylic acid [1-(5-acetyl-furan-2-ylmethyl)-1H-pyrazol-3-yl]-amide;
(E)-N-[1-(5-Acetyl-furan-2-ylmethyl)-1H-pyrazol-3-yl]-3-phenyl-acrylamide;
(E)-N-[1-(5-Acetyl-furan-2-ylmethyl)-1H-pyrazol-3-yl]-3-(2-trifluoromethyl-phenyl)-acrylamide;
(E)-N-[1-(5-Acetyl-furan-2-ylmethyl)-1H-pyrazol-3-yl]-3-(4-trifluoromethyl-phenyl)-acrylamide;
(E)-N-[1-(5-Acetyl-furan-2-ylmethyl)-1H-pyrazol-3-yl]-3-(2-chloro-6-fluoro-phenyl)-acrylamide;
(E)-N-[1-(5-Acetyl-furan-2-ylmethyl)-1H-pyrazol-3-yl]-3-(2,3-dimethoxy-phenyl)-acrylamide;
(E)-N-[1-(5-Acetyl-furan-2-ylmethyl)-1H-pyrazol-3-yl]-3-(2,3-dichloro-phenyl)-acrylamide;
(E)-N-[1-(5-Acetyl-furan-2-ylmethyl)-1H-pyrazol-3-yl]-3-(3-trifluoromethoxy-phenyl)-acrylamide;
(E)-N-[1-(5-Acetyl-furan-2-ylmethyl)-1H-pyrazol-3-yl]-3-(3-chloro-4-fluoro-phenyl)-acrylamide;
(E)-N-[1-(5-Acetyl-furan-2-ylmethyl)-1H-pyrazol-3-yl]-3-(2-chloro-3,6-difluoro-phenyl)-acrylamide;
(E)-N-[1-(5-Acetyl-furan-2-ylmethyl)-1H-pyrazol-3-yl]-3-(2,4-dichloro-phenyl)-acrylamide;
(E)-N-[1-(5-Acetyl-furan-2-ylmethyl)-1H-pyrazol-3-yl]-3-(2-chloro-4-fluoro-phenyl)-acrylamide;
(E)-N-[1-(5-Acetyl-furan-2-ylmethyl)-1H-pyrazol-3-yl]-3-(2-methoxy-phenyl)-acrylamide;
(E)-N-[1-(5-Acetyl-furan-2-ylmethyl)-1H-pyrazol-3-yl]-3-(2-fluoro-3-trifluoromethyl-phenyl)-acrylamide;
(E)-N-[1-(5-Acetyl-furan-2-ylmethyl)-1H-pyrazol-3-yl]-3-o-tolyl-acrylamide;
(E)-N-[1-(5-Acetyl-furan-2-ylmethyl)-1H-pyrazol-3-yl]-3-(3-chloro-phenyl)-acrylamide;
5-(4-Methoxy-phenyl)-oxazole-4-carboxylic acid [1-(5-acetyl-furan-2-ylmethyl)-1H-pyrazol-3-yl]-amide;
2-Methyl-5-m-tolyl-oxazole-4-carboxylic acid [1-(5-acetyl-furan-2-ylmethyl)-1H-pyrazol-3-yl]-amide;
(E)-N-[1-(5-Acetyl-furan-2-ylmethyl)-1H-pyrazol-3-yl]-3-(3-trifluoromethyl-phenyl)-acrylamide;
(E)-N-[1-(5-Acetyl-furan-2-ylmethyl)-1H-pyrazol-3-yl]-3-(4-methoxy-phenyl)-acrylamide;
(E)-N-[1-(5-Acetyl-furan-2-ylmethyl)-1H-pyrazol-3-yl]-3-p-tolyl-acrylamide;
(E)-N-[1-(5-Acetyl-furan-2-ylmethyl)-1H-pyrazol-3-yl]-3-(3-methoxy-phenyl)-acrylamide;
(E)-N-[1-(5-Acetyl-furan-2-ylmethyl)-1H-pyrazol-3-yl]-3-m-tolyl-acrylamide;
5-(3-Methoxy-phenyl)-oxazole-4-carboxylic acid [1-(5-acetyl-furan-2-ylmethyl)-1H-pyrazol-3-yl]-amide;
5-(4-Methoxy-phenyl)-2-methyl-oxazole-4-carboxylic acid [1-(5-acetyl-furan-2-ylmethyl)-1H-pyrazol-3-yl]-amide;
2-Methyl-5-o-tolyl-oxazole-4-carboxylic acid [1-(5-acetyl-furan-2-ylmethyl)-1H-pyrazol-3-yl]-amide;
[1-(5-Acetyl-furan-2-ylmethyl)-1H-pyrazol-4-yl]-carbamic acid benzyl ester;
[1-(5-Acetyl-furan-2-ylmethyl)-1H-pyrazol-4-yl]-carbamic acid 2-methyl-benzyl ester;
[1-(5-Acetyl-furan-2-ylmethyl)-1H-pyrazol-4-yl]carbamic acid 4-trifluoromethyl-benzyl ester;
[1-(5-Acetyl-furan-2-ylmethyl)-1H-pyrazol-4-yl]-carbamic acid 3-trifluoromethyl-benzyl ester;
[1-(5-Acetyl-furan-2-ylmethyl)-1H-pyrazol-4-yl]-carbamic acid 3-chloro-benzyl ester;
[1-(5-Acetyl-furan-2-ylmethyl)-1H-pyrazol-4-yl]-carbamic acid 2-chloro-4-fluoro-benzyl ester;
[1-(5-Acetyl-furan-2-ylmethyl)-1H-pyrazol-4-yl]-carbamic acid 2-ethyl-benzyl ester;
[1-(5-Acetyl-furan-2-ylmethyl)-1H-pyrazol-4-yl]-carbamic acid 2,6-dichloro-benzyl ester;

[1-(5-Acetyl-furan-2-ylmethyl)-1H-pyrazol-4-yl]-carbamic acid 3,4-dimethyl-benzyl ester;
[1-(5-Acetyl-furan-2-ylmethyl)-1H-pyrazol-4-yl]-carbamic acid 3,4-difluoro-benzyl ester;
[1-(5-Acetyl-furan-2-ylmethyl)-1H-pyrazol-4-yl]-carbamic acid 2-chloro-6-fluoro-benzyl ester;
[1-(5-Acetyl-furan-2-ylmethyl)-1H-pyrazol-4-yl]-carbamic acid naphthalen-1-ylmethyl ester;
[1-(5-Acetyl-furan-2-ylmethyl)-1H-pyrazol-4-yl]-carbamic acid 2,5-dimethyl-benzyl ester;
[1-(5-Acetyl-furan-2-ylmethyl)-1H-pyrazol-4-yl]-carbamic acid 2,4,6-trifluoro-benzyl ester;
[1-(5-Acetyl-furan-2-ylmethyl)-1H-pyrazol-4-yl]-carbamic acid 2,3-difluoro-benzyl ester;
[1-(5-Acetyl-furan-2-ylmethyl)-1H-pyrazol-4-yl]-carbamic acid 3-chloro-2,6-difluoro-benzyl ester;
[1-(5-Acetyl-furan-2-ylmethyl)-1H-pyrazol-4-yl]-carbamic acid 6-chloro-2-fluoro-3-methyl-benzyl ester;
[1-(5-Acetyl-furan-2-ylmethyl)-1H-pyrazol-4-yl]-carbamic acid 3-chloro-2-fluoro-benzyl ester;
[1-(5-Acetyl-furan-2-ylmethyl)-1H-pyrazol-4-yl]-carbamic acid 2-chloro-6-fluoro-3-methyl-benzyl ester;
[1-(5-Acetyl-furan-2-ylmethyl)-1H-pyrazol-4-yl]-carbamic acid 2,4,5-trifluoro-benzyl ester;
[1-(5-Acetyl-furan-2-ylmethyl)-1H-pyrazol-4-yl]-carbamic acid 2,6-difluoro-3-methyl-benzyl ester;
[1-(5-Acetyl-furan-2-ylmethyl)-1H-pyrazol-4-yl]-carbamic acid 2,3,4-trifluoro-benzyl ester;
[1-(5-Acetyl-furan-2-ylmethyl)-1H-pyrazol-4-yl]-carbamic acid 4-bromo-benzyl ester;
[1-(5-Acetyl-furan-2-ylmethyl)-1H-pyrazol-4-yl]-carbamic acid 2-trifluoromethyl-benzyl ester;
[1-(5-Acetyl-furan-2-ylmethyl)-1H-pyrazol-4-yl]-carbamic acid 2-fluoro-benzyl ester;
[1-(5-Acetyl-furan-2-ylmethyl)-1H-pyrazol-4-yl]-carbamic acid 4-chloro-benzyl ester;
[1-(5-Acetyl-furan-2-ylmethyl)-1H-pyrazol-4-yl]carbamic acid 3-methyl-benzyl ester;
5-Phenyl-oxazole-4-carboxylic acid [1-(5-acetyl-furan-2-ylmethyl)-1H-pyrazol-4-yl]-amide;
(E)-N-[1-(5-Acetyl-furan-2-ylmethyl)-1H-pyrazol-4-yl]-3-(2-trifluoromethyl-phenyl)-acrylamide;
(E)-N-[1-(5-Acetyl-furan-2-ylmethyl)-1H-pyrazol-4-yl]-3-(4-trifluoromethyl-phenyl)-acrylamide;
(E)-N-[1-(5-Acetyl-furan-2-ylmethyl)-1H-pyrazol-4-yl]-3-(2-chloro-6-fluoro-phenyl)-acrylamide;
(E)-N-[1-(5-Acetyl-furan-2-ylmethyl)-1H-pyrazol-4-yl]-3-(2,3-dimethoxy-phenyl)-acrylamide;
(E)-N-[1-(5-Acetyl-furan-2-ylmethyl)-1H-pyrazol-4-yl]-3-(2,3-dichloro-phenyl)-acrylamide;
(E)-N-[1-(5-Acetyl-furan-2-ylmethyl)-1H-pyrazol-4-yl]-3-(3-trifluoromethoxy-phenyl)-acrylamide;
(E)-N-[1-(5-Acetyl-furan-2-ylmethyl)-1H-pyrazol-4-yl]-3-(2-chloro-3,6-difluoro-phenyl)-acrylamide;
(E)-N-[1-(5-Acetyl-furan-2-ylmethyl)-1H-pyrazol-4-yl]-3-(2,4-dichloro-phenyl)-acrylamide;
(E)-N-[1-(5-Acetyl-furan-2-ylmethyl)-1H-pyrazol-4-yl]-3-(2-chloro-4-fluoro-phenyl)-acrylamide;
(E)-N-[1-(5-Acetyl-furan-2-ylmethyl)-1H-pyrazol-4-yl]-3-o-tolyl-acrylamide;
(E)-N-[1-(5-Acetyl-furan-2-ylmethyl)-1H-pyrazol-4-yl]-3-(3-chloro-phenyl)-acrylamide;
5-(4-Methoxy-phenyl)-oxazole-4-carboxylic acid [1-(5-acetyl-furan-2-ylmethyl)-1H-pyrazol-4-yl]-amide;
2-Methyl-5-m-tolyl-oxazole-4-carboxylic acid [1-(5-acetyl-furan-2-ylmethyl)-1H-pyrazol-4-yl] amide;
5-(4-Methoxy-phenyl)-2-methyl-oxazole-4-carboxylic acid [1-(5-acetyl-furan-2-ylmethyl)-1H-pyrazol-4-yl]-amide;
2-Methyl-5-m-tolyl-thiazole-4-carboxylic acid [1-(5-acetyl-furan-2-ylmethyl)-1H-pyrazol-4-yl]-amide;
(E)-N-[1-(5-Acetyl-furan-2-ylmethyl)-1H-pyrazol-4-yl]-3-(3-trifluoromethyl-phenyl)-acrylamide;
5-(3-Methoxy-phenyl)-2-methyl-oxazole-4-carboxylic acid [1-(5-acetyl-furan-2-ylmethyl)-1H-pyrazol-4-yl]-amide;
2-Methyl-5-phenyl-oxazole-4-carboxylic acid [1-(5-acetyl-furan-2-ylmethyl)-1H-pyrazol-4-yl]-amide;
(E)-N-[1-(5-Acetyl-furan-2-ylmethyl)-1H-pyrazol-4-yl]-3-(2-chloro-phenyl)-acrylamide;
5-m-Tolyl-oxazole-4-carboxylic acid [1-(5-acetyl-furan-2-ylmethyl)-1H-pyrazol-4-yl]-amide;
(E)-N-[1-(5-Acetyl-furan-2-ylmethyl)-1H-pyrazol-4-yl]-3-p-tolyl-acrylamide;
5-(3-Methoxy-phenyl)-oxazole-4-carboxylic acid [1-(5-acetyl-furan-2-ylmethyl)-1H-pyrazol-4-yl]-amide;
2-Methyl-5-o-tolyl-oxazole-4-carboxylic acid [1-(5-acetyl-furan-2-ylmethyl)-1H-pyrazol-4-yl]-amide;
5-(3-Chloro-phenyl)-thiazole-4-carboxylic acid [1-(5-acetyl-furan-2-ylmethyl)-1H-pyrazol-4-yl]-amide;
5-(2-Fluoro-phenyl)-thiazole-4-carboxylic acid [1-(5-acetyl-furan-2-ylmethyl)-1H-pyrazol-4-yl]-amide;
[1-(5-Oxo-hexyl)-1H-pyrazol-4-yl]-carbamic acid 2-chloro-benzyl ester;
[1-(5-Oxo-hexyl)-1H-pyrazol-4-yl]-carbamic acid 1-phenyl-ethyl ester;
[1-(5-Oxo-hexyl)-1H-pyrazol-4-yl]-carbamic acid 4-bromo-benzyl ester;
[1-(5-Oxo-hexyl)-1H-pyrazol-4-yl]-carbamic acid 2-trifluoromethyl-benzyl ester;
[1-(5-Oxo-hexyl)-1H-pyrazol-4-yl]-carbamic acid 2-fluoro-benzyl ester;
[1-(5-Oxo-hexyl)-1H-pyrazol-4-yl]-carbamic acid 4-chloro-benzyl ester;
[1-(5-Oxo-hexyl)-1H-pyrazol-4-yl]-carbamic acid 3-methyl-benzyl ester;
[1-(5-Oxo-hexyl)-1H-pyrazol-4-yl]-carbamic acid 3-trifluoromethyl-benzyl ester;
[1-(5-Oxo-hexyl)-1H-pyrazol-4-yl]-carbamic acid 3-chloro-benzyl ester;
[1-(5-Oxo-hexyl)-1H-pyrazol-4-yl]-carbamic acid 2-chloro-4-fluoro-benzyl ester;
[1-(5-Oxo-hexyl)-1H-pyrazol-4-yl]-carbamic acid 2-ethyl-benzyl ester;
[1-(5-Oxo-hexyl)-1H-pyrazol-4-yl]-carbamic acid 2,6-dichloro-benzyl ester;
[1-(5-Oxo-hexyl)-1H-pyrazol-4-yl]-carbamic acid 3,4-dimethyl-benzyl ester;
[1-(5-Oxo-hexyl)-1H-pyrazol-4-yl]-carbamic acid 3,4-difluoro-benzyl ester;
[1-(5-Oxo-hexyl)-1H-pyrazol-4-yl]-carbamic acid naphthalen-1-ylmethyl ester;
[1-(5-Oxo-hexyl)-1H-pyrazol-4-yl]-carbamic acid 2,5-dimethyl-benzyl ester;
[1-(5-Oxo-hexyl)-1H-pyrazol-4-yl]-carbamic acid 2,4,6-trifluoro-benzyl ester;
[1-(5-Oxo-hexyl)-1H-pyrazol-4-yl]-carbamic acid 2,3-difluoro-benzyl ester;
[1-(5-Oxo-hexyl)-1H-pyrazol-4-yl]-carbamic acid 3-chloro-2,6-difluoro-benzyl ester;
[1-(5-Oxo-hexyl)-1H-pyrazol-4-yl]-carbamic acid 6-chloro-2-fluoro-3-methyl-benzyl ester;

[1-(5-Oxo-hexyl)-1H-pyrazol-4-yl]-carbamic acid 3-chloro-2-fluoro-benzyl ester;
[1-(5-Oxo-hexyl)-1H-pyrazol-4-yl]-carbamic acid 2-chloro-6-fluoro-3-methyl-benzyl ester;
[1-(5-Oxo-hexyl)-1H-pyrazol-4-yl]-carbamic acid 2,6-difluoro-3-methyl-benzyl ester;
[1-(5-Oxo-hexyl)-1H-pyrazol-4-yl]-carbamic acid 2-fluoro-5-trifluoromethyl-benzyl ester;
[1-(5-Oxo-hexyl)-1H-pyrazol-4-yl]-carbamic acid 2,3,5-trifluoro-benzyl ester;
[1-(5-Oxo-hexyl)-1H-pyrazol-4-yl]-carbamic acid 2,3,4-trifluoro-benzyl ester;
5-Phenyl-oxazole-4-carboxylic acid [1-(5-oxo-hexyl)-1H-pyrazol-4-yl]-amide;
(E)-N-[1-(5-oxo-hexyl)-1H-pyrazol-4-yl]-3-(2-trifluoromethyl-phenyl)-acrylamide;
(E)-N-[1-(5-oxo-hexyl)-1H-pyrazol-4-yl]-3-o-tolyl-acrylamide;
(E)-3-(2-Chloro-phenyl)-N-[1-(5-oxo-hexyl)-1H-pyrazol-4-yl]-acrylamide;
2-Methyl-5-m-tolyl-oxazole-4-carboxylic acid [1-(5-oxo-hexyl)-1H-pyrazol-4-yl]-amide;
[1-(5-Oxo-hexyl)-1H-pyrazol-3-yl]-carbamic acid 2-chloro-benzyl ester;
[1-(5-Oxo-hexyl)-1H-pyrazol-3-yl]-carbamic acid benzyl ester;
[1-(5-Oxo-hexyl)-1H-pyrazol-3-yl]-carbamic acid 2-methyl-benzyl ester;
[1-(5-Oxo-hexyl)-1H-pyrazol-3-yl]-carbamic acid 3-trifluoromethyl-benzyl ester;
[1-(5-Oxo-hexyl)-1H-pyrazol-3-yl]-carbamic acid 3-chloro-benzyl ester;
[1-(5-Oxo-hexyl)-1H-pyrazol-3-yl]-carbamic acid 2-chloro-4-fluoro-benzyl ester;
[1-(5-Oxo-hexyl)-1H-pyrazol-3-yl]-carbamic acid 3,4-dimethyl-benzyl ester;
[1-(5-Oxo-hexyl)-1H-pyrazol-3-yl]-carbamic acid 3,4-difluoro-benzyl ester;
[1-(5-Oxo-hexyl)-1H-pyrazol-3-yl]-carbamic acid 2-chloro-6-fluoro-benzyl ester;
[1-(5-Oxo-hexyl)-1H-pyrazol-3-yl]-carbamic acid naphthalen-1-ylmethyl ester;
[1-(5-Oxo-hexyl)-1H-pyrazol-3-yl]-carbamic acid 2,5-dimethyl-benzyl ester;
[1-(5-Oxo-hexyl)-1H-pyrazol-3-yl]-carbamic acid 2,3-difluoro-benzyl ester;
[1-(5-Oxo-hexyl)-1H-pyrazol-3-yl]-carbamic acid 6-chloro-2-fluoro-3-methyl-benzyl ester;
[1-(5-Oxo-hexyl)-1H-pyrazol-3-yl]-carbamic acid 3-chloro-2-fluoro-benzyl ester;
[1-(5-Oxo-hexyl)-1H-pyrazol-3-yl]-carbamic acid 2-chloro-6-fluoro-3-methyl-benzyl ester;
[1-(5-Oxo-hexyl)-1H-pyrazol-3-yl]carbamic acid 2,6-difluoro-3-methyl-benzyl ester;
[1-(5-Oxo-hexyl)-1H-pyrazol-3-yl]-carbamic acid 2-ethyl-benzyl ester;
5-Phenyl-oxazole-4-carboxylic acid [1-(5-oxo-hexyl)-1H-pyrazol-3-yl]-amide;
(E)-N-[1-(5-oxo-hexyl)-1H-pyrazol-3-yl]-3-(2-trifluoromethyl-phenyl)-acrylamide;
(E)-N-[1-(5-oxo-hexyl)-1H-pyrazol-3-yl]-3-(4-trifluoromethyl-phenyl)-acrylamide;
(E)-3-(2,3-Dichloro-phenyl)-N-[1-(5-oxo-hexyl)-1H-pyrazol-3-yl]-acrylamide;
(E)-3-(2,4-Dichloro-phenyl)-N-[1-(5-oxo-hexyl)-1H-pyrazol-3-yl]-acrylamide;
(E)-3-(2-Chloro-4-fluoro-phenyl)-N-[1-(5-oxo-hexyl)-1H-pyrazol-3-yl]-acrylamide;
(E)-N-[1-(5-oxo-hexyl)-1H-pyrazol-3-yl]-3-o-tolyl-acrylamide;
2-Methyl-5-m-tolyl-oxazole-4-carboxylic acid [1-(5-oxo-hexyl)-1H-pyrazol-3-yl]-amide;
(E)-3-(3-Chloro-phenyl)-N-[1-(5-oxo-hexyl)-1H-pyrazol-3-yl]-acrylamide;
{1-[5-(1,1-Difluoro-ethyl)-furan-2-ylmethyl]-1H-pyrazol-3-yl}-carbamic acid 2-chloro-benzyl ester;
5-Phenyl-oxazole-4-carboxylic acid {1-[5-(1,1-difluoro-ethyl)-furan-2-ylmethyl]-1H-pyrazol-3-yl}-amide;
{1-[5-(1,1-Difluoro-ethyl)-furan-2-ylmethyl]-1H-pyrazol-4-yl}-carbamic acid 2-chloro-benzyl ester;
5-Phenyl-oxazole-4-carboxylic acid {1-[5-(1,1-difluoro-ethyl)-furan-2-ylmethyl]-1H-pyrazol-4-yl}-amide;
[1-(5,5-Difluoro-hexyl)-1H-pyrazol-3-yl]-carbamic acid 2-chloro-benzyl ester;
5-Phenyl-oxazole-4-carboxylic acid [1-(5,5-difluoro-hexyl)-1H-pyrazol-3-yl]-amide;
[1-(5,5-Difluoro-hexyl)-1H-pyrazol-4-yl]-carbamic acid 2-chloro-benzyl ester;
5-Phenyl-oxazole-4-carboxylic acid [1-(5,5-difluoro-hexyl)-1H-pyrazol-4-yl]-amide;
2-Cyclopropyl-5-phenyl-oxazole-4-carboxylic acid [1-(5-acetyl-furan-2-ylmethyl)-1H-pyrazol-4-yl]-amide;
2-Ethyl-5-phenyl-oxazole-4-carboxylic acid [1-(5-acetyl-furan-2-ylmethyl)-1H-pyrazol-4-yl]-amide;
{1-[5-(1,1-Difluoro-ethyl)-furan-2-ylmethyl]-1H-pyrazol-3-yl}-carbamic acid 6-chloro-2-fluoro-3-methyl-benzyl ester;
{1-[5-(1,1-Difluoro-ethyl)-furan-2-ylmethyl]-1H-pyrazol-3-yl-}carbamic acid 2-chloro-6-fluoro-3-methyl-benzyl ester;
[1-(5,5-Difluoro-hexyl)-1H-pyrazol-3-yl]-carbamic acid 2-chloro-6-fluoro-3-methyl-benzyl ester;
[1-(5,5-Difluoro-hexyl)-1H-pyrazol-3-yl]-carbamic acid 6-chloro-2-fluoro-3-methyl-benzyl ester;
2-Methyl-5-phenyl-oxazole-4-carboxylic acid [1-(5,5-difluoro-hexyl)-1H-pyrazol-4-yl]-amide;
2-Methyl-5-m-tolyl-oxazole-4-carboxylic acid [1-(5,5-difluoro-hexyl)-1H-pyrazol-4-yl]-amide;
(E)-N-[1-(5,5-Difluoro-hexyl)-1H-pyrazol-3-yl]-3-(4-trifluoromethyl-phenyl)-acrylamide;
(E)-N-[1-(5,5-Difluoro-hexyl)-1H-pyrazol-3-yl]-3-(2-trifluoromethyl-phenyl)-acrylamide;
[1-(5-Acetyl-furan-2-ylmethyl)-1H-pyrazol-3-yl]carbamic acid 2-chloro-benzyl ester;
[1-(5-Fluoro-hexyl)-1H-pyrazol-4-yl]-carbamic acid 2-chloro-benzyl ester;
(E)-N-[1-(5-Acetyl-furan-2-ylmethyl)-1H-pyrazol-3-yl]-3-(2-chloro-phenyl)-acrylamide;
{1-[5-(1,1-Difluoro-ethyl)-furan-2-ylmethyl]-1H-pyrazol-4-yl}-carbamic acid 6-chloro-2-fluoro-3-methyl-benzyl ester;
{1-[5-(1,1-Difluoro-ethyl)-furan-2-ylmethyl]-1H-pyrazol-4-yl}-carbamic acid 2-chloro-6-fluoro-3-methyl-benzyl ester;
[1-(5,5-Difluoro-hexyl)-1H-pyrazol-4-yl]-carbamic acid 2-chloro-6-fluoro-3-methyl-benzyl ester;
[1-(5,5-Difluoro-hexyl)-1H-pyrazol-4-yl]-carbamic acid 6-chloro-2-fluoro-3-methyl-benzyl ester;
5-m-Tolyl-oxazole-4-carboxylic acid {1-[5-(1,1-difluoro-ethyl)-furan-2-ylmethyl]-1H-pyrazol-4-yl}-amide;
5-(4-Methoxy-phenyl)-oxazole-4-carboxylic acid {1-[5-(1,1-difluoro-ethyl)-furan-2-ylmethyl]-1H-pyrazol-4-yl}-amide;

5-(4-Methoxy-phenyl)-2-methyl-oxazole-4-carboxylic acid {1-[5-(1,1-difluoro-ethyl)-furan-2-ylmethyl]-1H-pyrazol-4-yl}-amide;
(E)-N-{1-[5-(1,1-Difluoro-ethyl)-furan-2-ylmethyl]-1H-pyrazol-4-yl}-3-(4-trifluoromethyl-phenyl)-acrylamide;
(E)-N-{1-[5-(1,1-Difluoro-ethyl)-furan-2-ylmethyl]-1H-pyrazol-4-yl}-3-(2,3-dimethoxy-phenyl)-acrylamide;
(E)-N-{1-[5-(1,1-Difluoro-ethyl)-furan-2-ylmethyl]-1H-pyrazol-4-yl}-3-p-tolyl-acrylamide;
5-(3-Methoxy-phenyl)-2-methyl-oxazole-4-carboxylic acid {1-[5-(1,1-difluoro-ethyl)-furan-2-ylmethyl]-1H-pyrazol-4-yl}-amide;
5-(3-Chloro-phenyl)-thiazole-4-carboxylic acid {1-[5-(1,1-difluoro-ethyl)-furan-2-ylmethyl]-1H-pyrazol-4-yl}-amide;
(E)-N-{1-[5-(1,1-Difluoro-ethyl)-furan-2-ylmethyl]-1H-pyrazol-4-yl}-3-(4-methoxy-phenyl)-acrylamide;
(E)-N-{1-[5-(1,1-Difluoro-ethyl)-furan-2-ylmethyl]-1H-pyrazol-3-yl}-3-(3-trifluoromethyl-phenyl)-acrylamide;
(E)-3-(2,3-Dichloro-phenyl)-N-{1-[5-(1,1-difluoro-ethyl)-furan-2-ylmethyl]-1H-pyrazol-3-yl}-acrylamide;
(E)-N-{1-[5-(1,1-Difluoro-ethyl)-furan-2-ylmethyl]-1H-pyrazol-3-yl}-3-(2,3-dimethoxy-phenyl)-acrylamide;
(E)-3-(2-Chloro-4-fluoro-phenyl)-N-{1-[5-(1,1-difluoro-ethyl)-furan-2-ylmethyl]-1H-pyrazol-3-yl}-acrylamide;
(E)-N-{1-[5-(1,1-Difluoro-ethyl)-furan-2-ylmethyl]-1H-pyrazol-3-yl}-3-p-tolyl-acrylamide;
(E)-3-(2,4-Dichloro-phenyl)-N-{1-[5-(1,1-difluoro-ethyl)-furan-2-ylmethyl]-1H-pyrazol-3-yl}-acrylamide;
(E)-3-(2-Chloro-6-fluoro-phenyl)-N-{1-[5-(1,1-difluoro-ethyl)-furan-2-ylmethyl]-1H-pyrazol-3-yl}-acrylamide;
(E)-3-(2-Chloro-3,6-difluoro-phenyl)-N-{1-[5-(1,1-difluoro-ethyl)-furan-2-ylmethyl]-1H-pyrazol-3-yl}-acrylamide;
(E)-3-(3-Chloro-phenyl)-N-{1-[5-(1,1-difluoro-ethyl)-furan-2-ylmethyl]-1H-pyrazol-3-yl}-acrylamide;
(E)-N-{1-[5-(1,1-Difluoro-ethyl)-furan-2-ylmethyl]-1H-pyrazol-3-yl}-3-(2-fluoro-3-trifluoromethyl-phenyl)-acrylamide;
(E)-N-{1-[5-(1,1-Difluoro-ethyl)-furan-2-ylmethyl]-1H-pyrazol-3-yl}-3-m-tolyl-acrylamide;
(E)-N-{1-[5-(1,1-Difluoro-ethyl)-furan-2-ylmethyl]-1H-pyrazol-3-yl}-3-(3-methoxy-phenyl)-acrylamide;
(E)-N-{1-[5-(1,1-Difluoro-ethyl)-furan-2-ylmethyl]-1H-pyrazol-3-yl}-3-(4-methoxy-phenyl)-acrylamide;
2-Methyl-5-phenyl-oxazole-4-carboxylic acid {1-[5-(1,1-difluoro-ethyl)-furan-2-ylmethyl]-1H-pyrazol-4-yl}-amide;
2-Methyl-5-m-tolyl-oxazole-4-carboxylic acid {1-[5-(1,1-difluoro-ethyl)-furan-2-ylmethyl]-1H-pyrazol-4-yl}-amide;
2-Methyl-5-m-tolyl-oxazole-4-carboxylic acid {1-[5-(1,1-difluoro-ethyl)-furan-2-ylmethyl]-1H-pyrazol-3-yl}-amide;
5-(3-Methoxy-phenyl)-2-methyl-oxazole-4-carboxylic acid {1-[5-(1,1-difluoro-ethyl)-furan-2-ylmethyl]-1H-pyrazol-3-yl}-amide;
5-(3-Methoxy-phenyl)-oxazole-4-carboxylic acid {1-[5-(1,1-difluoro-ethyl)-furan-2-ylmethyl]-1H-pyrazol-4-yl}-amide;
5-(3-Methoxy-phenyl)-oxazole-4-carboxylic acid {1-[5-(1,1-difluoro-ethyl)-furan-2-ylmethyl]-1H-pyrazol-3-yl}-amide;
5-(4-Methoxy-phenyl)-oxazole-4-carboxylic acid {1-[5-(1,1-difluoro-ethyl)-furan-2-ylmethyl]-1H-pyrazol-3-yl}-amide;
(E)-N-[1-(5-Acetyl-furan-2-ylmethyl)-1H-pyrazol-4-yl]-3-(2-trifluoromethyl-phenyl)-acrylamide;
(E)-N-[1-(5-Acetyl-furan-2-ylmethyl)-1H-pyrazol-4-yl]-3-(4-trifluoromethyl-phenyl)-acrylamide;
(E)-N-[1-(5-Acetyl-furan-2-ylmethyl)-1H-pyrazol-3-yl]-3-(2-trifluoromethyl-phenyl)-acrylamide;
(E)-N-[1-(5-Acetyl-furan-2-ylmethyl)-1H-pyrazol-3-yl]-3-(4-trifluoromethyl-phenyl)-acrylamide;
(E)-N-[1-(5-Acetyl-furan-2-ylmethyl)-1H-pyrazol-3-yl]-3-(4-methoxy-phenyl)-acrylamide;
{1-[5-(1,1-Difluoro-ethyl)-furan-2-ylmethyl]-1H-pyrazol-4-yl}-carbamic acid 3-chloro-2-fluoro-benzyl ester;
{1-[5-(1,1-Difluoro-ethyl)-furan-2-ylmethyl]-1H-pyrazol-3-yl}-carbamic acid 3-trifluoromethyl-benzyl ester;
{1-[5-(1,1-Difluoro-ethyl)-furan-2-ylmethyl]-1H-pyrazol-4-yl}-carbamic acid 2-chloro-4-fluoro-benzyl ester;
[1-(5,5-Difluoro-hexyl)-1H-pyrazol-3-yl]-carbamic acid 2,6-difluoro-3-methyl-benzyl ester;
{1-[5-(1,1-Difluoro-ethyl)-furan-2-ylmethyl]-1H-pyrazol-4-yl}-carbamic acid 2-chloro-6-fluoro-benzyl ester;
{1-[5-(1,1-Difluoro-ethyl)-furan-2-ylmethyl]-1H-pyrazol-3-yl}-carbamic acid 2-fluoro-benzyl ester;
[1-(5,5-Difluoro-hexyl)-1H-pyrazol-3-yl]-carbamic acid 3-trifluoromethyl-benzyl ester;
{1-[5-(1,1-Difluoro-ethyl)-furan-2-ylmethyl]-1H-pyrazol-3-yl}-carbamic acid 3-chloro-benzyl ester;
[1-(5,5-Difluoro-hexyl)-1H-pyrazol-4-yl]-carbamic acid 3-trifluoromethyl-benzyl ester;
{1-[5-(1,1-Difluoro-ethyl)-furan-2-ylmethyl]-1H-pyrazol-4-yl}-carbamic acid 2,6-difluoro-3-methyl-benzyl ester;
{1-[5-(1,1-Difluoro-ethyl)-furan-2-ylmethyl]-1H-pyrazol-4-yl}-carbamic acid 2-fluoro-benzyl ester;
[1-(5,5-Difluoro-hexyl)-1H-pyrazol-3-yl]-carbamic acid 2-fluoro-benzyl ester;
{1-[5-(1,1-Difluoro-ethyl)-furan-2-ylmethyl]-1H-pyrazol-3-yl}-carbamic acid benzyl ester;
{1-[5-(1,1-Difluoro-ethyl)-furan-2-ylmethyl]-1H-pyrazol-4-yl}-carbamic acid 3-trifluoromethyl-benzyl ester;
[1-(5,5-Difluoro-hexyl)-1H-pyrazol-4-yl]-carbamic acid 2-fluoro-benzyl ester;
[1-(5,5-Difluoro-hexyl)-1H-pyrazol-3-yl]-carbamic acid 3-chloro-benzyl ester;
[1-(5,5-Difluoro-hexyl)-1H-pyrazol-3-yl]-carbamic acid 3,4-dimethyl-benzyl ester;
[1-(5,5-Difluoro-hexyl)-1H-pyrazol-3-yl]-carbamic acid 2-ethyl-benzyl ester;
{1-[5-(1,1-Difluoro-ethyl)-furan-2-ylmethyl]-1H-pyrazol-3-yl}-carbamic acid 3-methyl-benzyl ester;
[1-(5,5-Difluoro-hexyl)-1H-pyrazol-4-yl]carbamic acid 3-chloro-benzyl ester;
{1-[5-(1,1-Difluoro-ethyl)-furan-2-ylmethyl]-1H-pyrazol-3-yl}-carbamic acid 2-ethyl-benzyl ester;
{1-[5-(1,1-Difluoro-ethyl)-furan-2-ylmethyl]-1H-pyrazol-4-yl}-carbamic acid benzyl ester;
[1-(5,5-Difluoro-hexyl)-1H-pyrazol-3-yl]carbamic acid benzyl ester;
[1-(5,5-Difluoro-hexyl)-1H-pyrazol-4-yl]-carbamic acid 3,4-dimethyl-benzyl ester;
{1-[5-(1,1-Difluoro-ethyl)-furan-2-ylmethyl]-1H-pyrazol-4-yl}-carbamic acid 2-methyl-benzyl ester;

{1-[5-(1,1-Difluoro-ethyl)-furan-2-ylmethyl]-1H-pyrazol-4-yl}-carbamic acid 3-chloro-benzyl ester;
[1-(5,5-Difluoro-hexyl)-1H-pyrazol-3-yl]carbamic acid 2-methyl-benzyl ester;
{1-[5-(1,1-Difluoro-ethyl)-furan-2-ylmethyl]-1H-pyrazol-4-yl}-carbamic acid 3,4-dimethyl-benzyl ester;
[1-(5,5-Difluoro-hexyl)-1H-pyrazol-4-yl]-carbamic acid benzyl ester;
[1-(5,5-Difluoro-hexyl)-1H-pyrazol-3-yl]-carbamic acid 2,5-dimethyl-benzyl ester;
[1-(5,5-Difluoro-hexyl)-1H-pyrazol-3-yl]carbamic acid 3-methyl-benzyl ester;
[1-(5,5-Difluoro-hexyl)-1H-pyrazol-4-yl]carbamic acid 2-ethyl-benzyl ester;
[1-(5,5-Difluoro-hexyl)-1H-pyrazol-4-yl]-carbamic acid 2-methyl-benzyl ester;
[1-(5,5-Difluoro-hexyl)-1H-pyrazol-4-yl]carbamic acid 3-methyl-benzyl ester;
[1-(5,5-Difluoro-hexyl)-1H-pyrazol-4-yl]-carbamic acid 2,5-dimethyl-benzyl ester;
{1-[5-(1,1-Difluoro-ethyl)-furan-2-ylmethyl]-1H-pyrazol-4-yl}-carbamic acid 2-ethyl-benzyl ester;
{1-[5-(1,1-Difluoro-ethyl)-furan-2-ylmethyl]-1H-pyrazol-4-yl}-carbamic acid 3-methyl-benzyl ester;
{1-[5-(1,1-Difluoro-ethyl)-furan-2-ylmethyl]-1H-pyrazol-4-yl}-carbamic acid 2,5-dimethyl-benzyl ester;
(E)-N-[1-(5-Acetyl-furan-2-ylmethyl)-1H-pyrazol-3-yl]-3-(2,4-dimethoxy-phenyl)-acrylamide;
5-(3-Fluoro-phenyl)-2-methyl-oxazole-4-carboxylic acid [1-(5-acetyl-furan-2-ylmethyl)-1H-pyrazol-3-yl]-amide;
(E)-N-[1-(5-Acetyl-furan-2-ylmethyl)-1H-pyrazol-3-yl]-3-(4-chloro-phenyl)-acrylamide;
2-Methyl-5-(3-trifluoromethoxy-phenyl)-oxazole-4-carboxylic acid [1-(5-acetyl-furan-2-ylmethyl)-1H-pyrazol-3-yl]-amide;
5-(3,4-Dimethyl-phenyl)-oxazole-4-carboxylic acid [1-(5-acetyl-furan-2-ylmethyl)-1H-pyrazol-4-yl]-amide;
(E)-N-[1-(5-Acetyl-furan-2-ylmethyl)-1H-pyrazol-4-yl]-3-(2,4-dimethoxy-phenyl)-acrylamide;
5-(3,4-Dimethyl-phenyl)-oxazole-4-carboxylic acid [1-(5-acetyl-furan-2-ylmethyl)-1H-pyrazol-3-yl]-amide;
5-(3-Fluoro-phenyl)-2-methyl-oxazole-4-carboxylic acid [1-(5-acetyl-furan-2-ylmethyl)-1H-pyrazol-4-yl]-amide;
(E)-N-[1-(5-Acetyl-furan-2-ylmethyl)-1H-pyrazol-4-yl]-3-(4-methoxy-phenyl)-acrylamide;
2-Methyl-5-(3-trifluoromethyl-phenyl)-oxazole-4-carboxylic acid [1-(5-acetyl-furan-2-ylmethyl)-1H-pyrazol-4-yl]-amide;
(E)-N-[1-(5-Acetyl-furan-2-ylmethyl)-1H-pyrazol-4-yl]-3-(4-chloro-phenyl)-acrylamide;
5-(3-Chloro-phenyl)-2-methyl-oxazole-4-carboxylic acid [1-(5-acetyl-furan-2-ylmethyl)-1H-pyrazol-4-yl]-amide;
2-Methyl-5-(3-trifluoromethoxy-phenyl)-oxazole-4-carboxylic acid [1-(5-acetyl-furan-2-ylmethyl)-1H-pyrazol-4-yl]-amide;
5-Biphenyl-3-yl-2-methyl-oxazole-4-carboxylic acid [1-(5-acetyl-furan-2-ylmethyl)-1H-pyrazol-4-yl]-amide;
5-p-Tolyl-oxazole-4-carboxylic acid [1-(5-acetyl-furan-2-ylmethyl)-1H-pyrazol-4-yl]-amide;
5-p-Tolyl-oxazole-4-carboxylic acid [1-(5-acetyl-furan-2-ylmethyl)-1H-pyrazol-3-yl]-amide;
2-Methyl-5-(3-trifluoromethyl-phenyl)-oxazole-4-carboxylic acid [1-(5-acetyl-furan-2-ylmethyl)-1H-pyrazol-3-yl]-amide;
[1-(5-Acetyl-furan-2-ylmethyl)-1H-pyrazol-3-yl]-carbamic acid 4-fluoro-benzyl ester;
[1-(5-Acetyl-furan-2-ylmethyl)-1H-pyrazol-3-yl]-carbamic acid 3-bromo-benzyl ester;
[1-(5-Acetyl-furan-2-ylmethyl)-1H-pyrazol-4-yl]-carbamic acid 4-fluoro-benzyl ester;
[1-(5-Acetyl-furan-2-ylmethyl)-1H-pyrazol-4-yl]-carbamic acid 3-bromo-benzyl ester;
(E)-N-[1-(5-Acetyl-furan-2-ylmethyl)-1H-pyrazol-4-yl]-3-(2,3-difluoro-4-trifluoromethyl-phenyl)-acrylamide;
(E)-N-[1-(5-Acetyl-furan-2-ylmethyl)-1H-pyrazol-4-yl]-3-(2,5-difluoro-4-methoxy-phenyl)-acrylamide;
5-(4-Trifluoromethyl-phenyl)-oxazole-4-carboxylic acid [1-(5-acetyl-furan-2-ylmethyl)-1H-pyrazol-3-yl]-amide;
5-(3-Trifluoromethyl-phenyl)-oxazole-4-carboxylic acid [1-(5-acetyl-furan-2-ylmethyl)-1H-pyrazol-3-yl]-amide;
5-(3-Fluoro-phenyl)-oxazole-4-carboxylic acid [1-(5-acetyl-furan-2-ylmethyl)-1H-pyrazol-3-yl]-amide;
5-(4-Chloro-phenyl)-oxazole-4-carboxylic acid [1-(5-acetyl-furan-2-ylmethyl)-1H-pyrazol-3-yl]-amide;
5-(4-Fluoro-phenyl)-oxazole-4-carboxylic acid [1-(5-acetyl-furan-2-ylmethyl)-1H-pyrazol-3-yl]-amide;
5-(4-Trifluoromethoxy-phenyl)-oxazole-4-carboxylic acid [1-(5-acetyl-furan-2-ylmethyl)-1H-pyrazol-3-yl]-amide;
5-(4-Trifluoromethoxy-phenyl)-oxazole-4-carboxylic acid [1-(5-acetyl-furan-2-ylmethyl)-1H-pyrazol-4-yl]-amide;
5-(3-Trifluoromethyl-phenyl)-oxazole-4-carboxylic acid [1-(5-acetyl-furan-2-ylmethyl)-1H-pyrazol-4-yl]-amide;
(E)-N-[1-(5-Acetyl-furan-2-ylmethyl)-1H-pyrazol-3-yl]-3-(4-chloro-3,5-difluoro-phenyl)-acrylamide;
(E)-N-[1-(5-Acetyl-furan-2-ylmethyl)-1H-pyrazol-3-yl]-3-(2,5-difluoro-4-trifluoromethyl-phenyl)-acrylamide;
5-(4-Chloro-phenyl)-oxazole-4-carboxylic acid [1-(5-acetyl-furan-2-ylmethyl)-1H-pyrazol-4-yl]-amide;
5-(3-Chloro-phenyl)-oxazole-4-carboxylic acid [1-(5-acetyl-furan-2-ylmethyl)-1H-pyrazol-4-yl]-amide;
5-(3-Chloro-phenyl)-oxazole-4-carboxylic acid [1-(5-acetyl-furan-2-ylmethyl)-1H-pyrazol-3-yl]-amide;
5-(3-Fluoro-phenyl)-oxazole-4-carboxylic acid [1-(5-acetyl-furan-2-ylmethyl)-1H-pyrazol-4-yl]-amide;
5-Biphenyl-3-yl-2-methyl-oxazole-4-carboxylic acid [1-(5-acetyl-furan-2-ylmethyl)-1H-pyrazol-3-yl]-amide;
5-(3-Chloro-phenyl)-2-methyl-oxazole-4-carboxylic acid [1-(5-acetyl-furan-2-ylmethyl)-1H-pyrazol-3-yl]-amide;
5-Biphenyl-3-yl-oxazole-4-carboxylic acid [1-(5-acetyl-furan-2-ylmethyl)-1H-pyrazol-3-yl]-amide;
5-Biphenyl-3-yl-oxazole-4-carboxylic acid [1-(5-acetyl-furan-2-ylmethyl)-1H-pyrazol-4-yl]-amide;
5-(3-Methoxy-phenyl)-2-methyl-oxazole-4-carboxylic acid [1-(5-acetyl-furan-2-ylmethyl)-1H-pyrazol-3-yl]-amide;
5-m-Tolyl-oxazole-4-carboxylic acid [1-(5-acetyl-furan-2-ylmethyl)-1H-pyrazol-3-yl]-amide;
2-Methyl-5-phenyl-oxazole-4-carboxylic acid [1-(5-acetyl-furan-2-ylmethyl)-1H-pyrazol-3-yl]-amide;
[1-(5-Acetyl-thiophen-2-ylmethyl)-1H-pyrazol-4-yl]-carbamic acid 2-chloro-benzyl ester;
5-Phenyl-oxazole-4-carboxylic acid [1-(3-acetyl-isoxazol-5-ylmethyl)-1H-pyrazol-4-yl]-amide;
[1-(6-Acetyl-pyridin-2-ylmethyl)-1H-pyrazol-4-yl]-carbamic acid 2-chloro-benzyl ester;

5-Phenyl-oxazole-4-carboxylic acid [1-(6-acetyl-pyridin-2-ylmethyl)-1H-pyrazol-4-yl]-amide;
(E)-N-[1-(6-Acetyl-pyridin-2-ylmethyl)-1H-pyrazol-4-yl]-3-(4-trifluoromethyl-phenyl)-acrylamide;
[1-(3-Acetyl-benzyl)-1H-pyrazol-4-yl]carbamic acid 2-chloro-benzyl ester;
5-Phenyl-oxazole-4-carboxylic acid [1-(3-acetyl-benzyl)-1H-pyrazol-4-yl]-amide;
5-Pyridin-2-yl-oxazole-4-carboxylic acid [1-(5-acetyl-furan-2-ylmethyl)-1H-pyrazol-4-yl]-amide;
5-Phenyl-oxazole-4-carboxylic acid [1-(5-acetyl-thiophen-2-ylmethyl)-1H-pyrazol-4-yl]-amide;
(E)-N-[1-(5-Acetyl-thiophen-2-ylmethyl)-1H-pyrazol-4-yl]-3-(4-trifluoromethyl-phenyl)-acrylamide;
5-(3-Trifluoromethoxy-phenyl)-oxazole-4-carboxylic acid [1-(5-acetyl-furan-2-ylmethyl)-1H-pyrazol-3-yl]-amide;
5-(3-Trifluoromethoxy-phenyl)-oxazole-4-carboxylic acid [1-(5-acetyl-furan-2-ylmethyl)-1H-pyrazol-4-yl]-amide;
5-(3-Cyano-phenyl)-oxazole-4-carboxylic acid [1-(5-acetyl-furan-2-ylmethyl)-1H-pyrazol-4-yl]-amide;
5-(3-Carbamoyl-phenyl)-oxazole-4-carboxylic acid [1-(5-acetyl-furan-2-ylmethyl)-1H-pyrazol-4-yl]-amide;
5-(3-Dimethylamino-phenyl)-oxazole-4-carboxylic acid [1-(5-acetyl-furan-2-ylmethyl)-1H-pyrazol-4-yl]-amide;
5-Phenyl-oxazole-4-carboxylic acid [1-(5-acetyl-thiophen-2-ylmethyl)-1H-pyrazol-3-yl]-amide;
(E)-N-[1-(5-Acetyl-thiophen-2-ylmethyl)-1H-pyrazol-3-yl]-3-(4-trifluoromethyl-phenyl)-acrylamide;
[1-(5-Acetyl-thiophen-2-ylmethyl)-1H-pyrazol-3-yl]-carbamic acid 2-chloro-benzyl ester;
5-[3-(2-Methoxy-ethyl)-phenyl]-oxazole-4-carboxylic acid [1-(5-acetyl-furan-2-ylmethyl)-1H-pyrazol-3-yl]-amide;
5-(3-Cyano-phenyl)-oxazole-4-carboxylic acid [1-(5-acetyl-furan-2-ylmethyl)-1H-pyrazol-3-yl]-amide;
3-{4-[1-(5-Acetyl-furan-2-ylmethyl)-1H-pyrazol-3-ylcarbamoyl]-oxazol-5-yl}-benzoic acid tert-butyl ester;
[1-(5-Acetyl-pyridin-3-ylmethyl)-1H-pyrazol-4-yl]-carbamic acid 2-chloro-benzyl ester;
5-[3-(2-Hydroxy-ethyl)-phenyl]-oxazole-4-carboxylic acid [1-(5-acetyl-furan-2-ylmethyl)-1H-pyrazol-3-yl]-amide;
5-(3-Methoxymethyl-phenyl)-oxazole-4-carboxylic acid [1-(5-acetyl-furan-2-ylmethyl)-1H-pyrazol-3-yl]-amide;
[1-(4-Acetyl-pyridin-2-ylmethyl)-1H-pyrazol-4-yl]-carbamic acid 2-chloro-benzyl ester;
{4-[1-(5-Acetyl-furan-2-ylmethyl)-1H-pyrazol-3-ylcarbamoyl]-5-phenyl-oxazol-2-ylmethyl}-carbamic acid tert-butyl ester;
[1-(4-Acetyl-thiazol-2-ylmethyl)-1H-pyrazol-4-yl]-carbamic acid 2-chloro-benzyl ester;
5-Phenyl-oxazole-4-carboxylic acid [1-(4-acetyl-thiazol-2-ylmethyl)-1H-pyrazol-4-yl]-amide;
(E)-N-[1-(4-Acetyl-thiazol-2-ylmethyl)-1H-pyrazol-4-yl]-3-(4-trifluoromethyl-phenyl)-acrylamide;
2-Aminomethyl-5-phenyl-oxazole-4-carboxylic acid [1-(5-acetyl-furan-2-ylmethyl)-1H-pyrazol-3-yl]-amide;
2-Methyl-5-(3-trifluoromethoxy-phenyl)-oxazole-4-carboxylic acid [1-(5-acetyl-thiophen-2-ylmethyl)-1H-pyrazol-4-yl]-amide;
2-Methyl-5-(3-trifluoromethoxy-phenyl)-oxazole-4-carboxylic acid [1-(5-acetyl-thiophen-2-ylmethyl)-1H-pyrazol-3-yl]-amide;
5-m-Tolyl-oxazole-4-carboxylic acid [1-(5-acetyl-thiophen-2-ylmethyl)-1H-pyrazol-4-yl]-amide;
5-m-Tolyl-oxazole-4-carboxylic acid [1-(5-acetyl-thiophen-2-ylmethyl)-1H-pyrazol-3-yl]-amide;
2-Methyl-5-m-tolyl-thiazole-4-carboxylic acid [1-(5-acetyl-thiophen-2-ylmethyl)-1H-pyrazol-4-yl]-amide;
5-(4-Chloro-phenyl)-2-methyl-thiazole-4-carboxylic acid [1-(5-acetyl-thiophen-2-ylmethyl)-1H-pyrazol-4-yl]-amide;
5-(3-Cyano-phenyl)-oxazole-4-carboxylic acid [1-(5-acetyl-thiophen-2-ylmethyl)-1H-pyrazol-4-yl]-amide;
5-(3-Cyano-phenyl)-oxazole-4-carboxylic acid [1-(5-acetyl-thiophen-2-ylmethyl)-1H-pyrazol-3-yl]-amide;
5-(3-Dimethylamino-phenyl)-oxazole-4-carboxylic acid [1-(5-acetyl-thiophen-2-ylmethyl)-1H-pyrazol-4-yl]-amide;
5-(3-Dimethylamino-phenyl)-oxazole-4-carboxylic acid [1-(5-acetyl-thiophen-2-ylmethyl)-1H-pyrazol-3-yl]-amide;
2-Cyclopropyl-5-phenyl-oxazole-4-carboxylic acid [1-(5-acetyl-thiophen-2-ylmethyl)-1H-pyrazol-4-yl]-amide;
2-Cyclopropyl-5-phenyl-oxazole-4-carboxylic acid [1-(5-acetyl-thiophen-2-ylmethyl)-1H-pyrazol-3-yl]-amide;
5-(3-Methoxy-4-methyl-phenyl)-oxazole-4-carboxylic acid [1-(5-acetyl-thiophen-2-ylmethyl)-1H-pyrazol-4-yl]-amide;
5-(3-Hydroxymethyl-phenyl)-oxazole-4-carboxylic acid [1-(5-acetyl-furan-2-ylmethyl)-1H-pyrazol-3-yl]-amide;
5-[3-(2-Dimethylamino-ethyl)-phenyl]-oxazole-4-carboxylic acid [1-(5-acetyl-furan-2-ylmethyl)-1H-pyrazol-3-yl]-amide;
5-(3-Dimethylaminomethyl-phenyl)-oxazole-4-carboxylic acid [1-(5-acetyl-furan-2-ylmethyl)-1H-pyrazol-3-yl]-amide;
[1-(2-Acetyl-pyridin-4-ylmethyl)-1H-pyrazol-4-yl]-carbamic acid 2-chloro-benzyl ester;
5-Phenyl-oxazole-4-carboxylic acid [1-(5-acetyl-thiophen-3-ylmethyl)-1H-pyrazol-4-yl]-amide;
[1-(2-Acetyl-thiazol-4-ylmethyl)-1H-pyrazol-4-yl]-carbamic acid 2-chloro-benzyl ester;
(E)-N-[1-(6-Acetyl-pyridin-2-ylmethyl)-1H-pyrazol-3-yl]-3-(4-trifluoromethyl-phenyl)-acrylamide;
[1-(6-Acetyl-pyridin-2-ylmethyl)-1H-pyrazol-3-yl]-carbamic acid 2-chloro-benzyl ester;
5-(2-Fluoro-pyridin-4-yl)-oxazole-4-carboxylic acid [1-(5-acetyl-furan-2-ylmethyl)-1H-pyrazol-4-yl]-amide;
5-Phenyl-oxazole-4-carboxylic acid [1-(5-methanesulfonyl-furan-2-ylmethyl)-1H-pyrazol-4-yl]-amide;
5-Pyridin-4-yl-oxazole-4-carboxylic acid [1-(5-acetyl-furan-2-ylmethyl)-1H-pyrazol-4-yl]-amide;
5-(6-Methyl-pyridin-2-yl)-oxazole-4-carboxylic acid [1-(5-acetyl-furan-2-ylmethyl)-1H-pyrazol-4-yl]-amide;
2-Methoxymethyl-5-phenyl-oxazole-4-carboxylic acid [1-(5-acetyl-furan-2-ylmethyl)-1H-pyrazol-4-yl]-amide;
2-Methoxymethyl-5-phenyl-oxazole-4-carboxylic acid [1-(5-acetyl-furan-2-ylmethyl)-1H-pyrazol-3-yl]-amide;
{4-[1-(5-Acetyl-furan-2-ylmethyl)-1H-pyrazol-4-ylcarbamoyl]-5-phenyl-oxazol-2-ylmethyl}-carbamic acid tert-butyl ester;
5-(6-Trifluoromethyl-pyridin-2-yl)-oxazole-4-carboxylic acid [1-(5-acetyl-furan-2-ylmethyl)-1H-pyrazol-4-yl]-amide;
5-Isoxazol-5-yl-oxazole-4-carboxylic acid [1-(5-acetyl-furan-2-ylmethyl)-1H-pyrazol-4-yl]-amide;

5-Phenyl-oxazole-4-carboxylic acid [1-(2-acetyl-thiazol-4-ylmethyl)-1H-pyrazol-3-yl]-amide;
2-(2-Methoxy-ethyl)-5-phenyl-oxazole-4-carboxylic acid [1-(5-acetyl-furan-2-ylmethyl)-1H-pyrazol-4-yl]-amide;
2-(2-Methoxy-ethyl)-5-phenyl-oxazole-4-carboxylic acid [1-(5-acetyl-furan-2-ylmethyl)-1H-pyrazol-3-yl]-amide;
2-Isopropyl-5-phenyl-oxazole-4-carboxylic acid [1-(5-acetyl-furan-2-ylmethyl)-1H-pyrazol-4-yl]-amide;
2-Butyl-5-phenyl-oxazole-4-carboxylic acid [1-(5-acetyl-furan-2-ylmethyl)-1H-pyrazol-4-yl]-amide;
2-Isopropyl-5-phenyl-oxazole-4-carboxylic acid [1-(5-acetyl-furan-2-ylmethyl)-1H-pyrazol-3-yl]-amide;
2-Butyl-5-phenyl-oxazole-4-carboxylic acid [1-(5-acetyl-furan-2-ylmethyl)-1H-pyrazol-3-yl]-amide;
5-(3-Isopropoxymethyl-phenyl)-oxazole-4-carboxylic acid [1-(5-acetyl-furan-2-ylmethyl)-1H-pyrazol-3-yl]-amide;
5-[3-(2-Isopropoxy-ethyl)-phenyl]-oxazole-4-carboxylic acid [1-(5-acetyl-furan-2-ylmethyl)-1H-pyrazol-3-yl]-amide;
[1-(4-Acetyl-thiazol-2-ylmethyl)-1H-pyrazol-3-yl]-carbamic acid 2-chloro-benzyl ester;
5-Phenyl-oxazole-4-carboxylic acid [1-(4-acetyl-thiazol-2-ylmethyl)-1H-pyrazol-3-yl]-amide;
2-Benzyl-5-phenyl-oxazole-4-carboxylic acid [1-(5-acetyl-furan-2-ylmethyl)-1H-pyrazol-4-yl]-amide;
2-Benzyl-5-phenyl-oxazole-4-carboxylic acid [1-(5-acetyl-furan-2-ylmethyl)-1H-pyrazol-3-yl]-amide;
3-{4-[1-(5-Acetyl-furan-2-ylmethyl)-1H-pyrazol-3-ylcarbamoyl]-5-phenyl-oxazol-2-yl}-propionic acid tert-butyl ester;
5-Phenyl-oxazole-4-carboxylic acid [1-(5-acetyl-thiazol-2-ylmethyl)-1H-pyrazol-4-yl]-amide;
[1-(5-Acetyl-thiazol-2-ylmethyl)-1H-pyrazol-4-yl]-carbamic acid 2-chloro-benzyl ester;
5-Phenyl-oxazole-4-carboxylic acid [1-(2-acetyl-thiazol-5-ylmethyl)-1H-pyrazol-4-yl]-amide;
(E)-N-[1-(2-Acetyl-thiazol-5-ylmethyl)-1H-pyrazol-4-yl]-3-(4-trifluoromethyl-phenyl)-acrylamide;
[1-(2-Acetyl-thiazol-5-ylmethyl)-1H-pyrazol-4-yl]-carbamic acid 2-chloro-benzyl ester;
5-Phenyl-oxazole-4-carboxylic acid [1-(2-acetyl-oxazol-5-ylmethyl)-1H-pyrazol-3-yl]-amide;
5-Phenyl-oxazole-4-carboxylic acid [1-(4-acetyl-thiophen-2-ylmethyl)-1H-pyrazol-4-yl]-amide;
[1-(4-Acetyl-thiophen-2-ylmethyl)-1H-pyrazol-4-yl]-carbamic acid 2-chloro-benzyl ester;
2-Methyl-5-m-tolyl-oxazole-4-carboxylic acid [1-(4-acetyl-thiazol-2-ylmethyl)-1H-pyrazol-3-yl]-amide;
5-(3-Chloro-phenyl)-2-methyl-oxazole-4-carboxylic acid [1-(4-acetyl-thiazol-2-ylmethyl)-1H-pyrazol-3-yl]-amide;
5-m-Tolyl-oxazole-4-carboxylic acid [1-(4-acetyl-thiazol-2-ylmethyl)-1H-pyrazol-3-yl]-amide;
2-Methyl-5-phenyl-oxazole-4-carboxylic acid [1-(4-acetyl-thiazol-2-ylmethyl)-1H-pyrazol-3-yl]-amide;
2-Methyl-5-(3-trifluoromethyl-phenyl)-oxazole-4-carboxylic acid [1-(4-acetyl-thiazol-2-ylmethyl)-1H-pyrazol-3-yl]-amide;
5-(3-Fluoro-phenyl)-oxazole-4-carboxylic acid [1-(4-acetyl-thiazol-2-ylmethyl)-1H-pyrazol-3-yl]-amide;
5-(3-Dimethylamino-phenyl)-oxazole-4-carboxylic acid [1-(4-acetyl-thiazol-2-ylmethyl)-1H-pyrazol-3-yl]-amide;
5-(3-Chloro-phenyl)-oxazole-4-carboxylic acid [1-(4-acetyl-thiazol-2-ylmethyl)-1H-pyrazol-3-yl]-amide;
2-Methyl-5-(3-trifluoromethoxy-phenyl)-oxazole-4-carboxylic acid [1-(4-acetyl-thiazol-2-ylmethyl)-1H-pyrazol-3-yl]-amide;
5-(3-Trifluoromethoxy-phenyl)-oxazole-4-carboxylic acid [1-(4-acetyl-thiazol-2-ylmethyl)-1H-pyrazol-3-yl]-amide;
5-(3-Methoxy-phenyl)-oxazole-4-carboxylic acid [1-(4-acetyl-thiazol-2-ylmethyl)-1H-pyrazol-3-yl]-amide;
(E)-N-[1-(4-Acetyl-thiazol-2-ylmethyl)-1H-pyrazol-3-yl]-3-(4-trifluoromethyl-phenyl)-acrylamide;
(E)-N-[1-(4-Acetyl-thiazol-2-ylmethyl)-1H-pyrazol-3-yl]-3-(2-trifluoromethyl-phenyl)-acrylamide;
(E)-N-[1-(4-Acetyl-thiazol-2-ylmethyl)-1H-pyrazol-3-yl]-3-(3-trifluoromethoxy-phenyl)-acrylamide;
(E)-N-[1-(4-Acetyl-thiazol-2-ylmethyl)-1H-pyrazol-3-yl]-3-(2-chloro-4-fluoro-phenyl)-acrylamide;
5-(3-Methoxy-phenyl)-2-methyl-oxazole-4-carboxylic acid [1-(4-acetyl-thiazol-2-ylmethyl)-1H-pyrazol-3-yl]-amide;
5-(3-Fluoro-phenyl)-2-methyl-oxazole-4-carboxylic acid [1-(4-acetyl-thiazol-2-ylmethyl)-1H-pyrazol-3-yl]-amide;
5-Phenyl-oxazole-4-carboxylic acid [1-(4-acetyl-oxazol-2-ylmethyl)-1H-pyrazol-3-yl]-amide;
5-Phenyl-oxazole-4-carboxylic acid {1-[4-(1,1-difluoro-ethyl)-thiazol-2-ylmethyl]-1H-pyrazol-3-yl}-amide;
[1-(5-Oxo-hexyl)-1H-pyrazol-4-yl]carbamic acid benzothiazol-2-ylmethyl ester;
5-(6-Trifluoromethyl-pyridin-2-yl)-oxazole-4-carboxylic acid [1-(5-acetyl-furan-2-ylmethyl)-1H-pyrazol-3-yl]-amide;
(E)-N-[1-(5-Acetyl-furan-2-ylmethyl)-1H-pyrazol-4-yl]-3-(1H-indol-3-yl)-acrylamide;
5-Phenyl-oxazole-4-carboxylic acid [1-(5-acetyl-oxazol-2-ylmethyl)-1H-pyrazol-3-yl]-amide; or
[1-(2-Acetyl-oxazol-4-ylmethyl)-1H-pyrazol-4-yl]-carbamic acid 2-chloro-benzyl ester;
or a salt thereof.

11. A medicinal compound of comprising the formula according to claim 1, or a pharmaceutically acceptable salt thereof.

12. A pharmaceutical composition comprising as an active principle the compound of claim 1 or a pharmaceutically acceptable salt thereof, and at least one therapeutically inert excipient.

13. A method of treating a disease comprising the administration of a therapeutically effective amount of the compound of claim 1 or a pharmaceutically acceptable salt thereof, wherein the disease is selected from acute lung injury, adult/acute respiratory distress syndrome, asthma, hyper-neutrophilia, periodontitis, glomerulonephritis, cystic fibrosis, psoriasis, contact dermatitis, atopic dermatitis, dermatitis herpetiformis, scleroderma, hypersensitivity angiitis, urticaria, lupus erythematosus, epidermolysis, conjunctivitis, keratoconjunctivitis sicca, vernal conjunctivitis, inflammatory disease in which autoimmune reactions are implicated or which have an autoimmune component or aetiology, autoimmune inflammatory bowel disease, HIV-mediated retroviral infections, neuroinflammation, stroke, cerebral ischemia, Alzheimer's disease, Parkinson's disease, transmissible spongiform encephalopathies, mild cognitive impairment, dementia with Lewy bodies, Down's syndrome, cerebral hemorrhage with amyloidosis, progressive supranuclear palsy, multiple sclerosis, Creutzfeld Jakob disease, HIV-related dementia, amyotropic lateral sclerosis, inclusion-body myositis, adult onset diabetes or senile cardiac amyloidosis.

14. A method of treating a disease comprising the administration of a therapeutically effective amount of the composition of claim 12 or a pharmaceutically acceptable salt thereof, wherein the disease is selected from acute lung injury, adult/acute respiratory distress syndrome, asthma, hyper-neutrophilia, periodontitis, glomerulonephritis, cystic fibrosis, psoriasis, contact dermatitis, atopic dermatitis, dermatitis herpetiformis, scleroderma, hypersensitivity angiitis, urticaria, lupus erythematosus, epidermolysis, conjunctivitis, keratoconjunctivitis sicca, vernal conjunctivitis, inflammatory disease in which autoimmune reactions are implicated or which have an autoimmune component or aetiology, autoimmune inflammatory bowel disease, HIV-mediated retroviral infections, neuroinflammation, stroke, cerebral ischemia, Alzheimer's disease, Parkinson's disease, transmissible spongiform encephalopathies, mild cognitive impairment, dementia with Lewy bodies, Down's syndrome, cerebral hemorrhage with amyloidosis, progressive supranuclear palsy, multiple sclerosis, Creutzfeld Jakob disease, HIV-related dementia, amyotropic lateral sclerosis, inclusion-body myositis, adult onset diabetes or senile cardiac amyloidosis.

15. The compound of claim 6, wherein $R^3$ represents hydrogen or methyl; or a salt thereof.

16. The compound of claim 15, wherein $R^1$ represents phenyl, which is unsubstituted, mono-, di- or tri-substituted with halogen, $(C_1-C_4)$alkyl, $(C_1-C_4)$alkoxy, $(C_1-C_4)$fluoroalkyl, $(C_1-C_4)$fluoroalkoxy, phenyl, cyano, dimethylamino, —C(O)OtBu or $(C_1-C_4)$alkoxy-$(C_1-C_2)$alkyl;

or a salt thereof.

17. The compound of claim 16, wherein $R^2$ represents —CO—$(C_1-C_3)$alkyl or —CF$_2$—$(C_1-C_3)$alkyl; or a salt thereof.

* * * * *